(12) United States Patent
Bogoch et al.

(10) Patent No.: US 7,452,963 B2
(45) Date of Patent: Nov. 18, 2008

(54) REPLIKIN PEPTIDES AND ANTIBODIES THEREFORE

(76) Inventors: Samuel Bogoch, 49 E. 91st St., New York, NY (US) 10028; Elenore S. Bogoch, 49 E. 91st St., New York, NY (US) 10028

( * ) Notice: Subject to any disclaimer, the term of this patent is extended or adjusted under 35 U.S.C. 154(b) by 380 days.

(21) Appl. No.: 10/189,437

(22) Filed: Jul. 8, 2002

(65) Prior Publication Data

US 2003/0194414 A1  Oct. 16, 2003

Related U.S. Application Data

(63) Continuation-in-part of application No. 10/105,232, filed on Mar. 26, 2002, which is a continuation-in-part of application No. 09/984,057, filed on Oct. 26, 2001.

(60) Provisional application No. 60/303,396, filed on Jul. 9, 2001, provisional application No. 60/278,761, filed on Mar. 27, 2001.

(51) Int. Cl.
*A61K 38/03* (2006.01)
*A61K 38/16* (2006.01)

(52) U.S. Cl. .................................................. 530/300

(58) Field of Classification Search .................. 530/300
See application file for complete search history.

(56) References Cited

U.S. PATENT DOCUMENTS

| 5,104,854 | A |   | 4/1992  | Schlesinger et al. |         |
|-----------|---|---|---------|--------------------|---------|
| 5,231,167 | A | * | 7/1993  | Zanetti et al.     | 530/324 |
| 5,280,113 | A |   | 1/1994  | Rademacher         |         |
| 5,679,352 | A |   | 10/1997 | Chong              |         |
| 5,866,690 | A |   | 2/1999  | Bogoch             |         |
| 6,023,659 | A |   | 2/2000  | Seilhamer          |         |
| 6,070,126 | A |   | 5/2000  | Kokolus            |         |
| 6,242,578 | B1 |  | 6/2001  | Bogoch             |         |
| 6,256,647 | B1 |  | 7/2001  | Toh                |         |
| 6,638,505 | B2 |  | 10/2003 | Bogoch             |         |
| 2005/0271676 | A1 | | 12/2005 | Sette             |         |

FOREIGN PATENT DOCUMENTS

| EP | 0108564        |   | 5/1984  |
|----|----------------|---|---------|
| IT | 98MI0874 A1    | * | 10/1999 |
| WO | 96/32106       |   | 10/1996 |
| WO | WO 00/18351 A  |   | 4/2000  |
| WO | 0104135 A2     |   | 1/2001  |
| WO | 02085093 A2    |   | 10/2002 |
| WO | 03005880 A3    |   | 1/2003  |

OTHER PUBLICATIONS

Rodman et al. J. Exp. Med. 175: 1247-1253.*
Weber et al. Virology 1988, vol. 164, pp. 30-38.*
Gelder, CM et al., "Human CD4+ T-cell repertoire of responses to influenza A virus hemagglutinin after recent natural infection," J. Virol., 1995, vol. 69, No. 12, pp. 7497-7506.
Pannifer, et al. "Crystal structure of the anthrax lethal factor," *Nature*, vol. 414, pp. 229-233, (Nov. 2001).
Zhao, et al. "Neutralizing monoclonal antibody against Anthrax lethal factor inhibits intoxication in a mouse model," *Human Antibodies*, vol. 12, pp. 129-135, (2003).
Brown, L. R. et al., "Recognition of the influenza hemagglutinin by Class II MHC-restricted T lymphocytes and antibodies," *Journal of Immunology*, Oct. 15, 1991, pp. 2677-2684, vol. 147, No. 8, American Association of Immunologists, USA, XP002371257, ISSN: 0022-1767.
Atassi, M. Z. et al., "A novel approach for localization of the continuous protein antigenic sites by comprehensive synthetic surface scanning: Antibody and T cell activity to several influenza hemagglutinin synthetic sites," *Immunological Communications*, 1984, pp. 539-551, vol. 13, No. 6, Marcel Dekker, Inc., XP009062995, ISSN: 0090-0877.
Carr, C. M. et al. "A spring-loaded mechanism for the conformational change of influenza hemagglutinin," *Cell*, May 21, 1993, pp. 823-832, vol. 73, Cell Press, XP002059698; ISSN: 0092-8674.
Ben-Yedidia, T. et al., "Intranasal administration of peptide vaccine protects human/mouse radiation chimera from influenza infection," *International Immunology*, 1999, pp. 1043-1051, XP000914818, ISSN: 0953-8178.
Schenk, S. et al., "Four recombinant isoforms of *Cor a* 1, the major allergen of hazel pollen, show different reactivities with allergen-specific T-lymphocyte clones," *European Journal of Biochemistry*, 1994, pp. 717-722, vol. 224, XP002371408, ISSN: 0014-2956.
Orlando, C. et al., "A monoclonal antibody directed against the catalytic site of *Bacillus anthracis* adenylyl cyclase identifies a novel mammalian brain catalytic subunit," *Biochemistry*, 1992, pp. 3215-3222, vol. 31, American Chemical Society, XP002371438, ISSN: 0006-2960.
Supplementary Partial European Search Report 03721445.9, Dec. 12, 2006, EPO, International Searching Authority, Munich, DE.
PCT International Search Report, PCT/US2002/09240, Jan. 14, 2004, USPTO, International Searching Authority, Washington DC.
PCT International Preliminary Examination Report, PCT/US2002/09240, Feb. 5, 2004, USPTO, International Preliminary Examination Authority, Alexandria, VA, USA.
PCT International Search Report, PCT/US2002/21494, May 30, 2003, USPTO, International Searching Authority, Washington DC.
NCBI Accession No. NP 740460, residues 201-210.
PCT International Search Report, PCT/US2003/08990, Dec. 7, 2005, International Searching Authority, USPTO, Alexandria, VA, USA.
PCT International Search Report, PCT/US2004/017936, Apr. 28, 2005, EPO, International Searching Authority, Rijswijk, NL.
PCT Written Opinion of the International Searching Authority, PCT/US2004/017936, Apr. 7, 2005, EPO, International Searching Authority, Munich, DE.
PCT International Preliminary Report on Patentability, PCT/US2004/017936, Apr. 13, 2007, USPTO, International Preliminary Examining Authority, Alexandria, VA, USA.

(Continued)

*Primary Examiner*—Bruce Campell
*Assistant Examiner*—Myron G. Hill
(74) *Attorney, Agent, or Firm*—Kenyon & Kenyon LLP

(57) ABSTRACT

The present invention provides a new class of peptides related to rapid replication and their use in diagnosing, preventing and treating disease.

2 Claims, 9 Drawing Sheets

OTHER PUBLICATIONS

PCT International Preliminary Report on Patentability, PCT/US2005/014443, Nov. 1, 2006, WIPO, International Bureau of WIPO, Geneva, Switzerland.

PCT Written Opinion of the International Searching Authority, PCT/US2005/014443, Apr. 12, 2006, EPO, International Searching Authority, Munich, DE.

Bogoch, S. et al., "A Checklist for Suitability of Biomarkers as Surrogate Endpoints in Chemoprevention of Breast Cancer," Journal of Cellular Biochemistry, Supplement, Boston, US, vol. 19, pp. 173-185, XP009046492, ISSN: 0733-1959, 1994.

Bucher, D. et al., "M protein (M1) of influenza virus antigenic analysis and intracellular localization with monoclonal antibodies", J Virol. Sep. 1989; 63(9): pp. 3622-3633.

Chambers, T.M. et al., "Antigenic and molecular characterization of subtype H13 hemagglutinin of influenza virus," Database NCBI on STN, Accession No. HMIVT2, Virology, pp. 180-188, abstract, 1989, 172(1).

SHI, Immunogenicity and in vitro protective efficacy of a recombinant multistage Plasmodium falciparum candidate vaccine, PNAS vol. 96, No. 4, pp. 1615-1620.

Tanaka, T. et al., "Efficient Generation of Antibodies to Oncoproteins by using Synthetic Peptide Antigens." Proceedings of the National Academy of Sciences of USA, National Academy of Science, Washington, D.C., US, v. 82, No. 10, p. 3400-3404, tables 1, Peptide 21, XP000113798, ISSN: 0027-8424, May 1, 1985.

3Motif—Search Instructions, 3motif in three Dimensions, article titles "Submitting a protein sequence": http://brutlag.sanford.edu/3motif/search_instr.html).

NCBI accession # gi 75059 Jul. 16, 1999.

NCBI Listing JQ0032, residues 74-82, May 11, 2000.

NCBI Query Tutorial "Introduction" (http://ncbi.nim.nih.gov/Education/BLASTinfo/query_tutorial.html).

NCBI Query Tutorial "Introduction to a BLAST Query" (http://www.ncbi.nim.nih.gov/Education/BLASTinfo/tut1.html).

NCBI Query Tutorial "Setting up a BLAST Search" (http://www.ncbi.nim.nih.gov/Education/BLASTinfo/Blast_setup.html).

NCBI Blast Searching, Gene Gateway—Exploring Genes and Genetic Disorders, "Sequence similarity searching using NCBI Blast" (http:www.ORNL.gov/sci/techresources/Himan_Genome/chromosome/blast.shtml).

Abrams M. B. et al., "Early Detection and Monitoring of cancer with the Anti-Malignin Antibody Test," Cancer detection and Prevention, XX, XX, vol. 18, No. 1, 1994, pp. 65-78, XP000673180, ISSN:0361-090X.

Bogoch et al., "Aglyco Pathology of Viral Receptors in Dementias," Annals of the New York Academy of Sciences, New York Academy of Sciences, New York Academy of Sciences, New York, NY, US, vol. 757, 1995, pp.413-417, XP008003395, ISSN:0077-8923.

Keppeler et al., "Elongation of thr N-acyl side chain of sialic acid in MDCK II cells inhibits influenza A virus infection," abstract Biochemical amd Biophysical Research Communications, Dec. 18, 1998, vol. 253, No. 2. Database Medline on STN, National Library of Medicine, (Bethesda, MD, USA), No. 99097253.

Kornblith P. L. et al., "Growth-inhibitory effect of diphenylhydantoin on murine astrocytomas," Medline, XP002199627.

Margalit et al., "Prediction of Immunodomaint Helper T Cell Antigenic Sites From the Primary Sequence," Jour. Of Immunology, vol. 138, 2213-2229, Apr. 1, 1987.

Seal et al., "Elevation of Serum Protein-Bound Carbohydrates and Haptoglobin in Schrzophrenia," Clincal Chemistry; Oct. 1996, vol. 12, No. 10, pp. 709-716.

PCT International Search Report, PCT/US2005/014443, Oct. 21, 2006, EPO, International Searching Authority, Munich, DE.

EP Supplementary Search 99944002, Apr. 20, 2004.

Bogoch et al., "Rapid replication and Replikintm structures: basis of the AMASRTest and CAVAXR," Cancer Detection and Prevention Online, Feb. 9, 2002, XP002350483.

Brumeanu, T.M. et al., "Immunogenicity of a Contiguous T-B Synthetic Epitope of the A/PR/8/34 Influenaz Virus," Journal of Virology, Jul. 1997, vol. 71, No. 7, pp. 5473-5480.

GAO, Identification and characterization of T helper epitopes in the nucleoprotein of influenza A virus, J. Immunol. 1989, vol. 143, pp. 3007-3014.

PCT International Search Report, PCT/US2006/05343, Sep. 25, 2007, USPTO, International Searching Authority, Alexandria, VA, USA.

NCBI Accession # AAK38298, Apr. 19, 2001.

Yasuko, A-O, et al., "Intranasal administration of adjuvant-combined recombinant influenza virus HA vaccine protects mice from the lethal H5N1 virus infection." Microbes and Infection, vol. 8, Issues 12-13, pp. 2706-2714, Oct. 2006.

* cited by examiner

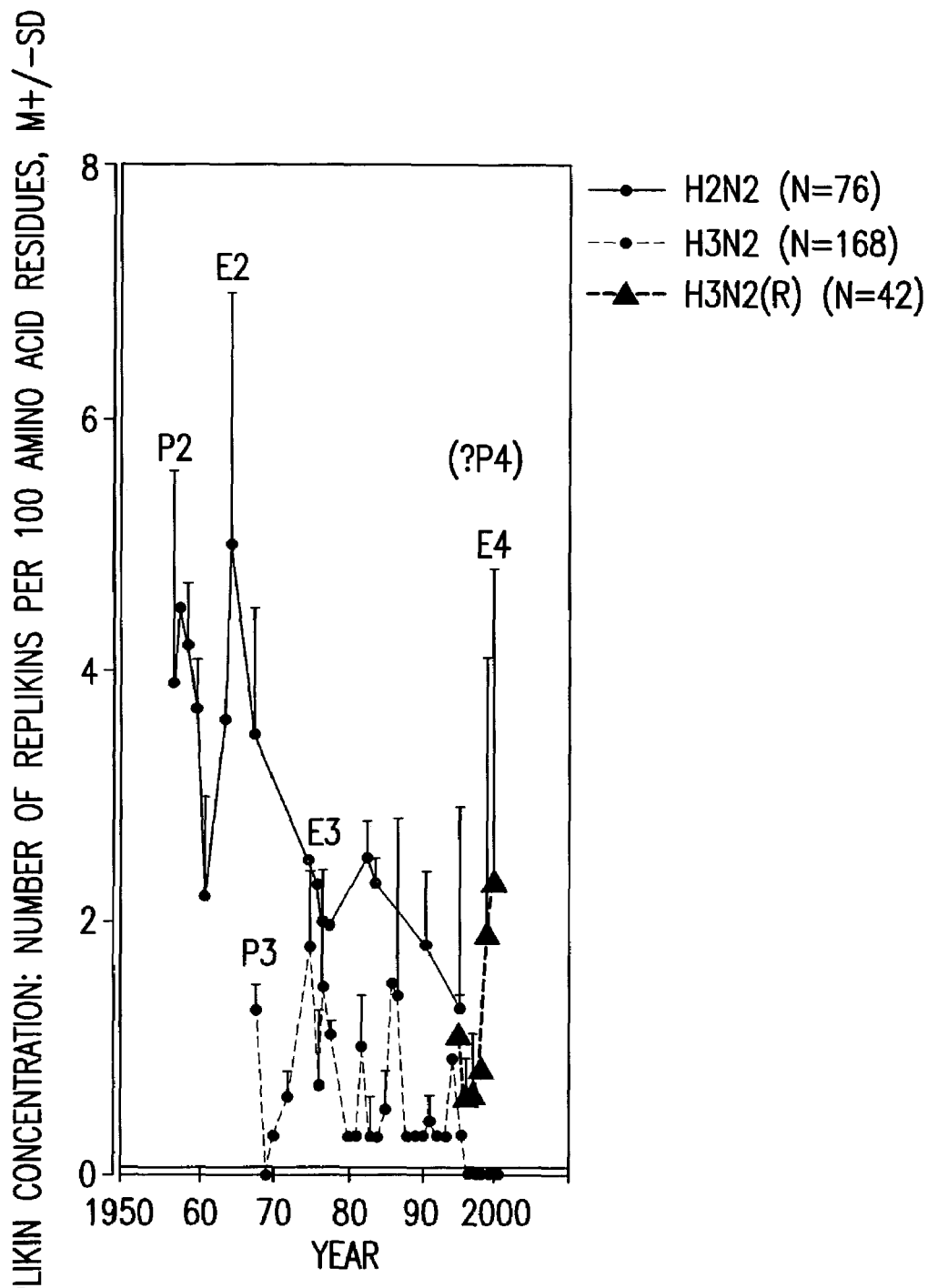

SEQUENCE LISTING

```
<160> NUMBER OF SEQ ID NOS: 729

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      glioma replikin

<400> SEQUENCE: 1

Lys Ala Gly Val Ala Phe Leu His Lys Lys
1               5                   10

<210> SEQ ID NO 2
<211> LENGTH: 13
<212> TYPE: PRT
<213> ORGANISM: Saccharomyces cerevisiae

<400> SEQUENCE: 2

His Ser Ile Lys Arg Glu Leu Gly Ile Ile Phe Asp Lys
1               5                   10

<210> SEQ ID NO 3
<211> LENGTH: 10
<212> TYPE: PRT
<213> ORGANISM: Gemini vinis virus

<400> SEQUENCE: 3

His Lys Gln Lys Ile Val Ala Pro Val Lys
1               5                   10

<210> SEQ ID NO 4
<211> LENGTH: 16
<212> TYPE: PRT
<213> ORGANISM: Unknown Organism
<220> FEATURE:
<223> OTHER INFORMATION: Description of Unknown Organism: Virus recognin
```

```
<400> SEQUENCE: 4

Tyr Lys Ala Gly Val Ala Phe Leu His Lys Lys Asn Asp Ile Asp Glu
 1               5                  10                  15

<210> SEQ ID NO 5
<211> LENGTH: 10
<212> TYPE: PRT
<213> ORGANISM: Human immunodeficiency virus type 1

<400> SEQUENCE: 5

Lys Cys Phe Asn Cys Gly Lys Glu Gly His
 1               5                  10

<210> SEQ ID NO 6
<211> LENGTH: 11
<212> TYPE: PRT
<213> ORGANISM: Human immunodeficiency virus type 1

<400> SEQUENCE: 6

Lys Val Tyr Leu Ala Trp Val Pro Ala His Lys
 1               5                  10

<210> SEQ ID NO 7
<211> LENGTH: 10
<212> TYPE: PRT
<213> ORGANISM: Human immunodeficiency virus type 2

<400> SEQUENCE: 7

Lys Cys Trp Asn Cys Gly Lys Glu Gly His
 1               5                  10

<210> SEQ ID NO 8
<211> LENGTH: 11
<212> TYPE: PRT
<213> ORGANISM: Maize streak virus

<400> SEQUENCE: 8

Lys Tyr Ile Val Cys Ala Arg Glu Ala His Lys
 1               5                  10

<210> SEQ ID NO 9
<211> LENGTH: 17
<212> TYPE: PRT
<213> ORGANISM: Maize streak virus

<400> SEQUENCE: 9

Lys Glu Lys Lys Pro Ser Lys Asp Glu Ile Met Arg Asp Ile Ile Ser
 1               5                  10                  15

His

<210> SEQ ID NO 10
<211> LENGTH: 9
<212> TYPE: PRT
<213> ORGANISM: Staphylococcus aureus

<400> SEQUENCE: 10

Lys Lys Glu Lys Thr Thr His Asn Lys
 1               5

<210> SEQ ID NO 11
<211> LENGTH: 10
<212> TYPE: PRT
<213> ORGANISM: Bovine herpesvirus 4
```

```
<400> SEQUENCE: 11

His Lys Ile Asn Ile Thr Asn Gly Gln Lys
 1               5                  10

<210> SEQ ID NO 12
<211> LENGTH: 10
<212> TYPE: PRT
<213> ORGANISM: Meleagrid herpesvirus 1

<400> SEQUENCE: 12

His Lys Asp Leu Tyr Arg Leu Leu Met Lys
 1               5                  10

<210> SEQ ID NO 13
<211> LENGTH: 15
<212> TYPE: PRT
<213> ORGANISM: Unknown Organsim
<220> FEATURE:
<223> OTHER INFORMATION: Description of Unknown Organism: Virus recognin

<400> SEQUENCE: 13

Lys Phe Arg Ile Asn Ala Lys Asn Tyr Phe Leu Thr Tyr Pro His
 1               5                  10                  15

<210> SEQ ID NO 14
<211> LENGTH: 19
<212> TYPE: PRT
<213> ORGANISM: Unknown Organism
<220> FEATURE:
<223> OTHER INFORMATION: Description of Unknown Organism: Virus recognin

<400> SEQUENCE: 14

Lys Asn Leu Glu Thr Pro Val Asn Lys Leu Phe Ile Arg Ile Cys Arg
 1               5                  10                  15

Glu Phe His

<210> SEQ ID NO 15
<211> LENGTH: 14
<212> TYPE: PRT
<213> ORGANISM: Unknown Organism
<220> FEATURE:
<223> OTHER INFORMATION: Description of Unknown Organism: Virus recognin

<400> SEQUENCE: 15

His Pro Asn Ile Gln Ala Ala Lys Ser Ser Thr Asp Val Lys
 1               5                  10

<210> SEQ ID NO 16
<211> LENGTH: 19
<212> TYPE: PRT
<213> ORGANISM: Unknown Organism
<220> FEATURE:
<223> OTHER INFORMATION: Description of Unknown Organism: Virus recognin

<400> SEQUENCE: 16

Lys Ser Ser Thr Asp Val Lys Ala Tyr Met Asp Lys Asp Gly Asp Val
 1               5                  10                  15

Leu Asp His

<210> SEQ ID NO 17
<211> LENGTH: 21
<212> TYPE: PRT
<213> ORGANISM: Unknown Organism
<220> FEATURE:
```

-continued

```
<223> OTHER INFORMATION: Description of Unknown Organism: Virus recognin

<400> SEQUENCE: 17

Lys Ala Ser Ala Leu Asn Ile Leu Arg Glu Lys Ala Pro Lys Asp Phe
 1               5                  10                  15

Val Leu Gln Phe His
            20

<210> SEQ ID NO 18
<211> LENGTH: 13
<212> TYPE: PRT
<213> ORGANISM: Hepatitis C virus

<400> SEQUENCE: 18

His Tyr Pro Pro Lys Pro Gly Cys Ile Val Pro Ala Lys
 1               5                  10

<210> SEQ ID NO 19
<211> LENGTH: 4
<212> TYPE: PRT
<213> ORGANISM: Homo sapiens

<400> SEQUENCE: 19

Tyr Lys Ala Gly
 1

<210> SEQ ID NO 20
<211> LENGTH: 6
<212> TYPE: PRT
<213> ORGANISM: Homo sapiens

<400> SEQUENCE: 20

Tyr Lys Ala Gly Val Ala
 1               5

<210> SEQ ID NO 21
<211> LENGTH: 7
<212> TYPE: PRT
<213> ORGANISM: Homo sapiens

<400> SEQUENCE: 21

Tyr Lys Ala Gly Val Ala Phe
 1               5

<210> SEQ ID NO 22
<211> LENGTH: 7
<212> TYPE: PRT
<213> ORGANISM: Homo sapiens

<400> SEQUENCE: 22

Tyr Lys Ala Gly Val Ala Phe
 1               5

<210> SEQ ID NO 23
<211> LENGTH: 9
<212> TYPE: PRT
<213> ORGANISM: Homo sapiens

<400> SEQUENCE: 23

Ala Gly Val Ala Phe His Lys Lys Asn
 1               5

<210> SEQ ID NO 24
<211> LENGTH: 4
```

```
<212> TYPE: PRT
<213> ORGANISM: Homo sapiens

<400> SEQUENCE: 24

Gly Val Ala Phe
 1

<210> SEQ ID NO 25
<211> LENGTH: 3
<212> TYPE: PRT
<213> ORGANISM: Homo sapiens

<400> SEQUENCE: 25

Val Ala Phe
 1

<210> SEQ ID NO 26
<211> LENGTH: 7
<212> TYPE: PRT
<213> ORGANISM: Homo sapiens

<400> SEQUENCE: 26

Val Ala Phe Leu His Lys Lys
 1               5

<210> SEQ ID NO 27
<211> LENGTH: 7
<212> TYPE: PRT
<213> ORGANISM: Homo sapiens

<400> SEQUENCE: 27

Val Ala Phe Leu His Lys Lys
 1               5

<210> SEQ ID NO 28
<211> LENGTH: 9
<212> TYPE: PRT
<213> ORGANISM: Homo sapiens

<400> SEQUENCE: 28

Val Ala Phe Leu His Lys Lys Asn Asp
 1               5

<210> SEQ ID NO 29
<211> LENGTH: 8
<212> TYPE: PRT
<213> ORGANISM: Homo sapiens

<400> SEQUENCE: 29

Val Ala Phe His Lys Lys Asn Asp
 1               5

<210> SEQ ID NO 30
<211> LENGTH: 4
<212> TYPE: PRT
<213> ORGANISM: Homo sapiens

<400> SEQUENCE: 30

Ala Phe Leu His
 1

<210> SEQ ID NO 31
<211> LENGTH: 8
<212> TYPE: PRT
<213> ORGANISM: Homo sapiens
```

```
<400> SEQUENCE: 31

His Lys Lys Asn Asp Ile Asp Glu
1               5

<210> SEQ ID NO 32
<211> LENGTH: 6
<212> TYPE: PRT
<213> ORGANISM: Homo sapiens

<400> SEQUENCE: 32

Lys Lys Asn Asp Ile Asp
1               5

<210> SEQ ID NO 33
<211> LENGTH: 6
<212> TYPE: PRT
<213> ORGANISM: Homo sapiens

<400> SEQUENCE: 33

Lys Asn Asp Ile Asp Glu
1               5

<210> SEQ ID NO 34
<211> LENGTH: 8
<212> TYPE: PRT
<213> ORGANISM: Caldophera prolifera

<400> SEQUENCE: 34

Lys Ala Ser Lys Phe Thr Lys His
1               5

<210> SEQ ID NO 35
<211> LENGTH: 12
<212> TYPE: PRT
<213> ORGANISM: Isolepis prolifera

<400> SEQUENCE: 35

Lys Ala Gln Ala Glu Thr Gly Glu Ile Lys Gly His
1               5                   10

<210> SEQ ID NO 36
<211> LENGTH: 10
<212> TYPE: PRT
<213> ORGANISM: Schizosaccharomyces pombe

<400> SEQUENCE: 36

Lys Ser Phe Lys Tyr Pro Lys Lys His Lys
1               5                   10

<210> SEQ ID NO 37
<211> LENGTH: 10
<212> TYPE: PRT
<213> ORGANISM: Oryza sativa

<400> SEQUENCE: 37

Lys Lys Ala Tyr Gly Asn Glu Leu His Lys
1               5                   10

<210> SEQ ID NO 38
<211> LENGTH: 9
<212> TYPE: PRT
<213> ORGANISM: Penicillium marneffei

<400> SEQUENCE: 38
```

```
Lys Val Asp Ile Val Thr His Gln Lys
 1               5
```

<210> SEQ ID NO 39
<211> LENGTH: 12
<212> TYPE: PRT
<213> ORGANISM: Diseula dcstructiva

<400> SEQUENCE: 39

```
Lys Leu Glu Glu Asp Ala Ala Tyr His Arg Lys Lys
 1               5                  10
```

<210> SEQ ID NO 40
<211> LENGTH: 17
<212> TYPE: PRT
<213> ORGANISM: Ophiostoma novo-ulmi

<400> SEQUENCE: 40

```
Lys Val Ile Leu Pro Leu Arg Gly Asn Ile Lys Gly Ile Phe Phe Lys
 1               5                  10                  15

His
```

<210> SEQ ID NO 41
<211> LENGTH: 11
<212> TYPE: PRT
<213> ORGANISM: Entamoeba invadens

<400> SEQUENCE: 41

```
Lys Leu Ile Leu Lys Gly Asp Leu Asn Lys His
 1               5                  10
```

<210> SEQ ID NO 42
<211> LENGTH: 8
<212> TYPE: PRT
<213> ORGANISM: Helicobacter pylori

<400> SEQUENCE: 42

```
Lys Ser Val His Ala Phe Leu Lys
 1               5
```

<210> SEQ ID NO 43
<211> LENGTH: 9
<212> TYPE: PRT
<213> ORGANISM: Mycoplasma pulmonis

<400> SEQUENCE: 43

```
Lys Val His Phe Phe Gln Leu Lys Lys
 1               5
```

<210> SEQ ID NO 44
<211> LENGTH: 9
<212> TYPE: PRT
<213> ORGANISM: Arabidopsis thaliana

<400> SEQUENCE: 44

```
Lys Asp His Asp Phe Asp Gly Asp Lys
 1               5
```

<210> SEQ ID NO 45
<211> LENGTH: 11
<212> TYPE: PRT
<213> ORGANISM: Arabidopsis thaliana

<400> SEQUENCE: 45

Lys Met Lys Gly Leu Lys Gln Lys Lys Ala His
1               5                   10

<210> SEQ ID NO 46
<211> LENGTH: 12
<212> TYPE: PRT
<213> ORGANISM: Arabidopsis thaliana

<400> SEQUENCE: 46

Lys Glu Leu Ser Ser Thr Thr Gln Glu Lys Ser His
1               5                   10

<210> SEQ ID NO 47
<211> LENGTH: 9
<212> TYPE: PRT
<213> ORGANISM: Feline immunodeficiency virus

<400> SEQUENCE: 47

His Leu Lys Asp Tyr Lys Leu Val Lys
1               5

<210> SEQ ID NO 48
<211> LENGTH: 7
<212> TYPE: PRT
<213> ORGANISM: Rous sarcoma virus

<400> SEQUENCE: 48

Lys Lys Leu Arg His Glu Lys
1               5

<210> SEQ ID NO 49
<211> LENGTH: 7
<212> TYPE: PRT
<213> ORGANISM: Avian sarcoma virus

<400> SEQUENCE: 49

Lys Lys Leu Arg His Asp Lys
1               5

<210> SEQ ID NO 50
<211> LENGTH: 7
<212> TYPE: PRT
<213> ORGANISM: Homo sapiens

<400> SEQUENCE: 50

Lys Lys Leu Arg His Asp Lys
1               5

<210> SEQ ID NO 51
<211> LENGTH: 7
<212> TYPE: PRT
<213> ORGANISM: Avian sarcoma virus

<400> SEQUENCE: 51

Lys Lys Leu Arg His Glu Lys
1               5

<210> SEQ ID NO 52
<211> LENGTH: 7
<212> TYPE: PRT
<213> ORGANISM: Homo sapiens

<400> SEQUENCE: 52

Lys Lys Leu Arg His Glu Lys

<210> SEQ ID NO 53
<211> LENGTH: 8
<212> TYPE: PRT
<213> ORGANISM: Homo sapiens

<400> SEQUENCE: 53

Lys Gln Ala His Glu Leu Ala Lys
1               5

<210> SEQ ID NO 54
<211> LENGTH: 8
<212> TYPE: PRT
<213> ORGANISM: Polyama virus

<400> SEQUENCE: 54

Lys Thr His Arg Phe Ser Lys His
1               5

<210> SEQ ID NO 55
<211> LENGTH: 8
<212> TYPE: PRT
<213> ORGANISM: Sindbis virus

<400> SEQUENCE: 55

Lys Asn Leu His Glu Lys Ile Lys
1               5

<210> SEQ ID NO 56
<211> LENGTH: 9
<212> TYPE: PRT
<213> ORGANISM: Human papilloamavirus type 71

<400> SEQUENCE: 56

Lys His Arg Pro Leu Leu Gln Leu Lys
1               5

<210> SEQ ID NO 57
<211> LENGTH: 7
<212> TYPE: PRT
<213> ORGANISM: Avian encephalomyelitis virus

<400> SEQUENCE: 57

Lys Ser Pro Asn His Val Lys
1               5

<210> SEQ ID NO 58
<211> LENGTH: 8
<212> TYPE: PRT
<213> ORGANISM: Feline sarcoma virus

<400> SEQUENCE: 58

Lys Asn Ile His Leu Glu Lys Lys
1               5

<210> SEQ ID NO 59
<211> LENGTH: 8
<212> TYPE: PRT
<213> ORGANISM: Homo sapiens

<400> SEQUENCE: 59

Lys Asn Ile His Leu Glu Lys Lys
1               5

```
<210> SEQ ID NO 60
<211> LENGTH: 10
<212> TYPE: PRT
<213> ORGANISM: Polyoma virus

<400> SEQUENCE: 60

Lys Pro His Leu Ala Gln Ser Leu Glu Lys
1               5                   10

<210> SEQ ID NO 61
<211> LENGTH: 9
<212> TYPE: PRT
<213> ORGANISM: Polyoma virus

<400> SEQUENCE: 61

Lys Gln His Arg Glu Leu Lys Asp Lys
1               5

<210> SEQ ID NO 62
<211> LENGTH: 9
<212> TYPE: PRT
<213> ORGANISM: Polyoma virus

<400> SEQUENCE: 62

Lys Gln His Arg Glu Leu Lys Asp Lys
1               5

<210> SEQ ID NO 63
<211> LENGTH: 12
<212> TYPE: PRT
<213> ORGANISM: Murine leukemia virus

<400> SEQUENCE: 63

Lys Val Pro Val Leu Ile Ser Pro Thr Leu Lys His
1               5                   10

<210> SEQ ID NO 64
<211> LENGTH: 13
<212> TYPE: PRT
<213> ORGANISM: Human T-cell lymphotropic virus type 2

<400> SEQUENCE: 64

Lys Ser Leu Leu Leu Glu Val Asp Lys Asp Ile Ser His
1               5                   10

<210> SEQ ID NO 65
<211> LENGTH: 13
<212> TYPE: PRT
<213> ORGANISM: Homo sapiens

<400> SEQUENCE: 65

Lys Ala Gly Ile Thr Ile Met Val Lys Arg Glu Tyr His
1               5                   10

<210> SEQ ID NO 66
<211> LENGTH: 8
<212> TYPE: PRT
<213> ORGANISM: Homo sapiens

<400> SEQUENCE: 66

Lys Ser Gly Lys His Leu Gly Lys
1               5

<210> SEQ ID NO 67
```

```
<211> LENGTH: 9
<212> TYPE: PRT
<213> ORGANISM: Homo sapiens

<400> SEQUENCE: 67

Lys Arg Arg Glu Gln Leu Lys His Lys
1               5

<210> SEQ ID NO 68
<211> LENGTH: 10
<212> TYPE: PRT
<213> ORGANISM: Homo sapiens

<400> SEQUENCE: 68

Lys Ser Phe Glu Val Ile Lys Val Ile His
1               5                   10

<210> SEQ ID NO 69
<211> LENGTH: 8
<212> TYPE: PRT
<213> ORGANISM: Homo sapiens

<400> SEQUENCE: 69

Lys Lys Lys His Thr Val Lys Lys
1               5

<210> SEQ ID NO 70
<211> LENGTH: 9
<212> TYPE: PRT
<213> ORGANISM: Homo sapiens

<400> SEQUENCE: 70

Lys Ala Gln Lys Asp His Leu Ser Lys
1               5

<210> SEQ ID NO 71
<211> LENGTH: 10
<212> TYPE: PRT
<213> ORGANISM: Homo sapiens

<400> SEQUENCE: 71

His Leu Lys Arg Val Lys Asp Leu Lys Lys
1               5                   10

<210> SEQ ID NO 72
<211> LENGTH: 11
<212> TYPE: PRT
<213> ORGANISM: Homo sapiens

<400> SEQUENCE: 72

Lys Tyr Gly Ser Pro Lys His Arg Leu Ile Lys
1               5                   10

<210> SEQ ID NO 73
<211> LENGTH: 13
<212> TYPE: PRT
<213> ORGANISM: Papilloma virus type 11

<400> SEQUENCE: 73

Lys Leu Lys His Ile Leu Gly Lys Ala Arg Phe Ile Lys
1               5                   10

<210> SEQ ID NO 74
<211> LENGTH: 12
<212> TYPE: PRT
```

```
<213> ORGANISM: Homo sapiens

<400> SEQUENCE: 74

Lys Gly Asp His Val Lys His Tyr Lys Ile Arg Lys
1               5                   10

<210> SEQ ID NO 75
<211> LENGTH: 13
<212> TYPE: PRT
<213> ORGANISM: Homo sapiens

<400> SEQUENCE: 75

Lys Glu Lys Leu Arg Asp Val Met Val Asp Arg His Lys
1               5                   10

<210> SEQ ID NO 76
<211> LENGTH: 15
<212> TYPE: PRT
<213> ORGANISM: Homo sapiens

<400> SEQUENCE: 76

Lys Leu Gln Ala Arg Gln Gln Leu Leu Lys Lys Ile Glu His
1               5                   10                  15

<210> SEQ ID NO 77
<211> LENGTH: 14
<212> TYPE: PRT
<213> ORGANISM: Homo sapiens

<400> SEQUENCE: 77

Lys Lys Gly Asn Arg Val Ser Pro Thr Met Lys Val Thr His
1               5                   10

<210> SEQ ID NO 78
<211> LENGTH: 9
<212> TYPE: PRT
<213> ORGANISM: Homo sapiens

<400> SEQUENCE: 78

Lys Glu Ile Pro Leu His Phe Arg Lys
1               5

<210> SEQ ID NO 79
<211> LENGTH: 8
<212> TYPE: PRT
<213> ORGANISM: Homo sapiens

<400> SEQUENCE: 79

Lys Lys Lys Pro His Ile Lys Lys
1               5

<210> SEQ ID NO 80
<211> LENGTH: 9
<212> TYPE: PRT
<213> ORGANISM: Homo sapiens

<400> SEQUENCE: 80

Lys Thr Arg His Asp Pro Leu Ala Lys
1               5

<210> SEQ ID NO 81
<211> LENGTH: 10
<212> TYPE: PRT
<213> ORGANISM: Homo sapiens
```

<400> SEQUENCE: 81

Lys His His Pro Lys Asp Asn Leu Ile Lys
1               5                   10

<210> SEQ ID NO 82
<211> LENGTH: 10
<212> TYPE: PRT
<213> ORGANISM: Homo sapiens

<400> SEQUENCE: 82

Lys His Lys Arg Lys Lys Phe Arg Gln Lys
1               5                   10

<210> SEQ ID NO 83
<211> LENGTH: 10
<212> TYPE: PRT
<213> ORGANISM: Homo sapiens

<400> SEQUENCE: 83

Lys Ala Gly Val Ala Phe Leu His Lys Lys
1               5                   10

<210> SEQ ID NO 84
<211> LENGTH: 10
<212> TYPE: PRT
<213> ORGANISM: Homo sapiens

<400> SEQUENCE: 84

Lys His Lys Arg Lys Lys Phe Arg Gln Lys
1               5                   10

<210> SEQ ID NO 85
<211> LENGTH: 10
<212> TYPE: PRT
<213> ORGANISM: Homo sapiens

<400> SEQUENCE: 85

Lys Lys Lys Ser Lys Lys His Lys Asp Lys
1               5                   10

<210> SEQ ID NO 86
<211> LENGTH: 11
<212> TYPE: PRT
<213> ORGANISM: Homo sapiens

<400> SEQUENCE: 86

His Lys Ser Glu Lys Pro Ala Leu Pro Arg Lys
1               5                   10

<210> SEQ ID NO 87
<211> LENGTH: 14
<212> TYPE: PRT
<213> ORGANISM: Homo sapiens

<400> SEQUENCE: 87

Lys Lys Lys Lys Pro Ser Arg Leu Lys Gly Asp Asn Glu Lys
1               5                   10

<210> SEQ ID NO 88
<211> LENGTH: 16
<212> TYPE: PRT
<213> ORGANISM: Homo sapiens

<400> SEQUENCE: 88

```
Lys Thr Lys Lys Gly Asn Arg Val Ser Pro Thr Met Lys Val Thr His
1               5                   10                  15

<210> SEQ ID NO 89
<211> LENGTH: 18
<212> TYPE: PRT
<213> ORGANISM: Homo sapiens

<400> SEQUENCE: 89

Lys His Lys Glu Lys Met Ser Lys Asp Gly Lys Lys Lys Lys Lys
1               5                   10                  15

Ser Lys

<210> SEQ ID NO 90
<211> LENGTH: 9
<212> TYPE: PRT
<213> ORGANISM: Legionella sp.

<400> SEQUENCE: 90

Lys Ile His Leu Ile Ser Val Lys Lys
1               5

<210> SEQ ID NO 91
<211> LENGTH: 8
<212> TYPE: PRT
<213> ORGANISM: Influenza B virus

<400> SEQUENCE: 91

Lys Ser His Phe Ala Asn Leu Lys
1               5

<210> SEQ ID NO 92
<211> LENGTH: 11
<212> TYPE: PRT
<213> ORGANISM: Influenza B virus

<400> SEQUENCE: 92

Lys Ser His Phe Ala Asn Leu Lys Gly Thr Lys
1               5                   10

<210> SEQ ID NO 93
<211> LENGTH: 19
<212> TYPE: PRT
<213> ORGANISM: Influenza B virus

<400> SEQUENCE: 93

Lys Ser His Phe Ala Asn Leu Lys Gly Thr Lys Thr Arg Gly Lys Leu
1               5                   10                  15

Cys Pro Lys

<210> SEQ ID NO 94
<211> LENGTH: 9
<212> TYPE: PRT
<213> ORGANISM: Influenza B virus

<400> SEQUENCE: 94

His Glu Lys Tyr Gly Gly Leu Asn Lys
1               5

<210> SEQ ID NO 95
<211> LENGTH: 11
<212> TYPE: PRT
<213> ORGANISM: Influenza B virus
```

```
<400> SEQUENCE: 95

His Glu Lys Tyr Gly Gly Leu Asn Lys Ser Lys
 1               5                  10

<210> SEQ ID NO 96
<211> LENGTH: 20
<212> TYPE: PRT
<213> ORGANISM: Influenza B virus

<400> SEQUENCE: 96

His Glu Lys Tyr Gly Gly Leu Asn Lys Ser Lys Pro Tyr Tyr Thr Gly
 1               5                  10                  15

Glu His Ala Lys
            20

<210> SEQ ID NO 97
<211> LENGTH: 13
<212> TYPE: PRT
<213> ORGANISM: Influenza B virus

<400> SEQUENCE: 97

His Ala Lys Ala Ile Gly Asn Cys Pro Ile Trp Val Lys
 1               5                  10

<210> SEQ ID NO 98
<211> LENGTH: 23
<212> TYPE: PRT
<213> ORGANISM: Influenza B virus

<400> SEQUENCE: 98

His Ala Lys Ala Ile Gly Asn Cys Pro Ile Trp Val Lys Thr Pro Leu
 1               5                  10                  15

Lys Leu Ala Asn Gly Thr Lys
            20

<210> SEQ ID NO 99
<211> LENGTH: 29
<212> TYPE: PRT
<213> ORGANISM: Influenza B virus

<400> SEQUENCE: 99

His Ala Lys Ala Ile Gly Asn Cys Pro Ile Trp Val Lys Thr Pro Leu
 1               5                  10                  15

Lys Leu Ala Asn Gly Thr Lys Tyr Arg Pro Pro Ala Lys
            20                  25

<210> SEQ ID NO 100
<211> LENGTH: 32
<212> TYPE: PRT
<213> ORGANISM: Influenza B virus

<400> SEQUENCE: 100

His Ala Lys Ala Ile Gly Asn Cys Pro Ile Trp Val Lys Thr Pro Leu
 1               5                  10                  15
Lys Leu Ala Asn Gly Thr Lys Tyr Arg Pro Pro Ala Lys Leu Leu Lys
            20                  25                  30

<210> SEQ ID NO 101
<211> LENGTH: 13
<212> TYPE: PRT
<213> ORGANISM: Influenza B virus

<400> SEQUENCE: 101
```

His Phe Ala Asn Leu Lys Gly Thr Lys Thr Arg Gly Lys
1               5                   10

<210> SEQ ID NO 102
<211> LENGTH: 17
<212> TYPE: PRT
<213> ORGANISM: Influenza B virus

<400> SEQUENCE: 102

His Phe Ala Asn Leu Lys Gly Thr Lys Thr Arg Gly Lys Leu Cys Pro
1               5                   10                  15
Lys

<210> SEQ ID NO 103
<211> LENGTH: 16
<212> TYPE: PRT
<213> ORGANISM: Influenza B virus

<400> SEQUENCE: 103

His Ser Asp Asn Glu Ile Gln Met Val Lys Leu Tyr Gly Asp Ser Lys
1               5                   10                  15

<210> SEQ ID NO 104
<211> LENGTH: 21
<212> TYPE: PRT
<213> ORGANISM: Influenza B virus

<400> SEQUENCE: 104

His Ser Asp Asn Glu Ile Gln Asp Lys Met Val Lys Leu Tyr Gly Asp
1               5                   10                  15
Ser Lys Pro Gln Lys
            20

<210> SEQ ID NO 105
<211> LENGTH: 19
<212> TYPE: PRT
<213> ORGANISM: Influenza B virus

<400> SEQUENCE: 105

His Ser Asp Asn Glu Ile Gln Met Val Lys Leu Tyr Gly Asp Ser Lys
1               5                   10                  15
Pro Gln Lys

<210> SEQ ID NO 106
<211> LENGTH: 9
<212> TYPE: PRT
<213> ORGANISM: Influenza B virus
<220> FEATURE:
<221> NAME/KEY: MOD_RES
<222> LOCATION: (2)
<223> OTHER INFORMATION: ala or val

<400> SEQUENCE: 106

Lys Xaa Ser Ile Leu His Glu Val Lys
1               5

<210> SEQ ID NO 107
<211> LENGTH: 15
<212> TYPE: PRT
<213> ORGANISM: Influenza B virus

<400> SEQUENCE: 107

Lys Cys Thr Gly Thr Ile Pro Ser Ala Lys Ala Ser Ile Leu His
1               5                   10                  15

<210> SEQ ID NO 108
<211> LENGTH: 18
<212> TYPE: PRT
<213> ORGANISM: Influenza B virus

<400> SEQUENCE: 108

Lys Cys Thr Gly Thr Ile Pro Ser Ala Lys Ala Ser Ile Leu His Glu
 1               5                  10                  15

Val Lys

<210> SEQ ID NO 109
<211> LENGTH: 16
<212> TYPE: PRT
<213> ORGANISM: Influenza B virus

<400> SEQUENCE: 109

Lys Tyr Gly Gly Leu Asn Lys Ser Lys Pro Tyr Tyr Thr Gly Glu His
 1               5                  10                  15

<210> SEQ ID NO 110
<211> LENGTH: 26
<212> TYPE: PRT
<213> ORGANISM: Influenza B virus

<400> SEQUENCE: 110

Lys Val Trp Cys Ala Ser Gly Arg Ser Lys Val Ile Lys Gly Ser Leu
1 5 10 15

Pro Leu Ile Gly Glu Ala Asp Cys Leu His
20 25

<210> SEQ ID NO 111
<211> LENGTH: 10
<212> TYPE: PRT
<213> ORGANISM: Influenza B virus

<400> SEQUENCE: 111

Lys Pro Tyr Tyr Thr Gly Glu His Ala Lys
1 5 10

<210> SEQ ID NO 112
<211> LENGTH: 18
<212> TYPE: PRT
<213> ORGANISM: Influenza B virus

<400> SEQUENCE: 112

Lys Cys Met Gly Thr Ile Pro Ser Ala Lys Ala Ser Ile Leu His Glu
1 5 10 15

Val Lys

<210> SEQ ID NO 113
<211> LENGTH: 15
<212> TYPE: PRT
<213> ORGANISM: Influenza B virus

<400> SEQUENCE: 113

His Asn Val Ile Asn Ala Glu Lys Ala Pro Gly Gly Pro Tyr Lys
1 5 10 15

<210> SEQ ID NO 114
<211> LENGTH: 16
<212> TYPE: PRT
<213> ORGANISM: Influenza B virus

```
<400> SEQUENCE: 114

His Ser Asp Asn Glu Thr Gln Met Ala Lys Leu Tyr Gly Asp Ser Lys
 1               5                   10                  15

<210> SEQ ID NO 115
<211> LENGTH: 18
<212> TYPE: PRT
<213> ORGANISM: Influenza B virus

<400> SEQUENCE: 115

His Gly Val Ala Val Ala Ala Asp Leu Lys Ser Thr Gln Glu Ala Ile
 1               5                   10                  15

Asn Lys

<210> SEQ ID NO 116
<211> LENGTH: 29
<212> TYPE: PRT
<213> ORGANISM: Influenza B virus

<400> SEQUENCE: 116

His Gly Val Ala Val Ala Ala Asp Leu Lys Ser Thr Gln Glu Ala Ile
 1               5                   10                  15

Asn Lys Asp Thr Ile Ser Thr Gln Glu Ala Ile Asn Lys
             20                  25

<210> SEQ ID NO 117
<211> LENGTH: 21
<212> TYPE: PRT
<213> ORGANISM: Influenza B virus

<400> SEQUENCE: 117

Lys Leu Tyr Gly Asp Ser Lys Pro Gln Lys Phe Thr Ser Ser Ala Asn
 1               5                   10                  15

Gly Val Thr Thr His
             20

<210> SEQ ID NO 118
<211> LENGTH: 19
<212> TYPE: PRT
<213> ORGANISM: Influenza B virus

<400> SEQUENCE: 118

His Ser Asp Asn Glu Thr Gln Met Ala Lys Leu Tyr Gly Asp Ser Lys
 1               5                   10                  15

Pro Gln Lys

<210> SEQ ID NO 119
<211> LENGTH: 13
<212> TYPE: PRT
<213> ORGANISM: Influenza B virus

<400> SEQUENCE: 119

His Phe Ala Asn Leu Lys Gly Thr Gln Thr Arg Gly Lys
 1               5                   10

<210> SEQ ID NO 120
<211> LENGTH: 12
<212> TYPE: PRT
<213> ORGANISM: Influenza B virus

<400> SEQUENCE: 120
```

```
Lys Pro Arg Ser Ala Leu Lys Cys Lys Gly Phe His
  1               5                  10
```

```
<210> SEQ ID NO 121
<211> LENGTH: 22
<212> TYPE: PRT
<213> ORGANISM: Influenza B virus
<220> FEATURE:
<221> NAME/KEY: MOD_RES
<222> LOCATION: (15)
<223> OTHER INFORMATION: gly or ala

<400> SEQUENCE: 121

Lys Ser Lys Pro Tyr Tyr Thr Gly Glu His Ala Lys Ala Ile Xaa Asn
  1               5                  10                  15

Cys Pro Ile Trp Val Lys
            20
```

```
<210> SEQ ID NO 122
<211> LENGTH: 16
<212> TYPE: PRT
<213> ORGANISM: Influenza virus
<220> FEATURE:
<221> NAME/KEY: MOD_RES
<222> LOCATION: (3)
<223> OTHER INFORMATION: val or ile
<220> FEATURE:
<221> NAME/KEY: MOD_RES
<222> LOCATION: (13)
<223> OTHER INFORMATION: arg or lys
<220> FEATURE:
<221> NAME/KEY: MOD_RES
<222> LOCATION: (14)
<223> OTHER INFORMATION: ser or thr
<220> FEATURE:
<221> NAME/KEY: MOD_RES
<222> LOCATION: (15)
<223> OTHER INFORMATION: thr or ala

<400> SEQUENCE: 122

His Pro Xaa Thr Ile Gly Glu Cys Pro Lys Tyr Val Xaa Xaa Xaa Lys
  1               5                  10                  15
```

```
<210> SEQ ID NO 123
<211> LENGTH: 21
<212> TYPE: PRT
<213> ORGANISM: Influenza virus
<220> FEATURE:
<221> NAME/KEY: MOD_RES
<222> LOCATION: (10)
<223> OTHER INFORMATION: glu or gly
<220> FEATURE:
<221> NAME/KEY: MOD_RES
<222> LOCATION: (13)
<223> OTHER INFORMATION: lys or arg
<220> FEATURE:
<221> NAME/KEY: MOD_RES
<222> LOCATION: (14)
<223> OTHER INFORMATION: asn or ser
<220> FEATURE:
<221> NAME/KEY: MOD_RES
<222> LOCATION: (17)
<223> OTHER INFORMATION: lys or arg

<400> SEQUENCE: 123

His Asp Ser Asn Val Lys Asn Leu Tyr Xaa Lys Val Xaa Xaa Gln Leu
  1               5                  10                  15

Xaa Asn Asn Ala Lys
            20
```

```
<210> SEQ ID NO 124
<211> LENGTH: 17
<212> TYPE: PRT
<213> ORGANISM: Influenza virus
<220> FEATURE:
<221> NAME/KEY: MOD_RES
<222> LOCATION: (10)
<223> OTHER INFORMATION: glu or gly
<220> FEATURE:
<221> NAME/KEY: MOD_RES
<222> LOCATION: (13)
<223> OTHER INFORMATION: lys or arg
<220> FEATURE:
<221> NAME/KEY: MOD_RES
<222> LOCATION: (14)
<223> OTHER INFORMATION: asn or ser

<400> SEQUENCE: 124

His Asp Ser Asn Val Lys Asn Leu Tyr Xaa Lys Val Xaa Xaa Gln Leu
 1               5                  10                  15

Lys

<210> SEQ ID NO 125
<211> LENGTH: 36
<212> TYPE: PRT
<213> ORGANISM: Influenza virus
<220> FEATURE:
<221> NAME/KEY: MOD_RES
<222> LOCATION: (4)..(5)
<223> OTHER INFORMATION: asn or asp
<220> FEATURE:
<221> NAME/KEY: MOD_RES
<222> LOCATION: (6)
<223> OTHER INFORMATION: ala, thr or glu
<220> FEATURE:
<221> NAME/KEY: MOD_RES
<222> LOCATION: (12)
<223> OTHER INFORMATION: arg or lys
<220> FEATURE:
<221> NAME/KEY: MOD_RES
<222> LOCATION: (31)
<223> OTHER INFORMATION: glu or lys

<400> SEQUENCE: 125

His Lys Cys Xaa Xaa Xaa Cys Met Glu Ser Val Xaa Asn Gly Thr Tyr
 1               5                  10                  15

Asp Tyr Pro Lys Tyr Ser Glu Glu Ser Lys Leu Asn Arg Glu Xaa Ile
            20                  25                  30

Asp Gly Val Lys
            35

<210> SEQ ID NO 126
<211> LENGTH: 26
<212> TYPE: PRT
<213> ORGANISM: Influenza virus
<220> FEATURE:
<221> NAME/KEY: MOD_RES
<222> LOCATION: (4)..(5)
<223> OTHER INFORMATION: asn or asp
<220> FEATURE:
<221> NAME/KEY: MOD_RES
<222> LOCATION: (6)
<223> OTHER INFORMATION: ala, thr or glu
<220> FEATURE:
<221> NAME/KEY: MOD_RES
<222> LOCATION: (12)
<223> OTHER INFORMATION: arg or lys

<400> SEQUENCE: 126

His Lys Cys Xaa Xaa Xaa Cys Met Glu Ser Val Xaa Asn Gly Thr Tyr
 1               5                  10                  15
```

```
Asp Tyr Pro Lys Tyr Ser Glu Glu Ser Lys
            20                  25
```

```
<210> SEQ ID NO 127
<211> LENGTH: 50
<212> TYPE: PRT
<213> ORGANISM: Influenza virus
<220> FEATURE:
<221> NAME/KEY: MOD_RES
<222> LOCATION: (4)
<223> OTHER INFORMATION: glu or gly
<220> FEATURE:
<221> NAME/KEY: MOD_RES
<222> LOCATION: (21)
<223> OTHER INFORMATION: asp or asn

<400> SEQUENCE: 127

His Gln Asn Xaa Gln Gly Ser Gly Tyr Ala Ala Asp Gln Lys Ser Thr
 1               5                  10                  15

Gln Asn Ala Ile Xaa Gly Ile Thr Asn Lys Val Asn Ser Val Ile Glu
            20                  25                  30

Lys Met Asn Thr Gln Phe Thr Ala Val Gly Lys Glu Phe Asn Lys Leu
        35                  40                  45

Glu Lys
     50
```

```
<210> SEQ ID NO 128
<211> LENGTH: 33
<212> TYPE: PRT
<213> ORGANISM: Influenza virus
<220> FEATURE:
<221> NAME/KEY: MOD_RES
<222> LOCATION: (4)
<223> OTHER INFORMATION: glu or gly
<220> FEATURE:
<221> NAME/KEY: MOD_RES
<222> LOCATION: (21)
<223> OTHER INFORMATION: asp or asn

<400> SEQUENCE: 128

His Gln Asn Xaa Gln Gly Ser Gly Tyr Ala Ala Asp Gln Lys Ser Thr
 1               5                  10                  15

Gln Asn Ala Ile Xaa Gly Ile Thr Asn Lys Val Asn Ser Val Ile Glu
            20                  25                  30

Lys
```

```
<210> SEQ ID NO 129
<211> LENGTH: 26
<212> TYPE: PRT
<213> ORGANISM: Influenza virus
<220> FEATURE:
<221> NAME/KEY: MOD_RES
<222> LOCATION: (4)
<223> OTHER INFORMATION: glu or gly
<220> FEATURE:
<221> NAME/KEY: MOD_RES
<222> LOCATION: (21)
<223> OTHER INFORMATION: asp or asn

<400> SEQUENCE: 129

His Gln Asn Xaa Gln Gly Ser Gly Tyr Ala Ala Asp Gln Lys Ser Thr
 1               5                  10                  15

Gln Asn Ala Ile Xaa Gly Ile Thr Asn Lys
            20                  25
```

```
<210> SEQ ID NO 130
<211> LENGTH: 14
<212> TYPE: PRT
<213> ORGANISM: Influenza virus

<400> SEQUENCE: 130

Lys Phe Glu Ile Phe Pro Lys Thr Ser Ser Trp Pro Asn His
 1               5                  10

<210> SEQ ID NO 131
<211> LENGTH: 27
<212> TYPE: PRT
<213> ORGANISM: Influenza virus
<220> FEATURE:
<221> NAME/KEY: MOD_RES
<222> LOCATION: (3)
<223> OTHER INFORMATION: asn, ser or thr
<220> FEATURE:
<221> NAME/KEY: MOD_RES
<222> LOCATION: (9)
<223> OTHER INFORMATION: asn or ser
<220> FEATURE:
<221> NAME/KEY: MOD_RES
<222> LOCATION: (13)
<223> OTHER INFORMATION: val or thr

<400> SEQUENCE: 131

Lys Gly Xaa Ser Tyr Pro Lys Leu Xaa Lys Ser Tyr Xaa Asn Asn Lys
 1               5                  10                  15

Gly Lys Glu Val Leu Val Leu Trp Gly Val His
            20                  25

<210> SEQ ID NO 132
<211> LENGTH: 18
<212> TYPE: PRT
<213> ORGANISM: Influenza virus
<220> FEATURE:
<221> NAME/KEY: MOD_RES
<222> LOCATION: (4)
<223> OTHER INFORMATION: val or thr

<400> SEQUENCE: 132

Lys Ser Tyr Xa

```
                    1               5                  10                  15
Asp Tyr Pro Lys Tyr Ser Glu Glu Ser Lys

```
<212> TYPE: PRT
<213> ORGANISM: Influenza virus
<220> FEATURE:
<221> NAME/KEY: MOD_RES
<222> LOCATION: (9)
<223> OTHER INFORMATION: lys or arg
<220> FEATURE:
<221> NAME/KEY: MOD_RES
<222> LOCATION: (16)
<223> OTHER INFORMATION: glu or gly

<400> SEQUENCE: 139

His Asn Gly Lys Ser Ser Phe Tyr Xaa Asn Leu Leu Trp Leu Thr Xaa
 1               5                  10                  15
Lys Asn Gly Leu Tyr Pro Asn Leu Ser Lys
            20                  25

<210> SEQ ID NO 140
<211> LENGTH: 17
<212> TYPE: PRT
<213> ORGANISM: Influenza virus
<220> FEATURE:
<221> NAME/KEY: MOD_RES
<222> LOCATION: (9)
<223> OTHER INFORMATION: lys or arg
<220> FEATURE:
<221> NAME/KEY: MOD_RES
<222> LOCATION: (16)
<223> OTHER INFORMATION: glu or gly

<400> SEQUENCE: 140

His Asn Gly Lys Ser Ser Phe Tyr Xaa Asn Leu Leu Trp Leu Thr Xaa
 1               5                  10                  15
Lys

<210> SEQ ID NO 141
<211> LENGTH: 40
<212> TYPE: PRT
<213> ORGANISM: Influenza virus

<400> SEQUENCE: 141

Lys Ser Ser Phe Tyr Lys Asn Leu Leu Trp Leu Thr Glu Lys Asn Gly
 1               5                  10                  15
Leu Tyr Pro Asn Leu Ser Lys Ser Tyr Val Asn Asn Lys Glu Lys Glu
            20                  25                  30
Val Leu Val Leu Trp Gly Val His
        35                  40

<210> SEQ ID NO 142
<211> LENGTH: 35
<212> TYPE: PRT
<213> ORGANISM: Influenza virus

<400> SEQUENCE: 142

Lys Asn Leu Leu Trp Leu Thr Glu Lys Asn Gly Leu Tyr Pro Asn Leu
 1               5                  10                  15
Ser Lys Ser Tyr Val Asn Asn Lys Glu Lys Glu Val Leu Val Leu Trp
            20                  25                  30
Gly Val His
        35

<210> SEQ ID NO 143
<211> LENGTH: 27
<212> TYPE: PRT
<213> ORGANISM: Influenza virus
```

<400> SEQUENCE: 143

Lys Asn Gly Leu Tyr Pro Asn Leu Ser Lys Ser Tyr Val Asn Asn Lys
1               5                   10                  15

Glu Lys Glu Val Leu Val Leu Trp Gly Val His
            20                  25

<210> SEQ ID NO 144
<211> LENGTH: 18
<212> TYPE: PRT
<213> ORGANISM: Influenza virus
<220> FEATURE:
<221> NAME/KEY: MOD_RES
<222> LOCATION: (4)
<223> OTHER INFORMATION: val or ala
<220> FEATURE:
<221> NAME/KEY: MOD_RES
<222> LOCATION: (12)
<223> OTHER INFORMATION: lys or not present
<220> FEATURE:
<221> NAME/KEY: MOD_RES
<222> LOCATION: (13)
<223> OTHER INFORMATION: val or not present

<400> SEQUENCE: 144

Lys Ser Tyr Xaa Asn Asn Lys Glu Lys Glu Val Xaa Xaa Leu Trp Gly
1               5                   10                  15

Val His

<210> SEQ ID NO 145
<211> LENGTH: 12
<212> TYPE: PRT
<213> ORGANISM: Influenza virus

<400> SEQUENCE: 145

Lys Glu Ser Ser Trp Pro Asn His Thr Val Thr Lys
1               5                   10

<210> SEQ ID NO 146
<211> LENGTH: 44
<212> TYPE: PRT
<213> ORGANISM: Influenza virus
<220> FEATURE:
<221> NAME/KEY: MOD_RES
<222> LOCATION: (4)
<223> OTHER INFORMATION: thr or asn

<400> SEQUENCE: 146

His Glu Thr Xaa Lys Gly Val Thr Ala Ala Cys Pro Tyr Ala Gly Ala
1               5                   10                  15

Ser Ser Phe Tyr Arg Asn Leu Leu Trp Leu Val Lys Lys Glu Asn Ser
            20                  25                  30

Tyr Pro Lys Leu Ser Lys Ser Tyr Val Asn Asn Lys
        35                  40

<210> SEQ ID NO 147
<211> LENGTH: 38
<212> TYPE: PRT
<213> ORGANISM: Influenza virus
<220> FEATURE:
<221> NAME/KEY: MOD_RES
<222> LOCATION: (4)
<223> OTHER INFORMATION: thr or asn

<400> SEQUENCE: 147

His Glu Thr Xaa Lys Gly Val Thr Ala Ala Cys Pro Tyr Ala Gly Ala
1               5                   10                  15

```
              1               5                  10                  15
Ser Ser Phe Tyr Arg Asn Leu Leu Trp Leu Val Lys Lys Glu Asn Ser
                    20                  25                  30

Tyr Pro Lys Leu Ser Lys
            35
```

<210> SEQ ID NO 148
<211> LENGTH: 22
<212> TYPE: PRT
<213> ORGANISM: Influenza virus

<400> SEQUENCE: 148

```
Lys Phe Glu Ile Phe Pro Lys Thr Ser Ser Trp Pro Asn Glu Val Leu
 1               5                  10                  15

Val Leu Trp Gly Val His
            20
```

<210> SEQ ID NO 149
<211> LENGTH: 8
<212> TYPE: PRT
<213> ORGANISM: Influenza virus

<400> SEQUENCE: 149

```
Lys Glu Arg Ser Trp Pro Lys His
 1               5
```

<210> SEQ ID NO 150
<211> LENGTH: 21
<212> TYPE: PRT
<213> ORGANISM: Influenza virus

<400> SEQUENCE: 150

```
Lys Leu Ser Lys Ser Tyr Val Asn Asn Lys Glu Lys Glu Val Leu Val
 1               5                  10                  15

Leu Trp Gln Val His
            20
```

<210> SEQ ID NO 151
<211> LENGTH: 15
<212> TYPE: PRT
<213> ORGANISM: Influenza virus

<400> SEQUENCE: 151

```
Lys Asn Asn Lys Glu Lys Glu Val Leu Val Leu Trp Gln Val His
 1               5                  10                  15
```

<210> SEQ ID NO 152
<211> LENGTH: 34
<212> TYPE: PRT
<213> ORGANISM: Influenza virus
<220> FEATURE:
<221> NAME/KEY: MOD_RES
<222> LOCATION: (2)
<223> OTHER INFORMATION: lys or asn
<220> FEATURE:
<221> NAME/KEY: MOD_RES
<222> LOCATION: (3)
<223> OTHER INFORMATION: gly or gln
<220> FEATURE:
<221> NAME/KEY: MOD_RES
<222> LOCATION: (9)
<223> OTHER INFORMATION: arg or lys
<220> FEATURE:
<221> NAME/KEY: MOD_RES
<222> LOCATION: (20)
<223> OTHER INFORMATION: lys or ser

```
<220> FEATURE:
<221> NAME/KEY: MOD_RES
<222> LOCATION: (23)
<223> OTHER INFORMATION: asn or thr

<400> SEQUENCE: 152

His Xaa Xaa Lys Ser Ser Phe Tyr Xaa Asn Leu Leu Trp Leu Thr Glu
 1               5                  10                  15

Lys Asn Gly Xaa Tyr Pro Xaa Leu Ser Lys Ser Tyr Ala Asn Asn Lys
            20                  25                  30

Glu Lys

<210> SEQ ID NO 153
<211> LENGTH: 17
<212> TYPE: PRT
<213> ORGANISM: Influenza virus
<220> FEATURE:
<221> NAME/KEY: MOD_RES
<222> LOCATION: (2)
<223> OTHER INFORMATION: lys or asn
<220> FEATURE:
<221> NAME/KEY: MOD_RES
<222> LOCATION: (3)
<223> OTHER INFORMATION: gly or gln
<220> FEATURE:
<221> NAME/KEY: MOD_RES
<222> LOCATION: (9)
<223> OTHER INFORMATION: arg or lys

<400> SEQUENCE: 153

His Xaa Xaa Lys Ser Ser Phe Tyr Xaa Asn Leu Leu Trp Leu Thr Glu
 1               5                  10                  15

Lys

<210> SEQ ID NO 154
<211> LENGTH: 9
<212> TYPE: PRT
<213> ORGANISM: Influenza virus

<400> SEQUENCE: 154

His Ala Lys Lys Ser Ser Phe Tyr Lys
 1               5

<210> SEQ ID NO 155
<211> LENGTH: 11
<212> TYPE: PRT
<213> ORGANISM: Influenza virus

<400> SEQUENCE: 155

His Asn Gly Lys Leu Cys Arg Leu Lys Gly Lys
 1               5                  10

<210> SEQ ID NO 156
<211> LENGTH: 9
<212> TYPE: PRT
<213> ORGANISM: Influenza virus
<220> FEATURE:
<221> NAME/KEY: MOD_RES
<222> LOCATION: (7)
<223> OTHER INFORMATION: gln or gly

<400> SEQUENCE: 156

His Tyr Lys Leu Asn Asn Xaa Lys Lys
 1               5

<210> SEQ ID NO 157
```

<211> LENGTH: 25
<212> TYPE: PRT
<213> ORGANISM: Influenza virus

<400> SEQUENCE: 157

His Asp Ile Tyr Arg Asp Glu Ala Ile Asn Asn Arg Phe Gln Ile Gln
1 5 10 15

Gly Val Lys Leu Thr Gln Gly Tyr Lys
20 25

<210> SEQ ID NO 158
<211> LENGTH: 11
<212> TYPE: PRT
<213> ORGANISM: Influenza virus

<400> SEQUENCE: 158

Lys Gly Asn Gly Cys Phe Glu Ile Phe His Lys
1 5 10

<210> SEQ ID NO 159
<211> LENGTH: 18
<212> TYPE: PRT
<213> ORGANISM: Influenza virus

<400> SEQUENCE: 159

Lys Leu Asn Arg Leu Ile Glu Lys Thr Asn Asp Lys Tyr His Gln Ile
1 5 10 15

Glu Lys

<210> SEQ ID NO 160
<211> LENGTH: 14
<212> TYPE: PRT
<213> ORGANISM: Influenza virus

<400> SEQUENCE: 160

Lys Leu Asn Arg Leu Ile Glu Lys Thr Asn Asp Lys Tyr His
1 5 10

<210> SEQ ID NO 161
<211> LENGTH: 13
<212> TYPE: PRT
<213> ORGANISM: Influenza virus

<400> SEQUENCE: 161

Lys Cys His Thr Asp Lys Gly Ser Leu Ser Thr Thr Lys
1 5 10

<210> SEQ ID NO 162
<211> LENGTH: 16
<212> TYPE: PRT
<213> ORGANISM: Influenza virus

<400> SEQUENCE: 162

Lys Ile Asn Asn Gly Asp Tyr Ala Lys Leu Tyr Ile Trp Gly Val His
1 5 10 15

<210> SEQ ID NO 163
<211> LENGTH: 17
<212> TYPE: PRT
<213> ORGANISM: Influenza virus

<400> SEQUENCE: 163

His Asn Gly Lys Leu Cys Arg Lys Gly Ile Ala Pro Leu Gln Leu Gly
1 5 10 15

Lys

<210> SEQ ID NO 164
<211> LENGTH: 38
<212> TYPE: PRT
<213> ORGANISM: Influenza virus

<400> SEQUENCE: 164

His Glu Thr Asn Arg Gln Val Thr Ala Ala Cys Pro Tyr Ala Gly Ala
1               5                   10                  15

Asn Ser Phe Phe Arg Asn Leu Ile Trp Leu Val Lys Lys Glu Ser Ser
            20                  25                  30

Tyr Pro Lys Leu Ser Lys
        35

<210> SEQ ID NO 165
<211> LENGTH: 35
<212> TYPE: PRT
<213> ORGANISM: Influenza virus

<400> SEQUENCE: 165

His Glu Thr Asn Arg Gln Val Thr Ala Ala Cys Pro Tyr Ala Gly Ala
1               5                   10                  15

Asn Ser Phe Phe Arg Asn Leu Ile Trp Leu Val Lys Lys Glu Ser Ser
            20                  25                  30

Tyr Pro Lys
        35

<210> SEQ ID NO 166
<211> LENGTH: 31
<212> TYPE: PRT
<213> ORGANISM: Influenza virus

<400> SEQUENCE: 166

His Pro Pro Thr Ser Thr Asp Gln Gln Ser Leu Tyr Gln Asn Ala Asp
1               5                   10                  15

Ala Tyr Ile Phe Val Gly Ser Ser Lys Tyr Asn Arg Lys Phe Lys
            20                  25                  30

<210> SEQ ID NO 167
<211> LENGTH: 35
<212> TYPE: PRT
<213> ORGANISM: Influenza virus

<400> SEQUENCE: 167

His Pro Pro Thr Ser Thr Asp Gln Gln Ser Leu Tyr Gln Asn Ala Asp
1               5                   10                  15

Ala Tyr Ile Phe Val Gly Ser Ser Lys Tyr Asn Arg Lys Phe Lys Pro
            20                  25                  30

Glu Ile Ala
        35

<210> SEQ ID NO 168
<211> LENGTH: 25
<212> TYPE: PRT
<213> ORGANISM: Influenza virus

<400> SEQUENCE: 168

His Asp Ile Tyr Arg Asp Glu Ala Ile Asn Asn Arg Phe Gln Ile Gln
1               5                   10                  15

Gly Val Lys Ile Thr Gln Gly Tyr Lys
            20                  25

<210> SEQ ID NO 169
<211> LENGTH: 43
<212> TYPE: PRT
<213> ORGANISM: Influenza virus

<400> SEQUENCE: 169

His Gln Asn Glu Gln Gly Ser Gly Tyr Ala Ala Asp Gln Lys Ser Thr
1               5                   10                  15

Gln Asn Ala Ile Asp Gly Ile Thr Asn Lys Val Asn Ser Val Ile Glu
            20                  25                  30

Lys Met Asn Thr Gln Phe Thr Ala Val Gly Lys
        35                  40

<210> SEQ ID NO 170
<211> LENGTH: 33
<212> TYPE: PRT
<213> ORGANISM: Influenza virus

<400> SEQUENCE: 170

His Gln Asn Glu Gln Gly Ser Gly Tyr Ala Ala Asp Gln Lys Ser Thr
1               5                   10                  15

Gln Asn Ala Ile Asp Gly Ile Thr Asn Lys Val Asn Ser Val Ile Glu
            20                  25                  30

Lys

<210> SEQ ID NO 171
<211> LENGTH: 50
<212> TYPE: PRT
<213> ORGANISM: Influenza virus

<400> SEQUENCE: 171

His Gln Asn Glu Gln Gly Ser Gly Tyr Ala Ala Asp Gln Lys Ser Thr
1               5                   10                  15

Gln Asn Ala Ile Asn Gly Ile Thr Asn Lys Val Asn Ser Val Ile Glu
            20                  25                  30

Lys Met Asn Thr Gln Phe Thr Ala Val Gly Lys Glu Phe Asn Lys Leu
        35                  40                  45

Glu Lys
    50

<210> SEQ ID NO 172
<211> LENGTH: 18
<212> TYPE: PRT
<213> ORGANISM: Influenza virus

<400> SEQUENCE: 172

His Asn Gly Lys Leu Cys Arg Leu Lys Gly Ile Ala Pro Leu Gln Leu
1               5                   10                  15

Gly Lys

<210> SEQ ID NO 173
<211> LENGTH: 12
<212> TYPE: PRT
<213> ORGANISM: Influenza virus

<400> SEQUENCE: 173

His Lys Cys Asn Asn Glu Cys Met Glu Ser Val Lys
1               5                   10

-continued

<210> SEQ ID NO 174
<211> LENGTH: 14
<212> TYPE: PRT
<213> ORGANISM: Influenza virus

<400> SEQUENCE: 174

```
Lys Phe Glu Ile Phe Pro Lys Ala Ser Ser Trp Pro Asn His
  1               5                  10
```

<210> SEQ ID NO 175
<211> LENGTH: 21
<212> TYPE: PRT
<213> ORGANISM: Influenza virus

<400> SEQUENCE: 175

```
His Asp Ser Asn Val Lys Asn Leu Tyr Glu Lys Val Arg Ser Gln Leu
  1               5                  10                  15

Arg Asn Asn Ala Lys
             20
```

<210> SEQ ID NO 176
<211> LENGTH: 22
<212> TYPE: PRT
<213> ORGANISM: Influenza virus

<400> SEQUENCE: 176

```
Lys Val Asn Ser Val Ile Lys Lys Met Asn Thr Gln Phe Ala Ala Val
  1               5                  10                  15

Gly Lys Glu Phe Asn His
             20
```

<210> SEQ ID NO 177
<211> LENGTH: 8
<212> TYPE: PRT
<213> ORGANISM: Influenza virus

<400> SEQUENCE: 177

```
Lys His Asn Gly Lys Leu Cys Lys
  1               5
```

<210> SEQ ID NO 178
<211> LENGTH: 28
<212> TYPE: PRT
<213> ORGANISM: Influenza virus

<400> SEQUENCE: 178

```
Lys Lys Gly Thr Ser Tyr Pro Lys Leu Ser Lys Ser Tyr Thr His Asn
  1               5                  10                  15

Lys Gly Lys Glu Val Leu Val Leu Trp Gly Val His
             20                  25
```

<210> SEQ ID NO 179
<211> LENGTH: 27
<212> TYPE: PRT
<213> ORGANISM: Influenza virus

<400> SEQUENCE: 179

```
Lys Gly Thr Ser Tyr Pro Lys Leu Ser Lys Ser Tyr Thr His Asn Lys
  1               5                  10                  15

Gly Lys Glu Val Leu Val Leu Trp Gly Val His
             20                  25

```
<210> SEQ ID NO 180
<211> LENGTH: 21
<212> TYPE: PRT
<213> ORGANISM: Influenza virus

<400> SEQUENCE: 180

Lys Leu Ser Lys Ser Tyr Thr His Asn Lys Gly Lys Glu Val Leu Val
 1               5                  10                  15

Leu Trp Gly Val His
            20

<210> SEQ ID NO 181
<211> LENGTH: 18
<212> TYPE: PRT
<213> ORGANISM: Influenza virus

<400> SEQUENCE: 181

Lys Ser Tyr Thr His Asn Lys Gly Lys Glu Val Leu Val Leu Trp Gly
 1               5                  10                  15

Val His

<210> SEQ ID NO 182
<211> LENGTH: 10
<212> TYPE: PRT
<213> ORGANISM: Influenza virus

<400> SEQUENCE: 182

Lys Gly Val Thr Ala Ser Cys Ser His Lys
 1               5                  10

<210> SEQ ID NO 183
<211> LENGTH: 34
<212> TYPE: PRT
<213> ORGANISM: Influenza virus

<400> SEQUENCE: 183

Lys Gly Val Thr Ala Ser Cys Ser His Lys Gly Arg Ser Ser Phe Tyr
 1               5                  10                  15

Arg Asn Leu Leu Trp Leu Thr Glu Lys Asn Gly Leu Tyr Pro Asn Leu
            20                  25                  30

Ser Lys

<210> SEQ ID NO 184
<211> LENGTH: 27
<212> TYPE: PRT
<213> ORGANISM: Influenza virus

<400> SEQUENCE: 184

Lys Gly Asn Ser Tyr Pro Lys Leu Ser Lys Ser Tyr Val Asn Asn Lys
 1               5                  10                  15

Glu Lys Glu Val Leu Val Leu Trp Gly Ile His
            20                  25

<210> SEQ ID NO 185
<211> LENGTH: 8
<212> TYPE: PRT
<213> ORGANISM: Influenza virus

<400> SEQUENCE: 185

Lys Glu Phe Asn His Leu Glu Lys
 1               5
```

<210> SEQ ID NO 186
<211> LENGTH: 39
<212> TYPE: PRT
<213> ORGANISM: Influenza virus

<400> SEQUENCE: 186

His Pro Pro Thr Ser Thr Asp Gln Gln Ser Leu Tyr Gln Asn Ala Asp
 1               5                  10                  15

Ala Tyr Val Phe Val Gly Ser Ser Lys Tyr Asn Lys Lys Phe Lys Pro
             20                  25                  30

Glu Ile Ala Thr Arg Pro Lys
         35

<210> SEQ ID NO 187
<211> LENGTH: 31
<212> TYPE: PRT
<213> ORGANISM: Influenza virus

<400> SEQUENCE: 187

His Pro Pro Thr Ser Thr Asp Gln Gln Ser Leu Tyr Gln Asn Ala Asp
 1               5                  10                  15

Ala Tyr Val Phe Val Gly Ser Ser Lys Tyr Asn Lys Lys Phe Lys
             20                  25                  30

<210> SEQ ID NO 188
<211> LENGTH: 31
<212> TYPE: PRT
<213> ORGANISM: Influenza virus

<400> SEQUENCE: 188

His Glu Gly Lys Ser Ser Phe Tyr Arg Asn Leu Leu Trp Leu Thr Glu
 1               5                  10                  15

Lys Glu Gly Ser Tyr Pro Lys Leu Lys Asn Ser Tyr Val Asn Lys
             20                  25                  30

<210> SEQ ID NO 189
<211> LENGTH: 23
<212> TYPE: PRT
<213> ORGANISM: Influenza virus

<400> SEQUENCE: 189

His Glu Gly Lys Ser Ser Phe Tyr Arg Asn Leu Leu Trp Leu Thr Glu
 1               5                  10                  15

Lys Glu Gly Ser Tyr Pro Lys
             20

<210> SEQ ID NO 190
<211> LENGTH: 26
<212> TYPE: PRT
<213> ORGANISM: Influenza virus

<400> SEQUENCE: 190

His Lys Cys Asp Asn Glu Cys Met Glu Ser Val Arg Asn Gly Thr Tyr
 1               5                  10                  15

Asp Tyr Pro Lys Tyr Ser Glu Glu Ser Lys
             20                  25

<210> SEQ ID NO 191
<211> LENGTH: 12
<212> TYPE: PRT
<213> ORGANISM: Influenza virus

<400> SEQUENCE: 191

Lys Glu Ser Ser Trp Pro Asn His Thr Val Thr Lys
1               5                   10

<210> SEQ ID NO 192
<211> LENGTH: 35
<212> TYPE: PRT
<213> ORGANISM: Influenza virus

<400> SEQUENCE: 192

Lys Asn Leu Leu Trp Leu Thr Glu Lys Asn Gly Leu Tyr Pro Asn Leu
1               5                   10                  15

Ser Lys Ser Tyr Val Asn Asn Lys Glu Lys Glu Ile Leu Val Leu Trp
            20                  25                  30

Gly Val His
        35

<210> SEQ ID NO 193
<211> LENGTH: 27
<212> TYPE: PRT
<213> ORGANISM: Influenza virus
<220> FEATURE:
<221> NAME/KEY: MOD_RES
<222> LOCATION: (9)
<223> OTHER INFORMATION: lys or met
<220> FEATURE:
<221> NAME/KEY: MOD_RES
<222> LOCATION: (10)
<223> OTHER INFORMATION: asn or not present
<220> FEATURE:
<221> NAME/KEY: MOD_RES
<222> LOCATION: (16)
<223> OTHER INFORMATION: glu or gly
<220> FEATURE:
<221> NAME/KEY: MOD_RES
<222> LOCATION: (17)
<223> OTHER INFORMATION: not present or lys

<400> SEQUENCE: 193

His Asn Gly Lys Ser Ser Phe Tyr Xaa Xaa Leu Leu Trp Leu Thr Xaa
1               5                   10                  15

Xaa Lys Asn Gly Leu Tyr Pro Asn Leu Ser Lys
            20                  25

<210> SEQ ID NO 194
<211> LENGTH: 17
<212> TYPE: PRT
<213> ORGANISM: Influenza virus

<400> SEQUENCE: 194

His Asn Gly Lys Ser Ser Phe Tyr Lys Asn Leu Leu Trp Leu Thr Glu
1               5                   10                  15

Lys

<210> SEQ ID NO 195
<211> LENGTH: 55
<212> TYPE: PRT
<213> ORGANISM: Influenza virus

<400> SEQUENCE: 195

His Thr Val Thr Lys Gly Val Thr Ala Ser Cys Ser His Asn Gly Lys
1               5                   10                  15

Ser Ser Phe Tyr Lys Asn Leu Leu Trp Leu Thr Glu Lys Asn Gly Leu
            20                  25                  30

```
Tyr Pro Asn Leu Ser Lys Ser Tyr Val Asn Asn Lys Glu Lys Glu Val
             35                  40                  45

Leu Val Leu Trp Gly Val His
     50                  55

<210> SEQ ID NO 196
<211> LENGTH: 38
<212> TYPE: PRT
<213> ORGANISM: Influenza virus
<220> FEATURE:
<221> NAME/KEY: MOD_RES
<222> LOCATION: (5)
<223> OTHER INFORMATION: lys or gly
<220> FEATURE:
<221> NAME/KEY: MOD_RES
<222> LOCATION: (8)
<223> OTHER INFORMATION: thr or ser
<220> FEATURE:
<221> NAME/KEY: MOD_RES
<222> LOCATION: (21)
<223> OTHER INFORMATION: lys or met
<220> FEATURE:
<221> NAME/KEY: MOD_RES
<222> LOCATION: (22)
<223> OTHER INFORMATION: asn or not present
<220> FEATURE:
<221> NAME/KEY: MOD_RES
<222> LOCATION: (28)
<223> OTHER INFORMATION: glu or gly
<220> FEATURE:
<221> NAME/KEY: MOD_RES
<222> LOCATION: (30)
<223> OTHER INFORMATION: asn present or not or lys

<400> SEQUENCE: 196

His Thr Val Thr Xaa Gly Val Xaa Ala Ser Cys Ser His Asn Gly Lys
 1               5                  10                  15

Ser Ser Phe Tyr Xaa Xaa Leu Leu Trp Leu Thr Xaa Lys Xaa Gly Leu
                 20                  25                  30

Tyr Pro Asn Leu Ser Lys
             35

<210> SEQ ID NO 197
<211> LENGTH: 29
<212> TYPE: PRT
<213> ORGANISM: Influenza virus

<400> SEQUENCE: 197

His Thr Val Thr Lys Gly Val Thr Ala Ser Cys Ser His Asn Gly Lys
 1               5

<210> SEQ ID NO 199
<211> LENGTH: 43
<212> TYPE: PRT
<213> ORGANISM: Influenza virus

<400> SEQUENCE: 199

His Gln Asn Glu Gln Gly Ser Gly Tyr Ala Ala Asp Gln Lys Ser Thr
1               5                   10                  15
Gln Asn Ala Ile Asn Gly Ile Thr Asn Lys Val Asn Ser Ile Ile Glu
            20                  25                  30
Lys Met Asn Thr Gln Phe Thr Ala Val Gly Lys
        35                  40

<210> SEQ ID NO 200
<211> LENGTH: 33
<212> TYPE: PRT
<213> ORGANISM: Influenza virus

<400> SEQUENCE: 200

His Gln Asn Glu Gln Gly Ser Gly Tyr Ala Ala Asp Gln Lys Ser Thr
1               5                   10                  15
Gln Asn Ala Ile Asn Gly Ile Thr Asn Lys Val Asn Ser Ile Ile Glu
            20                  25                  30
Lys

<210> SEQ ID NO 201
<211> LENGTH: 26
<212> TYPE: PRT
<213> ORGANISM: Influenza virus

<400> SEQUENCE: 201

His Gln Asn Glu Gln Gly Ser Gly Tyr Ala Ala Asp Gln Lys Ser Thr
1               5                   10                  15
Gln Asn Ala Ile Asn Gly Ile Thr Asn Lys
            20                  25

<210> SEQ ID NO 202
<211> LENGTH: 23
<212> TYPE: PRT
<213> ORGANISM: Influenza virus

<400> SEQUENCE: 202

His Ser Gly Ala Arg Ser Phe Tyr Arg Asn Leu Leu Trp Ile Val Lys
1               5                   10                  15
Lys Gly Asn Ser Tyr Pro Lys
            20

<210> SEQ ID NO 203
<211> LENGTH: 26
<212> TYPE: PRT
<213> ORGANISM: Influenza virus

<400> SEQUENCE: 203

His Ser Gly Ala Arg Ser Phe Tyr Arg Asn Leu Leu Trp Ile Val Lys
1               5                   10                  15
Lys Gly Asn Ser Tyr Pro Lys Leu Asn Lys
            20                  25

<210> SEQ ID NO 204
<211> LENGTH: 32
<212> TYPE: PRT
<213> ORGANISM: Influenza virus -continued

```
<400> SEQUENCE: 204

His Ser Gly Ala Arg Ser Phe Tyr Arg Asn Leu Leu Trp Ile Val Lys
  1               5                  10                  15

Lys Gly Asn Ser Tyr Pro Lys Leu Asn Lys Ser Tyr Thr Asn Asp Lys
             20                  25                  30

<210> SEQ ID NO 205
<211> LENGTH: 34
<212> TYPE: PRT
<213> ORGANISM: Influenza virus

<400> SEQUENCE: 205

His Ser Gly Ala Arg Ser Phe Tyr Arg Asn Leu Leu Trp Ile Val Lys
  1               5                  10                  15

Lys Gly Asn Ser Tyr Pro Lys Leu Asn Lys Ser Tyr Thr Asn Asp Lys
             20                  25                  30

Gly Lys

<210> SEQ ID NO 206
<211> LENGTH: 16
<212> TYPE: PRT
<213> ORGANISM: Influenza virus

<400> SEQUENCE: 206

His Thr Val Ser Lys Gly Val Thr Thr Ser Cys Ser His Asn Gly Lys
  1               5                  10                  15

<210> SEQ ID NO 207
<211> LENGTH: 12
<212> TYPE: PRT
<213> ORGANISM: Influenza virus

<400> SEQUENCE: 207

Lys Ala Thr Ser Trp Pro Asn His Glu Thr Thr Lys
  1               5                  10

<210> SEQ ID NO 208
<211> LENGTH: 12
<212> TYPE: PRT
<213> ORGANISM: Influenza virus

<400> SEQUENCE: 208

Lys Gln Val Thr Thr Ser Cys Ser His Asn Gln Lys
  1               5                  10

<210> SEQ ID NO 209
<211> LENGTH: 27
<212> TYPE: PRT
<213> ORGANISM: Influenza virus

<400> SEQUENCE: 209

Lys Gly Asn Ser Tyr Pro Lys Leu Asn Lys Ser Tyr Thr Asn Asp Lys
  1               5                  10                  15

Gly Lys Glu Val Leu Val Ile Trp Gly Val His
             20                  25

<210> SEQ ID NO 210
<211> LENGTH: 21
<212> TYPE: PRT
<213> ORGANISM: Influenza virus

<400> SEQUENCE: 210
```

-continued

Lys Leu Asn Lys Ser Tyr Thr Asn Asp Lys Gly Lys Glu Val Leu Val
1               5                   10                  15

Ile Trp Gly Val His
            20

<210> SEQ ID NO 211
<211> LENGTH: 18
<212> TYPE: PRT
<213> ORGANISM: Influenza virus

<400> SEQUENCE: 211

Lys Ser Tyr Thr Asn Asp Lys Gly Lys Glu Val Leu Val Ile Trp Gly
1               5                   10                  15

Val His

<210> SEQ ID NO 212
<211> LENGTH: 35
<212> TYPE: PRT
<213> ORGANISM: Influenza virus
<220> FEATURE:
<221> NAME/KEY: MOD_RES
<222> LOCATION: (16)
<223> OTHER INFORMATION: glu or gln
<220> FEATURE:
<221> NAME/KEY: MOD_RES
<222> LOCATION: (29)
<223> OTHER INFORMATION: val or ala

<400> SEQUENCE: 212

His Asn Gln Lys Ser Ser Phe Tyr Arg Asn Leu Leu Trp Leu Thr Xaa
1               5                   10                  15

Lys Asn Gly Leu Tyr Pro Asn Leu Ser Lys Ser Tyr Xaa Ala Asn Asn
            20                  25                  30

Lys Glu Lys
        35

<210> SEQ ID NO 213
<211> LENGTH: 16
<212> TYPE: PRT
<213> ORGANISM: Influenza virus

<400> SEQUENCE: 213

His Pro Ile Thr Ile Gly Glu Cys Pro Lys Tyr Val Arg Ser Ala Lys
1               5                   10                  15

<210> SEQ ID NO 214
<211> LENGTH: 43
<212> TYPE: PRT
<213> ORGANISM: Influenza virus

<400> SEQUENCE: 214

His Gln Asn Glu Gln Gly Ser Gly Tyr Ala Ala Asp Gln Lys Ser Thr
1               5                   10                  15

Gln Asn Ala Ile Asn Gly Ile Thr Asn Lys Val Asn Ser Val Ile Glu
            20                  25                  30

Lys Met Asn Thr Gln Phe Thr Ala Val Gly Lys
        35                  40

<210> SEQ ID NO 215
<211> LENGTH: 33
<212> TYPE: PRT
<213> ORGANISM: Influenza virus -continued

```
<400> SEQUENCE: 215

His Gln Asn Glu Gln Gly Ser Gly Tyr Ala Ala Asp Gln Lys Ser Thr
1               5                   10                  15

Gln Asn Ala Ile Asn Gly Ile Thr Asn Lys Val Asn Ser Val Ile Glu
            20                  25                  30

Lys

<210> SEQ ID NO 216
<211> LENGTH: 34
<212> TYPE: PRT
<213> ORGANISM: Influenza virus

<400> SEQUENCE: 216

His Asn Gly Lys Ser Ser Phe Tyr Arg Asn Leu Leu Trp Leu Thr Glu
1               5                   10                  15

Lys Asn Gly Leu Tyr Pro Asn Leu Ser Lys Ser Tyr Val Asn Asn Lys
            20                  25                  30

Glu Lys

<210> SEQ ID NO 217
<211> LENGTH: 11
<212> TYPE: PRT
<213> ORGANISM: Influenza virus

<400> SEQUENCE: 217

Lys His Phe Glu Lys Val Lys Ile Leu Pro Lys
1               5                   10

<210> SEQ ID NO 218
<211> LENGTH: 14
<212> TYPE: PRT
<213> ORGANISM: Influenza virus

<400> SEQUENCE: 218

Lys His Leu Leu Ser Ser Val Lys His Phe Glu Lys Val Lys
1               5                   10

<210> SEQ ID NO 219
<211> LENGTH: 13
<212> TYPE: PRT
<213> ORGANISM: Influenza virus
<220> FEATURE:
<221> NAME/KEY: MOD_RES
<222> LOCATION: (3)
<223> OTHER INFORMATION: lys, gln or met
<220> FEATURE:
<221> NAME/KEY: MOD_RES
<222> LOCATION: (4)
<223> OTHER INFORMATION: asp or asn

<400> SEQUENCE: 219

His Ala Xaa Xaa Ile Leu Glu Lys Thr His Asn Gly Lys
1               5                   10

<210> SEQ ID NO 220
<211> LENGTH: 16
<212> TYPE: PRT
<213> ORGANISM: Influenza virus
<220> FEATURE:
<221> NAME/KEY: MOD_RES
<222> LOCATION: (3)
<223> OTHER INFORMATION: lys, gln or met
<220> FEATURE:
<221> NAME/KEY: MOD_RES
<222> LOCATION: (4)
```

```
<223> OTHER INFORMATION: asp or asn
<220> FEATURE:
<221> NAME/KEY: MOD_RES
<222> LOCATION: (16)
<223> OTHER INFORMATION: lys or arg

<400> SEQUENCE: 220

His Ala Xaa Xaa Ile Leu Glu Lys Thr His Asn Gly Lys Leu Cys Xaa
  1               5                  10                  15

<210> SEQ ID NO 221
<211> LENGTH: 19
<212> TYPE: PRT
<213> ORGANISM: Influenza virus

<400> SEQUENCE: 221

His Asn Val His Pro Leu Thr Ile Gly Glu Cys Pro Lys Tyr Val Lys
  1               5                  10                  15

Ser Glu Lys

<210> SEQ ID NO 222
<211> LENGTH: 16
<212> TYPE: PRT
<213> ORGANISM: Influenza virus

<400> SEQUENCE:

```
<221> NAME/KEY: MOD_RES
<222> LOCATION: (26)
<223> OTHER INFORMATION: val or ile

<400> SEQUENCE: 225

Lys Gly Ser Asn Tyr Pro Xaa Ala Lys Xaa Ser Tyr Asn Asn Thr Ser
  1               5                  10                  15
Gly Glu Gln Met Leu Ile Ile Trp Gln Xaa His
             20                  25

<210> SEQ ID NO 226
<211> LENGTH: 36
<212> TYPE: PRT
<213> ORGANISM: Influenza virus

<400> SEQUENCE: 226

His Thr Thr Leu Gly Gln Ser Arg Ala Cys Ala Val Ser Gly Asn Pro
  1               5                  10                  15
Ser Phe Phe Arg Asn Met Val Trp Leu Thr Glu Lys Gly Ser Asn Tyr
             20                  25                  30
Pro Val Ala Lys
         35

<210> SEQ ID NO 227
<211> LENGTH: 7
<212> TYPE: PRT
<213> ORGANISM: Influenza virus

<400> SEQUENCE: 227

Lys His Phe Glu Lys Val Lys
  1               5

<210> SEQ ID NO 228
<211> LENGTH: 38
<212> TYPE: PRT
<213> ORGANISM: Influenza virus

<400> SEQUENCE: 228

Lys Ile Ser Lys Arg Gly Ser Ser Gly Ile Met Lys Thr Glu Gly Thr
  1               5                  10                  15
Leu Glu Asn Cys Glu Thr Lys Cys Gln Thr Pro Leu Gly Ala Ile Asn
             20                  25                  30
Thr Thr Leu Pro Phe His
         35

<210> SEQ ID NO 229
<211> LENGTH: 35
<212> TYPE: PRT
<213> ORGANISM: Influenza virus

<400> SEQUENCE: 229

Lys Arg Gly Ser Ser Gly Ile Met Lys Thr Glu Gly Thr Leu Glu Asn
  1               5                  10                  15
Cys Glu Thr Lys Cys Gln Thr Pro Leu Gly Ala Ile Asn Thr Thr Leu
             20                  25                  30
Pro Phe His
         35

<210> SEQ ID NO 230
<211> LENGTH: 27
<212> TYPE: PRT
<213> ORGANISM: Influenza virus
```

```
<400> SEQUENCE: 230

Lys Thr Glu Gly Thr Leu Glu Asn Cys Glu Thr Lys Cys Gln Thr Pro
1               5                   10                  15

Leu Gly Ala Ile Asn Thr Thr Leu Pro Phe His
            20                  25

<210> SEQ ID NO 231
<211> LENGTH: 38
<212> TYPE: PRT
<213> ORGANISM: Influenza virus

<400> SEQUENCE: 231

Lys Ile Ser Lys Arg Gly Ser Ser Gly Ile Met Lys Thr Glu Gly Thr
1               5                   10                  15

Leu Glu Asn Cys Glu Thr Lys Cys Gln Thr Pro Leu Gly Ala Ile Asn
            20                  25                  30

Thr Thr Leu Pro Phe His
        35

<210> SEQ ID NO 232
<211> LENGTH: 30
<212> TYPE: PRT
<213> ORGANISM: Influenza virus
<220> FEATURE:
<221> NAME/KEY: MOD_RES
<222> LOCATION: (29)
<223> OTHER INFORMATION: val or ile

<400> SEQUENCE: 232

Lys Thr Glu Gly Thr Leu Glu Asn Cys Glu Thr Lys Cys Gln Thr Pro
1               5                   10                  15

Leu Gly Ala Ile Asn Thr Thr Leu Pro Phe His Asn Xaa His
            20                  25                  30

<210> SEQ ID NO 233
<211> LENGTH: 38
<212> TYPE: PRT
<213> ORGANISM: Influenza virus

<400> SEQUENCE: 233

Lys Ile Ser Lys Arg Gly Ser Ser Gly Ile Met Lys Thr Glu Gly Thr
1               5                   10                  15

Leu Glu Asn Cys Glu Thr Lys Cys Gln Thr Pro Leu Gly Ala Ile Asn
            20                  25                  30

Thr Thr Leu Pro Phe His
        35

<210> SEQ ID NO 234
<211> LENGTH: 27
<212> TYPE: PRT
<213> ORGANISM: Influenza virus
<220> FEATURE:
<221> NAME/KEY: MOD_RES
<222> LOCATION: (2)
<223> OTHER INFORMATION: glu or gly

<400> SEQUENCE: 234

Lys Xaa Ser Asn Tyr Pro Val Ala Lys Gly Ser Tyr Asn Asn Thr Ser
1               5                   10                  15

Gly Glu Gln Met Leu Ile Ile Trp Gly Val His
            20                  25
```

-continued

<210> SEQ ID NO 235
<211> LENGTH: 16
<212> TYPE: PRT
<213> ORGANISM: Influenza virus

<400> SEQUENCE: 235

His Pro Leu Thr Ile Gly Glu Cys Pro Lys Tyr Val Lys Ser Glu Lys
 1               5                  10                  15

<210> SEQ ID NO 236
<211> LENGTH: 16
<212> TYPE: PRT
<213> ORGANISM: Influenza virus

<400> SEQUENCE: 236

Lys Cys Gln Thr Pro Leu Gly Ala Ile Lys Thr Thr Leu Pro Phe His
 1               5                  10                  15

<210> SEQ ID NO 237
<211> LENGTH: 58
<212> TYPE: PRT
<213> ORGANISM: Influenza virus
<220> FEATURE:
<221> NAME/KEY: MOD_RES
<222> LOCATION: (21)
<223> OTHER INFORMATION: phe or ile
<220> FEATURE:
<221> NAME/KEY: MOD_RES
<222> LOCATION: (47)
<223> OTHER INFORMATION: asn or ser

<400> SEQUENCE: 237

His His Ser Asn Asp Gln Gly Ser Gly Tyr Ala Ala Asp Lys Glu Ser
 1               5                  10                  15

Thr Gln Lys Ala Xaa Asp Gly Ile Thr Asn Lys Val Asn Ser Val Ile
                20                  25                  30

Glu Lys Met Asn Thr Gln Phe Glu Ala Val Gly Lys Leu Phe Xaa Asn
            35                  40                  45

Leu Glu Lys Leu Glu Asn Leu Asn Lys Lys
        50                  55

<210> SEQ ID NO 238
<211> LENGTH: 57
<212> TYPE: PRT
<213> ORGANISM: Influenza virus
<220> FEATURE:
<221> NAME/KEY: MOD_RES
<222> LOCATION: (20)
<223> OTHER INFORMATION: phe or ile
<220> FEATURE:
<221> NAME/KEY: MOD_RES
<222> LOCATION: (46)
<223> OTHER INFORMATION: asn or ser

<400> SEQUENCE: 238

His Ser Asn Asp Gln Gly Ser Gly Tyr Ala Ala Asp Lys Glu Ser Thr
 1               5                  10                  15

Gln Lys Ala Xaa Asp Gly Ile Thr Asn Lys Val Asn Ser Val Ile Glu
                20                  25                  30

Lys Met Asn Thr Gln Phe Glu Ala Val Gly Lys Leu Phe Xaa Asn Leu
            35                  40                  45

Glu Lys Leu Glu Asn Leu Asn Lys Lys
        50                  55

```
<210> SEQ ID NO 239
<211> LENGTH: 26
<212> TYPE: PRT
<213> ORGANISM: Influenza virus
<220> FEATURE:
<221> NAME/KEY: MOD_RES
<222> LOCATION: (20)
<223> OTHER INFORMATION: phe or ile

<400> SEQUENCE: 239

His Ser Asn Asp Gln Gly Ser Gly Tyr Ala Ala Asp Lys Glu Ser Thr
 1               5                  10                  15

Gln Lys Ala Xaa Asp Gly Ile Thr Asn Lys
            20                  25

<210> SEQ ID NO 240
<211> LENGTH: 21
<212> TYPE: PRT
<213> ORGANISM: Influenza virus

<400> SEQUENCE: 240

His Asp Ser Asn Val Arg Asn Leu Tyr Asp Lys Val Arg Met Gln Leu
 1               5                  10                  15

Arg Asp Asn Ala Lys
            20

<210> SEQ ID NO 241
<211> LENGTH: 30
<212> TYPE: PRT
<213> ORGANISM: Influenza virus

<400> SEQUENCE: 241

His Lys Cys Asp Asp Glu Cys Met Asn Ser Val Lys Asn Gly Thr Tyr
 1               5                  10                  15

Asp Tyr Pro Lys Leu Asn Arg Asn Glu Ile Lys Gly Val Lys
            20                  25                  30

<210> SEQ ID NO 242
<211> LENGTH: 27
<212> TYPE: PRT
<213> ORGANISM: Influenza virus

<400> SEQUENCE: 242

His Lys Cys Asp Asp Glu Cys Met Asn Ser Val Lys Asn Gly Thr Tyr
 1               5                  10                  15

Asp Tyr Pro Lys Leu Asn Arg Asn Glu Ile Lys
            20                  25

<210> SEQ ID NO 243
<211> LENGTH: 20
<212> TYPE: PRT
<213> ORGANISM: Influenza virus

<400> SEQUENCE: 243

His Lys Cys Asp Asp Glu Cys Met Asn Ser Val Lys Asn Gly Thr Tyr
 1               5                  10                  15

Asp Tyr Pro Lys
            20

<210> SEQ ID NO 244
<211> LENGTH: 12
<212> TYPE: PRT
<213> ORGANISM: Influenza virus
```

-continued

```
<400> SEQUENCE: 244

His Lys Cys Asp Asp Glu Cys Met Asn Ser Val Lys
 1               5                  10

<210> SEQ ID NO 245
<211> LENGTH: 27
<212> TYPE: PRT
<213> ORGANISM: Influenza virus

<400> SEQUENCE: 245

Lys Gly Ser Asn Tyr Pro Val Ala Lys Gly Ser Tyr Asn Asn Thr Asn
 1               5                  10                  15

Gly Glu Gln Ile Leu Ile Ile Trp Gly Val His
             20                  25

<210> SEQ ID NO 246
<211> LENGTH: 43
<212> TYPE: PRT
<213> ORGANISM: Influenza virus

<400> SEQUENCE: 246

His Ser Asn Asp Gln Gly Ser Gly Tyr Ala Ala Asp Lys Glu Ser Thr
 1               5                  10                  15

Gln Lys Ala Val Asp Gly Ile Thr Asn Lys Val Asn Ser Val Ile Glu
             20                  25                  30

Lys Met Asn Thr Gln Phe Glu Ala Val Gly Lys
         35                  40

<210> SEQ ID NO 247
<211> LENGTH: 35
<212> TYPE: PRT
<213> ORGANISM: Influenza virus

<400> SEQUENCE: 247

Lys Arg Gly Ser Ser Gly Ile Met Lys Thr Glu Gly Thr Leu Glu Asn
 1               5                  10                  15

Cys Glu Thr Lys Cys Gln Thr Pro Leu Gly Ala Ile Asn Thr Thr Leu
             20                  25                  30

Pro Phe His
         35

<210> SEQ ID NO 248
<211> LENGTH: 16
<212> TYPE: PRT
<213> ORGANISM: Influenza virus

<400> SEQUENCE: 248

His Pro Leu Thr Ile Gly Glu Cys Pro Lys Tyr Val Lys Ser Glu Lys
 1               5                  10                  15

<210> SEQ ID NO 249
<211> LENGTH: 16
<212> TYPE: PRT
<213> ORGANISM: Influenza virus

<400> SEQUENCE: 249

His Ala Lys Asp Ile Leu Glu Lys Thr His Asn Gly Lys Leu Cys Lys
 1               5                  10                  15

<210> SEQ ID NO 250
<211> LENGTH: 25
<212> TYPE: PRT
```

```
<213> ORGANISM: Influenza virus

<400> SEQUENCE: 250

His Asp Val Tyr Arg Asp Glu Ala Leu Asn Asn Arg Ph

```
<210> SEQ ID NO 256
<211> LENGTH: 8
<212> TYPE: PRT
<213> ORGANISM: Influenza virus

<400> SEQUENCE: 256

Lys Ile Cys Asn Asn Pro His Lys
  1               5

<210> SEQ ID NO 257
<211> LENGTH: 14
<212> TYPE: PRT
<213> ORGANISM: Influenza virus

<400> SEQUENCE: 257

Lys Leu Asn Arg Val Ile Lys Lys Thr Asn Glu Lys Phe His
  1               5                  10

<210> SEQ ID NO 258
<211> LENGTH: 24
<212> TYPE: PRT
<213> ORGANISM: Influenza virus
<220> FEATURE:
<221> NAME/KEY: MOD_RES
<222> LOCATION: (3)
<223> OTHER INFORMATION: ile or val
<220> FEATURE:
<221> NAME/KEY: MOD_RES
<222> LOCATION: (17)
<223> OTHER INFORMATION: gly or gln
<220> FEATURE:
<221> NAME/KEY: MOD_RES
<222> LOCATION: (20)
<223> OTHER INFORMATION: arg or lys
<220> FEATURE:
<221> NAME/KEY: MOD_RES
<222> LOCATION: (22)
<223> OTHER INFORMATION: gln or gly

<400> SEQUENCE: 258

His Asp Xaa Tyr Arg Asp Glu Ala Leu Asn Asn Arg Phe Gln Ile Lys
  1               5                  10                  15

Xaa Val Glu Xaa Ser Xaa Tyr Lys
             20

<210> SEQ ID NO 259
<211> LENGTH: 25
<212> TYPE: PRT
<213> ORGANISM: Influenza virus

<400> SEQUENCE: 259

His Gln Ile Glu Lys Glu Phe Ser Glu Val Glu Gly Arg Ile Gln Asp
  1               5                  10                  15

Leu Glu Lys Tyr Val Glu Asp Thr Lys
             20                  25

<210> SEQ ID NO 260
<211> LENGTH: 25
<212> TYPE: PRT
<213> ORGANISM: Influenza virus

<400> SEQUENCE: 260

Lys Tyr Val Glu Asp Thr Lys Ile Asp Leu Trp Ser Tyr Asn Ala Glu
  1               5                  10                  15

Leu Leu Val Ala Leu Glu Asn Gln His
             20                  25
```

-continued

```
<210> SEQ ID NO 261
<211> LENGTH: 49
<212> TYPE: PRT
<213> ORGANISM: Influenza virus

<400> SEQUENCE: 261

Lys Tyr Val Lys Gln Asn Ser Leu Lys Leu Ala Thr Gly Met Arg Asn
 1               5                  10                  15

Val Pro Glu Lys Gln Thr Arg Gly Leu Phe Gly Ala Ile Ala Gly Phe
            20                  25                  30

Ile Glu Asn Gly Trp Glu Gly Met Ile Asp Gly Trp Tyr Gly Phe Arg
        35                  40                  45

His

<210> SEQ ID NO 262
<211> LENGTH: 39
<212> TYPE: PRT
<213> ORGANISM: Influenza virus

<400> SEQUENCE: 262

Lys Glu Phe Ser Glu Val Glu Gly Arg Ile Gln Asp Leu Glu Lys Tyr
 1               5                  10                  15

Val Glu Asp Thr Lys Ile Asp Leu Trp Ser Tyr Asn Ala Glu Leu Leu
            20                  25                  30

Val Ala Leu Glu Asn Gln His
        35

<210> SEQ ID NO 263
<211> LENGTH: 33
<212> TYPE: PRT
<213> ORGANISM: Influenza virus
<220> FEATURE:
<221> NAME/KEY: MOD_RES
<222> LOCATION: (4)
<223> OTHER INFORMATION: ser or glu
<220> FEATURE:
<221> NAME/KEY: MOD_RES
<222> LOCATION: (5)
<223> OTHER INFORMATION: glu or gln
<220> FEATURE:
<221> NAME/KEY: MOD_RES
<222> LOCATION: (7)
<223> OTHER INFORMATION: thr or ser
<220> FEATURE:
<221> NAME/KEY: MOD_RES
<222> LOCATION: (9)
<223> OTHER INFORMATION: gln or tyr
<220> FEATURE:
<221> NAME/KEY: MOD_RES
<222> LOCATION: (13)
<223> OTHER INFORMATION: leu or gln
<220> FEATURE:
<221> NAME/KEY: MOD_RES
<222> LOCATION: (18)
<223> OTHER INFORMATION: ala or asn
<220> FEATURE:
<221> NAME/KEY: MOD_RES
<222> LOCATION: (20)
<223> OTHER INFORMATION: ile or leu
<220> FEATURE:
<221> NAME/KEY: MOD_RES
<222> LOCATION: (22)
<223> OTHER INFORMATION: gln or gly
<220> FEATURE:
<221> NAME/KEY: MOD_RES
<222> LOCATION: (24)
<223> OTHER INFORMATION: asn or thr
<220> FEATURE:
<221> NAME/KEY: MOD_RES
```

```
<222> LOCATION: (25)
<223> OTHER INFORMATION: gly or asn
<220> FEATURE:
<221> NAME/KEY: MOD_RES
<222> LOCATION: (27)
<223> OTHER INFORMATION: leu or val
<220> FEATURE:
<221> NAME/KEY: MOD_RES
<222> LOCATION: (29)
<223> OTHER INFORMATION: arg or ser
<220> FEATURE:
<221> NAME/KEY: MOD_RES
<222> LOCATION: (32)
<223> OTHER INFORMATION: glu or cys

<400> SEQUENCE: 263

His Gln Asn Xaa Xaa Gly Xaa Gly Xaa Ala Ala Asp Xaa Lys Ser Thr
 1               5                  10                  15

Gln Xaa Ala Xaa Asp Xaa Ile Xaa Xaa Lys Xaa Asn Xaa Val Ile Xaa
            20                  25                  30

Lys

<210> SEQ ID NO 264
<211> LENGTH: 18
<212> TYPE: PRT
<213> ORGANISM: Influenza virus
<220> FEATURE:
<221> NAME/KEY: MOD_RES
<222> LOCATION: (4)
<223> OTHER INFORMATION: gly or gln
<220> FEATURE:
<221> NAME/KEY: MOD_RES
<222> LOCATION: (6)
<223> OTHER INFORMATION: gln or arg
<220> FEATURE:
<221> NAME/KEY: MOD_RES
<222> LOCATION: (14)
<223> OTHER INFORMATION: val or ile
<220> FEATURE:
<221> NAME/KEY: MOD_RES
<222> LOCATION: (17)
<223> OTHER INFORMATION: ser or thr

<400> SEQUENCE: 264

His Cys Asp Xaa Phe Xaa Asn Glu Lys Trp Asp Leu Phe Xaa Glu Arg
 1               5                  10                  15

Xaa Lys

<210> SEQ ID NO 265
<211> LENGTH: 20
<212> TYPE: PRT
<213> ORGANISM: Influenza virus

<400> SEQUENCE: 265

His Thr Ile Asp Leu Thr Asp Ser Glu Met Asn Lys Lys Leu Phe Glu
 1               5                  10                  15

Arg Thr Arg Lys
            20

<210> SEQ ID NO 266
<211> LENGTH: 28
<212> TYPE: PRT
<213> ORGANISM: Influenza virus

<400> SEQUENCE: 266

Lys Ser Gly Ser Thr Tyr Pro Val Leu Lys Val Thr Met Pro Asn Asn
 1               5                  10                  15
```

```
Asp Asn Phe Asp Lys Leu Tyr Ile Trp Gly Val His
            20                  25
```

<210> SEQ ID NO 267
<211> LENGTH: 34
<212> TYPE: PRT
<213> ORGANISM: Influenza virus

<400> SEQUENCE: 267

```
Lys Leu Asn Trp Leu Thr Lys Ser Gly Asn Thr Tyr Pro Val Leu Asn
  1               5                  10                  15

Val Thr Met Pro Asn Asn Asp Asn Phe Asp Lys Leu Val Ile Trp Gly
             20                  25                  30

Val His
```

<210> SEQ ID NO 268
<211> LENGTH: 19
<212> TYPE: PRT
<213> ORGANISM: Influenza virus

<400> SEQUENCE: 268

```
His Thr Ile Asp Leu Thr Asp Ser Glu Met Asn Lys Leu Phe Glu Lys
  1               5                  10                  15

Thr Arg Lys
```

<210> SEQ ID NO 269
<211> LENGTH: 18
<212> TYPE: PRT
<213> ORGANISM: Influenza virus

<400> SEQUENCE: 269

```
Lys Leu Asn Arg Leu Ile Glu Lys Thr Asn Glu Lys Phe His Gln Thr
  1               5                  10                  15

Glu Lys
```

<210> SEQ ID NO 270
<211> LENGTH: 47
<212> TYPE: PRT
<213> ORGANISM: Influenza virus

<400> SEQUENCE: 270

```
His Thr Gly Lys Ser Ser Val Met Arg Ser Asp Ala Pro Ile Asp Phe
  1               5                  10                  15

Cys Asn Ser Glu Cys Ile Thr Pro Asn Gln Ser Ile Pro Asn Asp Lys
             20                  25                  30

Pro Phe Gln Asn Val Asn Lys Ile Thr Tyr Gly Ala Cys Pro Lys
         35                  40                  45
```

<210> SEQ ID NO 271
<211> LENGTH: 39
<212> TYPE: PRT
<213> ORGANISM: Influenza virus

<400> SEQUENCE: 271

```
His Thr Gly Lys Ser Ser Val Met Arg Ser Asp Ala Pro Ile Asp Phe
  1               5                  10                  15

Cys Asn Ser Glu Cys Ile Thr Pro Asn Gln Ser Ile Pro Asn Asp Lys
             20                  25                  30

Pro Phe Gln Asn Val Asn Lys
         35
```

-continued

<210> SEQ ID NO 272
<211> LENGTH: 33
<212> TYPE: PRT
<213> ORGANISM: Influenza virus

<400> SEQUENCE: 272

His Pro Ser Thr Asp Ser Asp Gln Thr Ser Leu Tyr Val Arg Ala Ser
1               5                   10                  15

Gly Arg Val Thr Val Ser Thr Lys Arg Ser Gln Gln Thr Val Ile Pro
            20                  25                  30

Lys

<210> SEQ ID NO 273
<211> LENGTH: 25
<212> TYPE: PRT
<213> ORGANISM: Influenza virus

<400> SEQUENCE: 273

Lys Tyr Val Glu Asp Thr Lys Ile Asp Leu Trp Ser Tyr Asn Ala Glu
1               5                   10                  15

Leu Leu Val Ala Leu Glu Asn Gln His
            20                  25

<210> SEQ ID NO 274
<211> LENGTH: 26
<212> TYPE: PRT
<213> ORGANISM: Influenza virus

<400> SEQUENCE: 274

Lys Leu Phe Glu Arg Thr Arg Lys Gln Leu Arg Glu Asn Ala Glu Asp
1               5                   10                  15

Met Gly Asn Gly Cys Phe Lys Ile Tyr His
            20                  25

<210> SEQ ID NO 275
<211> LENGTH: 16
<212> TYPE: PRT
<213> ORGANISM: Influenza virus

<400> SEQUENCE: 275

Lys Arg Arg Ser Ile Lys Ser Phe Phe Ser Arg Leu Asn Trp Leu His
1               5                   10                  15

<210> SEQ ID NO 276
<211> LENGTH: 16
<212> TYPE: PRT
<213> ORGANISM: Influenza virus
<220> FEATURE:
<221> NAME/KEY: MOD_RES
<222> LOCATION: (12)
<223> OTHER INFORMATION: val or arg

<400> SEQUENCE: 276

His Pro Val Thr Ile Gly Glu Cys Pro Lys Tyr Xaa Lys Ser Thr Lys
1               5                   10                  15

<210> SEQ ID NO 277
<211> LENGTH: 30
<212> TYPE: PRT
<213> ORGANISM: Influenza virus

<400> SEQUENCE: 277

Lys Gly Asn Ser Tyr Pro Lys Leu Ser Lys Leu Ser Lys Ser Tyr Ile

```
                1               5              10              15
Ile Asn Lys Lys Lys Glu Val Leu Val Ile Trp Gly Ile His
            20              25              30

<210> SEQ ID NO 278
<211> LENGTH: 24
<212> TYPE: PRT
<213> ORGANISM: Influenza virus
<220> FEATURE:
<221> NAME/KEY: MOD_RES
<222> LOCATION: (9)
<223> OTHER INFORMATION: val or tyr

<400> SEQUENCE: 278

Lys Leu Ser Lys Leu Ser Lys Ser Xaa Ile Ile Asn Lys Lys Lys Glu
 1               5              10                  15

Val Leu Val Ile Trp Gly Ile His
            20

<210> SEQ ID NO 279
<211> LENGTH: 21
<212> TYPE: PRT
<213> ORGANISM: Influenza virus
<220> FEATURE:
<221> NAME/KEY: MOD_RES
<222> LOCATION: (6)
<223> OTHER INFORMATION: val or tyr

<400> SEQUENCE: 279

Lys Leu Ser Lys Ser Xaa Ile Ile Asn Lys Lys Glu Val Leu Val
 1               5              10                  15

Ile Trp Gly Ile His
            20

<210> SEQ ID NO 280
<211> LENGTH: 46
<212> TYPE: PRT
<213> ORGANISM: Plasmodium falciparum

<400> SEQUENCE: 280

Lys Glu Glu Glu Glu Lys Glu Lys Glu Lys Glu Lys Glu Lys Glu Glu
 1               5              10                  15

Lys Glu Lys Glu Glu Lys Glu Lys Glu Lys Glu Lys Glu Lys Glu Glu
            20              25              30

Glu Lys Glu Lys Glu Lys Glu Glu Lys Glu Glu Glu Lys Lys
            35              40              45

<210> SEQ ID NO 281
<211> LENGTH: 48
<212> TYPE: PRT
<213> ORGANISM: Plasmodium falciparum

<400> SEQUENCE: 281

Lys Glu Glu Glu Glu Lys Glu Lys Glu Lys Glu Lys Glu Lys Glu Glu
 1               5              10                  15

Lys Glu Lys Glu Glu Lys Glu Lys Glu Lys Glu Lys Glu Lys Glu Glu
            20              25              30

Glu Lys Glu Lys Glu Lys Glu Glu Lys Glu Glu Glu Lys Lys Glu Lys
            35              40              45

<210> SEQ ID NO 282
<211> LENGTH: 47
<212> TYPE: PRT
```

```
<213> ORGANISM: Plasmodium falciparum

<400> SEQUENCE: 282

Lys Glu Glu Glu Glu Lys Glu Lys Glu Lys Glu Lys Glu Lys Glu Glu
 1               5                  10                  15

Lys Glu Lys Glu Glu Lys Glu Lys Glu Lys Glu Glu Lys Glu Lys Glu
            20                  25                  30

Glu Lys Glu Lys Glu Glu Lys Glu Glu Lys Glu Lys Lys
        35                  40                  45

<210> SEQ ID NO 283
<211> LENGTH: 10
<212> TYPE: PRT
<213> ORGANISM: Plasmodium falciparum

<400> SEQUENCE: 283

Lys Glu Glu Glu Glu Lys Glu Lys Glu Lys
 1               5                  10

<210> SEQ ID NO 284
<211> LENGTH: 19
<212> TYPE: PRT
<213> ORGANISM: Plasmodium falciparum

<400> SEQUENCE: 284

His Lys Lys Leu Ile Lys Ala Leu Lys Lys Asn Ile Glu Ser Ile Gln
 1               5                  10                  15

Asn Lys Lys

<210> SEQ ID NO 285
<211> LENGTH: 19
<212> TYPE: PRT
<213> ORGANISM: Plasmodium falciparum

<400> SEQUENCE: 285

His Lys Lys Leu Ile Lys Ala Leu Lys Lys Asn Ile Glu Ser Ile Gln
 1               5                  10                  15

Asn Lys Met

<210> SEQ ID NO 286
<211> LENGTH: 10
<212> TYPE: PRT
<213> ORGANISM: Plasmodium falciparum

<400> SEQUENCE: 286

His Lys Lys Leu Ile Lys Ala Leu Lys Lys
 1               5                  10

<210> SEQ ID NO 287
<211> LENGTH: 9
<212> TYPE: PRT
<213> ORGANISM: Plasmodium falciparum

<400> SEQUENCE: 287

His Lys Lys Leu Ile Lys Ala Leu Lys
 1               5

<210> SEQ ID NO 288
<211> LENGTH: 23
<212> TYPE: PRT
<213> ORGANISM: Plasmodium falciparum

<400> SEQUENCE: 288
```

Lys Ala Thr Tyr Ser Phe Val Asn Thr Lys Lys Ile Ile Ser Leu
1               5                   10                  15

Lys Ser Gln Gly His Lys Lys
            20

<210> SEQ ID NO 289
<211> LENGTH: 22
<212> TYPE: PRT
<213> ORGANISM: Plasmodium falciparum

<400> SEQUENCE: 289

Lys Ala Thr Tyr Ser Phe Val Asn Thr Lys Lys Ile Ile Ser Leu
1               5                   10                  15

Lys Ser Gln Gly His Lys
            20

<210> SEQ ID NO 290
<211> LENGTH: 21
<212> TYPE: PRT
<213> ORGANISM: Plasmodium falciparum

<400> SEQUENCE: 290

Lys Ala Thr Tyr Ser Phe Val Asn Thr Lys Lys Ile Ile Ser Leu
1               5                   10                  15

Lys Ser Gln Gly His
            20

<210> SEQ ID NO 291
<211> LENGTH: 29
<212> TYPE: PRT
<213> ORGANISM: Plasmodium falciparum

<400> SEQUENCE: 291

His Thr Tyr Val Lys Gly Lys Lys Ala Pro Ser Asp Pro Gln Cys Ala
1               5                   10                  15

Asp Ile Lys Glu Glu Cys Lys Glu Leu Leu Lys Glu Lys
            20                  25

<210> SEQ ID NO 292
<211> LENGTH: 11
<212> TYPE: PRT
<213> ORGANISM: Plasmodium falciparum

<400> SEQUENCE: 292

Lys Ile Ile Ser Leu Lys Ser Gln Gly His Lys
1               5                   10

<210> SEQ ID NO 293
<211> LENGTH: 21
<212> TYPE: PRT
<213> ORGANISM: Plasmodium falciparum

<400> SEQUENCE: 293

Lys Lys Lys Lys Phe Glu Pro Leu Lys Asn Gly Asn Val Ser Glu Thr
1               5                   10                  15

Ile Lys Leu Ile His
            20

<210> SEQ ID NO 294
<211> LENGTH: 20
<212> TYPE: PRT
<213> ORGANISM: Plasmodium falciparum -continued

<400> SEQUENCE: 294

Lys Lys Lys Phe Glu Pro Leu Lys Asn Gly Asn Val Ser Glu Thr Ile
1               5                   10                  15

Lys Leu Ile His
            20

<210> SEQ ID NO 295
<211> LENGTH: 19
<212> TYPE: PRT
<213> ORGANISM: Plasmodium falciparum

<400> SEQUENCE: 295

Lys Lys Phe Glu Pro Leu Lys Asn Gly Asn Val Ser Glu Thr Ile Lys
1               5                   10                  15

Leu Ile His

<210> SEQ ID NO 296
<211> LENGTH: 13
<212> TYPE: PRT
<213> ORGANISM: Plasmodium falciparum

<400> SEQUENCE: 296

Lys Asn Gly Asn Val Ser Glu Thr Ile Lys Leu Ile His
1               5                   10

<210> SEQ ID NO 297
<211> LENGTH: 11
<212> TYPE: PRT
<213> ORGANISM: Plasmodium falciparum

<400> SEQUENCE: 297

Lys Leu Ile His Leu Gly Asn Lys Asp Lys Lys
1               5                   10

<210> SEQ ID NO 298
<211> LENGTH: 36
<212> TYPE: PRT
<213> ORGANISM: Plasmodium falciparum

<400> SEQUENCE: 298

Lys Val Lys Lys Ile Gly Val Thr Leu Lys Lys Phe Glu Pro Leu Lys
1               5                   10                  15

Asn Gly Asn Val Ser Glu Thr Ile Lys Leu Ile His Leu Gly Asn Lys
            20                  25                  30

Asp Lys Lys His
        35

<210> SEQ ID NO 299
<211> LENGTH: 59
<212> TYPE: PRT
<213> ORGANISM: Plasmodium falciparum

<400> SEQUENCE: 299

His Leu Ile Tyr Lys Asn Lys Ser Tyr Asn Pro Leu Leu Leu Ser Cys
1               5                   10                  15

Val Lys Lys Met Asn Met Leu Lys Glu Asn Val Asp Tyr Ile Gln Asn
            20                  25                  30

Gln Asn Leu Phe Lys Glu Leu Met Asn Gln Lys Ala Thr Tyr Ser Phe
        35                  40                  45

Val Asn Thr Lys Lys Lys Ile Ile Ser Leu Lys

```
<210> SEQ ID NO 300
<211> LENGTH: 52
<212> TYPE: PRT
<213> ORGANISM: Plasmodium falciparum

<400> SEQUENCE: 300

His Leu Ile Tyr Lys Asn Lys Ser Tyr Asn Pro Leu Leu Leu Ser Cys
  1               5                  10                  15

Val Lys Lys Met Asn Met Leu Lys Glu Asn Val Asp Tyr Ile Gln Asn
             20                  25                  30

Gln Asn Leu Phe Lys Glu Leu Met Asn Gln Lys Ala Thr Tyr Ser Phe
         35                  40                  45

Val Asn Thr Lys
         50

<210> SEQ ID NO 301
<211> LENGTH: 43
<212> TYPE: PRT
<213> ORGANISM: Plasmodium falciparum

<400> SEQUENCE: 301

His Leu Ile Tyr Lys Asn Lys Ser Tyr Asn Pro Leu Leu Leu Ser Cys
  1               5                  10                  15

Val Lys Lys Met Asn Met Leu Lys Glu Asn Val Asp Tyr Ile Gln Asn
             20                  25                  30

Gln Asn Leu Phe Lys Glu Leu Met Asn Gln Lys
         35                  40

<210> SEQ ID NO 302
<211> LENGTH: 38
<212> TYPE: PRT
<213> ORGANISM: Plasmodium falciparum

<400> SEQUENCE: 302

His Leu Ile Tyr Lys Asn Lys Ser Tyr Asn Pro Leu Leu Leu Ser Cys
  1               5                  10                  15

Val Lys Lys Met Asn Met Leu Lys Glu Asn Val Asp Tyr Ile Gln Lys
             20                  25                  30

Asn Gln Asn Leu Phe Lys
         35

<210> SEQ ID NO 303
<211> LENGTH: 24
<212> TYPE: PRT
<213> ORGANISM: Plasmodium falciparum

<400> SEQUENCE: 303

His Leu Ile Tyr Lys Asn Lys Ser Tyr Asn Pro Leu Leu Leu Ser Cys
  1               5                  10                  15

Val Lys Lys Met Asn Met Leu Lys
             20

<210> SEQ ID NO 304
<211> LENGTH: 47
<212> TYPE: PRT
<213> ORGANISM: Plasmodium falciparum

<400> SEQUENCE: 304

Lys Ser Ala Asn Asn Ser Ala Asn Asn Gly Lys Lys Asn Asn Ala Glu
```

-continued

```
                1               5                  10                 15
Glu Met Lys Asn Leu Val Asn Phe Leu Gln Ser His Lys Lys Leu Ile
                    20                  25                  30

Lys Ala Leu Lys Lys Asn Ile Glu Ser Ile Gln Asn Lys Lys His
            35                  40                  45

<210> SEQ ID NO 305
<211> LENGTH: 37
<212> TYPE: PRT
<213> ORGANISM: Plasmodium falciparum

<400> SEQUENCE: 305

Lys Lys Asn Asn Ala Glu Glu Met Lys Asn Leu Val Asn Phe Leu Gln
  1               5                  10                  15

Ser His Lys Lys Leu Ile Lys Ala Leu Lys Lys Asn Ile Glu Ser Ile
                20                  25                  30

Gln Asn Lys Lys His
            35

<210> SEQ ID NO 306
<211> LENGTH: 29
<212> TYPE: PRT
<213> ORGANISM: Plasmodium falciparum

<400> SEQUENCE: 306

Lys Asn Leu Val Asn Phe Leu Gln Ser His Lys Lys Leu Ile Lys Ala
  1               5                  10                  15

Leu Lys Lys Asn Ile Glu Ser Ile Gln Asn Lys Lys His
                20                  25

<210> SEQ ID NO 307
<211> LENGTH: 19
<212> TYPE: PRT
<213> ORGANISM: Plasmodium falciparum

<400> SEQUENCE: 307

Lys Lys Leu Ile Lys Ala Leu Lys Lys Asn Ile Glu Ser Ile Gln Asn
  1               5                  10                  15

Lys Lys His

<210> SEQ ID NO 308
<211> LENGTH: 18
<212> TYPE: PRT
<213> ORGANISM: Plasmodium falciparum

<400> SEQUENCE: 308

Lys Leu Ile Lys Ala Leu Lys Lys Asn Ile Glu Ser Ile Gln Asn Lys
  1               5                  10                  15

Lys His

<210> SEQ ID NO 309
<211> LENGTH: 12
<212> TYPE: PRT
<213> ORGANISM: Plasmodium falciparum

<400> SEQUENCE: 309

Lys Lys Asn Ile Glu Ser Ile Gln Asn Lys Lys His
  1               5                  10

<210> SEQ ID NO 310
<211> LENGTH: 11
```

```
<212> TYPE: PRT
<213> ORGANISM: Plasmodium falciparum

<400> SEQUENCE: 310

Lys Asn Ile Glu Ser Ile Gln Asn Lys Lys His
 1               5                  10

<210> SEQ ID NO 311
<211> LENGTH: 17
<212> TYPE: PRT
<213> ORGANISM: Plasmodium falciparum

<400> SEQUENCE: 311

Lys Asn Asn Ala Glu Glu Met Lys Asn Leu Val Asn Phe Leu Gln Ser
 1               5                  10                  15

His

<210> SEQ ID NO 312
<211> LENGTH: 23
<212> TYPE: PRT
<213> ORGANISM: Plasmodium falciparum

<400> SEQUENCE: 312

Lys Lys Leu Ile Lys Ala Leu Lys Lys Asn Ile Glu Ser Ile Gln Asn
 1               5                  10                  15

Lys Lys Gln Gly His Lys Lys
            20

<210> SEQ ID NO 313
<211> LENGTH: 19
<212> TYPE: PRT
<213> ORGANISM: Plasmodium falciparum

<400> SEQUENCE: 313

Lys Lys Asn Asn Ala Glu Glu Met Lys Asn Leu Val Asn Phe Leu Gln
 1               5                  10                  15

Ser His Lys

<210> SEQ ID NO 314
<211> LENGTH: 17
<212> TYPE: PRT
<213> ORGANISM: Plasmodium falciparum

<400> SEQUENCE: 314

Lys Asn Asn Ala Glu Glu Met Lys Asn Leu Val Asn Phe Leu Gln Ser
 1               5                  10                  15

His

<210> SEQ ID NO 315
<211> LENGTH: 22
<212> TYPE: PRT
<213> ORGANISM: Plasmodium falciparum

<400> SEQUENCE: 315

Lys Leu Ile Lys Ala Leu Lys Lys Asn Ile Glu Ser Ile Gln Asn Lys
 1               5                  10                  15

Lys Gln Gly His Lys Lys
            20

<210> SEQ ID NO 316
<211> LENGTH: 28
<212> TYPE: PRT
```

<213> ORGANISM: Plasmodium falciparum

<400> SEQUENCE: 316

Lys Val Lys Lys Ile Gly Val Thr Leu Lys Lys Phe Glu Pro Leu Lys
 1               5                  10                  15

Asn Gly Asn Val Ser Glu Thr Ile Lys Leu Ile His
            20                  25

<210> SEQ ID NO 317
<211> LENGTH: 13
<212> TYPE: PRT
<213> ORGANISM: Plasmodium falciparum

<400> SEQUENCE: 317

Lys Asn Gly Asn Val Ser Glu Thr Ile Lys Leu Ile His
 1               5                  10

<210> SEQ ID NO 318
<211> LENGTH: 11
<212> TYPE: PRT
<213> ORGANISM: Plasmodium falciparum

<400> SEQUENCE: 318

Lys Leu Ile His Leu Gly Asn Lys Asp Lys Lys
 1               5                  10

<210> SEQ ID NO 319
<211> LENGTH: 28
<212> TYPE: PRT
<213> ORGANISM: Plasmodium falciparum

<400> SEQUENCE: 319

Lys Ser Ala Asn Asn Ser Ala Asn Asn Gly Lys Lys Asn Asn Ala Glu
 1               5                  10                  15

Glu Met Lys Asn Leu Val Asn Phe Leu Gln Ser His
            20                  25

<210> SEQ ID NO 320
<211> LENGTH: 18
<212> TYPE: PRT
<213> ORGANISM: Plasmodium falciparum

<400> SEQUENCE: 320

Lys Lys Asn Asn Ala Glu Glu Met Lys Asn Leu Val Asn Phe Leu Gln
 1               5                  10                  15

Ser His

<210> SEQ ID NO 321
<211> LENGTH: 19
<212> TYPE: PRT
<213> ORGANISM: Plasmodium falciparum

<400> SEQUENCE: 321

Lys Lys Leu Ile Lys Ala Leu Lys Lys Asn Ile Glu Ser Ile Gln Asn
 1               5                  10                  15

Lys Lys His

<210> SEQ ID NO 322
<211> LENGTH: 15
<212> TYPE: PRT
<213> ORGANISM: Plasmodium falciparum

<400> SEQUENCE: 322

```
Lys Ala Leu Lys Lys Asn Ile Glu Ser Ile Gln Asn Lys Lys His
 1               5                  10                  15

<210> SEQ ID NO 323
<211> LENGTH: 12
<212> TYPE: PRT
<213> ORGANISM: Plasmodium falciparum

<400> SEQUENCE: 323

Lys Lys Asn Ile Glu Ser Ile Gln Asn Lys Lys His
 1               5                  10

<210> SEQ ID NO 324
<211> LENGTH: 27
<212> TYPE: PRT
<213> ORGANISM: Plasmodium falciparum

<400> SEQUENCE: 324

Lys Glu Leu Met Asn Gln Lys Ala Thr Tyr Ser Phe Val Asn Thr Lys
 1               5                  10                  15

Lys Lys Ile Ile Ser Leu Lys Ser Gln Gly His
            20                  25

<210> SEQ ID NO 325
<211> LENGTH: 7
<212> TYPE: PRT
<213> ORGANISM: Plasmodium falciparum

<400> SEQUENCE: 325

Lys Ser Gln Gly His Lys Lys
 1               5

<210> SEQ ID NO 326
<211> LENGTH: 12
<212> TYPE: PRT
<213> ORGANISM: Plasmodium falciparum

<400> SEQUENCE: 326

Lys Lys Lys Ile Ile Ser Leu Lys Ser Gln Gly His
 1               5                  10

<210> SEQ ID NO 327
<211> LENGTH: 11
<212> TYPE: PRT
<213> ORGANISM: Plasmodium falciparum

<400> SEQUENCE: 327

Lys Lys Ile Ile Ser Leu Lys Ser Gln Gly His
 1               5                  10

<210> SEQ ID NO 328
<211> LENGTH: 12
<212> TYPE: PRT
<213> ORGANISM: Plasmodium falciparum

<400> SEQUENCE: 328

Lys Lys Asn Ile Glu Ser Ile Gln Asn Lys Lys His
 1               5                  10

<210> SEQ ID NO 329
<211> LENGTH: 11
<212> TYPE: PRT
<213> ORGANISM: Plasmodium falciparum
```

-continued

```
<400> SEQUENCE: 329

Lys Asn Ile Glu Ser Ile Gln Asn Lys Lys His
1               5                   10

<210> SEQ ID NO 330
<211> LENGTH: 29
<212> TYPE: PRT
<213> ORGANISM: Plasmodium falciparum

<400> SEQUENCE: 330

His Thr Tyr Val Lys Gly Lys Lys Ala Pro Ser Asp Pro Gln Cys Ala
1               5                   10                  15

Asp Ile Lys Glu Glu Cys Lys Glu Leu Leu Lys Glu Lys
            20                  25

<210> SEQ ID NO 331
<211> LENGTH: 27
<212> TYPE: PRT
<213> ORGANISM: Plasmodium falciparum

<400> SEQUENCE: 331

His Thr Tyr Val Lys Gly Lys Lys Ala Pro Ser Asp Pro Gln Cys Ala
1               5                   10                  15

Asp Ile Lys Glu Glu Cys Lys Glu Leu Leu Lys
            20                  25

<210> SEQ ID NO 332
<211> LENGTH: 29
<212> TYPE: PRT
<213> ORGANISM: Plasmodium falciparum

<400> SEQUENCE: 332

His Glu Asn Val Leu Ser Ala Ala Leu Glu Asn Thr Gln Ser Glu Glu
1               5                   10                  15

Glu Lys Lys Glu Val Ile Asp Val Ile Glu Glu Val Lys
            20                  25

<210> SEQ ID NO 333
<211> LENGTH: 48
<212> TYPE: PRT
<213> ORGANISM: Plasmodium falciparum

<400> SEQUENCE: 333

Lys Glu Asn Val Val Thr Thr Ile Leu Glu Lys Val Glu Glu Thr Thr
1               5                   10                  15

Ala Glu Ser Val Thr Thr Phe Ser Asn Ile Leu Glu Glu Ile Gln Glu
            20                  25                  30

Asn Thr Ile Thr Asn Asp Thr Ile Glu Glu Lys Leu Glu Glu Leu His
        35                  40                  45

<210> SEQ ID NO 334
<211> LENGTH: 14
<212> TYPE: PRT
<213> ORGANISM: Plasmodium falciparum

<400> SEQUENCE: 334

His Tyr Leu Gln Gln Met Lys Glu Lys Phe Ser Lys Glu Lys
1               5                   10

<210> SEQ ID NO 335
<211> LENGTH: 42
<212> TYPE: PRT
```

-continued

<213> ORGANISM: Plasmodium falciparum

<400> SEQUENCE: 335

His Tyr Leu Gln Gln Met Lys Glu Lys Phe Ser Lys Glu Lys Asn Asn
 1               5                   10                  15

Asn Val Ile Glu Val Thr Asn Lys Ala Glu Lys Lys Gly Asn Val Gln
            20                  25                  30

Val Thr Asn Lys Thr Glu Lys Thr Thr Lys
        35                  40

<210> SEQ ID NO 336
<211> LENGTH: 48
<212> TYPE: PRT
<213> ORGANISM: Plasmodium falciparum

<400> SEQUENCE: 336

His Tyr Leu Gln Gln Met Lys Glu Lys Phe Ser Lys Glu Lys Asn Asn
 1               5                   10                  15

Asn Val Ile Glu Val Thr Asn Lys Ala Glu Lys Lys Gly Asn Val Gln
            20                  25                  30

Val Thr Asn Lys Thr Glu Lys Thr Thr Lys Val Asp Lys Asn Asn Lys
        35                  40                  45

<210> SEQ ID NO 337
<211> LENGTH: 57
<212> TYPE: PRT
<213> ORGANISM: Plasmodium falciparum

<400> SEQUENCE: 337

His Tyr Leu Gln Gln Met Lys Glu Lys Phe Ser Lys Glu Lys Asn Asn
 1               5                   10                  15

Asn Val Ile Glu Val Thr Asn Lys Ala Glu Lys Lys Gly Asn Val Gln
            20                  25                  30

Val Thr Asn Lys Thr Glu Lys Thr Thr Lys Val Asp Lys Asn Asn Lys
        35                  40                  45

Val Pro Lys Lys Arg Arg Thr Gln Lys
        50                  55

<210> SEQ ID NO 338
<211> LENGTH: 59
<212> TYPE: PRT
<213> ORGANISM: Plasmodium falciparum

<400> SEQUENCE: 338

His Tyr Leu Gln Gln Met Lys Glu Lys Phe Ser Lys Glu Lys Asn Asn
 1               5                   10                  15

Asn Val Ile Glu Val Thr Asn Lys Ala Glu Lys Lys Gly Asn Val Gln
            20                  25                  30

Val Thr Asn Lys Thr Glu Lys Thr Thr Lys Val Asp Lys Asn Asn Lys
        35                  40                  45

Val Pro Lys Lys Arg Arg Thr Gln Lys Ser Lys
        50                  55

<210> SEQ ID NO 339
<211> LENGTH: 52
<212> TYPE: PRT
<213> ORGANISM: Plasmodium falciparum

<400> SEQUENCE: 339

His Val Asp Glu Val Met Lys Tyr Val Gln Lys Ile Asp Lys Glu Val

```
                1               5                  10                 15
Asp Lys Glu Val Ser Lys Ala Leu Glu Ser Lys Asn Asp Val Thr Asn
                    20                  25                  30

Val Leu Lys Gln Asn Gln Asp Phe Phe Ser Lys Val Lys Asn Phe Val
        35                  40                  45

Lys Lys Tyr Lys
    50

<210> SEQ ID NO 340
<211> LENGTH: 50
<212> TYPE: PRT
<213> ORGANISM: Plasmodium falciparum

<400> SEQUENCE: 340

His Val Asp Glu Val Met Lys Tyr Val Gln Lys Ile Asp Lys Glu Val
  1               5                  10                 15

Asp Lys Glu Val Ser Lys Ala Leu Glu Ser Lys Asn Asp Val Thr Asn
                    20                  25                  30

Val Leu Lys Gln Asn Gln Asp Phe Phe Ser Lys Val Lys Asn Phe Val
        35                  40                  45

Lys Lys
    50

<210> SEQ ID NO 341
<211> LENGTH: 43
<212> TYPE: PRT
<213> ORGANISM: Plasmodium falciparum

<400> SEQUENCE: 341

His Val Asp Glu Val Met Lys Tyr Val Gln Lys Ile Asp Lys Glu Val
  1               5                  10                 15

Asp Lys Glu Val Ser Lys Ala Leu Glu Ser Lys Asn Asp Val Thr Asn
                    20                  25                  30

Val Leu Lys Gln Asn Gln Asp Phe Phe Ser Lys
        35                  40

<210> SEQ ID NO 342
<211> LENGTH: 35
<212> TYPE: PRT
<213> ORGANISM: Plasmodium falciparum

<400> SEQUENCE: 342

His Val Asp Glu Val Met Lys Tyr Val Gln Lys Ile Asp Lys Glu Val
  1               5                  10                 15

Asp Lys Glu Val Ser Lys Ala Leu Glu Ser Lys Asn Asp Val Thr Asn
                    20                  25                  30

Val Leu Lys
        35

<210> SEQ ID NO 343
<211> LENGTH: 27
<212> TYPE: PRT
<213> ORGANISM: Plasmodium falciparum

<400> SEQUENCE: 343

His Val Asp Glu Val Met Lys Tyr Val Gln Lys Ile Asp Lys Glu Val
  1               5                  10                 15

Asp Lys Glu Val Ser Lys Ala Leu Glu Ser Lys
                    20                  25
```

<210> SEQ ID NO 344
<211> LENGTH: 22
<212> TYPE: PRT
<213> ORGANISM: Plasmodium falciparum

<400> SEQUENCE: 344

His Val Asp Glu Val Met Lys Tyr Val Gln Lys Ile Asp Lys Glu Val
 1               5                  10                  15

Asp Lys Glu Val Ser Lys
            20

<210> SEQ ID NO 345
<211> LENGTH: 18
<212> TYPE: PRT
<213> ORGANISM: Plasmodium falciparum

<400> SEQUENCE: 345

His Val Asp Glu Val Met Lys Tyr Val Gln Lys Ile Asp Lys Glu Val
 1               5                  10                  15

Asp Lys

<210> SEQ ID NO 346
<211> LENGTH: 14
<212> TYPE: PRT
<213> ORGANISM: Plasmodium falciparum

<400> SEQUENCE: 346

His Val Asp Glu Val Met Lys Tyr Val Gln Lys Ile Asp Lys
 1               5                  10

<210> SEQ ID NO 347
<211> LENGTH: 39
<212> TYPE: PRT
<213> ORGANISM: Plasmodium falciparum

<400> SEQUENCE: 347

Lys Asp Glu Val Ile Asp Leu Ile Val Gln Lys Glu Lys Arg Ile Glu
 1               5                  10                  15

Lys Val Lys Ala Lys Lys Lys Leu Glu Lys Lys Val Glu Glu Gly
            20                  25                  30

Val Ser Gly Leu Lys Lys His
        35

<210> SEQ ID NO 348
<211> LENGTH: 23
<212> TYPE: PRT
<213> ORGANISM: Plasmodium falciparum

<400> SEQUENCE: 348

Lys Val Lys Ala Lys Lys Lys Leu Glu Lys Lys Val Glu Glu Gly
 1               5                  10                  15

Val Ser Gly Leu Lys Lys His
            20

<210> SEQ ID NO 349
<211> LENGTH: 21
<212> TYPE: PRT
<213> ORGANISM: Plasmodium falciparum

<400> SEQUENCE: 349

Lys Ala Lys Lys Lys Lys Leu Glu Lys Lys Val Glu Glu Gly Val Ser
 1               5                  10                  15

Gly Leu Lys Lys His
            20

<210> SEQ ID NO 350
<211> LENGTH: 19
<212> TYPE: PRT
<213> ORGANISM: Plasmodium falciparum

<400> SEQUENCE: 350

Lys Lys Lys Lys Leu Glu Lys Lys Val Glu Glu Gly Val Ser Gly Leu
 1               5                  10                  15

Lys Lys His

<210> SEQ ID NO 351
<211> LENGTH: 18
<212> TYPE: PRT
<213> ORGANISM: Plasmodium falciparum

<400> SEQUENCE: 351

Lys Lys Lys Leu Glu Lys Lys Val Glu Glu Gly Val Ser Gly Leu Lys
 1               5                  10                  15

Lys His

<210> SEQ ID NO 352
<211> LENGTH: 17
<212> TYPE: PRT
<213> ORGANISM: Plasmodium falciparum

<400> SEQUENCE: 352

Lys Lys Leu Glu Lys Lys Val Glu Glu Gly Val Ser Gly Leu Lys Lys
 1               5                  10                  15

His

<210> SEQ ID NO 353
<211> LENGTH: 16
<212> TYPE: PRT
<213> ORGANISM: Plasmodium falciparum

<400> SEQUENCE: 353

Lys Leu Glu Lys Lys Val Glu Glu Gly Val Ser Gly Leu Lys Lys His
 1               5                  10                  15

<210> SEQ ID NO 354
<211> LENGTH: 13
<212> TYPE: PRT
<213> ORGANISM: Plasmodium falciparum

<400> SEQUENCE: 354

Lys Lys Val Glu Glu Gly Val Ser Gly Leu Lys Lys His
 1               5                  10

<210> SEQ ID NO 355
<211> LENGTH: 12
<212> TYPE: PRT
<213> ORGANISM: Plasmodium falciparum

<400> SEQUENCE: 355

Lys Val Glu Glu Gly Val Ser Gly Leu Lys Lys His
 1               5                  10

<210> SEQ ID NO 356
<211> LENGTH: 59

```
<212> TYPE: PRT
<213> ORGANISM: Plasmodium falciparum

<400> SEQUENCE: 356

His Val Glu Gln Asn Val Tyr Val Asp Val Asp Val Pro Ala Met Lys
1               5                   10                  15

Asp Gln Phe Leu Gly Ile Leu Asn Glu Ala Gly Gly Leu Lys Glu Met
            20                  25                  30

Phe Phe Asn Leu Glu Asp Val Phe Lys Ser Glu Ser Asp Val Ile Thr
        35                  40                  45

Val Glu Glu Ile Lys Asp Glu Pro Val Gln Lys
    50                  55

<210> SEQ ID NO 357
<211> LENGTH: 53
<212> TYPE: PRT
<213> ORGANISM: Plasmodium falciparum

<400> SEQUENCE: 357

His Ile Lys Gly Leu Glu Glu Asp Asp Leu Glu Glu Val Asp Asp Leu
1               5                   10                  15

Lys Gly Ser Ile Leu Asp Met Leu Lys Gly Asp Met Glu Leu Gly Asp
            20                  25                  30

Met Asp Lys Glu Ser Leu Glu Asp Val Thr Thr Lys Leu Gly Glu Arg
        35                  40                  45

Val Glu Ser Leu Lys
    50

<210> SEQ ID NO 358
<211> LENGTH: 44
<212> TYPE: PRT
<213> ORGANISM: Plasmodium falciparum

<400> SEQUENCE: 358

His Ile Lys Gly Leu Glu Glu Asp Asp Leu Glu Glu Val Asp Asp Leu
1               5                   10                  15

Lys Gly Ser Ile Leu Asp Met Leu Lys Gly Asp Met Glu Leu Gly Asp
            20                  25                  30

Met Asp Lys Glu Ser Leu Glu Asp Val Thr Thr Lys
        35                  40

<210> SEQ ID NO 359
<211> LENGTH: 35
<212> TYPE: PRT
<213> ORGANISM: Plasmodium falciparum

<400> SEQUENCE: 359

His Ile Lys Gly Leu Glu Glu Asp Asp Leu Glu Glu Val Asp Asp Leu
1               5                   10                  15

Lys Gly Ser Ile Leu Asp Met Leu Lys Gly Asp Met Glu Leu Gly Asp
            20                  25                  30

Met Asp Lys
        35

<210> SEQ ID NO 360
<211> LENGTH: 25
<212> TYPE: PRT
<213> ORGANISM: Plasmodium falciparum

<400> SEQUENCE: 360
```

His Ile Lys Gly Leu Glu Glu Asp Asp Leu Glu Glu Val Asp Asp Leu
1               5                   10                  15

Lys Gly Ser Ile Leu Asp Met Leu Lys
            20                  25

<210> SEQ ID NO 361
<211> LENGTH: 31
<212> TYPE: PRT
<213> ORGANISM: Plasmodium falciparum

<400> SEQUENCE: 361

His Ile Ile Ser Gly Asp Ala Asp Val Leu Ser Ser Ala Leu Gly Met
1               5                   10                  15

Asp Glu Glu Gln Met Lys Thr Arg Lys Lys Ala Gln Arg Pro Lys
            20                  25                  30

<210> SEQ ID NO 362
<211> LENGTH: 23
<212> TYPE: PRT
<213> ORGANISM: Plasmodium falciparum

<400> SEQUENCE: 362

His Asp Ile Thr Thr Thr Leu Asp Glu Val Val Glu Leu Lys Asp Val
1               5                   10                  15

Glu Glu Asp Lys Ile Glu Lys
            20

<210> SEQ ID NO 363
<211> LENGTH: 10
<212> TYPE: PRT
<213> ORGANISM: Plasmodium falciparum

<400> SEQUENCE: 363

Lys Lys Leu Glu Glu Val His Glu Leu Lys
1               5                   10

<210> SEQ ID NO 364
<211> LENGTH: 9
<212> TYPE: PRT
<213> ORGANISM: Plasmodium falciparum

<400> SEQUENCE: 364

Lys Leu Glu Glu Val His Glu Leu Lys
1               5

<210> SEQ ID NO 365
<211> LENGTH: 19
<212> TYPE: PRT
<213> ORGANISM: Plasmodium falciparum

<400> SEQUENCE: 365

Lys Thr Ile Glu Thr Asp Ile Leu Glu Glu Lys Lys Lys Glu Ile Glu
1               5                   10                  15

Lys Asp His

<210> SEQ ID NO 366
<211> LENGTH: 11
<212> TYPE: PRT
<213> ORGANISM: Plasmodium falciparum

<400> SEQUENCE: 366

Lys Lys Glu Ile Glu Lys Asp His Phe Glu Lys
1               5                   10

<210> SEQ ID NO 367
<211> LENGTH: 6
<212> TYPE: PRT
<213> ORGANISM: Plasmodium falciparum

<400> SEQUENCE: 367

Lys Asp His Phe Glu Lys
 1               5

<210> SEQ ID NO 368
<211> LENGTH: 11
<212> TYPE: PRT
<213> ORGANISM: Plasmodium falciparum

<400> SEQUENCE: 368

Lys Phe Glu Glu Glu Ala Glu Glu Ile Lys His
 1               5                  10

<210> SEQ ID NO 369
<211> LENGTH: 47
<212> TYPE: PRT
<213> ORGANISM: Plasmodium falciparum

<400> SEQUENCE: 369

Lys Asp Gly Asp Thr Lys Cys Thr Leu Glu Cys Ala Gln Gly Lys Lys
 1               5                  10                  15

Cys Ile Lys His Lys Ser Asp His Asn His Lys Ser Asp His Asn His
            20                  25                  30

Lys Ser Asp Pro Asn His Lys Lys Asn Asn Asn Asn Lys
        35                  40                  45

<210> SEQ ID NO 370
<211> LENGTH: 40
<212> TYPE: PRT
<213> ORGANISM: Plasmodium falciparum

<400> SEQUENCE: 370

Lys Asp Gly Asp Thr Lys Cys Thr Leu Glu Cys Ala Gln Gly Lys Lys
 1               5                  10                  15

Cys Ile Lys His Lys Ser Asp His Asn His Lys Ser Asp His Asn His
            20                  25                  30

Lys Ser Asp Pro Asn His Lys Lys
        35                  40

<210> SEQ ID NO 371
<211> LENGTH: 39
<212> TYPE: PRT
<213> ORGANISM: Plasmodium falciparum

<400> SEQUENCE: 371

Lys Asp Gly Asp Thr Lys Cys Thr Leu Glu Cys Ala Gln Gly Lys Lys
 1               5                  10                  15

Cys Ile Lys His Lys Ser Asp His Asn His Lys Ser Asp His Asn His
            20                  25                  30

Lys Ser Asp Pro Asn His Lys
        35

<210> SEQ ID NO 372
<211> LENGTH: 33
<212> TYPE: PRT
<213> ORGANISM: Plasmodium falciparum

<400> SEQUENCE: 372

Lys Asp Gly Asp Thr Lys Cys Thr Leu Glu Cys Ala Gln Gly Lys Lys
1               5                   10                  15

Cys Ile Lys His Lys Ser Asp His Asn His Lys Ser Asp His Asn His
            20                  25                  30

Lys

<210> SEQ ID NO 373
<211> LENGTH: 27
<212> TYPE: PRT
<213> ORGANISM: Plasmodium falciparum

<400> SEQUENCE: 373

Lys Asp Gly Asp Thr Lys Cys Thr Leu Glu Cys Ala Gln Gly Lys Lys
1               5                   10                  15

Cys Ile Lys His Lys Ser Asp His Asn His Lys
            20                  25

<210> SEQ ID NO 374
<211> LENGTH: 21
<212> TYPE: PRT
<213> ORGANISM: Plasmodium falciparum

<400> SEQUENCE: 374

Lys Asp Gly Asp Thr Lys Cys Thr Leu Glu Cys Ala Gln Gly Lys Lys
1               5                   10                  15

Cys Ile Lys His Lys
            20

<210> SEQ ID NO 375
<211> LENGTH: 16
<212> TYPE: PRT
<213> ORGANISM: Plasmodium falciparum

<400> SEQUENCE: 375

Lys Asp Gly Asp Thr Lys Cys Thr Leu Glu Cys Ala Gln Gly Lys Lys
1               5                   10                  15

<210> SEQ ID NO 376
<211> LENGTH: 15
<212> TYPE: PRT
<213> ORGANISM: Plasmodium falciparum

<400> SEQUENCE: 376

Lys Asp Gly Asp Thr Lys Cys Thr Leu Glu Cys Ala Gln Gly Lys
1               5                   10                  15

<210> SEQ ID NO 377
<211> LENGTH: 23
<212> TYPE: PRT
<213> ORGANISM: Plasmodium falciparum

<400> SEQUENCE: 377

Lys Cys Ile Gln Ala Glu Cys Asn Tyr Lys Glu Cys Gly Glu Gln Lys
1               5                   10                  15

Cys Val Trp Asp Gly Ile His
            20

<210> SEQ ID NO 378
<211> LENGTH: 14
<212> TYPE: PRT

<213> ORGANISM: Plasmodium falciparum

<400> SEQUENCE: 378

Lys Glu Cys Gly Glu Gln Lys Cys Val Trp Asp Gly Ile His
1               5                   10

<210> SEQ ID NO 379
<211> LENGTH: 32
<212> TYPE: PRT
<213> ORGANISM: Plasmodium falciparum

<400> SEQUENCE: 379

His Ile Glu Cys Lys Cys Asn Asn Asp Tyr Val Leu Thr Asn Arg Tyr
1               5                   10                  15

Glu Cys Glu Pro Lys Asn Lys Cys Thr Ser Leu Glu Asp Thr Asn Lys
                20                  25                  30

<210> SEQ ID NO 380
<211> LENGTH: 39
<212> TYPE: PRT
<213> ORGANISM: Plasmodium falciparum

<400> SEQUENCE: 380

Lys Ser Asp His Asn His Lys Ser Asp His Asn His Lys Ser Asp His
1               5                   10                  15

Asn His Lys Ser Asp His Asn His Lys Ser Asp Pro Asn His Lys Lys
                20                  25                  30

Lys Asn Asn Asn Asn Asn Lys
            35

<210> SEQ ID NO 381
<211> LENGTH: 33
<212> TYPE: PRT
<213> ORGANISM: Plasmodium falciparum

<400> SEQUENCE: 381

Lys Ser Asp His Asn His Lys Ser Asp His Asn His Lys Ser Asp His
1               5                   10                  15

Asn His Lys Ser Asp Pro Asn His Lys Lys Lys Asn Asn Asn Asn Asn
                20                  25                  30

Lys

<210> SEQ ID NO 382
<211> LENGTH: 27
<212> TYPE: PRT
<213> ORGANISM: Plasmodium falciparum

<400> SEQUENCE: 382

Lys Ser Asp His Asn His Lys Ser Asp His Asn His Lys Ser Asp Pro
1               5                   10                  15

Asn His Lys Lys Lys Asn Asn Asn Asn Asn Lys
                20                  25

<210> SEQ ID NO 383
<211> LENGTH: 21
<212> TYPE: PRT
<213> ORGANISM: Plasmodium falciparum

<400> SEQUENCE: 383

Lys Ser Asp His Asn His Lys Ser Asp Pro Asn His Lys Lys Lys Asn
1               5                   10                  15

Asn Asn Asn Asn Lys
            20

<210> SEQ ID NO 384
<211> LENGTH: 18
<212> TYPE: PRT
<213> ORGANISM: Plasmodium falciparum

<400> SEQUENCE: 384

Lys Lys Lys Asn Asn Asn Asn Lys Asp Asn Lys Ser Asp Pro Asn
1               5                   10                  15

His Lys

<210> SEQ ID NO 385
<211> LENGTH: 17
<212> TYPE: PRT
<213> ORGANISM: Plasmodium falciparum

<400> SEQUENCE: 385

Lys Lys Asn Asn Asn Asn Lys Asp Asn Lys Ser Asp Pro Asn His
1               5                   10                  15

Lys

<210> SEQ ID NO 386
<211> LENGTH: 16
<212> TYPE: PRT
<213> ORGANISM: Plasmodium falciparum

<400> SEQUENCE: 386

Lys Asn Asn Asn Asn Lys Asp Asn Lys Ser Asp Pro Asn His Lys
1               5                   10                  15

<210> SEQ ID NO 387
<211> LENGTH: 10
<212> TYPE: PRT
<213> ORGANISM: Plasmodium falciparum

<400> SEQUENCE: 387

Lys Asp Asn Lys Ser Asp Pro Asn His Lys
1               5                   10

<210> SEQ ID NO 388
<211> LENGTH: 7
<212> TYPE: PRT
<213> ORGANISM: Plasmodium falciparum

<400> SEQUENCE: 388

Lys Ser Asp Pro Asn His Lys
1               5

<210> SEQ ID NO 389
<211> LENGTH: 35
<212> TYPE: PRT
<213> ORGANISM: Plasmodium falciparum

<400> SEQUENCE: 389

His Ser Leu Tyr Ala Leu Gln Gln Asn Glu Glu Tyr Gln Lys Val Lys
1               5                   10                  15

Asn Glu Lys Asp Gln Asn Glu Ile Lys Lys Ile Lys Gln Leu Ile Glu
            20                  25                  30

Lys Asn Lys
        35

```
<210> SEQ ID NO 390
<211> LENGTH: 28
<212> TYPE: PRT
<213> ORGANISM: Plasmodium falciparum

<400> SEQUENCE: 390

His Ser Leu Tyr Ala Leu Gln Gln Asn Glu Glu Tyr Gln Lys Val Lys
 1               5                  10                  15

Asn Glu Lys Asp Gln Asn Glu Ile Lys Lys Ile Lys
            20                  25

<210> SEQ ID NO 391
<211> LENGTH: 26
<212> TYPE: PRT
<213> ORGANISM: Plasmodium falciparum

<400> SEQUENCE: 391

His Ser Leu Tyr Ala Leu Gln Gln Asn Glu Glu Tyr Gln Lys Val Lys
 1               5                  10                  15

Asn Glu Lys Asp Gln Asn Glu Ile Lys Lys
            20                  25

<210> SEQ ID NO 392
<211> LENGTH: 25
<212> TYPE: PRT
<213> ORGANISM: Plasmodium falciparum

<400> SEQUENCE: 392

His Ser Leu Tyr Ala Leu Gln Gln Asn Glu Glu Tyr Gln Lys Val Lys
 1               5                  10                  15

Asn Glu Lys Asp Gln Asn Glu Ile Lys
            20                  25

<210> SEQ ID NO 393
<211> LENGTH: 11
<212> TYPE: PRT
<213> ORGANISM: Plasmodium falciparum

<400> SEQUENCE: 393

His Lys Leu Glu Asn Leu Glu Glu Met Asp Lys
 1               5                  10

<210> SEQ ID NO 394
<211> LENGTH: 11
<212> TYPE: PRT
<213> ORGANISM: Plasmodium falciparum

<400> SEQUENCE: 394

Lys His Phe Asp Asp Asn Thr Asn Glu Gln Lys
 1               5                  10

<210> SEQ ID NO 395
<211> LENGTH: 8
<212> TYPE: PRT
<213> ORGANISM: Plasmodium falciparum

<400> SEQUENCE: 395

Lys Lys Glu Asp Asp Glu Lys His
 1               5

<210> SEQ ID NO 396
<211> LENGTH: 13
<212> TYPE: PRT
```

-continued

<213> ORGANISM: Plasmodium falciparum

<400> SEQUENCE: 396

Lys Glu Glu Asn Asn Lys Lys Glu Asp Asp Glu Lys His
 1               5                  10

<210> SEQ ID NO 397
<211> LENGTH: 21
<212> TYPE: PRT
<213> ORGANISM: Plasmodium falciparum

<400> SEQUENCE: 397

Lys Thr Ser Ser Gly Ile Leu Asn Lys Glu Glu Asn Asn Lys Lys Glu
 1               5                  10                  15

Asp Asp Glu Lys His
            20

<210> SEQ ID NO 398
<211> LENGTH: 7
<212> TYPE: PRT
<213> ORGANISM: Plasmodium falciparum

<400> SEQUENCE: 398

Lys Asn Ile His Ile Lys Lys
 1               5

<210> SEQ ID NO 399
<211> LENGTH: 13
<212> TYPE: PRT
<213> ORGANISM: Plasmodium falciparum

<400> SEQUENCE: 399

His Ile Lys Lys Lys Glu Gly Ile Asp Ile Gly Tyr Lys
 1               5                  10

<210> SEQ ID NO 400
<211> LENGTH: 21
<212> TYPE: PRT
<213> ORGANISM: Plasmodium falciparum

<400> SEQUENCE: 400

Lys Lys Met Trp Thr Cys Lys Leu Trp Asp Asn Lys Gly Asn Glu Ile
 1               5                  10                  15

Thr Lys Asn Ile His
            20

<210> SEQ ID NO 401
<211> LENGTH: 30
<212> TYPE: PRT
<213> ORGANISM: Plasmodium falciparum

<400> SEQUENCE: 401

Lys Lys Gly Ile Gln Trp Asn Leu Leu Lys Lys Met Trp Thr Cys Lys
 1               5                  10                  15

Leu Trp Asp Asn Lys Gly Asn Glu Ile Thr Lys Asn Ile His
            20                  25                  30

<210> SEQ ID NO 402
<211> LENGTH: 50
<212> TYPE: PRT
<213> ORGANISM: Plasmodium falciparum

<400> SEQUENCE: 402

-continued

```
Lys Glu Lys Lys Asp Ser Asn Glu Asn Arg Lys Lys Lys Gln Lys Glu
 1               5                  10                  15

Asp Lys Lys Asn Pro Asn Lys Leu Lys Lys Ile Glu Tyr Thr Asn Lys
            20                  25                  30

Ile Thr His Phe Phe Lys Ala Lys Asn Asn Lys Gln Gln Asn Asn Val
        35                  40                  45

Thr His
    50

<210> SEQ ID NO 403
<211> LENGTH: 48
<212> TYPE: PRT
<213> ORGANISM: Plasmodium falciparum

<400> SEQUENCE: 403

Lys Lys Asp Ser Asn Glu Asn Arg Lys Lys Lys Gln Lys Glu Asp Lys
 1               5                  10                  15

Lys Asn Pro Asn Lys Leu Lys Lys Ile Glu Tyr Thr Asn Lys Ile Thr
            20                  25                  30

His Phe Phe Lys Ala Lys Asn Asn Lys Gln Gln Asn Asn Val Thr His
        35                  40                  45

<210> SEQ ID NO 404
<211> LENGTH: 47
<212> TYPE: PRT
<213> ORGANISM: Plasmodium falciparum

<400> SEQUENCE: 404

Lys Asp Ser Asn Glu Asn Arg Lys Lys Lys Gln Lys Glu Asp Lys Lys
 1               5                  10                  15

Asn Pro Asn Lys Leu Lys Lys Ile Glu Tyr Thr Asn Lys Ile Thr His
            20                  25                  30

Phe Phe Lys Ala Lys Asn Asn Lys Gln Gln Asn Asn Val Thr His
        35                  40                  45

<210> SEQ ID NO 405
<211> LENGTH: 39
<212> TYPE: PRT
<213> ORGANISM: Plasmodium falciparum

<400> SEQUENCE: 405

Lys Lys Gln Lys Glu Asp Lys Lys Asn Pro Asn Lys Leu Lys Lys Ile
 1               5                  10                  15

Glu Tyr Thr Asn Lys Ile Thr His Phe Phe Lys Ala Lys Asn Asn Lys
            20                  25                  30

Gln Gln Asn Asn Val Thr His
        35

<210> SEQ ID NO 406
<211> LENGTH: 38
<212> TYPE: PRT
<213> ORGANISM: Plasmodium falciparum

<400> SEQUENCE: 406

Lys Gln Lys Glu Asp Lys Lys Asn Pro Asn Lys Leu Lys Lys Ile Glu
 1               5                  10                  15

Tyr Thr Asn Lys Ile Thr His Phe Phe Lys Ala Lys Asn Asn Lys Gln
            20                  25                  30

Gln Asn Asn Val Thr His
        35
```

<210> SEQ ID NO 407
<211> LENGTH: 36
<212> TYPE: PRT
<213> ORGANISM: Plasmodium falciparum

<400> SEQUENCE: 407

Lys Glu Asp Lys Lys Asn Pro Asn Lys Leu Lys Lys Ile Glu Tyr Thr
1               5                   10                  15

Asn Lys Ile Thr His Phe Phe Lys Ala Lys Asn Asn Lys Gln Gln Asn
            20                  25                  30

Asn Val Thr His
        35

<210> SEQ ID NO 408
<211> LENGTH: 32
<212> TYPE: PRT
<213> ORGANISM: Plasmodium falciparum

<400> SEQUENCE: 408

Lys Asn Pro Asn Lys Leu Lys Lys Ile Glu Tyr Thr Asn Lys Ile Thr
1               5                   10                  15

His Phe Phe Lys Ala Lys Asn Asn Lys Gln Gln Asn Asn Val Thr His
            20                  25                  30

<210> SEQ ID NO 409
<211> LENGTH: 26
<212> TYPE: PRT
<213> ORGANISM: Plasmodium falciparum

<400> SEQUENCE: 409

Lys Lys Ile Glu Tyr Thr Asn Lys Ile Thr His Phe Phe Lys Ala Lys
1               5                   10                  15

Asn Asn Lys Gln Gln Asn Asn Val Thr His
            20                  25

<210> SEQ ID NO 410
<211> LENGTH: 25
<212> TYPE: PRT
<213> ORGANISM: Plasmodium falciparum

<400> SEQUENCE: 410

Lys Ile Glu Tyr Thr Asn Lys Ile Thr His Phe Phe Lys Ala Lys Asn
1               5                   10                  15

Asn Lys Gln Gln Asn Asn Val Thr His
            20                  25

<210> SEQ ID NO 411
<211> LENGTH: 19
<212> TYPE: PRT
<213> ORGANISM: Plasmodium falciparum

<400> SEQUENCE: 411

Lys Ile Thr His Phe Phe Lys Ala Lys Asn Asn Lys Gln Gln Asn Asn
1               5                   10                  15

Val Thr His

<210> SEQ ID NO 412
<211> LENGTH: 48
<212> TYPE: PRT
<213> ORGANISM: Plasmodium falciparum

<400> SEQUENCE: 412

His Lys Asn Asn Glu Asp Ile Lys Asn Asp Asn Ser Lys Asp Ile Lys
1               5                   10                  15

Asn Asp Asn Ser Lys Asp Ile Lys Asn Asp Asn Ser Lys Asp Ile Lys
            20                  25                  30

Asn Asp Asn Asn Glu Asp Ile Lys Asn Asp Asn Ser Lys Asp Ile Lys
        35                  40                  45

<210> SEQ ID NO 413
<211> LENGTH: 45
<212> TYPE: PRT
<213> ORGANISM: Plasmodium falciparum

<400> SEQUENCE: 413

His Lys Asn Asn Glu Asp Ile Lys Asn Asp Asn Ser Lys Asp Ile Lys
1               5                   10                  15

Asn Asp Asn Ser Lys Asp Ile Lys Asn Asp Asn Ser Lys Asp Ile Lys
            20                  25                  30

Asn Asp Asn Asn Glu Asp Ile Lys Asn Asp Asn Ser Lys
        35                  40                  45

<210> SEQ ID NO 414
<211> LENGTH: 40
<212> TYPE: PRT
<213> ORGANISM: Plasmodium falciparum

<400> SEQUENCE: 414

His Lys Asn Asn Glu Asp Ile Lys Asn Asp Asn Ser Lys Asp Ile Lys
1               5                   10                  15

Asn Asp Asn Ser Lys Asp Ile Lys Asn Asp Asn Ser Lys Asp Ile Lys
            20                  25                  30

Asn Asp Asn Asn Glu Asp Ile Lys
        35                  40

<210> SEQ ID NO 415
<211> LENGTH: 32
<212> TYPE: PRT
<213> ORGANISM: Plasmodium falciparum

<400> SEQUENCE: 415

His Lys Asn Asn Glu Asp Ile Lys Asn Asp Asn Ser Lys Asp Ile Lys
1               5                   10                  15

Asn Asp Asn Ser Lys Asp Ile Lys Asn Asp Asn Ser Lys Asp Ile Lys
            20                  25                  30

<210> SEQ ID NO 416
<211> LENGTH: 29
<212> TYPE: PRT
<213> ORGANISM: Plasmodium falciparum

<400> SEQUENCE: 416

His Lys Asn Asn Glu Asp Ile Lys Asn Asp Asn Ser Lys Asp Ile Lys
1               5                   10                  15

Asn Asp Asn Ser Lys Asp Ile Lys Asn Asp Asn Ser Lys
            20                  25

<210> SEQ ID NO 417
<211> LENGTH: 24
<212> TYPE: PRT
<213> ORGANISM: Plasmodium falciparum -continued

<400> SEQUENCE: 417

His Lys Asn Asn Glu Asp Ile Lys Asn Asp Asn Ser Lys Asp Ile Lys
1               5                   10                  15

Asn Asp Asn Ser Lys Asp Ile Lys
            20

<210> SEQ ID NO 418
<211> LENGTH: 21
<212> TYPE: PRT
<213> ORGANISM: Plasmodium falciparum

<400> SEQUENCE: 418

His Lys Asn Asn Glu Asp Ile Lys Asn Asp Asn Ser Lys Asp Ile Lys
1               5                   10                  15

Asn Asp Asn Ser Lys
            20

<210> SEQ ID NO 419
<211> LENGTH: 16
<212> TYPE: PRT
<213> ORGANISM: Plasmodium falciparum

<400> SEQUENCE: 419

His Lys Asn Asn Glu Asp Ile Lys Asn Asp Asn Ser Lys Asp Ile Lys
1               5                   10                  15

<210> SEQ ID NO 420
<211> LENGTH: 8
<212> TYPE: PRT
<213> ORGANISM: Plasmodium falciparum

<400> SEQUENCE: 420

His Lys Asn Asn Glu Asp Ile Lys
1               5

<210> SEQ ID NO 421
<211> LENGTH: 31
<212> TYPE: PRT
<213> ORGANISM: Plasmodium falciparum

<400> SEQUENCE: 421

Lys Lys Tyr Asp Asp Leu Gln Asn Lys Tyr Asn Ile Leu Asn Lys Leu
1               5                   10                  15

Lys Asn Ser Leu Glu Glu Lys Asn Glu Glu Leu Lys Lys Tyr His
            20                  25                  30

<210> SEQ ID NO 422
<211> LENGTH: 30
<212> TYPE: PRT
<213> ORGANISM: Plasmodium falciparum

<400> SEQUENCE: 422

Lys Tyr Asp Asp Leu Gln Asn Lys Tyr Asn Ile Leu Asn Lys Leu Lys
1               5                   10                  15

Asn Ser Leu Glu Glu Lys Asn Glu Glu Leu Lys Lys Tyr His
            20                  25                  30

<210> SEQ ID NO 423
<211> LENGTH: 23
<212> TYPE: PRT
<213> ORGANISM: Plasmodium falciparum

<400> SEQUENCE: 423

Lys Tyr Asn Ile Leu Asn Lys Leu Lys Asn Ser Leu Glu Glu Lys Asn
1               5                   10                  15

Glu Glu Leu Lys Lys Tyr His
            20

<210> SEQ ID NO 424
<211> LENGTH: 17
<212> TYPE: PRT
<213> ORGANISM: Plasmodium falciparum

<400> SEQUENCE: 424

Lys Leu Lys Asn Ser Leu Glu Glu Lys Asn Glu Glu Leu Lys Lys Tyr
1               5                   10                  15

His

<210> SEQ ID NO 425
<211> LENGTH: 15
<212> TYPE: PRT
<213> ORGANISM: Plasmodium falciparum

<400> SEQUENCE: 425

Lys Asn Ser Leu Glu Glu Lys Asn Glu Glu Leu Lys Lys Tyr His
1               5                   10                  15

<210> SEQ ID NO 426
<211> LENGTH: 9
<212> TYPE: PRT
<213> ORGANISM: Plasmodium falciparum

<400> SEQUENCE: 426

Lys Asn Glu Glu Leu Lys Lys Tyr His
1               5

<210> SEQ ID NO 427
<211> LENGTH: 35
<212> TYPE: PRT
<213> ORGANISM: Plasmodium falciparum

<400> SEQUENCE: 427

His Met Gly Asn Asn Gln Asp Ile Asn Glu Asn Val Tyr Asn Ile Lys
1               5                   10                  15

Pro Gln Glu Phe Lys Glu Glu Glu Glu Asp Ile Ser Met Val Asn
            20                  25                  30

Thr Lys Lys
        35

<210> SEQ ID NO 428
<211> LENGTH: 17
<212> TYPE: PRT
<213> ORGANISM: Plasmodium falciparum

<400> SEQUENCE: 428

Lys Asn Ser Asn Glu Leu Lys Arg Ile Asn Asp Asn Phe Phe Lys Leu
1               5                   10                  15

His

<210> SEQ ID NO 429
<211> LENGTH: 55
<212> TYPE: PRT
<213> ORGANISM: Plasmodium falciparum

<400> SEQUENCE: 429

```
Lys Pro Cys Leu Tyr Lys Lys Cys Lys Ile Ser Gln Cys Leu Tyr Lys
 1               5                  10                  15

Lys Cys Lys Ile Ser Gln Val Trp Trp Cys Met Pro Val Lys Asp Thr
                20                  25                  30

Phe Asn Thr Tyr Glu Arg Asn Val Leu Asn Ser Lys Ile Glu Asn
            35                  40                  45

Asn Ile Glu Lys Ile Pro His
        50                  55

<210> SEQ ID NO 430
<211> LENGTH: 40
<212> TYPE: PRT
<213> ORGANISM: Plasmodium falciparum

<400> SEQUENCE: 430

His Ile Asn Asn Glu Tyr Thr Asn Lys Asn Pro Lys Asn Cys Leu Leu
 1               5                  10                  15

Tyr Lys Asn Glu Glu Arg Asn Tyr Asn Asp Asn Asn Ile Lys Asp Tyr
                20                  25                  30

Ile Asn Ser Met Asn Phe Lys Lys
            35                  40

<210> SEQ ID NO 431
<211> LENGTH: 39
<212> TYPE: PRT
<213> ORGANISM: Plasmodium falciparum

<400> SEQUENCE: 431

His Ile Asn Asn Glu Tyr Thr Asn Lys Asn Pro Lys Asn Cys Leu Leu
 1               5                  10                  15

Tyr Lys Asn Glu Glu Arg Asn Tyr Asn Asp Asn Asn Ile Lys Asp Tyr
                20                  25                  30

Ile Asn Ser Met Asn Phe Lys
            35

<210> SEQ ID NO 432
<211> LENGTH: 18
<212> TYPE: PRT
<213> ORGANISM: Plasmodium falciparum

<400> SEQUENCE: 432

His Ile Asn Asn Glu Tyr Thr Asn Lys Asn Pro Lys Asn Cys Leu Leu
 1               5                  10                  15

Tyr Lys

<210> SEQ ID NO 433
<211> LENGTH: 23
<212> TYPE: PRT
<213> ORGANISM: Plasmodium falciparum

<400> SEQUENCE: 433

Lys Asn Lys Thr Asn Gln Ser Lys Gly Val Lys Gly Glu Tyr Glu Lys
 1               5                  10                  15

Lys Lys Glu Thr Asn Gly His
                20

<210> SEQ ID NO 434
<211> LENGTH: 21
<212> TYPE: PRT
<213> ORGANISM: Plasmodium falciparum
```

<400> SEQUENCE: 434

Lys Thr Asn Gln Ser Lys Gly Val Lys Gly Glu Tyr Glu Lys Lys
1               5                   10                  15

Glu Thr Asn Gly His
            20

<210> SEQ ID NO 435
<211> LENGTH: 16
<212> TYPE: PRT
<213> ORGANISM: Plasmodium falciparum

<400> SEQUENCE: 435

Lys Gly Val Lys Gly Glu Tyr Glu Lys Lys Glu Thr Asn Gly His
1               5                   10                  15

<210> SEQ ID NO 436
<211> LENGTH: 13
<212> TYPE: PRT
<213> ORGANISM: Plasmodium falciparum

<400> SEQUENCE: 436

Lys Gly Glu Tyr Glu Lys Lys Lys Glu Thr Asn Gly His
1               5                   10

<210> SEQ ID NO 437
<211> LENGTH: 28
<212> TYPE: PRT
<213> ORGANISM: Plasmodium falciparum

<400> SEQUENCE: 437

Lys Ser Gly Met Tyr Thr Asn Glu Gly Asn Lys Ser Cys Glu Cys Ser
1               5                   10                  15

Tyr Lys Lys Lys Ser Ser Ser Ser Asn Lys Val His
            20                  25

<210> SEQ ID NO 438
<211> LENGTH: 18
<212> TYPE: PRT
<213> ORGANISM: Plasmodium falciparum

<400> SEQUENCE: 438

Lys Ser Cys Glu Cys Ser Tyr Lys Lys Lys Ser Ser Ser Ser Asn Lys
1               5                   10                  15

Val His

<210> SEQ ID NO 439
<211> LENGTH: 11
<212> TYPE: PRT
<213> ORGANISM: Plasmodium falciparum

<400> SEQUENCE: 439

Lys Lys Lys Ser Ser Ser Ser Asn Lys Val His
1               5                   10

<210> SEQ ID NO 440
<211> LENGTH: 10
<212> TYPE: PRT
<213> ORGANISM: Plasmodium falciparum

<400> SEQUENCE: 440

Lys Lys Ser Ser Ser Ser Asn Lys Val His
1               5                   10

<210> SEQ ID NO 441
<211> LENGTH: 9
<212> TYPE: PRT
<213> ORGANISM: Plasmodium falciparum

<400> SEQUENCE: 441

Lys Ser Ser Ser Asn Lys Val His
 1               5

<210> SEQ ID NO 442
<211> LENGTH: 30
<212> TYPE: PRT
<213> ORGANISM: Plasmodium falciparum

<400> SEQUENCE: 442

His Ile Met Leu Lys Ser Gly Met Tyr Thr Asn Glu Gly Asn Lys Ser
 1               5                  10                  15

Cys Glu Cys Ser Tyr Lys Lys Lys Ser Ser Ser Asn Lys
            20                  25                  30

<210> SEQ ID NO 443
<211> LENGTH: 24
<212> TYPE: PRT
<213> ORGANISM: Plasmodium falciparum

<400> SEQUENCE: 443

His Ile Met Leu Lys Ser Gly Met Tyr Thr Asn Glu Gly Asn Lys Ser
 1               5                  10                  15

Cys Glu Cys Ser Tyr Lys Lys Lys
            20

<210> SEQ ID NO 444
<211> LENGTH: 23
<212> TYPE: PRT
<213> ORGANISM: Plasmodium falciparum

<400> SEQUENCE: 444

His Ile Met Leu Lys Ser Gly Met Tyr Thr Asn Glu Gly Asn Lys Ser
 1               5                  10                  15

Cys Glu Cys Ser Tyr Lys Lys
            20

<210> SEQ ID NO 445
<211> LENGTH: 22
<212> TYPE: PRT
<213> ORGANISM: Plasmodium falciparum

<400> SEQUENCE: 445

His Ile Met Leu Lys Ser Gly Met Tyr Thr Asn Glu Gly Asn Lys Ser
 1               5                  10                  15

Cys Glu Cys Ser Tyr Lys
            20

<210> SEQ ID NO 446
<211> LENGTH: 50
<212> TYPE: PRT
<213> ORGANISM: Plasmodium falciparum

<400> SEQUENCE: 446

Lys Pro Leu Ala Lys Leu Arg Lys Arg Glu Lys Thr Gln Ile Asn Lys
 1               5                  10                  15

```
Thr Lys Tyr Glu Arg Gly Asp Val Ile Ile Asp Asn Thr Glu Ile Gln
            20                  25                  30

Lys Ile Ile Ile Arg Asp Tyr His Glu Thr Leu Asn Val His Lys Leu
        35                  40                  45

Asp His
    50

<210> SEQ ID NO 447
<211> LENGTH: 43
<212> TYPE: PRT
<213> ORGANISM: Plasmodium falciparum

<400> SEQUENCE: 447

Lys Arg Glu Lys Thr Gln Ile Asn Lys Thr Lys Tyr Glu Arg Gly Asp
1               5                   10                  15

Val Ile Ile Asp Asn Thr Glu Ile Gln Lys Ile Ile Ile Arg Asp Tyr
            20                  25                  30

His Glu Thr Leu Asn Val His Lys Leu Asp His
        35                  40

<210> SEQ ID NO 448
<211> LENGTH: 40
<212> TYPE: PRT
<213> ORGANISM: Plasmodium falciparum

<400> SEQUENCE: 448

Lys Thr Gln Ile Asn Lys Thr Lys Tyr Glu Arg Gly Asp Val Ile Ile
1               5                   10                  15

Asp Asn Thr Glu Ile Gln Lys Ile Ile Ile Arg Asp Tyr His Glu Thr
            20                  25                  30

Leu Asn Val His Lys Leu Asp His
        35                  40

<210> SEQ ID NO 449
<211> LENGTH: 46
<212> TYPE: PRT
<213> ORGANISM: Plasmodium falciparum

<400> SEQUENCE: 449

Lys Pro Leu Ala Lys Leu Arg Lys Arg Glu Lys Thr Gln Ile Asn Lys
1               5                   10                  15

Thr Lys Tyr Glu Arg Gly Asp Val Ile Ile Asp Asn Thr Glu Ile Gln
            20                  25                  30

Lys Ile Ile Ile Arg Asp Tyr His Glu Thr Leu Asn Val His
        35                  40                  45

<210> SEQ ID NO 450
<211> LENGTH: 40
<212> TYPE: PRT
<213> ORGANISM: Plasmodium falciparum

<400> SEQUENCE: 450

Lys Pro Leu Ala Lys Leu Arg Lys Arg Glu Lys Thr Gln Ile Asn Lys
1               5                   10                  15

Thr Lys Tyr Glu Arg Gly Asp Val Ile Ile Asp Asn Thr Glu Ile Gln
            20                  25                  30

Lys Ile Ile Ile Arg Asp Tyr His
        35                  40

<210> SEQ ID NO 451
```

```
<211> LENGTH: 36
<212> TYPE: PRT
<213> ORGANISM: Plasmodium falciparum

<400> SEQUENCE: 451

Lys Leu Arg Lys Arg Glu Lys Thr Gln Ile Asn Lys Thr Lys Tyr Glu
 1               5                  10                  15

Arg Gly Asp Val Ile Ile Asp Asn Thr Glu Ile Gln Lys Ile Ile Ile
            20                  25                  30

Arg Asp Tyr His
        35

<210> SEQ ID NO 452
<211> LENGTH: 33
<212> TYPE: PRT
<213> ORGANISM: Plasmodium falciparum

<400> SEQUENCE: 452

Lys Arg Glu Lys Thr Gln Ile Asn Lys Thr Lys Tyr Glu Arg Gly Asp
 1               5                  10                  15

Val Ile Ile Asp Asn Thr Glu Ile Gln Lys Ile Ile Ile Arg Asp Tyr
            20                  25                  30

His

<210> SEQ ID NO 453
<211> LENGTH: 30
<212> TYPE: PRT
<213> ORGANISM: Plasmodium falciparum

<400> SEQUENCE: 453

Lys Thr Gln Ile Asn Lys Thr Lys Tyr Glu Arg Gly Asp Val Ile Ile
 1               5                  10                  15

Asp Asn Thr Glu Ile Gln Lys Ile Ile Ile Arg Asp Tyr His
            20                  25                  30

<210> SEQ ID NO 454
<211> LENGTH: 41
<212> TYPE: PRT
<213> ORGANISM: Plasmodium falciparum

<400> SEQUENCE: 454

Lys Lys Asp Lys Glu Lys Lys Asp Ser Asn Glu Asn Arg Lys Lys
 1               5                  10                  15

Lys Gln Lys Glu Asp Lys Lys Asn Pro Asn Asp Asn Lys Leu Lys Lys
            20                  25                  30

Ile Glu Tyr Thr Asn Lys Ile Thr His
        35                  40

<210> SEQ ID NO 455
<211> LENGTH: 40
<212> TYPE: PRT
<213> ORGANISM: Plasmodium falciparum

<400> SEQUENCE: 455

Lys Asp Lys Glu Lys Lys Lys Asp Ser Asn Glu Asn Arg Lys Lys Lys
 1               5                  10                  15

Gln Lys Glu Asp Lys Lys Asn Pro Asn Asp Asn Lys Leu Lys Lys Ile
            20                  25                  30

Glu Tyr Thr Asn Lys Ile Thr His
        35                  40
```

```
<210> SEQ ID NO 456
<211> LENGTH: 38
<212> TYPE: PRT
<213> ORGANISM: Plasmodium falciparum

<400> SEQUENCE: 456

Lys Glu Lys Lys Lys Asp Ser Asn Glu Asn Arg Lys Lys Gln Lys
 1               5                  10                  15

Glu Asp Lys Lys Asn Pro Asn Asp Asn Lys Leu Lys Lys Ile Glu Tyr
                20                  25                  30

Thr Asn Lys Ile Thr His
            35

<210> SEQ ID NO 457
<211> LENGTH: 36
<212> TYPE: PRT
<213> ORGANISM: Plasmodium falciparum

<400> SEQUENCE: 457

Lys Lys Lys Asp Ser Asn Glu Asn Arg Lys Lys Lys Gln Lys Glu Asp
 1               5                  10                  15

Lys Lys Asn Pro Asn Asp Asn Lys Leu Lys Lys Ile Glu Tyr Thr Asn
                20                  25                  30

Lys Ile Thr His
            35

<210> SEQ ID NO 458
<211> LENGTH: 35
<212> TYPE: PRT
<213> ORGANISM: Plasmodium falciparum

<400> SEQUENCE: 458

Lys Lys Asp Ser Asn Glu Asn Arg Lys Lys Lys Gln Lys Glu Asp Lys
 1               5                  10                  15

Lys Asn Pro Asn Asp Asn Lys Leu Lys Lys Ile Glu Tyr Thr Asn Lys
                20                  25                  30

Ile Thr His
        35

<210> SEQ ID NO 459
<211> LENGTH: 34
<212> TYPE: PRT
<213> ORGANISM: Plasmodium falciparum

<400> SEQUENCE: 459

Lys Asp Ser Asn Glu Asn Arg Lys Lys Lys Gln Lys Glu Asp Lys Lys
 1               5                  10                  15

Asn Pro Asn Asp Asn Lys Leu Lys Lys Ile Glu Tyr Thr Asn Lys Ile
                20                  25                  30

Thr His

<210> SEQ ID NO 460
<211> LENGTH: 27
<212> TYPE: PRT
<213> ORGANISM: Plasmodium falciparum

<400> SEQUENCE: 460

Lys Lys Lys Gln Lys Glu Asp Lys Lys Asn Pro Asn Asp Asn Lys Leu
 1               5                  10                  15

Lys Lys Ile Glu Tyr Thr Asn Lys Ile Thr His
```

<210> SEQ ID NO 461
<211> LENGTH: 26
<212> TYPE: PRT
<213> ORGANISM: Plasmodium falciparum

<400> SEQUENCE: 461

Lys Lys Gln Lys Glu Asp Lys Lys Asn Pro Asn Asp Asn Lys Leu Lys
1               5                   10                  15

Lys Ile Glu Tyr Thr Asn Lys Ile Thr His
            20                  25

<210> SEQ ID NO 462
<211> LENGTH: 25
<212> TYPE: PRT
<213> ORGANISM: Plasmodium falciparum

<400> SEQUENCE: 462

Lys Gln Lys Glu Asp Lys Lys Asn Pro Asn Asp Asn Lys Leu Lys Lys
1               5                   10                  15

Ile Glu Tyr Thr Asn Lys Ile Thr His
            20                  25

<210> SEQ ID NO 463
<211> LENGTH: 23
<212> TYPE: PRT
<213> ORGANISM: Plasmodium falciparum

<400> SEQUENCE: 463

Lys Glu Asp Lys Lys Asn Pro Asn Asp Asn Lys Leu Lys Lys Ile Glu
1               5                   10                  15

Tyr Thr Asn Lys Ile Thr His
            20

<210> SEQ ID NO 464
<211> LENGTH: 20
<212> TYPE: PRT
<213> ORGANISM: Plasmodium falciparum

<400> SEQUENCE: 464

Lys Lys Asn Pro Asn Asp Asn Lys Leu Lys Lys Ile Glu Tyr Thr Asn
1               5                   10                  15

Lys Ile Thr His
            20

<210> SEQ ID NO 465
<211> LENGTH: 19
<212> TYPE: PRT
<213> ORGANISM: Plasmodium falciparum

<400> SEQUENCE: 465

Lys Asn Pro Asn Asp Asn Lys Leu Lys Lys Ile Glu Tyr Thr Asn Lys
1               5                   10                  15

Ile Thr His

<210> SEQ ID NO 466
<211> LENGTH: 13
<212> TYPE: PRT
<213> ORGANISM: Plasmodium falciparum

<400> SEQUENCE: 466

```
Lys Leu Lys Lys Ile Glu Tyr Thr Asn Lys Ile Thr His
1               5                   10
```

<210> SEQ ID NO 467
<211> LENGTH: 11
<212> TYPE: PRT
<213> ORGANISM: Plasmodium falciparum

<400> SEQUENCE: 467

```
Lys Lys Ile Glu Tyr Thr Asn Lys Ile Thr His
1               5                   10
```

<210> SEQ ID NO 468
<211> LENGTH: 10
<212> TYPE: PRT
<213> ORGANISM: Plasmodium falciparum

<400> SEQUENCE: 468

```
Lys Ile Glu Tyr Thr Asn Lys Ile Thr His
1               5                   10
```

<210> SEQ ID NO 469
<211> LENGTH: 44
<212> TYPE: PRT
<213> ORGANISM: Plasmodium falciparum

<400> SEQUENCE: 469

```
His Gly Gln Ile Lys Ile Glu Asp Val Asn Asn Glu Asn Phe Asn Asn
1               5                   10                  15

Glu Gln Met Lys Asn Lys Tyr Asn Asp Glu Glu Lys Met Asp Ile Ser
            20                  25                  30

Lys Ser Lys Ser Leu Lys Ser Asp Phe Leu Glu Lys
        35                  40
```

<210> SEQ ID NO 470
<211> LENGTH: 38
<212> TYPE: PRT
<213> ORGANISM: Plasmodium falciparum

<400> SEQUENCE: 470

```
His Gly Gln Ile Lys Ile Glu Asp Val Asn Asn Glu Asn Phe Asn Asn
1               5                   10                  15

Glu Gln Met Lys Asn Lys Tyr Asn Asp Glu Glu Lys Met Asp Ile Ser
            20                  25                  30

Lys Ser Lys Ser Leu Lys
        35
```

<210> SEQ ID NO 471
<211> LENGTH: 35
<212> TYPE: PRT
<213> ORGANISM: Plasmodium falciparum

<400> SEQUENCE: 471

```
His Gly Gln Ile Lys Ile Glu Asp Val Asn Asn Glu Asn Phe Asn Asn
1               5                   10                  15

Glu Gln Met Lys Asn Lys Tyr Asn Asp Glu Glu Lys Met Asp Ile Ser
            20                  25                  30

Lys Ser Lys
        35
```

<210> SEQ ID NO 472
<211> LENGTH: 33

```
<212> TYPE: PRT
<213> ORGANISM: Plasmodium falciparum

<400> SEQUENCE: 472

His Gly Gln Ile Lys Ile Glu Asp Val Asn Asn Glu Asn Phe Asn Asn
 1               5                  10                  15

Glu Gln Met Lys Asn Lys Tyr Asn Asp Glu Glu Lys Met Asp Ile Ser
            20                  25                  30

Lys

<210> SEQ ID NO 473
<211> LENGTH: 31
<212> TYPE: PRT
<213> ORGANISM: Plasmodium falciparum

<400> SEQUENCE: 473

Lys Lys Tyr Asp Asp Leu Gln Asn Lys Tyr Asn Ile Leu Asn Lys Leu
 1               5                  10                  15

Lys Asn Ser Leu Glu Glu Lys Asn Glu Glu Leu Lys Lys Tyr His
            20                  25                  30

<210> SEQ ID NO 474
<211> LENGTH: 30
<212> TYPE: PRT
<213> ORGANISM: Plasmodium falciparum

<400> SEQUENCE: 474

Lys Tyr Asp Asp Leu Gln Asn Lys Tyr Asn Ile Leu Asn Lys Leu Lys
 1               5                  10                  15

Asn Ser Leu Glu Glu Lys Asn Glu Glu Leu Lys Lys Tyr His
            20                  25                  30

<210> SEQ ID NO 475
<211> LENGTH: 23
<212> TYPE: PRT
<213> ORGANISM: Plasmodium falciparum

<400> SEQUENCE: 475

Lys Tyr Asn Ile Leu Asn Lys Leu Lys Asn Ser Leu Glu Glu Lys Asn
 1               5                  10                  15

Glu Glu Leu Lys Lys Tyr His
            20

<210> SEQ ID NO 476
<211> LENGTH: 17
<212> TYPE: PRT
<213> ORGANISM: Plasmodium falciparum

<400> SEQUENCE: 476

Lys Leu Lys Asn Ser Leu Glu Glu Lys Asn Glu Glu Leu Lys Lys Tyr
 1               5                  10                  15

His

<210> SEQ ID NO 477
<211> LENGTH: 15
<212> TYPE: PRT
<213> ORGANISM: Plasmodium falciparum

<400> SEQUENCE: 477

Lys Asn Ser Leu Glu Glu Lys Asn Glu Glu Leu Lys Lys Tyr His
 1               5                  10                  15
```

<210> SEQ ID NO 478
<211> LENGTH: 9
<212> TYPE: PRT
<213> ORGANISM: Plasmodium falciparum

<400> SEQUENCE: 478

Lys Asn Glu Glu Leu Lys Lys Tyr His
 1               5

<210> SEQ ID NO 479
<211> LENGTH: 44
<212> TYPE: PRT
<213> ORGANISM: Plasmodium falciparum

<400> SEQUENCE: 479

His Met Gly Asn Asn Gln Asp Ile Asn Glu Asn Val Tyr Asn Ile Lys
 1               5                  10                  15

Pro Gln Glu Phe Lys Glu Glu Glu Glu Asp Ile Ser Met Val Asn
            20                  25                  30

Thr Lys Lys Cys Asp Asp Ile Gln Glu Asn Ile Lys
        35                  40

<210> SEQ ID NO 480
<211> LENGTH: 50
<212> TYPE: PRT
<213> ORGANISM: Plasmodium falciparum

<400> SEQUENCE: 480

Lys Thr Asn Leu Tyr Asn Ile Tyr Asn Asn Lys Asn Asp Asp Lys Asp
 1               5                  10                  15

Asn Ile Leu Asp Asn Glu Asn Arg Glu Gly Leu Tyr Leu Cys Asp Val
            20                  25                  30

Met Lys Asn Ser Asn Glu Leu Lys Arg Ile Asn Asp Asn Phe Phe Lys
        35                  40                  45

Leu His
    50

<210> SEQ ID NO 481
<211> LENGTH: 17
<212> TYPE: PRT
<213> ORGANISM: Plasmodium falciparum

<400> SEQUENCE: 481

Lys Asn Ser Asn Glu Leu Lys Arg Ile Asn Asp Asn Phe Phe Lys Leu
 1               5                  10                  15

His

<210> SEQ ID NO 482
<211> LENGTH: 11
<212> TYPE: PRT
<213> ORGANISM: Plasmodium falciparum

<400> SEQUENCE: 482

Lys Arg Ile Asn Asp Asn Phe Phe Lys Leu His
 1               5                  10

<210> SEQ ID NO 483
<211> LENGTH: 40
<212> TYPE: PRT
<213> ORGANISM: Plasmodium falciparum

<400> SEQUENCE: 483

His Ile Asn Asn Glu Tyr Thr Asn Lys Asn Pro Lys Asn Cys Leu Leu
1               5                   10                  15

Tyr Lys Asn Glu Glu Arg Asn Tyr Asn Asp Asn Asn Ile Lys Asp Tyr
            20                  25                  30

Ile Asn Ser Met Asn Phe Lys Lys
        35                  40

<210> SEQ ID NO 484
<211> LENGTH: 39
<212> TYPE: PRT
<213> ORGANISM: Plasmodium falciparum

<400> SEQUENCE: 484

His Ile Asn Asn Glu Tyr Thr Asn Lys Asn Pro Lys Asn Cys Leu Leu
1               5                   10                  15

Tyr Lys Asn Glu Glu Arg Asn Tyr Asn Asp Asn Asn Ile Lys Asp Tyr
            20                  25                  30

Ile Asn Ser Met Asn Phe Lys
        35

<210> SEQ ID NO 485
<211> LENGTH: 18
<212> TYPE: PRT
<213> ORGANISM: Plasmodium falciparum

<400> SEQUENCE: 485

His Ile Asn Asn Glu Tyr Thr Asn Lys Asn Pro Lys Asn Cys Leu Leu
1               5                   10                  15

Tyr Lys

<210> SEQ ID NO 486
<211> LENGTH: 45
<212> TYPE: PRT
<213> ORGANISM: Plasmodium falciparum

<400> SEQUENCE: 486

Lys Pro Cys Leu Tyr Lys Lys Cys Lys Ile Ser Gln Val Trp Trp Cys
1               5                   10                  15

Met Pro Val Lys Asp Thr Phe Asn Thr Tyr Glu Arg Asn Asn Val Leu
            20                  25                  30

Asn Ser Lys Ile Glu Asn Asn Ile Glu Lys Ile Pro His
        35                  40                  45

<210> SEQ ID NO 487
<211> LENGTH: 39
<212> TYPE: PRT
<213> ORGANISM: Plasmodium falciparum

<400> SEQUENCE: 487

Lys Cys Lys Ile Ser Gln Val Trp Trp Cys Met Pro Val Lys Asp Thr
1               5                   10                  15

Phe Asn Thr Tyr Glu Arg Asn Asn Val Leu Asn Ser Lys Ile Glu Asn
            20                  25                  30

Asn Ile Glu Lys Ile Pro His
        35

<210> SEQ ID NO 488
<211> LENGTH: 11
<212> TYPE: PRT
<213> ORGANISM: Plasmodium falciparum -continued

```
<400> SEQUENCE: 488

Lys Ile Glu Asn Asn Ile Glu Lys Ile Pro His
  1               5                  10

<210> SEQ ID NO 489
<211> LENGTH: 23
<212> TYPE: PRT
<213> ORGANISM: Plasmodium falciparum

<400> SEQUENCE: 489

Lys Asn Lys Thr Asn Gly Ser Lys Gly Val Lys Gly Glu Tyr Glu Lys
  1               5                  10                  15

Lys Lys Glu Thr Asn Gly His
             20

<210> SEQ ID NO 490
<211> LENGTH: 21
<212> TYPE: PRT
<213> ORGANISM: Plasmodium falciparum

<400> SEQUENCE: 490

Lys Thr Asn Gly Ser Lys Gly Val Lys Gly Glu Tyr Glu Lys Lys Lys
  1               5                  10                  15

Glu Thr Asn Gly His
             20

<210> SEQ ID NO 491
<211> LENGTH: 16
<212> TYPE: PRT
<213> ORGANISM: Plasmodium falciparum

<400> SEQUENCE: 491

Lys Gly Val Lys Gly Glu Tyr Glu Lys Lys Lys Glu Thr Asn Gly His
  1               5                  10                  15

<210> SEQ ID NO 492
<211> LENGTH: 13
<212> TYPE: PRT
<213> ORGANISM: Plasmodium falciparum

<400> SEQUENCE: 492

Lys Gly Glu Tyr Glu Lys Lys Lys Glu Thr Asn Gly His
  1               5                  10

<210> SEQ ID NO 493
<211> LENGTH: 60
<212> TYPE: PRT
<213> ORGANISM: Plasmodium falciparum

<400> SEQUENCE: 493

Lys Thr Ile Glu Lys Ile Asn Lys Ser Lys Ser Trp Phe Phe Glu Glu
  1               5                  10                  15

Leu Asp Glu Ile Asp Lys Pro Leu Ala Lys Leu Arg Lys Arg Glu Lys
             20                  25                  30

Thr Gln Ile Asn Lys Thr Lys Tyr Glu Arg Gly Asp Val Ile Ile Asp
             35                  40                  45

Asn Thr Glu Ile Gln Lys Ile Ile Arg Asp Tyr His
             50                  55                  60

<210> SEQ ID NO 494
<211> LENGTH: 56
```

```
<212> TYPE: PRT
<213> ORGANISM: Plasmodium falciparum

<400> SEQUENCE: 494

Lys Ile Asn Lys Ser Lys Ser Trp Phe Phe Glu Glu Leu Asp Glu Ile
 1               5                  10                  15

Asp Lys Pro Leu Ala Lys Leu Arg Lys Arg Glu Lys Thr Gln Ile Asn
            20                  25                  30

Lys Thr Lys Tyr Glu Arg Gly Asp Val Ile Ile Asp Asn Thr Glu Ile
        35                  40                  45

Gln Lys Ile Ile Arg Asp Tyr His
    50                  55

<210> SEQ ID NO 495
<211> LENGTH: 39
<212> TYPE: PRT
<213> ORGANISM: Plasmodium falciparum

<400> SEQUENCE: 495

Lys Pro Leu Ala Lys Leu Arg Lys Arg Glu Lys Thr Gln Ile Asn Lys
 1               5                  10                  15

Thr Lys Tyr Glu Arg Gly Asp Val Ile Ile Asp Asn Thr Glu Ile Gln
            20                  25                  30

Lys Ile Ile Arg Asp Tyr His
        35

<210> SEQ ID NO 496
<211> LENGTH: 32
<212> TYPE: PRT
<213> ORGANISM: Plasmodium falciparum

<400> SEQUENCE: 496

His Ile Met Leu Lys Ser Gln Met Tyr Thr Asn Glu Gly Asn Lys Ser
 1               5                  10                  15

Cys Glu Cys Ser Tyr Lys Lys Lys Ser Ser Ser Asn Lys Val His
            20                  25                  30

<210> SEQ ID NO 497
<211> LENGTH: 35
<212> TYPE: PRT
<213> ORGANISM: Plasmodium falciparum

<400> SEQUENCE: 497

Lys Leu Arg Lys Arg Glu Lys Thr Gln Ile Asn Lys Thr Lys Tyr Glu
 1               5                  10                  15

Arg Gly Asp Val Ile Ile Asp Asn Thr Glu Ile Gln Lys Ile Ile Arg
            20                  25                  30

Asp Tyr His
        35

<210> SEQ ID NO 498
<211> LENGTH: 32
<212> TYPE: PRT
<213> ORGANISM: Plasmodium falciparum

<400> SEQUENCE: 498

Lys Arg Glu Lys Thr Gln Ile Asn Lys Thr Lys Tyr Glu Arg Gly Asp
 1               5                  10                  15

Val Ile Ile Asp Asn Thr Glu Ile Gln Lys Ile Ile Arg Asp Tyr His
            20                  25                  30
```

<210> SEQ ID NO 499
<211> LENGTH: 29
<212> TYPE: PRT
<213> ORGANISM: Plasmodium falciparum

<400> SEQUENCE: 499

Lys Thr Gln Ile Asn Lys Thr Lys Tyr Glu Arg Gly Asp Val Ile Ile
 1               5                  10                  15

Asp Asn Thr Glu Ile Gln Lys Ile Ile Arg Asp Tyr His
            20                  25

<210> SEQ ID NO 500
<211> LENGTH: 48
<212> TYPE: PRT
<213> ORGANISM: Plasmodium falciparum

<400> SEQUENCE: 500

Lys Pro Leu Ala Lys Leu Arg Lys Arg Glu Lys Thr Gln Ile Asn Lys
 1               5                  10                  15

Thr Lys Tyr Glu Arg Gly Asp Val Ile Ile Asp Asn Thr Glu Ile Gln
            20                  25                  30

Lys Ile Ile Arg Asp Tyr His Thr Leu Asn Val His Lys Leu Asp His
        35                  40                  45

<210> SEQ ID NO 501
<211> LENGTH: 44
<212> TYPE: PRT
<213> ORGANISM: Plasmodium falciparum

<400> SEQUENCE: 501

Lys Leu Arg Lys Arg Glu Lys Thr Gln Ile Asn Lys Thr Lys Tyr Glu
 1               5                  10                  15

Arg Gly Asp Val Ile Ile Asp Asn Thr Glu Ile Gln Lys Ile Ile Arg
            20                  25                  30

Asp Tyr His Thr Leu Asn Val His Lys Leu Asp His
        35                  40

<210> SEQ ID NO 502
<211> LENGTH: 41
<212> TYPE: PRT
<213> ORGANISM: Plasmodium falciparum

<400> SEQUENCE: 502

Lys Arg Glu Lys Thr Gln Ile Asn Lys Thr Lys Tyr Glu Arg Gly Asp
 1               5                  10                  15

Val Ile Ile Asp Asn Thr Glu Ile Gln Lys Ile Ile Arg Asp Tyr His
            20                  25                  30

Thr Leu Asn Val His Lys Leu Asp His
        35                  40

<210> SEQ ID NO 503
<211> LENGTH: 38
<212> TYPE: PRT
<213> ORGANISM: Plasmodium falciparum

<400> SEQUENCE: 503

Lys Thr Gln Ile Asn Lys Thr Lys Tyr Glu Arg Gly Asp Val Ile Ile
 1               5                  10                  15

Asp Asn Thr Glu Ile Gln Lys Ile Ile Arg Asp Tyr His Thr Leu Asn
            20                  25                  30

Val His Lys Leu Asp His
            35

<210> SEQ ID NO 504
<211> LENGTH: 44
<212> TYPE: PRT
<213> ORGANISM: Plasmodium falciparum

<400> SEQUENCE: 504

Lys Pro Leu Ala Lys Leu Arg Lys Arg Glu Lys Thr Gln Ile Asn Lys
 1               5                  10                  15

Thr Lys Tyr Glu Arg Gly Asp Val Ile Ile Asp Asn Thr Glu Ile Gln
            20                  25                  30

Lys Ile Ile Arg Asp Tyr His Thr Leu Asn Val His
        35                  40

<210> SEQ ID NO 505
<211> LENGTH: 40
<212> TYPE: PRT
<213> ORGANISM: Plasmodium falciparum

<400> SEQUENCE: 505

Lys Leu Arg Lys Arg Glu Lys Thr Gln Ile Asn Lys Thr Lys Tyr Glu
 1               5                  10                  15

Arg Gly Asp Val Ile Ile Asp Asn Thr Glu Ile Gln Lys Ile Ile Arg
            20                  25                  30

Asp Tyr His Thr Leu Asn Val His
        35                  40

<210> SEQ ID NO 506
<211> LENGTH: 37
<212> TYPE: PRT
<213> ORGANISM: Plasmodium falciparum

<400> SEQUENCE: 506

Lys Arg Glu Lys Thr Gln Ile Asn Lys Thr Lys Tyr Glu Arg Gly Asp
 1               5                  10                  15

Val Ile Ile Asp Asn Thr Glu Ile Gln Lys Ile Ile Arg Asp Tyr His
            20                  25                  30

Thr Leu Asn Val His
        35

<210> SEQ ID NO 507
<211> LENGTH: 34
<212> TYPE: PRT
<213> ORGANISM: Plasmodium falciparum

<400> SEQUENCE: 507

Lys Thr Gln Ile Asn Lys Thr Lys Tyr Glu Arg Gly Asp Val Ile Ile
 1               5                  10                  15

Asp Asn Thr Glu Ile Gln Lys Ile Ile Arg Asp Tyr His Thr Leu Asn
            20                  25                  30

Val His

<210> SEQ ID NO 508
<211> LENGTH: 32
<212> TYPE: PRT
<213> ORGANISM: Plasmodium falciparum

<400> SEQUENCE: 508

His Ile Met Leu Lys Ser Gln Met Tyr Thr Asn Glu Gly Asn Lys Ser

```
             1               5                  10                 15
Cys Glu Cys Ser Tyr Lys Lys Ser Ser Ser Asn Lys Val His
                        20                  25                  30

<210> SEQ ID NO 509
<211> LENGTH: 28
<212> TYPE: PRT
<213> ORGANISM: Plasmodium falciparum

<400> SEQUENCE: 509

Lys Ser Gln Met Tyr Thr Asn Glu Gly Asn Lys Ser Cys Glu Cys Ser
 1               5                  10                  15

Tyr Lys Lys Lys Ser Ser Ser Asn Lys Val His
                20                  25

<210> SEQ ID NO 510
<211> LENGTH: 18
<212> TYPE: PRT
<213> ORGANISM: Plasmodium falciparum

<400> SEQUENCE: 510

Lys Ser Cys Glu Cys Ser Tyr Lys Lys Lys Ser Ser Ser Asn Lys
 1               5                  10                  15

Val His

<210> SEQ ID NO 511
<211> LENGTH: 11
<212> TYPE: PRT
<213> ORGANISM: Plasmodium falciparum

<400> SEQUENCE: 511

Lys Lys Lys Ser Ser Ser Ser Asn Lys Val His
 1               5                  10

<210> SEQ ID NO 512
<211> LENGTH: 10
<212> TYPE: PRT
<213> ORGANISM: Plasmodium falciparum

<400> SEQUENCE: 512

Lys Lys Ser Ser Ser Ser Asn Lys Val His
 1               5                  10

<210> SEQ ID NO 513
<211> LENGTH: 9
<212> TYPE: PRT
<213> ORGANISM: Plasmodium falciparum

<400> SEQUENCE: 513

Lys Ser Ser Ser Ser Asn Lys Val His
 1               5

<210> SEQ ID NO 514
<211> LENGTH: 30
<212> TYPE: PRT
<213> ORGANISM: Plasmodium falciparum

<400> SEQUENCE: 514

His Ile Met Leu Lys Ser Gln Met Tyr Thr Asn Glu Gly Asn Lys Ser
 1               5                  10                  15

Cys Glu Cys Ser Tyr Lys Lys Lys Ser Ser Ser Asn Lys
                20                  25                  30
```

<210> SEQ ID NO 515
<211> LENGTH: 24
<212> TYPE: PRT
<213> ORGANISM: Plasmodium falciparum

<400> SEQUENCE: 515

His Ile Met Leu Lys Ser Gln Met Tyr Thr Asn Glu Gly Asn Lys Ser
 1               5                  10                  15

Cys Glu Cys Ser Tyr Lys Lys Lys
            20

<210> SEQ ID NO 516
<211> LENGTH: 23
<212> TYPE: PRT
<213> ORGANISM: Plasmodium falciparum

<400> SEQUENCE: 516

His Ile Met Leu Lys Ser Gln Met Tyr Thr Asn Glu Gly Asn Lys Ser
 1               5                  10                  15

Cys Glu Cys Ser Tyr Lys Lys
            20

<210> SEQ ID NO 517
<211> LENGTH: 22
<212> TYPE: PRT
<213> ORGANISM: Plasmodium falciparum

<400> SEQUENCE: 517

His Ile Met Leu Lys Ser Gln Met Tyr Thr Asn Glu Gly Asn Lys Ser
 1               5                  10                  15

Cys Glu Cys Ser Tyr Lys
            20

<210> SEQ ID NO 518
<211> LENGTH: 36
<212> TYPE: PRT
<213> ORGANISM: Plasmodium falciparum

<400> SEQUENCE: 518

His Asn Asn His Asn Ile Gln Ile Tyr Lys Asp Lys Arg Ile Asn Phe
 1               5                  10                  15

Met Asn Pro His Lys Val Met Tyr His Asp Asn Met Ser Lys Asn Glu
            20                  25                  30

Arg Thr Glu Lys
        35

<210> SEQ ID NO 519
<211> LENGTH: 30
<212> TYPE: PRT
<213> ORGANISM: Plasmodium falciparum

<400> SEQUENCE: 519

His Asn Asn His Asn Ile Gln Ile Tyr Lys Asp Lys Arg Ile Asn Phe
 1               5                  10                  15

Met Asn Pro His Lys Val Met Tyr His Asp Asn Met Ser Lys
            20                  25                  30

<210> SEQ ID NO 520
<211> LENGTH: 21
<212> TYPE: PRT
<213> ORGANISM: Plasmodium falciparum

```
<400> SEQUENCE: 520

His Asn Asn His Asn Ile Gln Ile Tyr Lys Asp Lys Arg Ile Asn Phe
  1               5                  10                  15

Met Asn Pro His Lys
         20

<210> SEQ ID NO 521
<211> LENGTH: 17
<212> TYPE: PRT
<213> ORGANISM: Plasmodium falciparum

<400> SEQUENCE: 521

His Lys Val Met Tyr His Asp Asn Met Ser Lys Asn Glu Arg Thr Glu
  1               5                  10                  15

Lys

<210> SEQ ID NO 522
<211> LENGTH: 11
<212> TYPE: PRT
<213> ORGANISM: Plasmodium falciparum

<400> SEQUENCE: 522

His Lys Val Met Tyr His Asp Asn Met Ser Lys
  1               5                  10

<210> SEQ ID NO 523
<211> LENGTH: 40
<212> TYPE: PRT
<213> ORGANISM: Homo sapiens

<400> SEQUENCE: 523

His Arg Glu Ile Cys Thr Ile Gln Ser Ser Gly Gly Ile Met Leu Leu
  1               5                  10                  15

Lys Asp Gln Val Leu Arg Cys Ser Lys Ile Ala Gly Val Lys Val Ala
                 20                  25                  30

Glu Ile Thr Glu Leu Ile Leu Lys
         35                  40

<210> SEQ ID NO 524
<211> LENGTH: 25
<212> TYPE: PRT
<213> ORGANISM: Homo sapiens

<400> SEQUENCE: 524

His Arg Glu Ile Cys Thr Ile Gln Ser Ser Gly Gly Ile Met Leu Leu
  1               5                  10                  15

Lys Asp Gln Val Leu Arg Cys Ser Lys
                 20                  25

<210> SEQ ID NO 525
<211> LENGTH: 47
<212> TYPE: PRT
<213> ORGANISM: Homo sapiens

<400> SEQUENCE: 525

His Arg Glu Ile Cys Thr Ile Gln Ser Ser Gly Gly Ile Met Leu Leu
  1               5                  10                  15

Lys Asp Gln Val Leu Arg Cys Ser Lys Ile Ala Gly Val Lys Val Ala
                 20                  25                  30

Glu Ile Thr Glu Leu Ile Leu Lys Ala Leu Glu Asn Asp Gln Lys
         35                  40                  45
```

<210> SEQ ID NO 526
<211> LENGTH: 40
<212> TYPE: PRT
<213> ORGANISM: Homo sapiens

<400> SEQUENCE: 526

His Arg Glu Ile Cys Thr Ile Gln Ala Ala Gly Gly Ile Met Leu Leu
1               5                   10                  15

Lys Asp Gln Val Leu Arg Cys Ser Lys Ile Ala Gly Val Lys Val Ala
            20                  25                  30

Glu Ile Thr Glu Leu Ile Leu Lys
        35                  40

<210> SEQ ID NO 527
<211> LENGTH: 23
<212> TYPE: PRT
<213> ORGANISM: Homo sapiens

<400> SEQUENCE: 527

Lys Lys Met Gln Gln Glu Asn Met Lys Pro Gln Glu Gln Leu Thr Leu
1               5                   10                  15

Glu Pro Tyr Glu Arg Asp His
            20

<210> SEQ ID NO 528
<211> LENGTH: 22
<212> TYPE: PRT
<213> ORGANISM: Homo sapiens

<400> SEQUENCE: 528

Lys Met Gln Gln Glu Asn Met Lys Pro Gln Glu Gln Leu Thr Leu Glu
1               5                   10                  15

Pro Tyr Glu Arg Asp His
            20

<210> SEQ ID NO 529
<211> LENGTH: 38
<212> TYPE: PRT
<213> ORGANISM: Homo sapiens

<400> SEQUENCE: 529

His Glu Met Glu Glu Ser Lys Lys Asn Arg Val Glu Ile Asn Asp Val
1               5                   10                  15

Glu Pro Glu Val Phe Lys Glu Met Met Cys Phe Ile Tyr Thr Gly Lys
            20                  25                  30

Ala Pro Asn Leu Asp Lys
        35

<210> SEQ ID NO 530
<211> LENGTH: 32
<212> TYPE: PRT
<213> ORGANISM: Homo sapiens

<400> SEQUENCE: 530

His Glu Met Glu Glu Ser Lys Lys Asn Arg Val Glu Ile Asn Asp Val
1               5                   10                  15

Glu Pro Glu Val Phe Lys Glu Met Met Cys Phe Ile Tyr Thr Gly Lys
            20                  25                  30

<210> SEQ ID NO 531

```
<211> LENGTH: 9
<212> TYPE: PRT
<213> ORGANISM: Homo sapiens

<400> SEQUENCE: 531

Lys His Gly Glu Leu Lys Val Tyr Lys
 1               5

<210> SEQ ID NO 532
<211> LENGTH: 14
<212> TYPE: PRT
<213> ORGANISM: Homo sapiens

<400> SEQUENCE: 532

Lys Leu Ile Leu Gly Pro Gln Glu Glu Lys Gly Lys Gln His
 1               5                  10

<210> SEQ ID NO 533
<211> LENGTH: 7
<212> TYPE: PRT
<213> ORGANISM: Homo sapiens

<400> SEQUENCE: 533

Lys Asn Arg Ile His His Lys
 1               5

<210> SEQ ID NO 534
<211> LENGTH: 17
<212> TYPE: PRT
<213> ORGANISM: Homo sapiens

<400> SEQUENCE: 534

His His Asn Ser Ser Arg Lys Ser Thr Lys Lys Thr Asn Gln Ser Ser
 1               5                  10                  15

Lys

<210> SEQ ID NO 535
<211> LENGTH: 16
<212> TYPE: PRT
<213> ORGANISM: Homo sapiens

<400> SEQUENCE: 535

His Asn Ser Ser Arg Lys Ser Thr Lys Lys Thr Asn Gln Ser Ser Lys
 1               5                  10                  15

<210> SEQ ID NO 536
<211> LENGTH: 20
<212> TYPE: PRT
<213> ORGANISM: Homo sapiens

<400> SEQUENCE: 536

Lys His His Asn Ile Leu Pro Lys Thr Leu Ala Asn Asp Lys His Ser
 1               5                  10                  15

His Lys Pro His
            20

<210> SEQ ID NO 537
<211> LENGTH: 17
<212> TYPE: PRT
<213> ORGANISM: Homo sapiens

<400> SEQUENCE: 537

His His Asn Ile Leu Pro Lys Thr Leu Ala Asn Asp Lys His Ser His
 1               5                  10                  15
```

Lys

<210> SEQ ID NO 538
<211> LENGTH: 16
<212> TYPE: PRT
<213> ORGANISM: Homo sapiens

<400> SEQUENCE: 538

His Asn Ile Leu Pro Lys Thr Leu Ala Asn Asp Lys His Ser His Lys
1               5                   10                  15

<210> SEQ ID NO 539
<211> LENGTH: 12
<212> TYPE: PRT
<213> ORGANISM: Homo sapiens

<400> SEQUENCE: 539

His Asn Ile Leu Pro Lys Thr Leu Ala Asn Asp Lys
1               5                   10

<210> SEQ ID NO 540
<211> LENGTH: 18
<212> TYPE: PRT
<213> ORGANISM: Homo sapiens

<400> SEQUENCE: 540

Lys Asn Thr Pro Asp Ser Lys Lys Ile Ser Ser Arg Asn Ile Asn Asp
1               5                   10                  15

His His

<210> SEQ ID NO 541
<211> LENGTH: 17
<212> TYPE: PRT
<213> ORGANISM: Homo sapiens

<400> SEQUENCE: 541

Lys Asn Thr Pro Asp Ser Lys Lys Ile Ser Ser Arg Asn Ile Asn Asp
1               5                   10                  15

His

<210> SEQ ID NO 542
<211> LENGTH: 27
<212> TYPE: PRT
<213> ORGANISM: Homo sapiens

<400> SEQUENCE: 542

Lys Asp Thr Cys Ile Gln Ser Pro Ser Lys Glu Cys Gln Lys Ser His
1               5                   10                  15

Pro Lys Ser Val Pro Val Ser Ser Lys Lys Lys
            20                  25

<210> SEQ ID NO 543
<211> LENGTH: 26
<212> TYPE: PRT
<213> ORGANISM: Homo sapiens

<400> SEQUENCE: 543

Lys Asp Thr Cys Ile Gln Ser Pro Ser Lys Glu Cys Gln Lys Ser His
1               5                   10                  15

Pro Lys Ser Val Pro Val Ser Ser Lys Lys
            20                  25

```
<210> SEQ ID NO 544
<211> LENGTH: 12
<212> TYPE: PRT
<213> ORGANISM: Homo sapiens

<400> SEQUENCE: 544

His Pro Lys Ser Val Pro Val Ser Ser Lys Lys Lys
  1               5                  10

<210> SEQ ID NO 545
<211> LENGTH: 11
<212> TYPE: PRT
<213> ORGANISM: Homo sapiens

<400> SEQUENCE: 545

His Pro Lys Ser Val Pro Val Ser Ser Lys Lys
  1               5                  10

<210> SEQ ID NO 546
<211> LENGTH: 10
<212> TYPE: PRT
<213> ORGANISM: Homo sapiens

<400> SEQUENCE: 546

His Pro Lys Ser Val Pro Val Ser Ser Lys
  1               5                  10

<210> SEQ ID NO 547
<211> LENGTH: 14
<212> TYPE: PRT
<213> ORGANISM: Homo sapiens

<400> SEQUENCE: 547

Lys Ala Leu Gln Glu Lys Val Glu Ile Lys Gln Leu Asn His
  1               5                  10

<210> SEQ ID NO 548
<211> LENGTH: 42
<212> TYPE: PRT
<213> ORGANISM: Homo sapiens

<400> SEQUENCE: 548

Lys Thr Leu Phe Pro Leu Ile Glu Ala Lys Lys Lys Asp Gln Val Thr
  1               5                  10                  15

Ala Gln Glu Ile Phe Gln Asp Asn His Glu Asp Gly Pro Thr Ala Lys
             20                  25                  30

Lys Leu Lys Thr Glu Gln Gly Gly Ala His
         35                  40

<210> SEQ ID NO 549
<211> LENGTH: 25
<212> TYPE: PRT
<213> ORGANISM: Homo sapiens

<400> SEQUENCE: 549

Lys Thr Leu Phe Pro Leu Ile Glu Ala Lys Lys Lys Asp Gln Val Thr
  1               5                  10                  15

Ala Gln Glu Ile Phe Gln Asp Asn His
             20                  25

<210> SEQ ID NO 550
<211> LENGTH: 14
<212> TYPE: PRT
```

```
<213> ORGANISM: Homo sapiens

<400> SEQUENCE: 550

Lys Leu Cys Val Phe Lys Lys Ile Glu Arg His Ser Ile His
 1               5                  10

<210> SEQ ID NO 551
<211> LENGTH: 11
<212> TYPE: PRT
<213> ORGANISM: Homo sapiens

<400> SEQUENCE: 551

Lys Leu Cys Val Phe Lys Lys Ile Glu Arg His
 1               5                  10

<210> SEQ ID NO 552
<211> LENGTH: 22
<212> TYPE: PRT
<213> ORGANISM: Homo sapiens

<400> SEQUENCE: 552

His Gly Pro Ser Phe Pro Leu Lys Gly Ile Thr Glu Gln Gln Lys Glu
 1               5                  10                  15

Gly Leu Glu Ile Val Lys
            20

<210> SEQ ID NO 553
<211> LENGTH: 15
<212> TYPE: PRT
<213> ORGANISM: Homo sapiens

<400> SEQUENCE: 553

His Gly Pro Ser Phe Pro Leu Lys Gly Ile Thr Glu Gln Gln Lys
 1               5                  10                  15

<210> SEQ ID NO 554
<211> LENGTH: 13
<212> TYPE: PRT
<213> ORGANISM: Homo sapiens

<400> SEQUENCE: 554

His Thr Leu Leu Lys Ile Leu Ser Thr Phe Leu Phe Lys
 1               5                  10

<210> SEQ ID NO 555
<211> LENGTH: 14
<212> TYPE: PRT
<213> ORGANISM: Homo sapiens

<400> SEQUENCE: 555

His Leu Leu Gly Asn Asn Asp Lys Asn Leu Leu Pro Ser Lys
 1               5                  10

<210> SEQ ID NO 556
<211> LENGTH: 19
<212> TYPE: PRT
<213> ORGANISM: Homo sapiens

<400> SEQUENCE: 556

His Arg His Glu Gly Val Phe Ile Cys Arg Gly Lys Glu Asp Ala Leu
 1               5                  10                  15

Val Thr Lys
```

```
<210> SEQ ID NO 557
<211> LENGTH: 17
<212> TYPE: PRT
<213> ORGANISM: Homo sapiens

<400> SEQUENCE: 557

His Glu Gly Val Phe Ile Cys Arg Gly Lys Glu Asp Ala Leu Val Thr
 1               5                  10                  15
Lys

<210> SEQ ID NO 558
<211> LENGTH: 20
<212> TYPE: PRT
<213> ORGANISM: Homo sapiens

<400> SEQUENCE: 558

His Ser Gly Gly Asn Arg Gly Arg Gly Arg Gly Gly Lys Arg Gly Asn
 1               5                  10                  15
Gln Ser Gly Lys
            20

<210> SEQ ID NO 559
<211> LENGTH: 15
<212> TYPE: PRT
<213> ORGANISM: Homo sapiens

<400> SEQUENCE: 559

Lys Arg Gly Asn Gln Ser Gly Lys Asn Val Met Val Glu Pro His
 1               5                  10                  15

<210> SEQ ID NO 560
<211> LENGTH: 17
<212> TYPE: PRT
<213> ORGANISM: Homo sapiens

<400> SEQUENCE: 560

Lys Arg Gly Asn Gln Ser Gly Lys Asn Val Met Val Glu Pro His Arg
 1               5                  10                  15
His

<210> SEQ ID NO 561
<211> LENGTH: 23
<212> TYPE: PRT
<213> ORGANISM: Homo sapiens

<400> SEQUENCE: 561

Lys Lys Met Gln Gln Glu Asn Met Lys Pro Gln Glu Gln Leu Thr Leu
 1               5                  10                  15
Glu Pro Tyr Glu Arg Asp His
            20

<210> SEQ ID NO 562
<211> LENGTH: 22
<212> TYPE: PRT
<213> ORGANISM: Homo sapiens

<400> SEQUENCE: 562

Lys Met Gln Gln Glu Asn Met Lys Pro Gln Glu Gln Leu Thr Leu Glu
 1               5                  10                  15
Pro Tyr Glu Arg Asp His
            20
```

<210> SEQ ID NO 563
<211> LENGTH: 16
<212> TYPE: PRT
<213> ORGANISM: Homo sapiens

<400> SEQUENCE: 563

His Ala Tyr Pro Glu Asp Ala Glu Asn Lys Glu Lys Glu Thr Ala Lys
 1               5                  10                  15

<210> SEQ ID NO 564
<211> LENGTH: 22
<212> TYPE: PRT
<213> ORGANISM: Homo sapiens

<400> SEQUENCE: 564

Lys Glu Ala Asn Val Lys Cys Pro Gln Ile Val Ile Ala Phe Tyr Glu
 1               5                  10                  15

Glu Arg Leu Thr Trp His
            20

<210> SEQ ID NO 565
<211> LENGTH: 25
<212> TYPE: PRT
<213> ORGANISM: Homo sapiens

<400> SEQUENCE: 565

Lys Val Leu Asp Arg Arg Val Val Lys Gly Gln Val Glu Tyr Leu Leu
 1               5                  10                  15

Lys Trp Lys Gly Phe Ser Glu Glu His
            20                  25

<210> SEQ ID NO 566
<211> LENGTH: 17
<212> TYPE: PRT
<213> ORGANISM: Homo sapiens

<400> SEQUENCE: 566

Lys Gly Gln Val Glu Tyr Leu Leu Lys Trp Lys Gly Phe Ser Glu Glu
 1               5                  10                  15

His

<210> SEQ ID NO 567
<211> LENGTH: 32
<212> TYPE: PRT
<213> ORGANISM: Homo sapiens

<400> SEQUENCE: 567

Lys Ser Glu Val Ala Ala Gly Val Lys Lys Ser Gly Pro Leu Pro Ser
 1               5                  10                  15

Ala Glu Arg Leu Glu Asn Val Leu Phe Gly Pro His Asp Cys Ser His
            20                  25                  30

<210> SEQ ID NO 568
<211> LENGTH: 28
<212> TYPE: PRT
<213> ORGANISM: Homo sapiens

<400> SEQUENCE: 568

Lys Ser Glu Val Ala Ala Gly Val Lys Lys Ser Gly Pro Leu Pro Ser
 1               5                  10                  15

Ala Glu Arg Leu Glu Asn Val Leu Phe Gly Pro His
            20                  25

```
<210> SEQ ID NO 569
<211> LENGTH: 28
<212> TYPE: PRT
<213> ORGANISM: Homo sapiens

<400> SEQUENCE: 569

Lys Ala Ala Glu Tyr Gly Lys Lys Ala Lys Ser Glu Thr Phe Arg Leu
 1               5                  10                  15

Leu His Ala Lys Asn Ile Ile Arg Pro Gln Leu Lys
            20                  25

<210> SEQ ID NO 570
<211> LENGTH: 20
<212> TYPE: PRT
<213> ORGANISM: Homo sapiens

<400> SEQUENCE: 570

Lys Ala Ala Glu Tyr Gly Lys Lys Ala Lys Ser Glu Thr Phe Arg Leu
 1               5                  10                  15

Leu His Ala Lys
            20

<210> SEQ ID NO 571
<211> LENGTH: 11
<212> TYPE: PRT
<213> ORGANISM: Homo sapiens

<400> SEQUENCE: 571

Lys Ser Glu Thr Phe Arg Leu Leu His Ala Lys
 1               5                  10

<210> SEQ ID NO 572
<211> LENGTH: 11
<212> TYPE: PRT
<213> ORGANISM: Homo sapiens

<400> SEQUENCE: 572

His Ala Lys Asn Ile Ile Arg Pro Gln Leu Lys
 1               5                  10

<210> SEQ ID NO 573
<211> LENGTH: 12
<212> TYPE: PRT
<213> ORGANISM: Homo sapiens

<400> SEQUENCE: 573

His Met Met Leu Lys Ile Ala Glu Glu Leu Pro Lys
 1               5                  10

<210> SEQ ID NO 574
<211> LENGTH: 17
<212> TYPE: PRT
<213> ORGANISM: Homo sapiens

<400> SEQUENCE: 574

His Ser Leu Asp His Leu Leu Lys Leu Tyr Cys Asn Val Asp Ser Asn
 1               5                  10                  15

Lys

<210> SEQ ID NO 575
<211> LENGTH: 13
<212> TYPE: PRT
<213> ORGANISM: Homo sapiens
```

```
<400> SEQUENCE: 575

His Leu Leu Lys Leu Tyr Cys Asn Val Asp Ser Asn Lys
1               5                   10

<210> SEQ ID NO 576
<211> LENGTH: 10
<212> TYPE: PRT
<213> ORGANISM: Homo sapiens

<400> SEQUENCE: 576

Lys Ala Lys Glu Arg Leu Glu Ala Lys His
1               5                   10

<210> SEQ ID NO 577
<211> LENGTH: 8
<212> TYPE: PRT
<213> ORGANISM: Homo sapiens

<400> SEQUENCE: 577

Lys Asp Arg Gln His Thr Leu Lys
1               5

<210> SEQ ID NO 578
<211> LENGTH: 9
<212> TYPE: PRT
<213> ORGANISM: Homo sapiens

<400> SEQUENCE: 578

Lys Asp Arg Gln His Thr Leu Lys His
1               5

<210> SEQ ID NO 579
<211> LENGTH: 12
<212> TYPE: PRT
<213> ORGANISM: Homo sapiens

<400> SEQUENCE: 579

Lys Glu Thr Cys Ser Glu Lys Ser Thr Asn Leu His
1               5                   10

<210> SEQ ID NO 580
<211> LENGTH: 16
<212> TYPE: PRT
<213> ORGANISM: Homo sapiens

<400> SEQUENCE: 580

Lys Thr Glu Glu Ile Ser Glu Val Lys Met Asp Ala Glu Phe Gly His
1               5                   10                  15

<210> SEQ ID NO 581
<211> LENGTH: 24
<212> TYPE: PRT
<213> ORGANISM: Homo sapiens

<400> SEQUENCE: 581

Lys Thr Glu Glu Ile Ser Glu Val Lys Met Asp Ala Glu Phe Gly His
1               5                   10                  15
Asp Ser Gly Phe Glu Val Arg His
            20

<210> SEQ ID NO 582
<211> LENGTH: 17
<212> TYPE: PRT
```

-continued

<213> ORGANISM: Homo sapiens

<400> SEQUENCE: 582

Lys Lys Tyr Val Arg Ala Glu Gln Lys Asp Arg Gln His Thr Leu Lys
 1               5                  10                  15

His

<210> SEQ ID NO 583
<211> LENGTH: 16
<212> TYPE: PRT
<213> ORGANISM: Homo sapiens

<400> SEQUENCE: 583

Lys Tyr Val Arg Ala Glu Gln Lys Asp Arg Gln His Thr Leu Lys His
 1               5                  10                  15

<210> SEQ ID NO 584
<211> LENGTH: 13
<212> TYPE: PRT
<213> ORGANISM: Homo sapiens

<400> SEQUENCE: 584

Lys Lys Tyr Val Arg Ala Glu Gln Lys Asp Arg Gln His
 1               5                  10

<210> SEQ ID NO 585
<211> LENGTH: 13
<212> TYPE: PRT
<213> ORGANISM: Homo sapiens

<400> SEQUENCE: 585

Lys Tyr Val Arg Ala Glu Gln Lys Asp Arg Gln His Thr
 1               5                  10

<210> SEQ ID NO 586
<211> LENGTH: 16
<212> TYPE: PRT
<213> ORGANISM: Homo sapiens

<400> SEQUENCE: 586

His His Val Phe Asn Met Leu Lys Lys Tyr Val Arg Ala Glu Gln Lys
 1               5                  10                  15

<210> SEQ ID NO 587
<211> LENGTH: 15
<212> TYPE: PRT
<213> ORGANISM: Homo sapiens

<400> SEQUENCE: 587

His Val Phe Asn Met Leu Lys Lys Tyr Val Arg Ala Glu Gln Lys
 1               5                  10                  15

<210> SEQ ID NO 588
<211> LENGTH: 24
<212> TYPE: PRT
<213> ORGANISM: Homo sapiens

<400> SEQUENCE: 588

His His Val Phe Asn Met Leu Lys Lys Tyr Val Arg Ala Glu Gln Lys
 1               5                  10                  15

Asp Arg Gln His Thr Leu Lys His
                20

```
<210> SEQ ID NO 589
<211> LENGTH: 23
<212> TYPE: PRT
<213> ORGANISM: Homo sapiens

<400> SEQUENCE: 589

His Val Phe Asn Met Leu Lys Lys Tyr Val Arg Ala Glu Gln Lys Asp
 1               5                  10                  15

Arg Gln His Thr Leu Lys His
            20

<210> SEQ ID NO 590
<211> LENGTH: 15
<212> TYPE: PRT
<213> ORGANISM: Homo sapiens

<400> SEQUENCE: 590

His Ala His Phe Gln Lys Ala Lys Glu Arg Leu Glu Ala Lys His
 1               5                  10                  15

<210> SEQ ID NO 591
<211> LENGTH: 14
<212> TYPE: PRT
<213> ORGANISM: Homo sapiens

<400> SEQUENCE: 591

His Ala His Phe Gln Lys Ala Lys Glu Arg Leu Glu Ala Lys
 1               5                  10

<210> SEQ ID NO 592
<211> LENGTH: 12
<212> TYPE: PRT
<213> ORGANISM: Homo sapiens

<400> SEQUENCE: 592

His Phe Gln Lys Ala Lys Glu Arg Leu Glu Ala Lys
 1               5                  10

<210> SEQ ID NO 593
<211> LENGTH: 30
<212> TYPE: PRT
<213> ORGANISM: Homo sapiens

<400> SEQUENCE: 593

His Gln Glu Arg Met Asp Val Cys Glu Thr His Leu His Trp His Thr
 1               5                  10                  15

Val Ala Lys Glu Thr Cys Ser Glu Lys Ser Thr Asn Leu His
            20                  25                  30

<210> SEQ ID NO 594
<211> LENGTH: 25
<212> TYPE: PRT
<213> ORGANISM: Homo sapiens

<400> SEQUENCE: 594

His Gln Glu Arg Met Asp Val Cys Glu Thr His Leu His Trp His Thr
 1               5                  10                  15

Val Ala Lys Glu Thr Cys Ser Glu Lys
            20                  25

<210> SEQ ID NO 595
<211> LENGTH: 13
<212> TYPE: PRT
<213> ORGANISM: Homo sapiens
```

```
<400> SEQUENCE: 595

His Trp His Thr Val Ala Lys Glu Thr Cys Ser Glu Lys
 1               5                  10

<210> SEQ ID NO 596
<211> LENGTH: 11
<212> TYPE: PRT
<213> ORGANISM: Homo sapiens

<400> SEQUENCE: 596

His Thr Val Ala Lys Glu Thr Cys Ser Glu Lys
 1               5                  10

<210> SEQ ID NO 597
<211> LENGTH: 15
<212> TYPE: PRT
<213> ORGANISM: Homo sapiens

<400> SEQUENCE: 597

His Leu His Trp His Thr Val Ala Lys Glu Thr Cys Ser Glu Lys
 1               5                  10                  15

<210> SEQ ID NO 598
<211> LENGTH: 23
<212> TYPE: PRT
<213> ORGANISM: Homo sapiens

<400> SEQUENCE: 598

His Met Asn Val Gln Asn Gly Lys Trp Glu Ser Asp Pro Ser Gly Thr
 1               5                  10                  15

Lys Thr Cys Ile Gly Thr Lys
                20

<210> SEQ ID NO 599
<211> LENGTH: 17
<212> TYPE: PRT
<213> ORGANISM: Homo sapiens

<400> SEQUENCE: 599

His Met Asn Val Gln Asn Gly Lys Trp Glu Ser Asp Pro Ser Gly Thr
 1               5                  10                  15

Lys

<210> SEQ ID NO 600
<211> LENGTH: 19
<212> TYPE: PRT
<213> ORGANISM: Human immunodeficiency virus

<400> SEQUENCE: 600

His Cys Leu Val Cys Phe Gln Lys Lys Gly Leu Gly Ile Ser Tyr Gly
 1               5                  10                  15

Arg Lys Lys

<210> SEQ ID NO 601
<211> LENGTH: 27
<212> TYPE: PRT
<213> ORGANISM: Triticum aestivum

<400> SEQUENCE: 601

His Lys Asp Arg Leu Thr Lys Lys Val Val Asp Ile Ala Arg Glu Val
 1               5                  10                  15
```

```
Ala Lys Val Asp Val Pro Glu Tyr Arg Arg His
            20                  25

<210> SEQ ID NO 602
<211> LENGTH: 27
<212> TYPE: PRT
<213> ORGANISM: Triticum aestivum

<400> SEQUENCE: 602

His Lys Glu Arg Leu Asp Arg Lys Val Val Asp Val Ala Arg Glu Val
  1               5                  10                  15

Ala Lys Val Glu Val Pro Ser Tyr Arg Arg His
            20                  25

<210> SEQ ID NO 603
<211> LENGTH: 27
<212> TYPE: PRT
<213> ORGANISM: Triticum aestivum

<400> SEQUENCE: 603

His Lys Glu Arg Leu Asp Arg Lys Val Val Asp Val Ala Arg Glu Val
  1               5                  10                  15

Ala Lys Met Glu Val Pro Ser Tyr Arg Arg His
            20                  25

<210> SEQ ID NO 604
<211> LENGTH: 23
<212> TYPE: PRT
<213> ORGANISM: Triticum aestivum

<400> SEQUENCE: 604

His Leu Gln Pro Lys Trp Lys Pro Ser Leu Ser Trp Phe Lys Asn Ala
  1               5                  10                  15

Glu Ser Arg Leu Asn His His
            20

<210> SEQ ID NO 605
<211> LENGTH: 14
<212> TYPE: PRT
<213> ORGANISM: Triticum aestivum

<400> SEQUENCE: 605

His Leu Gln Pro Lys Trp Lys Pro Ser Leu Ser Trp Phe Lys
  1               5                  10

<210> SEQ ID NO 606
<211> LENGTH: 19
<212> TYPE: PRT
<213> ORGANISM: Triticum aestivum

<400> SEQUENCE: 606

Lys Trp Lys Pro Ser Leu Ser Trp Phe Lys Asn Ala Glu Ser Arg Leu
  1               5                  10                  15

Asn His His

<210> SEQ ID NO 607
<211> LENGTH: 18
<212> TYPE: PRT
<213> ORGANISM: Triticum aestivum

<400> SEQUENCE: 607

Lys Trp Lys Pro Ser Leu Ser Trp Phe Lys Asn Ala Glu Ser Arg Leu
  1               5                  10                  15
```

Asn His

<210> SEQ ID NO 608
<211> LENGTH: 17
<212> TYPE: PRT
<213> ORGANISM: Triticum aestivum

<400> SEQUENCE: 608

Lys Pro Ser Leu Ser Trp Phe Lys Asn Ala Glu Ser Arg Leu Asn His
 1               5                  10                  15

His

<210> SEQ ID NO 609
<211> LENGTH: 16
<212> TYPE: PRT
<213> ORGANISM: Triticum aestivum

<400> SEQUENCE: 609

Lys Pro Ser Leu Ser Trp Phe Lys Asn Ala Glu Ser Arg Leu Asn His
 1               5                  10                  15

<210> SEQ ID NO 610
<211> LENGTH: 32
<212> TYPE: PRT
<213> ORGANISM: Triticum aestivum

<400> SEQUENCE: 610

His His Ala Ile Ala Leu Gly Leu His Thr Thr Thr Leu Ile Leu Val
 1               5                  10                  15

Lys Gly Ala Leu Asp Ala Arg Gly Ser Lys Leu Met Pro Asp Lys Lys
            20                  25                  30

<210> SEQ ID NO 611
<211> LENGTH: 31
<212> TYPE: PRT
<213> ORGANISM: Triticum aestivum

<400> SEQUENCE: 611

His Ala Ile Ala Leu Gly Leu His Thr Thr Thr Leu Ile Leu Val Lys
 1               5                  10                  15

Gly Ala Leu Asp Ala Arg Gly Ser Lys Leu Met Pro Asp Lys Lys
            20                  25                  30

<210> SEQ ID NO 612
<211> LENGTH: 26
<212> TYPE: PRT
<213> ORGANISM: Triticum aestivum

<400> SEQUENCE: 612

His His Ala Ile Ala Leu Gly Leu His Thr Thr Thr Leu Ile Leu Val
 1               5                  10                  15

Lys Gly Ala Leu Asp Ala Arg Gly Ser Lys
            20                  25

<210> SEQ ID NO 613
<211> LENGTH: 25
<212> TYPE: PRT
<213> ORGANISM: Triticum aestivum

<400> SEQUENCE: 613

His Ala Ile Ala Leu Gly Leu His Thr Thr Thr Leu Ile Leu Val Lys
 1               5                  10                  15

Gly Ala Leu Asp Ala Arg Gly Ser Lys
            20                  25

<210> SEQ ID NO 614
<211> LENGTH: 24
<212> TYPE: PRT
<213> ORGANISM: Triticum aestivum

<400> SEQUENCE: 614

His Thr Thr Thr Leu Ile Leu Val Lys Gly Ala Leu Asp Ala Arg Gly
 1               5                  10                  15

Ser Lys Leu Met Pro Asp Lys Lys
            20

<210> SEQ ID NO 615
<211> LENGTH: 23
<212> TYPE: PRT
<213> ORGANISM: Triticum aestivum

<400> SEQUENCE: 615

His Thr Thr Thr Leu Ile Leu Val Lys Gly Ala Leu Asp Ala Arg Gly
 1               5                  10                  15

Ser Lys Leu Met Pro Asp Lys
            20

<210> SEQ ID NO 616
<211> LENGTH: 18
<212> TYPE: PRT
<213> ORGANISM: Triticum aestivum

<400> SEQUENCE: 616

His Thr Thr Thr Leu Ile Leu Val Lys Gly Ala Leu Asp Ala Arg Gly
 1               5                  10                  15

Ser Lys

<210> SEQ ID NO 617
<211> LENGTH: 44
<212> TYPE: PRT
<213> ORGANISM: Triticum aestivum

<400> SEQUENCE: 617

His His His Leu Ala Ile Ala Ile Leu Phe Leu Ile Ala Gly His Met
 1               5                  10                  15

Tyr Arg Thr Asn Trp Gly Ile Gly His Gly Leu Lys Asp Ile Leu Glu
            20                  25                  30

Ala His Lys Gly Pro Phe Thr Gly Gln Gly His Lys
        35                  40

<210> SEQ ID NO 618
<211> LENGTH: 43
<212> TYPE: PRT
<213> ORGANISM: Triticum aestivum

<400> SEQUENCE: 618

His His Leu Ala Ile Ala Ile Leu Phe Leu Ile Ala Gly His Met Tyr
 1               5                  10                  15

Arg Thr Asn Trp Gly Ile Gly His Gly Leu Lys Asp Ile Leu Glu Ala
            20                  25                  30

His Lys Gly Pro Phe Thr Gly Gln Gly His Lys
        35                  40

```
<210> SEQ ID NO 619
<211> LENGTH: 42
<212> TYPE: PRT
<213> ORGANISM: Triticum aestivum

<400> SEQUENCE: 619

His Leu Ala Ile Ala Ile Leu Phe Leu Ile Ala Gly His Met Tyr Arg
 1               5                  10                  15

Thr Asn Trp Gly Ile Gly His Gly Leu Lys Asp Ile Leu Glu Ala His
            20                  25                  30

Lys Gly Pro Phe Thr Gly Gln Gly His Lys
        35                  40

<210> SEQ ID NO 620
<211> LENGTH: 30
<212> TYPE: PRT
<213> ORGANISM: Triticum aestivum

<400> SEQUENCE: 620

His Met Tyr Arg Thr Asn Trp Gly Ile Gly His Gly Leu Lys Asp Ile
 1               5                  10                  15

Leu Glu Ala His Lys Gly Pro Phe Thr Gly Gln Gly His Lys
            20                  25                  30

<210> SEQ ID NO 621
<211> LENGTH: 20
<212> TYPE: PRT
<213> ORGANISM: Triticum aestivum

<400> SEQUENCE: 621

His Gly Leu Lys Asp Ile Leu Glu Ala His Lys Gly Pro Phe Thr Gly
 1               5                  10                  15

Gln Gly His Lys
            20

<210> SEQ ID NO 622
<211> LENGTH: 17
<212> TYPE: PRT
<213> ORGANISM: Triticum aestivum

<400> SEQUENCE: 622

Lys Asp Ile Leu Glu Ala His Lys Gly Pro Phe Thr Gly Gln Gly His
 1               5                  10                  15

Lys

<210> SEQ ID NO 623
<211> LENGTH: 11
<212> TYPE: PRT
<213> ORGANISM: Triticum aestivum

<400> SEQUENCE: 623

His Lys Gly Pro Phe Thr Gly Gln Gly His Lys
 1               5                  10

<210> SEQ ID NO 624
<211> LENGTH: 10
<212> TYPE: PRT
<213> ORGANISM: Triticum aestivum

<400> SEQUENCE: 624

Lys Gly Pro Phe Thr Gly Gln Gly His Lys
 1               5                  10
```

<210> SEQ ID NO 625
<211> LENGTH: 16
<212> TYPE: PRT
<213> ORGANISM: Oryza sativa

<400> SEQUENCE: 625

Lys Phe Pro Asp Val Ile His Ala Phe Lys Pro Asn Pro Arg Ser His
 1               5                  10                  15

<210> SEQ ID NO 626
<211> LENGTH: 10
<212> TYPE: PRT
<213> ORGANISM: Oryza sativa

<400> SEQUENCE: 626

Lys Phe Pro Asp Val Ile His Ala Phe Lys
 1               5                  10

<210> SEQ ID NO 627
<211> LENGTH: 10
<212> TYPE: PRT
<213> ORGANISM: Oryza sativa

<400> SEQUENCE: 627

Lys Ala Arg Tyr Val Lys Phe His Trp Lys
 1               5                  10

<210> SEQ ID NO 628
<211> LENGTH: 33
<212> TYPE: PRT
<213> ORGANISM: Oryza sativa

<400> SEQUENCE: 628

His Pro Lys Val Ser Pro Glu Leu Arg Ala Ile Trp Val Asn Tyr Leu
 1               5                  10                  15

Ser Gln Cys Asp Glu Ser Leu Gly Val Lys Ile Ala Asn Leu Asn Val
             20                  25                  30

Lys

<210> SEQ ID NO 629
<211> LENGTH: 45
<212> TYPE: PRT
<213> ORGANISM: Oryza sativa

<400> SEQUENCE: 629

His Arg Asp Glu Glu Val Asp Tyr Tyr Pro Ser Arg His Ala Pro Leu
 1               5                  10                  15

Arg His Ala Pro Pro Thr Pro Ile Thr Pro Arg Pro Val Val Gly Arg
             20                  25                  30

Arg Gln Lys Ala Thr Ile His Lys Gln Asn Asp Phe Lys
         35                  40                  45

<210> SEQ ID NO 630
<211> LENGTH: 11
<212> TYPE: PRT
<213> ORGANISM: Oryza sativa

<400> SEQUENCE: 630

Lys Ala Thr Ile His Lys Gln Asn Asp Phe Lys
 1               5                  10

```
<210> SEQ ID NO 631
<211> LENGTH: 27
<212> TYPE: PRT
<213> ORGANISM: Oryza sativa

<400> SEQUENCE: 631

His Ala Pro Pro Thr Pro Ile Pro Arg Pro Val Gly Arg Arg Gln
 1               5                  10                  15

Lys Ala Thr Ile His Lys Gln Asn Asp Phe Lys
            20                  25

<210> SEQ ID NO 632
<211> LENGTH: 49
<212> TYPE: PRT
<213> ORGANISM: Oryza sativa

<400> SEQUENCE: 632

Lys Phe Arg Pro Ser Ser Ser Phe Asp Thr Lys Thr Thr Thr Thr Asn
 1               5                  10                  15

Ala Gly Ala Pro Val Trp Asn Asp Asn Glu Ala Leu Thr Val Gly Pro
            20                  25                  30

Arg Gly Pro Ile Leu Leu Glu Asp Tyr His Leu Ile Glu Lys Val Ala
        35                  40                  45

His

<210> SEQ ID NO 633
<211> LENGTH: 42
<212> TYPE: PRT
<213> ORGANISM: Oryza sativa

<400> SEQUENCE: 633

Lys Phe Arg Pro Ser Ser Ser Phe Asp Thr Lys Thr Thr Thr Thr Asn
 1               5                  10                  15

Ala Gly Ala Pro Val Trp Asn Asp Asn Glu Ala Leu Thr Val Gly Pro
            20                  25                  30

Arg Gly Pro Ile Leu Leu Glu Asp Tyr His
        35                  40

<210> SEQ ID NO 634
<211> LENGTH: 9
<212> TYPE: PRT
<213> ORGANISM: Oryza sativa

<400> SEQUENCE: 634

Lys Val Lys Ala His Phe Gln Lys His
 1               5

<210> SEQ ID NO 635
<211> LENGTH: 8
<212> TYPE: PRT
<213> ORGANISM: Oryza sativa

<400> SEQUENCE: 635

Lys Val Lys Ala His Phe Gln Lys
 1               5

<210> SEQ ID NO 636
<211> LENGTH: 12
<212> TYPE: PRT
<213> ORGANISM: Oryza sativa

<400> SEQUENCE: 636
```

-continued

```
Lys Asp Tyr Glu Ile Asp Lys Asp Leu Ile His
1               5                   10
```

<210> SEQ ID NO 637
<211> LENGTH: 20
<212> TYPE: PRT
<213> ORGANISM: Oryza sativa

<400> SEQUENCE: 637

```
His Met Lys Gln Cys Phe Ala Phe Cys Ala Val Phe Pro Lys Asp Tyr
1               5                   10                  15

Glu Ile Asp Lys
            20
```

<210> SEQ ID NO 638
<211> LENGTH: 14
<212> TYPE: PRT
<213> ORGANISM: Oryza sativa

<400> SEQUENCE: 638

```
His Met Lys Gln Cys Phe Ala Phe Cys Ala Val Phe Pro Lys
1               5                   10
```

<210> SEQ ID NO 639
<211> LENGTH: 49
<212> TYPE: PRT
<213> ORGANISM: Oryza sativa

<400> SEQUENCE: 639

```
His Val Phe Trp Glu Leu Val Trp Arg Ser Phe Phe Gln Asn Val Lys
1               5                   10                  15

Gln Ile Gly Ser Ile Phe Gln Arg Lys Val Tyr Arg Tyr Gly Gln Ser
                20                  25                  30

Asp Val Thr Thr Ser Lys Ile His Asp Leu Met His Asp Leu Ala Val
            35                  40                  45

His
```

<210> SEQ ID NO 640
<211> LENGTH: 34
<212> TYPE: PRT
<213> ORGANISM: Oryza sativa

<400> SEQUENCE: 640

```
Lys Gln Ile Gly Ser Ile Phe Gln Arg Lys Val Tyr Arg Tyr Gly Gln
1               5                   10                  15

Ser Asp Val Thr Thr Ser Lys Ile His Asp Leu Met His Asp Leu Ala
                20                  25                  30

Val His
```

<210> SEQ ID NO 641
<211> LENGTH: 29
<212> TYPE: PRT
<213> ORGANISM: Oryza sativa

<400> SEQUENCE: 641

```
Lys Gln Ile Gly Ser Ile Phe Gln Arg Lys Val Tyr Arg Tyr Gly Gln
1               5                   10                  15

Ser Asp Val Thr Thr Ser Lys Ile His Asp Leu Met His
                20                  25
```

<210> SEQ ID NO 642

```
<211> LENGTH: 25
<212> TYPE: PRT
<213> ORGANISM: Oryza sativa

<400> SEQUENCE: 642

Lys Gln Ile Gly Ser Ile Phe Gln Arg Lys Val Tyr Arg Tyr Gly Gln
 1               5                  10                  15

Ser Asp Val Thr Thr Ser Lys Ile His
            20                  25

<210> SEQ ID NO 643
<211> LENGTH: 9
<212> TYPE: PRT
<213> ORGANISM: Oryza sativa

<400> SEQUENCE: 643

Lys His Gly Val Ser Ala Gly Ile Lys
 1               5

<210> SEQ ID NO 644
<211> LENGTH: 15
<212> TYPE: PRT
<213> ORGANISM: Oryza sativa

<400> SEQUENCE: 644

His Thr Val Phe Asp Tyr Gly Lys Met Arg Val Gly Phe Ala Lys
 1               5                  10                  15

<210> SEQ ID NO 645
<211> LENGTH: 17
<212> TYPE: PRT
<213> ORGANISM: Oryza sativa

<400> SEQUENCE: 645

His Ser Arg Tyr Lys Ser Gly Gln Ser Ser Thr Tyr Gln Lys Asn Gly
 1               5                  10                  15

Lys

<210> SEQ ID NO 646
<211> LENGTH: 29
<212> TYPE: PRT
<213> ORGANISM: Oryza sativa

<400> SEQUENCE: 646

Lys Gln Glu Ala Met Val Leu Lys Gln Glu Ile Asn Leu Leu Gln Lys
 1               5                  10                  15

Gly Leu Arg Tyr Ile Tyr Gly Asn Arg Ala Asn Glu His
            20                  25

<210> SEQ ID NO 647
<211> LENGTH: 22
<212> TYPE: PRT
<213> ORGANISM: Oryza sativa

<400> SEQUENCE: 647

Lys Gln Glu Ile Asn Leu Leu Gln Lys Gly Leu Arg Tyr Ile Tyr Gly
 1               5                  10                  15

Asn Arg Ala Asn Glu His
            20

<210> SEQ ID NO 648
<211> LENGTH: 38
<212> TYPE: PRT
```

```
<213> ORGANISM: Oryza sativa

<400> SEQUENCE: 648

Lys Ser Lys Glu Gly Met Leu Lys Ala Ala Asn Glu Ile Leu Gln Glu
 1               5                  10                  15

Lys Ile Val Glu Gln Asn Gly Leu Ile Asp Val Gly Met Met Val Ala
             20                  25                  30

Asp Gln Gln Asn Gly His
         35

<210> SEQ ID NO 649
<211> LENGTH: 31
<212> TYPE: PRT
<213> ORGANISM: Oryza sativa

<400> SEQUENCE: 649

Lys Ala Ala Asn Glu Ile Leu Gln Glu Lys Ile Val Glu Gln Asn Gly
 1               5                  10                  15

Leu Ile Asp Val Gly Met Met Val Ala Asp Gln Gln Asn Gly His
             20                  25                  30

<210> SEQ ID NO 650
<211> LENGTH: 11
<212> TYPE: PRT
<213> ORGANISM: Zea mays

<400> SEQUENCE: 650

Lys Val Leu Ala Ala His Arg Tyr Gly Ile Lys
 1               5                  10

<210> SEQ ID NO 651
<211> LENGTH: 17
<212> TYPE: PRT
<213> ORGANISM: Zea mays

<400> SEQUENCE: 651

Lys Leu Lys Ile Ala Met Lys His Leu Ile Pro Arg Val Leu Glu Gln
 1               5                  10                  15

His

<210> SEQ ID NO 652
<211> LENGTH: 8
<212> TYPE: PRT
<213> ORGANISM: Zea mays

<400> SEQUENCE: 652

Lys Leu Lys Ile Ala Met Lys His
 1               5

<210> SEQ ID NO 653
<211> LENGTH: 33
<212> TYPE: PRT
<213> ORGANISM: Zea mays

<400> SEQUENCE: 653

Lys Thr Ser Leu Ala Ser Ser Ile Ala Lys Ala Leu Asn Arg Lys Phe
 1               5                  10                  15

Ile Arg Ile Ser Leu Gly Gly Val Lys Asp Glu Ala Asp Ile Arg Gly
             20                  25                  30

His
```

```
<210> SEQ ID NO 654
<211> LENGTH: 24
<212> TYPE: PRT
<213> ORGANISM: Zea mays

<400> SEQUENCE: 654

Lys Ala Leu Asn Arg Lys Phe Ile Arg Ile Ser Leu Gly Gly Val Lys
 1               5                  10                  15

Asp Glu Ala Asp Ile Arg Gly His
            20

<210> SEQ ID NO 655
<211> LENGTH: 19
<212> TYPE: PRT
<213> ORGANISM: Zea mays

<400> SEQUENCE: 655

Lys Phe Ile Arg Ile Ser Leu Gly Gly Val Lys Asp Glu Ala Asp Ile
 1               5                  10                  15

Arg Gly His

<210> SEQ ID NO 656
<211> LENGTH: 37
<212> TYPE: PRT
<213> ORGANISM: Zea mays

<400> SEQUENCE: 656

Lys Val Arg Leu Ser Lys Ala Thr Glu Leu Val Asp Arg His Leu Gln
 1               5                  10                  15

Ser Ile Leu Val Ala Glu Lys Ile Thr Gln Lys Val Glu Gly Gln Leu
            20                  25                  30

Ser Lys Ser Gln Lys
        35

<210> SEQ ID NO 657
<211> LENGTH: 24
<212> TYPE: PRT
<213> ORGANISM: Zea mays

<400> SEQUENCE: 657

His Leu Gln Ser Ile Leu Val Ala Glu Lys Ile Thr Gln Lys Val Glu
 1               5                  10                  15

Gly Gln Leu Ser Lys Ser Gln Lys
            20

<210> SEQ ID NO 658
<211> LENGTH: 14
<212> TYPE: PRT
<213> ORGANISM: Zea mays

<400> SEQUENCE: 658

Lys Val Arg Leu Ser Lys Ala Thr Glu Leu Val Asp Arg His
 1               5                  10

<210> SEQ ID NO 659
<211> LENGTH: 34
<212> TYPE: PRT
<213> ORGANISM: Zea mays

<400> SEQUENCE: 659

Lys Val Gly Gly Ser Ala Val Glu Ser Ser Lys Gln Asp Thr Lys Asn
 1               5                  10                  15
```

```
Gly Lys Glu Pro Ile His Trp His Ser Lys Gly Val Ala Ala Arg Ala
            20                  25                  30

Leu His

<210> SEQ ID NO 660
<211> LENGTH: 24
<212> TYPE: PRT
<213> ORGANISM: Zea mays

<400> SEQUENCE: 660

Lys Val Gly Gly Ser Ala Val Glu Ser Ser Lys Gln Asp Thr Lys Asn
  1               5                  10                  15

Gly Lys Glu Pro Ile His Trp His
            20

<210> SEQ ID NO 661
<211> LENGTH: 22
<212> TYPE: PRT
<213> ORGANISM: Zea mays

<400> SEQUENCE: 661

Lys Val Gly Gly Ser Ala Val Glu Ser Ser Lys Gln Asp Thr Lys Asn
  1               5                  10                  15

Gly Lys Glu Pro Ile His
            20

<210> SEQ ID NO 662
<211> LENGTH: 24
<212> TYPE: PRT
<213> ORGANISM: Zea mays

<400> SEQUENCE: 662

Lys Gln Asp Thr Lys Asn Gly Lys Glu Pro Ile His Trp His Ser Lys
  1               5                  10                  15

Gly Val Ala Ala Arg Ala Leu His
            20

<210> SEQ ID NO 663
<211> LENGTH: 12
<212> TYPE: PRT
<213> ORGANISM: Zea mays

<400> SEQUENCE: 663

Lys Gln Asp Thr Lys Asn Gly Lys Glu Pro Ile His
  1               5                  10

<210> SEQ ID NO 664
<211> LENGTH: 33
<212> TYPE: PRT
<213> ORGANISM: Zea mays

<400> SEQUENCE: 664

His Arg Asp Leu Arg Arg Ala Arg Ala Ala Leu Asn Ile Val Pro
  1               5                  10                  15

Thr Ser Thr Gly Ala Ala Lys Ala Val Ser Leu Val Leu Pro Asn Leu
            20                  25                  30

Lys

<210> SEQ ID NO 665
<211> LENGTH: 18
<212> TYPE: PRT
<213> ORGANISM: Zea mays
```

-continued

<400> SEQUENCE: 665

Lys Val Leu Asp Gln Lys Phe Gly Ile Ile Lys Gly Thr Met Thr Thr
1               5                   10                  15

Thr His

<210> SEQ ID NO 666
<211> LENGTH: 16
<212> TYPE: PRT
<213> ORGANISM: Zea mays

<400> SEQUENCE: 666

His Ile Gln Ala Gly Ala Lys Lys Val Leu Ile Thr Ala Pro Gly Lys
1               5                   10                  15

<210> SEQ ID NO 667
<211> LENGTH: 28
<212> TYPE: PRT
<213> ORGANISM: Zea mays

<400> SEQUENCE: 667

His Gly Arg Gly Asp Ala Ser Pro Leu Asp Val Ile Ala Ile Asn Asp
1               5                   10                  15

Thr Gly Gly Val Lys Gln Ala Ser His Leu Leu Lys
            20                  25

<210> SEQ ID NO 668
<211> LENGTH: 51
<212> TYPE: PRT
<213> ORGANISM: Zea mays

<400> SEQUENCE: 668

Lys Val Arg Arg Val Leu Ser Lys Asp Tyr Ser Ser Leu Lys Gln Leu
1               5                   10                  15

Met Thr Leu Met Met Asp Asp Asp Ile Ser Lys His Leu Gln Ile Ile
            20                  25                  30

Glu Ser Gly Leu Glu Glu Arg Glu Asp Lys Val Trp Met Lys Glu Asn
        35                  40                  45

Ile Ile Lys
    50

<210> SEQ ID NO 669
<211> LENGTH: 28
<212> TYPE: PRT
<213> ORGANISM: Zea mays

<400> SEQUENCE: 669

Lys Val Arg Arg Val Leu Ser Lys Asp Tyr Ser Ser Leu Lys Gln Leu
1               5                   10                  15

Met Thr Leu Met Met Asp Asp Asp Ile Ser Lys His
            20                  25

<210> SEQ ID NO 670
<211> LENGTH: 24
<212> TYPE: PRT
<213> ORGANISM: Zea mays

<400> SEQUENCE: 670

His Leu Gln Ile Ile Glu Ser Gly Leu Glu Glu Arg Glu Asp Lys Val
1               5                   10                  15

Trp Met Lys Glu Asn Ile Ile Lys

-continued

```
                20

<210> SEQ ID NO 671
<211> LENGTH: 17
<212> TYPE: PRT
<213> ORGANISM: Zea mays

<400> SEQUENCE: 671

His Asp Leu Arg Glu Asn Ile Ile Met Lys Ala Asp Leu Ala Ser
 1               5                  10                  15

Lys

<210> SEQ ID NO 672
<211> LENGTH: 18
<212> TYPE: PRT
<213> ORGANISM: Zea mays

<400> SEQUENCE: 672

His Val Gln Asn Leu Glu Asn Val Ile Gly Lys Asp Glu Ala Leu Ala
 1               5                  10                  15

Ser Lys

<210> SEQ ID NO 673
<211> LENGTH: 21
<212> TYPE: PRT
<213> ORGANISM: Zea mays

<400> SEQUENCE: 673

Lys Lys Gln Gly Tyr Glu Leu Arg Gln Leu Lys Asp Leu Asn Glu Leu
 1               5                  10                  15

Gly Gly Ser Leu His
                20

<210> SEQ ID NO 674
<211> LENGTH: 20
<212> TYPE: PRT
<213> ORGANISM: Zea mays

<400> SEQUENCE: 674

Lys Gln Gly Tyr Glu Leu Arg Gln Leu Lys Asp Leu Asn Glu Leu Gly
 1               5                  10                  15

Gly Ser Leu His
            20

<210> SEQ ID NO 675
<211> LENGTH: 28
<212> TYPE: PRT
<213> ORGANISM: Zea mays

<400> SEQUENCE: 675

Lys Leu Tyr Leu Lys Ser Arg Leu Lys Glu Leu Ile Leu Glu Trp Ser
 1               5                  10                  15

Ser Glu Asn Gly Met Asp Ala Met Asn Ile Leu His
            20                  25

<210> SEQ ID NO 676
<211> LENGTH: 39
<212> TYPE: PRT
<213> ORGANISM: Zea mays

<400> SEQUENCE: 676

His Leu Gln Leu Leu Gln Leu Asn Gly Met Val Glu Arg Leu Pro Asn
```

-continued

```
                1               5                  10                 15
Lys Val Cys Asn Leu Ser Lys Leu Arg Tyr Leu Arg Gly Tyr Lys Asp
               20                 25                  30

Gln Ile Pro Asn Ile Gly Lys
         35

<210> SEQ ID NO 677
<211> LENGTH: 31
<212> TYPE: PRT
<213> ORGANISM: Zea mays

<400> SEQUENCE: 677

His Leu Gln Leu Leu Gln Leu Asn Gly Met Val Glu Arg Leu Pro Asn
  1               5                  10                  15

Lys Val Cys Asn Leu Ser Lys Leu Arg Tyr Leu Arg Gly Tyr Lys
               20                  25                  30

<210> SEQ ID NO 678
<211> LENGTH: 23
<212> TYPE: PRT
<213> ORGANISM: Zea mays

<400> SEQUENCE: 678

His Leu Gln Leu Leu Gln Leu Asn Gly Met Val Glu Arg Leu Pro Asn
  1               5                  10                  15

Lys Val Cys Asn Leu Ser Lys
               20

<210> SEQ ID NO 679
<211> LENGTH: 14
<212> TYPE: PRT
<213> ORGANISM: Zea mays

<400> SEQUENCE: 679

His Asn Ser Asn Lys Leu Pro Lys Ser Val Gly Glu Leu Lys
  1               5                  10

<210> SEQ ID NO 680
<211> LENGTH: 11
<212> TYPE: PRT
<213> ORGANISM: Zea mays

<400> SEQUENCE: 680

Lys Leu Pro Lys Ser Val Gly Glu Leu Lys His
  1               5                  10

<210> SEQ ID NO 681
<211> LENGTH: 18
<212> TYPE: PRT
<213> ORGANISM: Zea mays

<400> SEQUENCE: 681

His Leu Ser Val Arg Val Glu Ser Met Gln Lys His Lys Glu Ile Ile
  1               5                  10                  15

Tyr Lys

<210> SEQ ID NO 682
<211> LENGTH: 8
<212> TYPE: PRT
<213> ORGANISM: Zea mays

<400> SEQUENCE: 682
```

```
Lys His Lys Glu Ile Ile Tyr Lys
 1               5
```

<210> SEQ ID NO 683
<211> LENGTH: 23
<212> TYPE: PRT
<213> ORGANISM: Zea mays

<400> SEQUENCE: 683

```
Lys Leu Arg Asp Ile Leu Gln Glu Ser Gln Lys Phe Leu Leu Val Leu
 1               5                  10                  15

Asp Leu Ala Leu Phe Lys His
            20
```

<210> SEQ ID NO 684
<211> LENGTH: 46
<212> TYPE: PRT
<213> ORGANISM: Zea mays

<400> SEQUENCE: 684

```
His Ala Phe Ser Gly Ala Glu Ile Lys Asp Gln Leu Leu Arg Met Lys
 1               5                  10                  15

Leu Gln Asp Thr Ala Glu Cys Ile Ala Lys Arg Leu Gly Gln Cys Pro
            20                  25                  30

Leu Ala Ala Lys Val Leu Gly Ser Arg Met Cys Arg Arg Lys
        35                  40                  45
```

<210> SEQ ID NO 685
<211> LENGTH: 16
<212> TYPE: PRT
<213> ORGANISM: Zea mays

<400> SEQUENCE: 685

```
His Ala Phe Ser Gly Ala Glu Ile Lys Asp Gln Leu Leu Arg Met Lys
 1               5                  10                  15
```

<210> SEQ ID NO 686
<211> LENGTH: 47
<212> TYPE: PRT
<213> ORGANISM: Zea mays

<400> SEQUENCE: 686

```
Lys Leu Gln Asp Thr Ala Glu Glu Ile Ala Lys Arg Leu Gly Gln Cys
 1               5                  10                  15

Pro Leu Ala Ala Lys Val Leu Gly Ser Arg Met Cys Arg Arg Lys Asp
            20                  25                  30

Ile Ala Glu Trp Lys Ala Ala Asp Val Trp Phe Glu Lys Ser His
        35                  40                  45
```

<210> SEQ ID NO 687
<211> LENGTH: 27
<212> TYPE: PRT
<213> ORGANISM: Zea mays

<400> SEQUENCE: 687

```
Lys Val Leu Gly Ser Arg Met Cys Arg Arg Lys Asp Ile Ala Glu Trp
 1               5                  10                  15

Lys Ala Ala Asp Val Trp Phe Glu Lys Ser His
            20                  25
```

<210> SEQ ID NO 688
<211> LENGTH: 17

```
<212> TYPE: PRT
<213> ORGANISM: Zea mays

<400> SEQUENCE: 688

Lys Asp Ile Ala Glu Trp Lys Ala Ala Asp Val Trp Phe Glu Lys Ser
 1               5                  10                  15

His

<210> SEQ ID NO 689
<211> LENGTH: 11
<212> TYPE: PRT
<213> ORGANISM: Zea mays

<400> SEQUENCE: 689

Lys Ala Ala Asp Val Trp Phe Glu Lys Ser His
 1               5                  10

<210> SEQ ID NO 690
<211> LENGTH: 40
<212> TYPE: PRT
<213> ORGANISM: Zea mays

<400> SEQUENCE: 690

His Val Pro Thr Thr Thr Ser Leu Pro Thr Ser Lys Val Phe Gly Arg
 1               5                  10                  15

Asn Ser Asp Arg Asp Arg Ile Val Lys Phe Leu Leu Gly Lys Thr Thr
                20                  25                  30

Thr Ala Glu Ala Ser Ser Thr Lys
            35                  40

<210> SEQ ID NO 691
<211> LENGTH: 18
<212> TYPE: PRT
<213> ORGANISM: Zea mays

<400> SEQUENCE: 691

Lys Ala Ile Leu Thr Glu Ala Lys Gln Leu Arg Asp Leu Leu Gly Leu
 1               5                  10                  15

Pro His

<210> SEQ ID NO 692
<211> LENGTH: 29
<212> TYPE: PRT
<213> ORGANISM: Zea mays

<400> SEQUENCE: 692

Lys Ala Lys Ala Lys Ser Gly Lys Gly Pro Leu Leu Arg Glu Asp Glu
 1               5                  10                  15

Ser Ser Ser Thr Ala Thr Thr Val Met Lys Pro Phe His
                20                  25

<210> SEQ ID NO 693
<211> LENGTH: 29
<212> TYPE: PRT
<213> ORGANISM: Zea mays

<400> SEQUENCE: 693

Lys Ser Pro His Arg Gly Lys Leu Glu Ser Trp Leu Arg Arg Leu Lys
 1               5                  10                  15

Glu Ala Phe Tyr Asp Ala Glu Asp Leu Leu Asp Glu His
                20                  25
```

```
<210> SEQ ID NO 694
<211> LENGTH: 16
<212> TYPE: PRT
<213> ORGANISM: Zea mays

<400> SEQUENCE: 694

Lys Ser Pro His Arg Gly Lys Leu Glu Ser Trp Leu Arg Arg Leu Lys
 1               5                  10                  15

<210> SEQ ID NO 695
<211> LENGTH: 13
<212> TYPE: PRT
<213> ORGANISM: Zea mays

<400> SEQUENCE: 695

His Arg Gly Lys Leu Glu Ser Trp Leu Arg Arg Leu Lys
 1               5                  10

<210> SEQ ID NO 696
<211> LENGTH: 7
<212> TYPE: PRT
<213> ORGANISM: Zea mays

<400> SEQUENCE: 696

Lys Ser Pro His Arg Gly Lys
 1               5

<210> SEQ ID NO 697
<211> LENGTH: 8
<212> TYPE: PRT
<213> ORGANISM: Zea mays

<400> SEQUENCE: 697

Lys Gln Ala Ser His Leu Leu Lys
 1               5

<210> SEQ ID NO 698
<211> LENGTH: 23
<212> TYPE: PRT
<213> ORGANISM: Artificial Sequence
<220> FEATURE:
<223> OTHER INFORMATION: Description of Artificial Sequence: Replikin
      formula sequence
<220> FEATURE:
<221> NAME/KEY: MOD_RES
<222> LOCATION: (1)
<223> OTHER INFORMATION: lys, his, arg, tyr, ile, ser, val, ala, phe,
      pro or gln
<220> FEATURE:
<221> NAME/KEY: MOD_RES
<222> LOCATION: (3)
<223> OTHER INFORMATION: ser, cys or trp
<220> FEATURE:
<221> NAME/KEY: MOD_RES
<222> LOCATION: (4)
<223> OTHER INFORMATION: tyr, phe or pro
<220> FEATURE:
<221> NAME/KEY: MOD_RES
<222> LOCATION: (7)
<223> OTHER INFORMATION: leu, gln, ser, ala or arg
<220> FEATURE:
<221> NAME/KEY: MOD_RES
<222> LOCATION: (8)
<223> OTHER INFORMATION: val, ile or leu
<220> FEATURE:
<221> NAME/KEY: MOD_RES
<222> LOCATION: (10)
<223> OTHER INFORMATION: phe or leu
<220> FEATURE:
<221> NAME/KEY: MOD_RES
```

-continued

```
<222> LOCATION: (11)
<223> OTHER INFORMATION: gln, his, ile, leu, met or asn
<220> FEATURE:
<221> NAME/KEY: MOD_RES
<222> LOCATION: (12)
<223> OTHER INFORMATION: lys, thr, asn, met or ser
<220> FEATURE:
<221> NAME/KEY: MOD_RES
<222> LOCATION: (14)
<223> OTHER INFORMATION: gly, ala, gln or arg
<220> FEATURE:
<221> NAME/KEY: MOD_RES
<222> LOCATION: (16)
<223> OTHER INFORMATION: gly, ala, val or ser
<220> FEATURE:
<221> NAME/KEY: MOD_RES
<222> LOCATION: (17)
<223> OTHER INFORMATION: ile or leu
<220> FEATURE:
<221> NAME/KEY: MOD_RES
<222> LOCATION: (18)
<223> OTHER INFORMATION: ser or tyr
<220> FEATURE:
<221> NAME/KEY: MOD_RES
<222> LOCATION: (19)
<223> OTHER INFORMATION: tyr or his
<220> FEATURE:
<221> NAME/KEY: MOD_RES
<222> LOCATION: (20)
<223> OTHER INFORMATION: gly or gln

<400> SEQUENCE: 698

Xaa Cys Xaa Xaa His Cys Xaa Xaa Cys Xaa Xaa Xaa Lys Xaa Leu Xaa
 1               5                  10                  15
Xaa Xaa Xaa Xaa Arg Lys Lys
            20

<210> SEQ ID NO 699
<211> LENGTH: 8
<212> TYPE: PRT
<213> ORGANISM: Mycobacterium leprae

<400> SEQUENCE: 699

Lys Val Met Arg Thr Asp Lys His
 1               5

<210> SEQ ID NO 700
<211> LENGTH: 17
<212> TYPE: PRT
<213> ORGANISM: Mycobacterium tuberculosis

<400> SEQUENCE: 700

His Pro Arg Pro Lys Val Ala Ala Ala Leu Lys Asp Ser Tyr Arg Leu
 1               5                  10                  15
Lys

<210> SEQ ID NO 701
<211> LENGTH: 11
<212> TYPE: PRT
<213> ORGANISM: Mycobacterium tuberculosis

<400> SEQUENCE: 701

His Pro Arg Pro Lys Val Ala Ala Ala Leu Lys
 1               5                  10

<210> SEQ ID NO 702
<211> LENGTH: 19
<212> TYPE: PRT
<213> ORGANISM: Mycobacterium tuberculosis
```

-continued

<400> SEQUENCE: 702

Lys Ser Ala Gln Lys Trp Pro Asp Lys Phe Leu Ala Gly Ala Ala Gln
1               5                   10                  15

Val Ala His

<210> SEQ ID NO 703
<211> LENGTH: 15
<212> TYPE: PRT
<213> ORGANISM: Escherichia coli

<400> SEQUENCE: 703

His Ala Trp Gln His Gln Gly Lys Thr Leu Phe Ile Ser Arg Lys
1               5                   10                  15

<210> SEQ ID NO 704
<211> LENGTH: 11
<212> TYPE: PRT
<213> ORGANISM: Escherichia coli

<400> SEQUENCE: 704

His Gln Gly Lys Thr Leu Phe Ile Ser Arg Lys
1               5                   10

<210> SEQ ID NO 705
<211> LENGTH: 19
<212> TYPE: PRT
<213> ORGANISM: Agrobacterium tumefaciens

<400> SEQUENCE: 705

His Ser Asp Gln Gln Leu Ala Val Met Ile Ala Ala Lys Arg Leu Asp
1               5                   10                  15

Asp Tyr Lys

<210> SEQ ID NO 706
<211> LENGTH: 33
<212> TYPE: PRT
<213> ORGANISM: Agrobacterium tumefaciens

<400> SEQUENCE: 706

His Leu Leu Asp His Pro Ala Ser Val Gly Gln Leu Asp Leu Arg Ala
1               5                   10                  15

Met Leu Ala Val Glu Glu Val Lys Ile Asp Asn Pro Val Tyr Met Glu
            20                  25                  30

Lys

<210> SEQ ID NO 707
<211> LENGTH: 29
<212> TYPE: PRT
<213> ORGANISM: Agrobacterium tumefaciens

<400> SEQUENCE: 707

His Pro Ala Ser Val Gly Gln Leu Asp Leu Arg Ala Met Leu Ala Val
1               5                   10                  15

Glu Glu Val Lys Ile Asp Asn Pro Val Tyr Met Glu Lys
            20                  25

<210> SEQ ID NO 708
<211> LENGTH: 39
<212> TYPE: PRT
<213> ORGANISM: Agrobacterium tumefaciens -continued

<400> SEQUENCE: 708

Lys Cys Val Met Ala Lys Asn Cys Asn Ile Lys Cys Pro Ala Gly Leu
1               5                   10                  15

Thr Thr Asn Gln Glu Ala Phe Asn Gly Asp Pro Arg Ala Leu Ala Gln
            20                  25                  30

Tyr Leu Met Asn Ile Ala His
        35

<210> SEQ ID NO 709
<211> LENGTH: 34
<212> TYPE: PRT
<213> ORGANISM: Agrobacterium tumefaciens

<400> SEQUENCE: 709

Lys Asn Cys Asn Ile Lys Cys Pro Ala Gly Leu Thr Thr Asn Gln Glu
1               5                   10                  15

Ala Phe Asn Gly Asp Pro Arg Ala Leu Ala Gln Tyr Leu Met Asn Ile
            20                  25                  30

Ala His

<210> SEQ ID NO 710
<211> LENGTH: 27
<212> TYPE: PRT
<213> ORGANISM: Agrobacterium tumefaciens

<400> SEQUENCE: 710

His His Asp Thr Tyr Ser Ile Glu Asp Leu Ala Gln Leu Ile His Asp
1               5                   10                  15

Ala Lys Ala Ala Arg Val Arg Val Ile Val Lys
            20                  25

<210> SEQ ID NO 711
<211> LENGTH: 26
<212> TYPE: PRT
<213> ORGANISM: Agrobacterium tumefaciens

<400> SEQUENCE: 711

His Asp Thr Tyr Ser Ile Glu Asp Leu Ala Gln Leu Ile His Asp Ala
1               5                   10                  15

Lys Ala Ala Arg Val Arg Val Ile Val Lys
            20                  25

<210> SEQ ID NO 712
<211> LENGTH: 13
<212> TYPE: PRT
<213> ORGANISM: Agrobacterium tumefaciens

<400> SEQUENCE: 712

His Asp Ala Lys Ala Ala Arg Val Arg Val Ile Val Lys
1               5                   10

<210> SEQ ID NO 713
<211> LENGTH: 42
<212> TYPE: PRT
<213> ORGANISM: Agrobacterium tumefaciens

<400> SEQUENCE: 713

Lys Ile Gly Gln Gly Ala Lys Pro Gly Glu Gly Gly Gln Leu Pro Ser
1               5                   10                  15

Pro Lys Val Thr Val Glu Ile Ala Ala Ala Arg Gly Gly Thr Pro Gly
            20                  25                  30

```
Val Glu Leu Val Ser Pro Pro His His
        35                  40

<210> SEQ ID NO 714
<211> LENGTH: 41
<212> TYPE: PRT
<213> ORGANISM: Agrobacterium tumefaciens

<400> SEQUENCE: 714

Lys Ile Gly Gln Gly Ala Lys Pro Gly Glu Gly Gly Gln Leu Pro Ser
  1               5                  10                  15

Pro Lys Val Thr Val Glu Ile Ala Ala Ala Arg Gly Gly Thr Pro Gly
             20                  25                  30

Val Glu Leu Val Ser Pro Pro His
        35                  40

<210> SEQ ID NO 715
<211> LENGTH: 46
<212> TYPE: PRT
<213> ORGANISM: Agrobacterium tumefaciens

<400> SEQUENCE: 715

Lys Ala Ser Glu Ile Thr Lys Thr Leu Ala Ser Gly Ala Met Ser His
  1               5                  10                  15

Gly Ala Leu Val Ala Ala Ala His Glu Ala Val Ala His Gly Thr Asn
             20                  25                  30

Met Val Gly Gly Met Ser Asn Ser Gly Glu Gly Gly Glu His
        35                  40                  45

<210> SEQ ID NO 716
<211> LENGTH: 29
<212> TYPE: PRT
<213> ORGANISM: Agrobacterium tumefaciens

<400> SEQUENCE: 716

Lys Ala Ser Glu Ile Thr Lys Thr Leu Ala Ser Gly Ala Met Ser His
  1               5                  10                  15

Gly Ala Leu Val Ala Ala Ala His Glu Ala Val Ala His
             20                  25

<210> SEQ ID NO 717
<211> LENGTH: 24
<212> TYPE: PRT
<213> ORGANISM: Agrobacterium tumefaciens

<400> SEQUENCE: 717

Lys Ala Ser Glu Ile Thr Lys Thr Leu Ala Ser Gly Ala Met Ser His
  1               5                  10                  15

Gly Ala Leu Val Ala Ala Ala His
             20

<210> SEQ ID NO 718
<211> LENGTH: 16
<212> TYPE: PRT
<213> ORGANISM: Agrobacterium tumefaciens

<400> SEQUENCE: 718

Lys Ala Ser Glu Ile Thr Lys Thr Leu Ala Ser Gly Ala Met Ser His
  1               5                  10                  15

<210> SEQ ID NO 719
```

```
<211> LENGTH: 27
<212> TYPE: PRT
<213> ORGANISM: Agrobacterium tumefaciens

<400> SEQUENCE: 719

Lys Arg Tyr Phe Pro Asn Val Lys Thr Pro Val Gly Gly Val Thr Phe
 1               5                  10                  15
Ala Val Ile Ala Gln Ala Val Ala Asp Trp His
             20                  25

<210> SEQ ID NO 720
<211> LENGTH: 48
<212> TYPE: PRT
<213> ORGANISM: Agrobacterium tumefaciens

<400> SEQUENCE: 720

His His Ile Ala Ala Gly Leu Gly Phe Gly Ala Ser Ala Val Tyr Pro
 1               5                  10                  15
Leu Gly Val Gln Phe Arg Ala Glu Glu Lys Phe Gly Ala Asp Ala Asp
             20                  25                  30
Lys Ala Phe Lys Arg Phe Ala Lys Ala Ala Glu Lys Ser Leu Met Lys
         35                  40                  45

<210> SEQ ID NO 721
<211> LENGTH: 48
<212> TYPE: PRT
<213> ORGANISM: Agrobacterium tumefaciens

<400> SEQUENCE: 721

His His Ile Ala Ala Gly Leu Gly Phe Gly Ala Ser Ala Val Tyr Pro
 1               5                  10                  15
Leu Gly Val Gln Phe Arg Ala Glu Glu Lys Phe Gly Ala Asp Ala Asp
             20                  25                  30
Lys Ala Phe Lys Arg Phe Ala Lys Ala Ala Glu Lys Ser Leu Met Lys
         35                  40                  45

<210> SEQ ID NO 722
<211> LENGTH: 44
<212> TYPE: PRT
<213> ORGANISM: Agrobacterium tumefaciens

<400> SEQUENCE: 722

His His Ile Ala Ala Gly Leu Gly Phe Gly Ala Ser Ala Val Tyr Pro
 1               5                  10                  15
Leu Gly Val Gln Phe Arg Ala Glu Glu Lys Phe Gly Ala Asp Ala Asp
             20                  25                  30
Lys Ala Phe Lys Arg Phe Ala Lys Ala Ala Glu Lys
         35                  40

<210> SEQ ID NO 723
<211> LENGTH: 40
<212> TYPE: PRT
<213> ORGANISM: Agrobacterium tumefaciens

<400> SEQUENCE: 723

His His Ile Ala Ala Gly Leu Gly Phe Gly Ala Ser Ala Val Tyr Pro
 1               5                  10                  15
Leu Gly Val Gln Phe Arg Ala Glu Glu Lys Phe Gly Ala Asp Ala Asp
             20                  25                  30
Lys Ala Phe Lys Arg Phe Ala Lys
         35                  40
```

<210> SEQ ID NO 724
<211> LENGTH: 33
<212> TYPE: PRT
<213> ORGANISM: Agrobacterium tumefaciens

<400> SEQUENCE: 724

His His Ile Ala Ala Gly Leu Gly Phe Gly Ala Ser Ala Val Tyr Pro
1               5                   10                  15

Leu Gly Val Gln Phe Arg Ala Glu Glu Lys Phe Gly Ala Asp Ala Asp
            20                  25                  30

Lys

<210> SEQ ID NO 725
<211> LENGTH: 47
<212> TYPE: PRT
<213> ORGANISM: Agrobacterium tumefaciens

<400> SEQUENCE: 725

His Ile Ala Ala Gly Leu Gly Phe Gly Ala Ser Ala Val Tyr Pro Leu
1               5                   10                  15

Gly Val Gln Phe Arg Ala Glu Glu Lys Phe Gly Ala Asp Ala Asp Lys
            20                  25                  30

Ala Phe Lys Arg Phe Ala Lys Ala Ala Glu Lys Ser Leu Met Lys
        35                  40                  45

<210> SEQ ID NO 726
<211> LENGTH: 43
<212> TYPE: PRT
<213> ORGANISM: Agrobacterium tumefaciens

<400> SEQUENCE: 726

His Ile Ala Ala Gly Leu Gly Phe Gly Ala Ser Ala Val Tyr Pro Leu
1               5                   10                  15

Gly Val Gln Phe Arg Ala Glu Glu Lys Phe Gly Ala Asp Ala Asp Lys
            20                  25                  30

Ala Phe Lys Arg Phe Ala Lys Ala Ala Glu Lys
        35                  40

<210> SEQ ID NO 727
<211> LENGTH: 39
<212> TYPE: PRT
<213> ORGANISM: Agrobacterium tumefaciens

<400> SEQUENCE: 727

His Ile Ala Ala Gly Leu Gly Phe Gly Ala Ser Ala Val Tyr Pro Leu
1               5                   10                  15

Gly Val Gln Phe Arg Ala Glu Glu Lys Phe Gly Ala Asp Ala Asp Lys
            20                  25                  30

Ala Phe Lys Arg Phe Ala Lys
        35

<210> SEQ ID NO 728
<211> LENGTH: 32
<212> TYPE: PRT
<213> ORGANISM: Agrobacterium tumefaciens

<400> SEQUENCE: 728

His Ile Ala Ala Gly Leu Gly Phe Gly Ala Ser Ala Val Tyr Pro Leu
1               5                   10                  15

-continued

```
Gly Val Gln Phe Arg Ala Glu Glu Lys Phe Gly Ala Asp Ala Asp Lys
            20                  25                  30

<210> SEQ ID NO 729
<211> LENGTH: 28
<212> TYPE: PRT
<213> ORGANISM: Agrobacterium tumefaciens

<400> SEQUENCE: 729

Lys Phe Gly Leu Tyr Asp Ala Ala Phe Glu Lys Ser Ser Cys Gly Val
  1               5                  10                  15

Gly Phe Ile Thr Arg Lys Asp Gly Val Gln Thr His
            20                  25
```

REPLIKIN PEPTIDES AND ANTIBODIES THEREFORE

CROSS REFERENCE TO OTHER APPLICATIONS

This application is a Continuation-In-Part of U.S. application Ser. No. 10/105,232, filed Mar. 26, 2002, which is a Continunation-In-Part of U.S. Ser. No. 09/984,057, filed Oct. 26, 2001, which claims priority from Provisional Applications 60/303,396, filed Jul. 9, 2001 and 60/278,761 filed Mar. 27, 2001, the subject matter of which is incorporated herein by reference.

FIELD OF THE INVENTION

This invention relates to the identification and use of Replikins, a newly discovered class of peptides that share structural characteristics. In particular, this invention relates to Replikins which have been found in viruses, bacteria, fungus, cancer associated proteins, plants and unicellular parasites and their use as targets in the development of methods of treating or preventing diseases. Further, this invention relates to the use of Replikins in the detection of these diseases. Also this invention relates to the use of Replikins to stimulate growth of plants used for food.

INTRODUCTION AND BACKGROUND OF THE INVENTION

Rapid replication is characteristic of virulence in certain bacteria, viruses and malignancies, but no chemistry common to rapid replication in different organisms has been described previously. This patent application discloses a new class of protein structures related to rapid replication. A new family of conserved small proteins related to rapid replication, named Replikins, which are used to predict and control rapid replication in multiple organisms and diseases and to induce rapid replication in plant and animal life.

We constructed an algorithm search for Replikins. In applying the algorithm invented herein not only was the function of the epitope revealed—rapid replication, but an entire family of homologues whose function is related to rapid replication was discovered, which we named Replikins.

The algorithm is based on the following: 1) Evidence that the immune system looks to parts rather than a whole protein in recognition. Protein chains are first hydrolyzed by the immune system into smaller pieces, frequently six (6) to ten (10) amino acids long, as part of the immune systems' process of recognition of foreign structures against which it may mount an immune defense. By way of example, the immune system recognizes the presence of disease by chopping up proteins of the disease agent into smaller peptide sequences and reading them. This principle is used as a basis for the algorithm with which to search for homologues of the malignin cancer epitope, once the structure of the epitope was known; 2) The specific structure of the malignin epitope, in which two of the three lysines (K's) are eight residues apart is in accordance with the apparent 'rules' used by the immune system for recognition referred to above (6-10 amino acids long); 3) The fact that the malignin cancer epitope was shown to be a very strong antigen, that is—a generator of a strong immune response; that there are three lysines (K's) in the 10-mer peptide glioma Replikin and that K's are known to bind frequently to DNA and RNA as potential anchors for the entry of viruses; and 4) One histidine (H) is included in the sequence of the malignin epitope, between the two K's which are eight (8) residues apart, suggesting a connection to the metals of redox systems which are required to provide the energy for replication.

Engineered enzymes and catalytic antibodies, possessing tailored binding pockets with appropriately positioned functional groups have been successful in catalyzing a number of chemical transformations, sometimes with impressive efficiencies. Just as two or more separate proteins with specific and quite different functions are now often recognized to be synthesized together by organisms, and then separately cleaved to 'go about their separate functions', so the Replikin structure is a unique protein with a unique function that appears to be recognized separately by the immune system and may be now rationally engineered—e.g. synthesized to produce a functional unit.

From a proteomic point of view, this template based on the newly determined glioma peptide sequence has led to the discovery of a wide class of proteins with related conserved structures and a particular function, in this case replication. Examples of the increase in Replikin concentration with virulence of a disease appear in diseases including, influenza, HIV, cancer and tomato leaf curl virus. This class of structures is related to the phenomenon of rapid replication in organisms as diverse as yeast, algae, plants, the gemini curl leaf tomato virus, HIV and cancer.

In addition to detecting the presence of Replikins in rapidly replicating organisms, we found that 1) Replikin concentration (number of Replikins per 100 amino acids) and 2) Replikin compositions in specific functional states dependant on rapid replication, provide the basis for the finding that Replikins are related quantitatively as well as qualitatively to the rate of replication of the organism in which they reside. Examples of these functional proofs include the relationship found between rapid replication and virulence in glioblastoma cells, between Replikins in influenza virus and the prediction of influenza pandemics and epidemics, and the relationship between Replikin concentration and rapid replication in HIV.

The first functional basis for Replikins' role in rapid replication was found in the properties of the glioma Replikin, a 10 KD peptide called Malignin in brain glioblastoma multiforme (glioma)—a 250 KD cell protein. Antimalignin antibody increased in concentration in serum (AMAS), measured by an early stage diagnostic test for cancer now used for most or all cell types. Malignin was so named because in tissue culture the expression of this peptide and its concentration per milligram membrane protein extractable increased with increased rate of cell division per unit time. Not only is there an increase in the amount of malignin in proportion to the cell number increase but the amount of malignin is enriched, that is—increased ten fold whereas the cell number increased only five fold.

The structure of malignin protein was determined through hydrolysis and mass spectrometry which revealed what proved to be a novel 16 mer peptide sequence. We searched for the 16 mer peptide sequence which we have named a Glioma Replikin protein in databases for the healthy human genome and found that it was not present in these databases.

As such, the fixed requirement algorithm was used to search in other organisms for the Glioma Replikin protein or homologues thereof. Over 4,000 protein sequences in the "Pub Med" database were searched and homologues were found in viruses and plant forms specifically associated with rapid replication. Homologues of such Replikin proteins occurred frequently in proteins called 'replicating proteins' by their investigators.

Homologues of the Replikin sequence were found in all tumor viruses (that is viruses that cause cancer), and in 'replicating proteins' of algae, plants, fungi, viruses and bacteria.

That malignin is enriched ten-fold compared to the five-fold increase in cell number and membrane protein concentration in rapid replication of glioma cells suggests an integral relationship of the Replikins to replication. When the glioma replikin was synthesized in vitro and administered as a synthetic vaccine to rabbits, abundant antimalignin antibody was produced—establishing rigourously the antigenic basis of the antimalignin antibody in serum (AMAS) test, and providing the first potential synthetic cancer vaccine and the prototype for Replikin vaccines in other organisms.

The demonstration of the relationship of the Replikins to replication and the natural immune response to cancer Replikins (overriding cell type) based upon the shared specificity of cancer Replikins, permits passive augmentation of immunity with antimalignin antibody and active augmentation with synthetic Replikin vaccines.

A study of 8,090 serum specimens from cancer patients and controls has demonstrated that the concentration of antimalignin antibody increases with age in healthy individuals, as the incidence of cancer in the population increases, and increases further two to three-fold in early malignancy, regardless of cell type. In vitro this antibody is cytotoxic to cancer cells at picograms (femtomoles) per cancer cell, and in vivo the concentration of antimalignin antibody relates quantitatively to the survival of cancer patients. As shown in glioma cells, the stage in cancer at which cells only have been transformed to the immortal malignant state but remain quiescent or dormant, now can be distinguished from the more active life-threatening replicating state which is characterized by the increased concentration of Replikins. In addition, clues to the viral pathogenesis of cancer may be found in the fact that glioma glycoprotein 10B has a 50% reduction in carbohydrate residues when compared to the normal 10B. This reduction is associated with virus entry in other instances and so may be evidence of the attachment of virus for the delivery of virus Replikins to the 10B of glial cells as a step in the transformation to the malignant state.

The sharing of immunological specificity by diverse members of the class, as demonstrated with antimalignin antibody for the glioma and related cancer Replikins, suggests that B cells and their product antibodies may recognize Replikins by means of a similar recognition 'language'. With the discovery of the Replikins, this shared immunological specificity may explain what was previously difficult to understand: why the antimalignin antibody is elevated in all cancers, and is cytotoxic to cancer cells and related to survival of cancer patients in most or all cell types. Thus antimalignin antibody is produced against cancer Replikins, which share immunological specificity and which are related to the phenomenon of rapid replication, not to cell type.

A second functional basis for the Replikins' role in rapid replication is the study of data from the past 100 years on influenza virus hemagglutinin protein sequences and epidemiology of influenza epidemics and pandemics. To date, only serological hemagglutinin and antibody classification, but no strain-specific conserved peptide sequences have previously been described in influenza, and no changes in concentration and composition of any strain-specific peptide sequences have been described previously which correlate with epidemiologically documented epidemics or rapid replication.

A four to ten-fold increase in the concentration of strain-specific influenza Replikins in one of each of the four major strains, influenza B, (A)H1N1, (A)H2N2 and (A)H3N2 was found, and that such increase of Replikin concentration was related to influenza epidemics caused specifically by each strain from 1902 to 2001. These increases in concentration were then shown to be due to the reappearance of at least one specific Replikin composition from 1 to up to 64 years after its disappearance, plus the emergence of new strain-specific Replikin compositions. Previously, no strain-specific chemical structures were known with which to predict which strains would predominate in coming influenza seasons, nor to devise annual mixtures of whole-virus strains for vaccines. The recent sharp increase in H3N2 Replikin concentration (1997 to 2000), the largest in H3N2's history, and the reappearance of specific Replikin compositions which were last seen in the high mortality H3N2 pandemic of 1968 and in the two high mortality epidemics of 1975 and 1977, but were absent for 20-25 years, together may be a warning of coming epidemics.

Synthetic Replikins are new vaccines. This high degree of conservation of Replikin structures observed whereby the identical structure can persist for 100 years, or reappear after an absence of from one to 64 years reappears indicates that what was previously thought to be change in virulence due to random substitution of amino acids in influenza proteins is more likely to be change due to an organized process of conservation of Replikins. In fact, if random substitutions of each amino acid occurred, the chance against an average length influenza Replikin sequence being conserved for one year (let alone 100) is calculated to be in the order of 2 to the $27^{th}$ power to 1.

The significant conservation of Replikins is not unique to influenza virus is also present in foot and mouth disease virus type O and in HIV, as well as in wheat.

A third functional basis for Replikins' role in rapid replication is the increase in Replikin concentration shown to be related to rapid replication in HIV. The Replikin concentration in the slow-growing low-titre strain of HIV (NS1, "Bru"), prevalent in early stage infection, was found to be one-sixth of the Replikin concentration in the rapidly-growing high-titre strain of HIV (SI, "Lai"), prevalent in late stage HIV infection.

Other examples are given of the relation of Replikins to rapid replication. For example, in tomato curl leaf gemini virus, which devastates tomato crops, the first 161 amino acids of the 'replicating protein', which have been shown to bind to DNA, contain five Replikins.

In malaria, legendary for rapid replication, trypanosomes are released from the liver in tens of thousands from one trypanosome. Multiple, novel, almost 'flamboyant' Replikin structures with concentrations of up to 36 overlapping Replikins per 100 amino acids are found therein.

The increase in Replikin concentration in influenza epidemics is functionally comparable to the glioma Replikin's increase in concentration during rapid replication of malignant glioma cells and comparable to rapid replication in HIV and in a diverse range of other organisms. Replikins thus are associated with and appear to be part of the structural bases of rapid replication in different organisms.

Replikin concentration and composition therefore provide new methods to detect and to control the process of replication, which is central to the survival and dominance of each biological population. The discovery of these new proteins related to rapid replication provides new opportunities 1) for detection of pathogens by qualitative and quantitative determinations of Replikins, 2) for the control of a broad range of diseases in which rapid replication is a key factor by targeting native Replikins and by using synthetic Replikins as vaccines, and 3) for the use of Replikins to foster growth of algal and plant foods.

There is a significant number of diseases and pathogens which have proved difficult to detect and treat and for which there is no effective vaccine. Thus, for each disorder there is a need for developing a target that will provide effective methods of detecting, treating or preventing these diseases and pathogens.

SUMMARY OF THE INVENTION

The present invention provides a method for identifying nucleotide or amino acid sequences that include a Replikin sequence. The method is referred to herein as a 3-point-recognition method. By use of the "3-point recognition" method, namely, peptides comprising from 7 to about 50 amino acids including:
(1) at least one lysine residue located six to ten amino acid residues from a second lysine residue;
(2) at least one histidine residue; and
(3) at least 6% lysine residues (Replikin)—constituting a new class of peptides was revealed in algae, yeast, flungi, amoebae, bacteria, plant and virus proteins having replication, transformation, or redox functions.

In one aspect of the invention there are provided isolated or synthesized peptides containing a Replikin sequence. The peptides comprise from 7 to about 50 amino acids including:
(1) at least one lysine residue located six to ten amino acid residues from a second lysine residues;
(2) at least one histidine residue; and
(3) at least 6% lysine residues.

The present invention also provides methods for detecting the presence of a contaminating organism in a body sample or environmental sample comprising:
(1) isolating nucleic acids from the body sample or environmental sample;
(2) screening the nucleic acids for the presence of a Replikin structure; and
(3) correlating the presence of a Replikin structure with the presence of the contaminating organism.

In another aspect of the invention there is provided a process for stimulating the immune system of a subject to produce antibodies that bind specifically to a Replikin sequence, said process comprising administering to the subject an effective amount of a dosage of a composition comprising at least one Replikin peptide. One embodiment comprises at least one peptide that is present in an emerging strain of the organism if such new strain emerges.

The present invention also provides antibodies that bind specifically to a Replikin, as defined herein, as well as antibody cocktails containing a plurality of antibodies that specifically bind to Replikins. In one embodiment of the invention, there are provided compositions comprising an antibody or antibodies that specifically bind to a Replikin and a pharmaceutically acceptable carrier.

In one aspect of the invention there are provided isolated, or separated from other proteins, recombinant, or synthesized peptides or other methods containing a viral Replikin sequence. The viral Replikin peptides comprise from 7 to about 50 amino acids including:
(1) at least one lysine residue located six to ten amino acid residues from a second lysine residue;
(2) at least one histidine residue; and
(3) at least 6% lysine residues. (viral Replikin).

The present invention also provides methods for detecting the presence of a contaminating virus in a body sample or environmental sample comprising:
(1) isolating nucleic acids from the body sample or environmental sample;
(2) screening the nucleic acids for the presence of a viral Replikin structure; and
(3) correlating the presence of viral Replikin structures, their concentration and composition, with the presence of the contaminating virus.

In another aspect of the invention there is provided a process for stimulating the immune system of a subject to produce antibodies that bind specifically to a viral Replikin sequence, said process comprising administering to the subject an effective amount of a dosage of a composition comprising at least one Replikin peptide. One embodiment comprises at least one peptide that is present in an emerging strain of the virus if such new strain emerges.

The present invention also provides antibodies that bind specifically to a viral Replikin, as defined herein, as well as antibody cocktails containing a plurality of antibodies that specifically bind to viral Replikins. In one embodiment of the invention, there are provided compositions comprising an antibody or antibodies that specifically bind to a viral Replikin and a pharmaceutically acceptable carrier.

The present invention also provides therapeutic compositions comprising one or more of isolated virus peptides having from 7 to about 50 amino acids comprising:
(1) at least one lysine residue located six to ten residues from a second lysine residue;
(2) at least one histidine residue; and
(3) at least 6% lysine residues, and a pharmaceutically acceptable carrier.

In another aspect of the invention there is provided an antisense nucleic acid molecule complementary to a virus Replikin mRNA sequence, said Replikin mRNA sequence denoting from 7 to about 50 amino acids comprising:
(1) at least one lysine residue located six to ten residues from a second lysine residue;
(2) at least one histidine residue; and
(3) at least 6% lysine residues.

In yet another aspect of the invention there is provided a method of simulating the immune system of a subject to produce antibodies to viruses, said method comprising: administering an effective amount of at least one virus Replikin peptide having from 7 to about 50 amino acids comprising:
(1) at least one lysine residue located six to ten amino acid residues from a second lysine residue;
(2) at least one histidine residue; and
(3) at least 6% lysine residues.

In another aspect, there is provided a method of selecting a virus peptide for inclusion in a preventive or therapeutic virus vaccine comprising:
(1) obtaining at least one isolate of each strain of a plurality of strains of said virus;
(2) analyzing the amino acid sequence of the at least one isolate of each strain of the plurality of strains of the virus for the presence and concentration of Replikin sequences;
(3) comparing the concentration of Replikin sequences in the amino acid sequence of the at least one isolate of each strain of the plurality of strains of the virus to the concentration of Replikin sequences observed in the amino acid sequence of each of the strains at least one earlier time period to provide the concentration of Replikins for at least two time periods, said at least one earlier time period being within about six months to about three years prior to step (1);
(4) indentifying the strain of the virus having the highest increase in concentration of Replikin sequences during the at least two time periods; and (5) selecting at least one Replikin sequence present in the strain of the virus peptide identified in step (4) as a peptide for inclusion in the virus vaccine.

The present invention also provides a method of making a preventive or therapeutic virus vaccine comprising:
(1) identifying a strain of a virus as an emerging strain,
(2) selecting at least one Replikin sequence present in the emerging strain as a peptide template for the virus vaccine manufacture,
(3) synthesizing peptides having the amino acid sequence of the at least one Replikin sequence selected in step (2), and
(4) combining a therapeutically effective amount of the peptides of step (3) with a pharmaceutically acceptable carrier and/or adjuvant.

In another aspect, the invention is directed to a method of identifying an emerging strain of a virus for diagnostic, preventive or therapeutic purposes comprising:
(1) obtaining at least one isolate of each strain of a plurality of strains of the virus;
(2) analyzing the amino acid sequence of the at least one isolate of each strain of the plurality of strains of the virus for the presence and concentration of Replikin sequences;
(3) comparing the concentration of Replikin sequences in the amino acid sequence of the at least one isolate of each strain of the plurality of strains of the virus to the concentration of Replikin sequences observed in the amino acid sequence of each of the strains at at least one earlier time period to provide the concentration of Replikins for at least two time periods, said at least one earlier time period being within about six months to about three years prior to step (1); and
(4) identifying the strain of the virus having the highest increase in concentration of Replikin sequences during the at least two time periods.

In yet another aspect of the invention, there is provided a preventive or therapeutic virus vaccine comprising at least one isolated Replikin present in a protein of an emerging strain of the virus and a pharmaceutically acceptable carrier and/or adjuvant.

Also provided by the present invention is a method of preventing or treating a virus infection comprising administering to a patient in need thereof a preventive or therapeutic virus vaccine comprising at least one isolated Replikin present in a protein of an emerging strain of the virus and a pharmaceutically acceptable carrier and/or adjuvant.

Influenza

Influenza is an acute respiratory illness of global importance. Despite international attempts to control influenza virus outbreaks through vaccination, influenza infections remain an important cause of morbidity and mortality. Worldwide influenza epidemics and pandemics have occurred at irregular and previously unpredictable intervals throughout history and it is expected that they will continue to occur in the future. The impact of both pandemic and epidemic influenza is substantial in terms of morbidity, mortality and economic cost.

Influenza vaccines remain the most effective defense against influenza virus, but because of the ability of the virus to mutate and the availability of non-human host reservoirs, it is expected that influenza will remain an emergent or re-emergent infection. Global influenza surveillance indicates that influenza viruses may vary within a country and between countries and continents during an influenza season. Virological surveillance is of importance in monitoring antigenic shift and drift. Disease surveillance is also important in assessing the impact of epidemics. Both types of information have provided the basis of the vaccine composition and the correct use of antivirals. However, to date there has been only annual post hoc hematological classification of the increasing number of emerging influenza virus strains, and no specific chemical structure of the viruses has been identified as an indicator of approaching influenza epidemics or pandemics. Currently, the only basis for annual classification of influenza virus as active, inactive or prevalent in a given year is the activities of the virus hemagglutinin and neuramimidase proteins. No influenza viral chemical structure has been identified prior to this application that can be used for quantitative warning of epidemics or pandemics or to design more effective and safer vaccines.

Because of the annual administration of influenza vaccines and the short period of time when a vaccine can be administered, strategies directed at improving vaccine coverage are of critical importance.

In one aspect of the invention there are provided isolated or synthesized influenza virus peptides containing a Replikin sequence. The influenza Replikin virus peptides comprise from 7 to about 50 amino acids including:
(1) at least one lysine residue located six to ten amino acid residues from a second lysine residue;
(2) at least one histidine residue; and
(3) at least 6% lysine residues. (Influenza Replikin).

In another aspect of the invention, there is provided a process for stimulating the immune system of a subject to produce antibodies that bind specifically to an influenza virus Replikin sequence, said process comprising administering to the subject an effective amount of dosage of a composition comprising at least one influenza virus Replikin peptide. In a preferred embodiment the composition comprises at least on peptide that is present in an emerging strain of influenza virus.

The present invention also provides antibodies that bind specifically to an influenza virus Replikin, as defined herein, as well as antibody cocktails containing a plurality of antibodies that specifically bind to influenza virus Replikins. In one embodiment of the invention, there are provided compositions comprising an antibody or antibodies that specifically bind to an influenza Replikin and a pharmaceutically acceptable carrier.

The present invention also provides therapeutic compositions comprising one or more of isolated influenza virus peptides having from 7 to about 50 amino acids comprising:
(1) at least one lysine residue located six to ten residues form a second lysine residue;
(2) at least one histidine residue; and
(3) at least 6% lysine residues, and a pharmaceutical acceptable carrier.

In another aspect of the invention there is provided an antisense nucleic acid molecule complementary to an influenza virus hemagglutinin Replikin mRNA sequence, said Replikin mRNA sequence denoting from 7 to about 50 amino acids comprising:
(1) at least one lysine residue located six to ten residues from a second lysine residue;
(2) at least one histidine residue; and
(3) at least 6% lysine residues.

In yet another aspect of the invention there is provided a method of simulating the immune system of a subject to produce antibodies to influenza virus comprising administering an effective amount of at least one influenza virus Rep likin peptide having from 7 to about 50 amino acids comprising:
(1) at least one lysine residue located six to ten amino acid residues from a second lysine residue;
(2) at least one histidine residue; and
(3) at least 6% lysine residues.

In another aspect, there is provided a method of selecting an influenza virus peptide for inclusion in a preventive or therapeutic influenza virus vaccine comprising:
(1) obtaining at least one isolate of each strain of a plurality of strains of influenza virus;
(2) analyzing the hemagglutinin amino acid sequence of the at least one isolate of each strain of the plurality of strains of influenza virus for the presence and concentration of Replikin sequences;
(3) comparing the concentration of Replikin sequences in the hemagglutinin amino acid sequence of the at least one isolate of each strain of the plurality of strains of influenza virus to the concentration of Replikin sequences observed in the hemagglutinin amino acid sequence of each of the strains at least one earlier time period to provide the concentration of Replikins for at least two time periods, said at least one earlier time period being within about six months to about three years prior to step (1);
(4) identifying the strain of influenza virus having the highest increase in concentration of Replikin sequences during the at least two time periods;
(5) selecting at least one Replikin sequence present in the strain of influenza virus peptide identified in step (4) as a peptide for inclusion in an influenza virus vaccine.

The present invention also provides a method of making a preventive or therapeutic influenza virus vaccine comprising:
(1) identifying a strain of influenza virus as an emerging strain;
(2) selecting at least one Replikin sequence present in the emerging strain as a peptide template for influenza virus vaccine manufacture;
(3) synthesizing peptides having the amino acid sequence of the at least one Replikin sequence selected in step (2), and
(4) combining a therapeutically effective amount of the peptides of step (3) with a pharmaceutically acceptable carrier and/or adjuvant.

In another aspect, the invention is directed to a method of identifying an emerging strain of influenza virus for diagnostic, preventive or therapeutic purposes comprising:
(1) obtaining at least one isolate of each strain of a plurality of strains of influenza virus;
(2) analyzing the hemagglutinin amino acid sequence of the at least one isolate of each strain of the plurality of strains of influenza virus for the presence and concentration of Replikin sequences;
(3) comparing the concentration of Replikin sequences in the hemagglutinin amino acid sequence of the at least one isolate of each strain of the plurality of strains of influenza virus to the concentration of Replikin sequences observed in the hemagglutinin amino acid sequence of each of the strains at at least one earlier time period to provide the concentration of Replikins for at least two time periods, said at least one earlier time period being within about six months to about three years prior to step (1); and
(4) identifying the strain of influenza virus having the highest increase in concentration of Replikin sequences during the at least two time periods.

In yet another aspect of the invention, there is provided a preventive or therapeutic influenza virus vaccine comprising at least one isolated Replikin present in the hemagglutinin protein of an emerging strain of influenza virus and a pharmaceutically acceptable carrier and/or adjuvant.

Also provided by the present invention is a method of preventing or treating influenza virus infection comprising administering to a patient in need thereof a preventive or therapeutic vaccine comprising at least one isolated Replikin present in the hemagglutinin protein of an emerging strain of influenza virus and a pharmaceutically acceptable carrier and/or adjuvant.

Trypanosomes

In one aspect of the invention there are provided isolated or synthesized trypanosome peptides containing a Replikin sequence. The trypanosome Replikin peptides comprise from 7 to about 50 amino acids including:
(1) at least one lysine residue located six to ten amino acid residues from a second lysine residue;
(2) at least one histidine residue; and
(3) at least 6% lysine residues. (Trypanosome Replikins).

Malaria

One trypanosome disorder which has proved difficult to treat and for which there is no effective vaccine is malaria. Malaria causes much death, and physical and economic hardship in tropical regions. Malaria is caused mainly by *Plasmodium falciparum*, which has proved to be extremely resistant to treatment and to date, a vaccine for malaria has remained elusive. Thus there is a need for effective malaria vaccines and methods of treating or preventing the disease. This application provides the basis for such vaccines and methods of treatment and prevention. All of the methods described above for production of and treatment with Replikin virus vaccines and Replikin influenza virus vaccines are applicable to the production of and treatment with Replikin malaria vaccines.

In the present invention, there are provided vaccines and methods for preventing or treating malaria. The malaria vaccines comprise at least one isolated *Plasmodium falciparum* Replikin. The present invention also provides methods for treating or preventing malaria comprising administering to a patient an effective amount of preventive or therapeutic vaccine comprising at least one isolated *Plasmodium falciparum* Replikin.

Also provided by the present invention are antibodies, antibody cocktails and compositions that comprise antibodies that specifically bind to a Replikin or Replikins present in a malaria antigen of *Plasmodium falciparum*.

Another example of a trypanosome which may be treated under the present invention as is the case for malaria, the Replikins of Treponema Pallidum (syphilis), can be used for detection, prevention, treatment of syphilis.

Bacteria

In one aspect of the invention there are provided isolated or synthesized bacterial peptides containing a Replikin sequence (bacterial Replikins). The bacterial peptides comprise from 7 to about 50 amino acids including:
(1) at least one lysine residue located six to ten amino acid residues from a second lysine residue;
(2) at least one histidine residue; and
(3) at least 6% lysine residues. (bacterial Replikins). U.S. application Ser. No. 10/105,232 filed Mar. 26, 2002 is incorporated by reference in its entirety, including but not limited to the bacterial sequence listing and information.

The present invention also provides methods for detecting the presence of a contaminating bacterial organism in a body sample or environmental sample comprising:
(1) isolating nucleic acids from the body sample or environmental sample;
(2) screening the nucleic acids for the presence of a Replikin structure; and
(3) correlating the presence of a Replikin structure with the presence of the contaminating organism.

In another aspect of the invention there is provided a process for stimulating the immune system of a subject to produce antibodies that bind specifically to a bacterial Replikin sequence, said process comprising administering to the subject an effective amount of a dosage of a composition comprising at least one bacterial Replikin peptide. One embodiment comprises at least one bacterial peptide that is present in an emerging strain of the bacterial organism if such new strain emerges.

The present invention also provides antibodies that bind specifically to a bacterial Replikin, as defined herein, as well as antibody cocktails containing a plurality of antibodies that specifically bind to bacterial Replikins. In one embodiment of the invention, there are provided compositions comprising an antibody or antibodies that specifically bind to a bacterial Replikin and a pharmaceutically acceptable carrier.

The present invention also provides therapeutic compositions comprising one or more of isolated bacterial peptides having from 7 to about 50 amino acids comprising:
(1) at least one lysine residue located six to ten residues from a second lysine residue;
(2) at least one histidine residue;
(3) at least 6% lysine residues; and
(4) a pharmaceutically acceptable carrier.

In another aspect of the invention there is provided an antisense nucleic acid molecule complementary to a bacterial Replikin mRNA sequence, said Replikin mRNA sequence denoting from 7 to about 50 amino acids comprising:
(1) at least one lysine residue located six to ten residues from a second lysine residue;
(2) at least one histidine residue; and
(3) at least 6% lysine residues.

In yet another aspect of the invention there is provided a method of simulating the immune system of a subject to produce antibodies to bacteria comprising administering an effective amount of at least one bacterial Replikin peptide having from 7 to about 50 amino acids comprising:
(1) at least one lysine residue located six to ten amino acid residues from a second lysine residue;
(2) at least one histidine residue; and
(3) at least 6% lysine residues.

In another aspect, there is provided a method of selecting a bacterial Replikin peptide for inclusion in a preventive or therapeutic bacterial vaccine comprising:
(1) obtaining at least one isolate of each strain of a plurality of strains of the bacteria;
(2) analyzing the amino acid sequence of the at least one isolate of each strain of the plurality of strains of the bacteria for the presence and concentration of bacterial Replikin sequences;
(3) comparing the concentration of bacterial Replikin sequences in the amino acid sequence of the at least one isolate of each strain of the plurality of strains of the bacteria to the concentration of bacterial Replikin sequences observed in the amino acid sequence of each of the strains at at least one earlier time period to provide the concentration of bacterial Replikins for at least two time periods, said at least one earlier time period being within about six months to about three years prior to step (1), or earlier in rapidly mutating bacteria;
(4) identifying the strain of the bacteria having the highest increase in concentration of bacterial Replikin sequences during the at least two time periods; and
(5) selecting at least one bacterial Replikin sequence present in the strain of the bacterial peptide identified in step (4) as a peptide for inclusion in the bacterial vaccine.

The present invention also provides a method of making a preventive or therapeutic bacterial vaccine comprising:
(1) identifying a strain of a bacteria as an emerging strain;
(2) selecting at least one bacterial Replikin sequence present in the emerging strain as a peptide template for the bacterial vaccine manufacture;
(3) synthesizing peptides having the amino acid sequence of the at least one bacterial Replikin sequence selected in step (2); and
(4) combining a therapeutically effective amount of the peptides of step (3) with a pharmaceutically acceptable carrier and/or adjuvant.

In another aspect, the invention is directed to a method of identifying an emerging strain of bacteria for diagnostic, preventive or therapeutic purposes comprising:
(1) obtaining at least one isolate of each strain of a plurality of strains of the bacteria;
(2) analyzing the amino acid sequence of the at least one isolate of each strain of the plurality of strains of the bacteria for the presence and concentration of bacterial Replikin sequences;
(3) comparing the concentration of bacterial Replikin sequences in the amino acid sequence of the at least one isolate of each strain of the plurality of strains of the bacteria to the concentration of bacterial Replikin sequences observed in the amino acid sequence of each of the strains at at least one earlier time period to provide the concentration of bacterial Replikins for at least two time periods, said at least one earlier time period being within about six months to about three years prior to step (1); and
(4) identifying the strain of the bacteria having the highest increase in concentration of bacterial Replikin sequences during the at least two time periods.

In yet another aspect of the invention, there is provided a preventive or therapeutic bacterial vaccine comprising at least one isolated bacterial Replikin present in a protein of an emerging strain of the bacteria and a pharmaceutically acceptable carrier and/or adjuvant.

Two important sub-species of bacteria, classified under mycobacteria, are *Mycobacterium leprae* (leprosy) whose 30-s ribosomal protein has a C-terminal Replikin and *Mycobacterium tuberculosis* (tuberculosis) whose ATPase has three Replikins:

Replikin in 30s ribosomal protein s6 of *Mycobacterium leprae* (leprosy) is:
kvmrtdkh (SEQ ID NO. 699)
Replikins in the ATPase of *Mycobacterium tuberculosis* are:
hprpkvaaalkdsyrlk (SEQ ID NO. 700)
hprpkvaaalk (SEQ ID NO. 701)
ksaqkwpdkflagaaqvah (SEQ ID NO. 702)
Replikins in the B-D-galactosidase of *E. coli*:
hawqhqgktlfisrk (SEQ ID NO. 703)
hqgktlfisrk (SEQ ID NO. 704)
Replikins in *Agrobacterium tumefaciens*:
hsdqqlavmiaakrlddyk (SEQ ID NO. 705)
hlldhpasvgqldlramlaveevkidnpvymek (SEQ ID NO. 706)

hpasvgqldlramlaveevkidnpvymek (SEQ ID NO. 707)
kcvmakncnikcpaglttnqeafngdpralaqylmniah (SEQ ID NO. 708)
kncnikcpaglttnqeafngdpralaqylmniah (SEQ ID NO. 709)
hhdtysiedlaqlihdakaarvrvivk (SEQ ID NO. 710)
hdtysiedlaqlihdakaarvrvivk (SEQ ID NO. 711)
hdakaarvrvivk (SEQ ID NO. 712)
kigqgakpgeggqlpspkvtveiaaarggtpgvelvsppphh (SEQ ID NO. 713)
kigqgakpgeggqlpspkvtveiaaarggtpgvelvsppph (SEQ ID NO. 714)
kaseitktlasgamshgalvaaaheavahgtnmvggmsnsgeggeh (SEQ ID NO. 715)
kaseitktlasgamshgalvaaaheavah (SEQ ID NO. 716)
kaseitktlasgamshgalvaaah (SEQ ID NO. 717)
kaseitktlasgamsh (SEQ ID NO. 718)
kryfpnvktpvggvtfaviaqavadwh (SEQ ID NO. 719)
hhiaaglgfgasavyplgvqfraeekfgadadkafkrfakaaekslmk (SEQ ID NO. 720)
hhiaaglgfgasavyplgvqfraeekfgadadkafkrfakaaekslmk (SEQ ID NO. 721)
hhiaaglgfgasavyplgvqfraeekfgadadkafkrfakaaek (SEQ ID NO. 722)
hhiaaglgfgasavyplgvqfraeekfgadadkafkrfak (SEQ ID NO. 723)
hhiaaglgfgasavyplgvqfraeekfgadadk (SEQ ID NO. 724)
hiaaglgfgasavyplgvqfraeekfgadadkafkrfakaaekslmk (SEQ ID NO. 725)
hiaaglgfgasavyplgvqfraeekfgadadkafkrfakaaek (SEQ ID NO. 726)
hiaaglgfgasavyplgvqfraeekfgadadkafkrfak (SEQ ID NO. 727)
hiaaglgfgasavyplgvqfraeekfgadadk (SEQ ID NO. 728)
kfglydaafeksscgvgfitrkdgvqth (SEQ ID NO. 729)

Also provided by the present invention is a method of preventing or treating a bacterial infection comprising administering to a patient in need thereof a preventive or therapeutic vaccine comprising at least one isolated bacterial Replikin present in a protein of an emerging strain of the bacteria and a pharmaceutically acceptable carrier and/or adjuvant.

Fungus

In one aspect of the invention there are provided isolated or synthesized fungal peptides containing a Replikin sequence. The fungal Replikin peptides comprise from 7 to about 50 amino acids including:

(1) at least one lysine residue located six to ten amino acid residues from a second lysine residue;
(2) at least one histidine residue; and
(3) at least 6% lysine residues (fungal Replikins).

All of the methods described above for production of and treatment with bacterial Replikin vaccines are applicable to the production of and treatment with fungal Replikin vaccines.

In another aspect of the invention there is provided a process for stimulating the immune system of a subject to produce antibodies that bind specifically to a fungal Replikin sequence, said process comprising administering to the subject an effective amount of a dosage of a composition comprising at least one fungal Replikin peptide.

The present invention also provides antibodies that bind specifically to a fungal Replikin, as defined herein, as well as antibody cocktails containing a plurality of antibodies that specifically bind to viral Replikins. In one embodiment of the invention, there are provided compositions comprising an antibody or antibodies that specifically bind to a fungal Replikin and a pharmaceutically acceptable carrier.

The present invention also provides therapeutic compositions comprising one or more of isolated fungal peptides having from 7 to about 50 amino acids comprising:

(1) at least one lysine residue located six to ten residues from a second lysine residue;
(2) at least one histidine residue;
(3) at least 6% lysine residues; and
(4) a pharmaceutically acceptable carrier.

In another aspect of the invention there is provided an antisense nucleic acid molecule complementary to an fungal Replikin mRNA sequence, said Replikin mRNA sequence having from 7 to about 50 amino acids comprising:

(1) at least one lysine residue located six to ten residues from a second lysine residue;
(2) at least one histidine residue; and
(3) at least 6% lysine residues.

In another aspect of the invention there is provided a process for stimulating the immune system of a subject to produce antibodies that bind specifically to a fungal Replikin sequence, said process comprising administering to the subject an effective amount of a dosage of a composition comprising at least one Replikin peptide.

Increasing Replication

In yet another aspect of the invention there is provided a method for increasing the replication rate of an organism comprising transforming a gene encoding an enzyme or other protein having a replication function in the organism with at least one Replikin structure.

Definitions

As used herein, the term "peptide" or "protein" refers to a compound of two or more amino acids in which the carboxyl group of one is united with an amino group of another, forming a peptide bond. The term peptide is also used to denote the amino acid sequence encoding such a compound. As used herein, "isolated" or "synthesized" peptide or biologically active portion thereof refers to a peptide that is substantially free of cellular material or other contaminating peptides from the cell or tissue source from which the peptide is derived, or substantially free from chemical precursors or other chemicals when chemically synthesized by any method, or substantially free from contaminating peptides when synthesized by recombinant gene techniques.

As used herein, a Replikin peptide or Replikin protein is an amino acid sequence having 7 to about 50 amino acids comprising:

(1) at least one lysine residue located six to ten amino acid residues from a second lysine residue;
(2) at least one histidine residue;
(3) at least 6% lysine residues.

Similarly, a Replikin sequence is the amino acid sequence encoding such a peptide or protein.

As used herein, "emerging strain" as used herein refers to a strain of a virus, bacterium, fungus, or other organisms identified as having an increased increasing concentration of Replikin sequences in one or more of its protein sequences relative to the concentration of Replikins in other strains of such organism. The increase or increasing concentration of Replikins occurs over a period of at least about six months, and preferably over a period of at least about one year, most preferably over a period of at least about three years or more, for example, in influenza virus, but may be a much shorter period of time for bacteria and other organisms.

As used herein, "mutation" refers to change in this structure and properties of an organism caused by substitution of amino acids. In contrast, the term "conservation" as used herein, refers to conservation of particular amino acids due to lack of substitution.

BRIEF DESCRIPTION OF THE DRAWINGS

FIG. 8 is a graph of the Replikin concentration observed in hemagglutinin of influenza A strains, H2N2 and H3N2, as well as an emerging strain defined by its constituent Replikins, designated H3N2(R), on a year by year basis from 1950 to 2001.

DETAILED DESCRIPTION OF THE INVENTION

Figure 1:
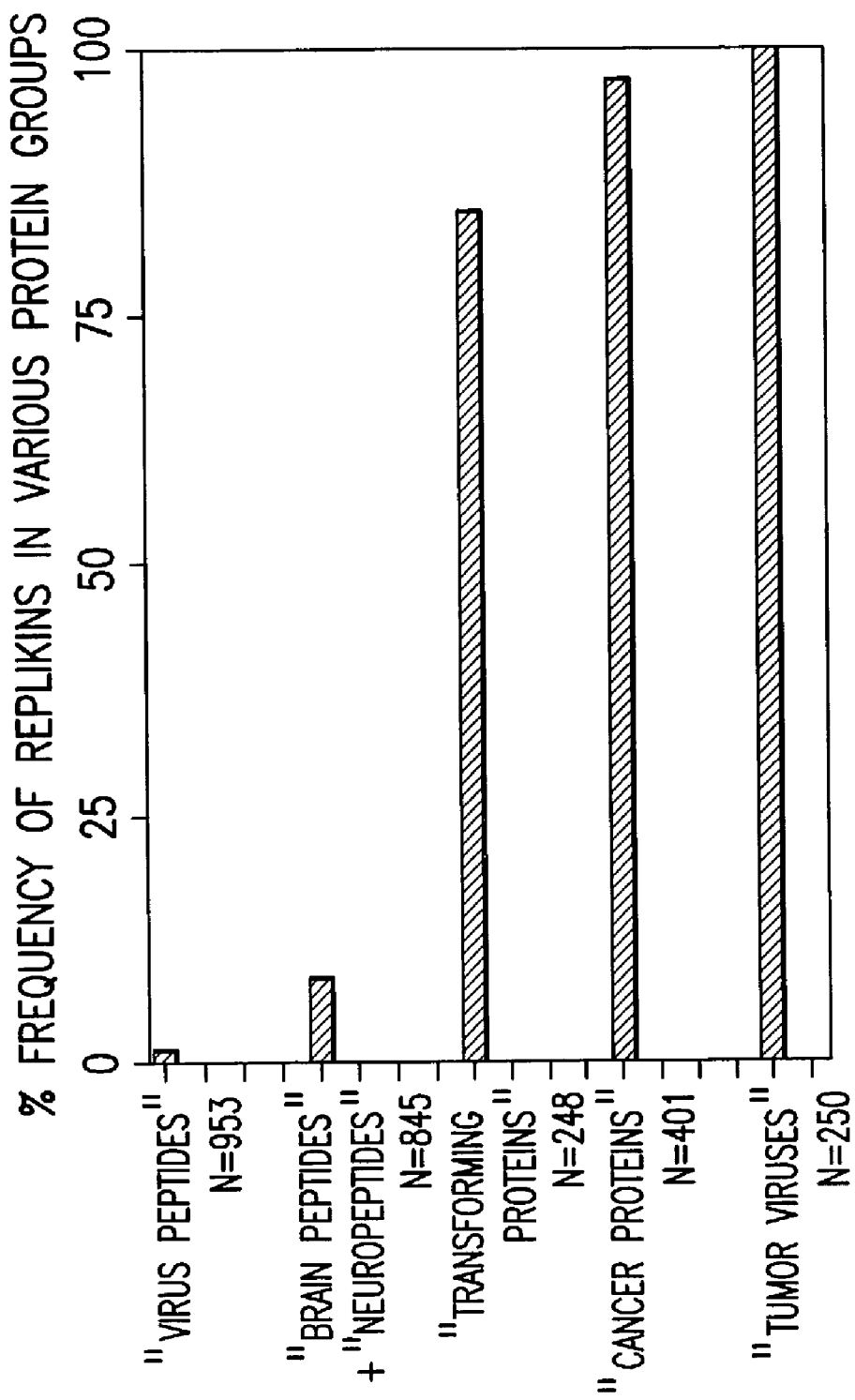
FIG. 1 is a bar graph depicting the frequency of occurrence of Replikins in various organisms.

The identification of a new family of small peptides related to the phenomenon of rapid replication, referred to herein as Replikins, provides targets for detection of pathogens in a sample and developing therapies, including vaccine development. In general, knowledge of and identification of this family of peptides enables development of effective therapies and vaccines for any organism that harbors Replikins. Identification of this family of peptides also provides for the detection of viruses and virus vaccine development.

For example, identification of this family of peptides provides for the detection of influenza virus and provides new targets for influenza treatment. Identification of this family of peptides also provides for example, for the detection of malaria and provides new targets for malaria vaccine development. Further examples provided by the identification of this family of peptides include the detection of infectious disease Replikins, cancer immune Replikins and structural protein Replikins.

Rapid replication is characteristic of virulence in certain bacteria, viruses and malignancies, but no chemistry common to rapid replication in different organisms has been described. We have found a family of conserved small protein sequences related to rapid replication, which we have named Replikins. Such Replikins offer new targets for developing effective detection methods and therapies. The first Replikin found was the glioma Replikin, which was identified in brain glioblastoma multiforme (glioma) cell protein called malignin.

Hydrolysis and mass spectrometry of malignin revealed the novel 16 mer peptide sequence which contains the glioma Replikin. This Replikin was not found in databases for the normal healthy human genome and therefore appeared to be derived from some source outside the body.

We have devised an algorithm to search for the glioma Replikin or homologue thereof. Homologues were not common in over 4,000 protein sequences, but were found, surprisingly, in all tumor viruses, and in the replicating proteins of algae, plants, fungi, viruses and bacteria.

We have identified that both 1) Replikin concentration (number of Replikins per 100 amino acids) and 2) Replikin composition correlate with the functional phenomenon of rapid replication. These relationships provide functional basis for the determination that Replikins are related quantitatively as well as qualitatively to the rate of replication.

The first functional basis for Replikins role to rapid replication is seen in glioma replication. The fact that glioma malignin is enriched ten-fold compared to the five-fold increase in cell number and membrane protein concentration in rapid replication of glioma cells suggests an integral relationship of the Replikins to replication. When the glioma Replikin was synthesized in vitro and administered as a synthetic vaccine to rabbits, abundant antimalignin antibody was produced. This establishes the antigenic basis of the antimalignin antibody in serum (AMAS) test, and provides the first potential synthetic cancer vaccine and the prototype for Replikin vaccines in other organisms. With the demonstration of this natural immune relationship of the Replikins to replication and this natural immune response to cancer Replikins, which overrides cell type, based upon the shared specificity of cancer Replikins and rapid replication, both passive augmentation of this immunity with antimalignin antibody and active augmentation with synthetic Replikin vaccines now is possible.

The relationship between the presence of antimalignin antibody and survival in patients was shown in a study of 8,090 serum specimens from cancer patients. The study showed that the concentration of antimalignin antibody increases with age, as the incidence of cancer in the population increases, and increases further two to three-fold in early malignancy, regardless of cell type. In vitro, the antimalignin antibody is cytotoxic to cancer cells at picograms (femtomoles) per cancer cell, and in vivo the concentration of antimalignin antibody relates quantitatively to the survival of cancer patients. As shown in glioma cells, the stage in cancer at which cells have only been transformed to the immortal malignant state but remain quiescent or dormant, now can be distinguished from the more active life-threatening replicating state, which is characterized by the increased concentration of Replikins. In addition, clues to the viral pathogenesis of cancer may be found in the fact that glioma glycoprotein 10B has a 50% reduction in carbohydrate residues when compared to the normal 10B. This reduction is associated with virus entry in other instances, and so may be evidence of the attachment of virus for the delivery of virus Replikins to the 10B of glial cells as a step in the transformation to the malignant state.

Our study concerning influenza virus hemagglutinin protein sequences and influenza epidemiology over the past 100 years, has provided a second functional basis for the relations of Replikins to rapid replication. Only serological hemagglutinin and antibody classification, but no strain-specific conserved peptide sequences have previously been described in influenza. Further, no changes in concentration and composition of any strain-specific peptide sequences have been described previously that correlate with epidemiologically documented epidemics or rapid replication. In this study, a four to ten-fold increase in the concentration of strain-specific influenza Replikins in one of each of the four major strains, influenza B, (A)H1N1, (A)H2N2 and (A)143N2, is shown to relate to influenza epidemics caused by each strain from 1902 to 2001.

We then showed that these increases in concentration are due to the reappearance of at least one specific Replikin composition from 1 to up to 64 years after its disappearance, plus the emergence of new strain-specific Replikin compositions. Previously, no strain-specific chemical structures were known with which to predict the strains that would predominate in coming influenza seasons, nor to devise annual mixtures of whole-virus strains for vaccines. The recent sharp increase in H3N2 Replikin concentration (1997 to 2000), the largest in H3N2's history, and the reappearance of specific Replikin compositions that were last seen in the high mortality H3N2 pandemic of 1968, and in the two high mortality epidemics of 1975 and 1977, but were absent for 20-25 years, together may be a warning of coming epidemics. This high degree of conservation of Replikin structures observed, whereby the identical structure can persist for 100 years, or reappear after an absence of from one to 64 years, indicate that what was previously thought to be change due to random substitution of amino acids in influenza proteins is more likely to be change due to an organized process of conservation of Replikins.

The conservation of Replikins is not unique to influenza virus but was also observed in other sources, for example in foot and mouth disease virus, type 0, HIV tat, and wheat.

A third functional basis for Replikins' role in rapid replication is seen in the increase in rapid replication in HIV. Replikin concentration was shown to be related to rapid replication in HIV. We found the Replikin concentration in the slow growing low-titre strain of HIV (NS1, "Bru"), which is prevalent in early stage infection, to be one-sixth of the Replikin concentration in the rapidly-growing high-titre strain of HIV (SI, "Lai") (prevalent in late stage HIV infection).

Further examples demonstrate the relationship of Replikins to rapid replication. In the "replicating protein," of tomato curl leaf gemini virus which devastates tomato crops, the first 161 amino acids, the sequence which has been shown to bind to DNA, was shown to contain five Replikins. In malaria, legendary for rapid replication when trypanosomes are released from the liver in the tens of thousands from one trypanosome, multiple, novel, almost 'flamboyant' Replikin structures have been found with concentrations of up to 36 overlapping Replikins per 100 amino acids.

The conservation of any structure is critical to whether that structure provides a stable invariant target to attack and destroy or to stimulate. When a structure is tied in some way to a basic survival mechanism of the organism, the structures tend to be conserved. A varying structure provides an inconstant target, which is a good strategy for avoiding attackers, such as antibodies that have been generated specifically against the prior structure and thus are ineffective against the modified form. This strategy is used by influenza virus, for example, so that a previous vaccine may be quite ineffective against the current virulent virus.

Replikins as Stable Targets for Treatment

Both bacteria and HIV have both Replikin and non-Replikin amino acids. In HIV, for example, there has been a recent increase in drug-resistance from 9% to 13% due to mutation, that is substitution of non-Replikin amino acids. (See detailed analysis of TAT protein of HIV discussed herein). In bacteria, the development of 'resistant strains' is due to a similar mechanism. However, we have found that Replikin structures do not mutate or change to the same degree as non Replikin amino acids (see also discussion of foot and mouth disease virus conservation of Replikins discussed herein). The Replikin structures, as opposed to the non-Replikin structures are conserved and thus provide new constant targets for treatment.

Certain structures too closely related to survival functions apparently cannot change constantly. Because an essential component of the Replikin structure is histidine (h), which is know for its frequent binding to metal groups in redox enzymes and probable source of energy needed for replication, and since this histidine structure remains constant, this structure remains all the more attractive a target for destruction or stimulation.

From a proteomic point of view, inventors construction of a template based on the newly determined glioma peptide sequence led them to the discovery of a wide class of proteins with related conserved structures and a particular function, in this case replication. Examples of the increase in Replikin concentration with virulence of a disease include, influenza, HIV, cancer and tomato leaf curl virus. This newly recognized class of structures is related to the phenomenon of rapid replication in organisms as diverse as yeast, algae, plants, the gemini curl leaf tomato virus, HIV and cancer.

Replikin concentration and composition provide new quantitative methods to detect and control the process of replication, which is central to the survival and dominance of each biological population. The sharing of immunological specificity by diverse members of the class, as demonstrated with antimalignin antibody for the glioma and related cancer Replikins, suggests that B cells and their product antibodies may recognize Replikins by means of a similar recognition language.

Examples of peptide sequences of cancer Replikins or as containing a Replikin, i.e., a homologue of the glioma peptide, kagvaflhkk, may be found in such cancers of, but not limited to, the lung, brain, liver, soft-tissue, salivary gland, nasopharynx, esophagus, stomach, colon, rectum, gallbladder, breast, prostate, uterus, cervix, bladder, eye, forms of melanoma, lymphoma, leukemia, and kidney.

Replikins provide for: 1) detection of pathogens by qualitative and quantitative determinations of Replikins; 2) treatment and control of a broad range of diseases in which rapid replication is a key factor by targeting native Replikins and by using synthetic Replikins as vaccines; and 3) fostering increased growth rates of algal and plant foods.

The first Replikin sequence to be identified was the cancer cell Replikin found in a brain cancer protein, malignin, which was demonstrated to be enriched ten-fold during rapid anaerobic replication of glioblastoma multiforme (glioma) cells. (FIG. 2) Malignin is a 10 KDa portion of the 250 KDa glycoprotein 10B, which was isolated in vivo and in vitro from membranes of glioblastoma multiforme (glioma) cells. Hydrolysis and mass spectroscopy of malignin revealed a 16-mer peptide sequence, ykagvaflhkkndide (SEQ ID NO.: 4), which is referred to herein as the glioma Replikin and which includes the shorter peptide, kagvaflhkk (SEQ ID NO.: 1), both of which apparently are absent in the normal human genome.

TABLE 1

16-mer peptide sequence ykagvaflhkkndide obtained
from malignin by hydrolysis and mass spectrometry

| | | | | Method By Which Fragment Obtained | | | |
|---|---|---|---|---|---|---|---|
| Seq ID No. | Fragment Identified | MH+ (mass) | Sequence | Auto-hydrolysis of malignin free in solution | Auto-hydrolysis of malignin immobilized on bromoacetyl cellulose | Microwaved 5 seconds | Microwaved 30 seconds |
| 19 | 1-3 | 381.21 | ( )yka(g) | | | | + |
| 20 | 1-5 | 537.30 | ( )ykagv(a) | | + | | |
| 21 | 2-6 | 445.28 | (y)kagva(f) | | + | | |
| 22 | 2-7 | 592.35 | (Y)kagvaf(l) | | | + | |
| 23 | 4-11 | 899.55 | (a)gvaflhkk(n) | | | | + |
| 24 | 5-7 | 336.19 | (g)vaf(l) | | | | + |
| 25 | 6-7 | 237.12 | (v)af(l) | + | | | |
| 26 | 6-10 | 615.36 | (v)aflhk(k) | | | | + |
| 27 | 6-10 | 615.36 | (v)aflhk(k) | + | | | |
| 28 | 6-12 | 857.50 | (v)aflhkkn(d) | | + | | |
| 29 | 6-12 | 857.50 | (v)afhkkn(d) | + | | | |
| 30 | 7-8 | 279.17 | (a)fl(h) | | | + | |
| 31 | 10-16 | 861.43 | (h)kkndide( ) | | + | | |
| 32 | 11-14 | 489.27 | (k)kndi(d) | | + | | |
| 33 | 12-15 | 476.2- | (k)ndid(e) | + | | | |

When the 16-mer glioma Replikin was synthesized and injected as a synthetic vaccine into rabbits, abundant antimalignin antibody was produced. (Bogoch et al., Cancer Detection and Prevention, 26 (Suppl. 1): 402 (2002)). The concentration of antimalignin antibody in serum in vivo has been shown to relate quantitatively to the survival of cancer patients. (Bogoch et al., Protides of Biological Fluids, 31:739-747 (1984). In vitro antimalignin antibodies have been shown to be cytotoxic to cancer cells at a concentration of picograms (femtomolar) per cancer cell. (Bogoch et al., Cancer Detection and Prevention, 26 (Suppl. 1): 402 (2002).

Studies carried out by the inventors showed that the glioma Replikin is not represented in the normal healthy human genome. Consequently, a search for the origin and possible homologues of the Replikin sequence was undertaken by analysis of published sequences of various organisms.

By using the 16-mer glioma Replikin sequence as a template and constructing a recognition proteomic system to visually scan the amino acid sequences of proteins of several different organisms, a new class of peptides, the Replikins, was identified. The present invention provides a method for identifying nucleotide or amino acid sequences that include a Replikin sequence. The method is referred to herein as a 3-point-recognition method. The three point recognition method comprises: a peptide from 7 to about 50 amino acids including:

(1) at least one lysine residue located six to ten amino acid residues from a second lysine residue;
(2) at least one histidine residue; and
(3) at least 6% lysine residues. (Replikin).

These peptides or proteins constitute a new class of peptides in species including algae, yeast, fungi, amoebae, bacteria, plant, virus and cancer proteins having replication, transformation, or redox functions. Replikin peptides have been found to be concentrated in larger 'replicating' and 'transforming' proteins (so designated by their investigators, See Table 2) and cancer cell proteins. No sequences were found to be identical to the malignin 16-mer peptide.

TABLE 2

Examples of Replikins in various organisms - prototype: Glioma Replikin* kagvaflhkk
(SEQ ID No.: 1)

| | SEQ ID NO. | | |
|---|---|---|---|
| Algae: | 34 | *Caldophera prolifera* | kaskftkh |
| | 35 | *Isolepis prolifera* | kaqaetgeikgh |
| Yeast: | 36 | *Schizosaccharomyces pombe* | ksfkypkkhk |
| | 37 | *Oryza sativa* | kkaygnelhk |
| | 2 | *Sacch. cerevisiae* replication binding protein | hsikrelgiifdk |
| Fungi: | 38 | Isocitrate lyase ICl 1, *Penicillium marneffei* | kvdivthqk |
| | 39 | DNA-dependent RNA polymerase 11, Diseula destructiva | kleedaayhrkk |
| | 40 | *Ophiostoma* novo-ulm 1, RNA in Dutch elm disease fungus | kvilplrgnikgiffkh |
| Amoeba: | 41 | *Entamoeba invadens*, histone H2B | klilkgdlnkh |
| Bacteria: | 42 | Pribosomal protein replication factor, *Helicobacter pylori* | ksvhaflk |
| | 10 | Replication-associated protein Staph. Aureus | |
| | 43 | Mycoplasma pulmonic, chromosome replication | kkektthnk |
| | 90 | Macrophage infectivity potentiator, *L. legionella* | kvhffqlkk |

TABLE 2-continued

Examples of Replikins in various organisms - prototype: Glioma Replikin* kagvaflhkk
(SEQ ID No.: 1)

| | SEQ ID NO. | | |
|---|---|---|---|
| Plants: | 44 | Arabidopsis thaliana, prolifera | kdhdfdgdk |
| | 45 | Arabidopsis thaliana, cytoplasmic ribosomal | kmkglkqkkah |
| | 46 | Arabidopsis thaliana, DNA binding protein | kelssttqeksh |
| Viruses: | 9 | Replication associated protein A [Maize streak virus] | Kekkpskdeimrdiish |
| | 11 | Bovine herpes virus 4, DNA replication protein | hkinitngqk |
| | 12 | Meleagrid herpesvirus 1, replication binding protein | hkdlyrllmk |
| | 47 | Feline immunodeficiency | hlkdyklvk |
| | 3 | Foot and Mouth Disease (O) | hkqkivapvk |
| | 5 | HIV Type 1 | kcfncgkegh |
| | 7 | HIV Type 2 | kcwncgkegh |
| Tumor | 48 | Rous sarcoma virus tyrosine-protein kinase | kklrhek |
| Viruses: | 49 | v-yes, avian sarcoma | kklrhdk |
| | 50 | c-yes, colon cancer, malignant melanoma | kklrhdk |
| | 51 | v-srcC, avian sarcoma | kklrhek |
| | 52 | c-src, colon, mammary, panrcreatic cancer | kklrhek |
| | 53 | Neuroblastoma RAS viral (v-ras) oncogene | kqahelak |
| | 54 | VP1 (major capsid protein) [Polyamavirus sp.] | kthrfskh |
| | 55 | Sindbis | knlhekik |
| | 56 | E1 [Human papilloamavirus type 71] | khrpllqlk |
| | 57 | v-erbB from AEV and c-erb | kspnhvk |
| | 58 | v-fms (feline sarcoma) | knihlekk |
| | 59 | c-fms (acute and chronic myelomonocytic tumors) | knihlekk |
| | 60 | large t-antigen I [Polyomavirus sp.l | kphlaqslek |
| | 61 | middle t-antigen [Polyomavirus sp,l- | kqhrelkdk |
| | 62 | small t-antigen [Polyomavirus spJ, | kqhrelkdk |
| | 63 | v-abl, murine acute leukemia | kvpvlisptlkh |
| | 64 | Human T-cell lymphotropic virus typo 2 | kslllevdkdish |
| | 65 | c-kit, GI tumors, small cell lung carcinoma | kagitimvkreyh |
| | 18 | Hepatitis C | hyppkpgcivpak |
| Trans- | 66 | Transforming protein myb | Ksgkhlgk |
| Forming | 67 | Transforming protein myc, Burkitt lymphoma | krreqlkhk |
| Proteins: | 68 | Ras-related GTP-binding protein | ksfevikvih |
| | 69 | Transforming protein ras (teratocarcinoma) | kkkhtvkk |
| | 70 | TRAF-associated NF•kB activator TANK | kaqkdhlsk |
| | 71 | RFP transforming protein | hlkrvkdlkk |
| | 72 | Transforming protein D (S.C.) | kygspkhrlik |
| | 73 | Papilloma virus type 11, transforming protein | klkhilgkarfik |
| | 74 | Protein tryosine kinasc (EC 2.7.1.ll2slk | kgdhvkhykirk |
| | 75 | Transforming protein (ax1(–)) | keklrdvmvdrhk |
| | 76 | Transforming protein (N-myc) | klqarqqqllkkieh |
| | 77 | Fibroblast growth factor 4 (Kaposi sarcoma) | kkgnrvsptmkvth |
| Cancer | 78 | Matrix metaloproteinase 7 (uterine) | keiplhfrk |
| Cell | 79 | Transcription factor 7-like | kkkphikk |
| Proteins: | 80 | Breast cancer antigen NY-BR-87 | ktrhdplak |
| | 81 | BRCA-1-Associated Ring Domain Protein (breast) | khhpkdnlik |
| | 82 | 'Autoantigen from a breast tumor' | khkrkkfrqk |
| | 83 | Glioma Replikin (this study) | kagvaflhkk |
| | 84 | Ovarian cancer antigen | khkrkkfrqk |
| | 85 | EE L leukemia | kkkskkhkdk |
| | 86 | Proto-oncogene tyrosine-protein kinase C-ABLE | hksekpalprk |
| | 87 | Adenomatosis polyposis coli | kkkkpsrlkgdnek |
| | 88 | Gastric cancer transforming protein | ktkkgnrvsptmkvth |
| | 89 | Transforming protein (K-RAS 2B), lung | khkekmskdgkkkkkksk |

Identification of an amino acid sequence as a Replikin or as containing a Replikin, i.e., a homologue of the glioma peptide, kagvaflhkk, requires that the three following requirements be met. According to the three point recognition system the sequences have three elements: (1) at least one lysine residue located six to ten residues from another lysine residue; (2) at least one histidine residue; and (3) a composition of at least 6% lysine within an amino acid sequence of 7 to about 50 residues.

Databases were searched using the National Library of Medicine keyword "PubMed" descriptor for protein sequences containing Replikin sequences. Over 4,000 protein sequences were visually examined for homologues. Sequences of all individual proteins within each group of PubMed-classified proteins were visually scanned for peptides meeting the three above-listed requirements. An infrequent occurrence of homologues was observed in "virus peptides" as a whole (1.5%) (N=953), and in other peptides not designated as associated with malignant transformation or replication such as "brain peptides" and "neuropeptides" (together 8.5%) (N=845). However, surprisingly, homologues were significantly more frequently identified in large "replicating proteins," which were identified as having an established function in replication in bacteria, algae, and viruses. Even more surprising was the finding that Replikin homologues occurred in 100% of "tumor viruses" (N=250), in 97% of "cancer proteins" (N=401), and in 85% of "transforming viruses" (N=248). These results suggest that there are shared properties of cancer pathogenesis regardless of cell type and suggest a role of viruses in carcinogenesis, i.e., conversion of cells from a transformed albeit dormant state to a more virulent actively replicating state.

Homologues of the following amino acid sequence, kagvaflhkk, as defined by the three point recognition method, were found in such viruses, or viral peptides, as, but not limited to, adenovirus, lentivirus, a-virus, retrovirus, andeno-associated virus, human immunodeficiency virus, hepatitis virus, influenza virus, maize streak virus, herpes virus, bovine herpes virus, feline immunodeficiency virus, foot and mouth disease virus, small pox virus, rous sarcoma virus, neuroblastoma RAS viral oncogene, polyamavirus, sindbis, human papilloma virus, myelomonocytic tumor virus, murine acute leukemia, T-cell lymphotropic virus, and tomato leaf curl virus.

Replikins are present in such bacteria as, but not limited to, *Acetobacter, Achromobacter, Actinomyces, Aerobacter, Alcaligenes, Arthrobacter, Azotobacter, Bacillus, Brevibacterium, Chainia, Clostridium, Corynebacterium, Erwinia, Escheria, Lebsiella, Lactobacillus, Haemophilus, Flavobacterium, Methylomonas, Micrococcus, Mycobacterium, Micronomspora, Mycoplasma, Neisseria, Nocardia, Proteus, Pseudomonas, Rhizobium, Salmonella, Serratia, Staphylococcus, Streptocossus, Streptomyces, Streptosporangium, Streptovirticillium, Vibrio*, peptide, and *Xanthomas*.

Replikins are present in such fungi as, but not limited to, *Penicillium*, Diseula, Ophiostoma novo-ulim, Mycophycophta, *Phytophthora infestans, Absidia, Aspergillus, Candida, Cephalosporium, Fusarium, Hansenula, Mucor, Paecilomyces, Pichia, Rhizopus, Torulopsis, Trichoderma*, and *Erysiphe*.

Replikins are present in such yeast as, but not limited to, *Saccharomyces, Cryptococcus*, including *Cryptococcus neoformas, Schizosaccharomyces*, and *Oryza*.

Replikins are present in algae such as, but not limited to, Caldophera, Isolepisprolifera, Chondrus, Gracilaria, Gelidium, Caulerpa, Laurencia, Cladophexa, Sargassum, Penicillos, Halimeda, Laminaria, Fucus, Ascophyllum, Undari, Rhodymenia, Macrocystis, Eucheuma, Ahnfeltia, and Pteroclasia.

Replikins are present in amoeba such as, but not limited to, *Entamoeba* (including *Entamoeba invadens*), *Amoebidae, Acanthamoeba* and *Naegleria*.

Replikins are present in plants such as, but not limited to, *Arabidopsis*, wheat, rice, and maize.

Auxiliary Specifications

To permit classification of subtypes of Replikins, additional or "auxiliary specifications" to the basic "3-point-recognition" requirements may be added: (a) on a structural basis, such as the common occurrence of adjacent di- and polylysines in cancer cell proteins (e.g., transforming protein P21B(K-RAS 2B), lung, Table 2, SEQ ID NO.: 89), and other adjacent di-amino acids in TOLL-like receptors, or b) on a functional basis, such as exhibiting ATPase, tyrosine kinase or redox activity as seen in Table 2.

Functional Derivatives

"Functional derivatives" of the Replikins as described herein are fragments, variants, analogs, or chemical derivatives of the Replikins, which retain at least a portion of the immunological cross reactivity with an antibody specific for the Replikin. A fragment of the Replikin peptide refers to any subset of the molecule. Variant peptides may be made by direct chemical synthesis, for example, using methods well known in the art. An analog of a Replikin to a non-natural protein substantially similar to either the entire protein or a fragment thereof. Chemical derivatives of a Replikin contain additional chemical moieties not normally a part of the peptide or peptide fragment.

Figure 2:
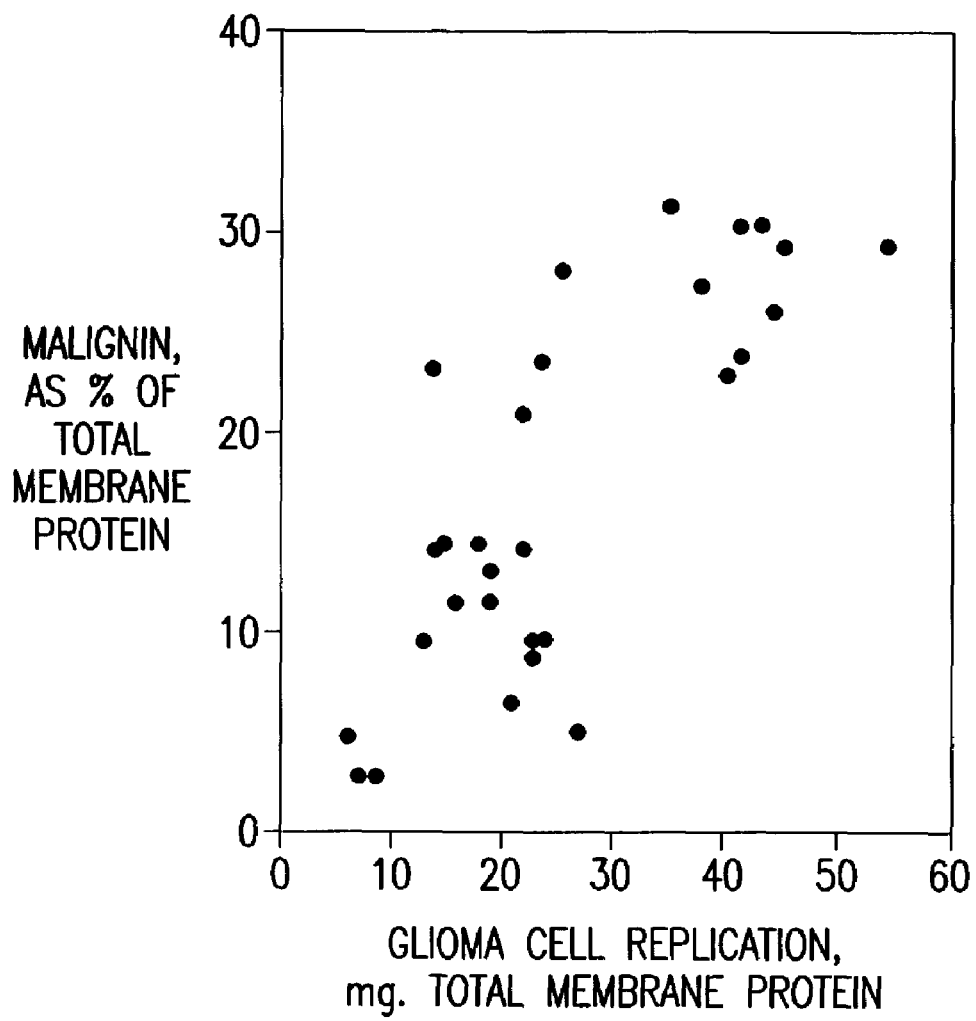
FIG. 2 is a graph depicting the percentage of malignin per milligram total membrane protein during anaerobic replication of glioblastoma cells.

As seen in FIG. 2, during anaerobic respiration when the rate of cell replication is increased, malignin is enriched. That is, malignin is found to increase not simply in proportion to the increase in cell number and total membrane proteins, but is enriched as much as ten-fold in concentration, starting with 3% at rest and reaching 30% of total membrane protein. This clear demonstration of a marked increase in Replikin concentration with glioma cell replication points to, and is consistent with, the presence of Replikins identified with the 3-point recognition method in various organisms. For example, Replikins were identified in such proteins as "*Saccharomyces cerevisiae* replication binding protein" (SEQ ID NO.: 2) (hsikrelgiifdk); the "replication associated protein A of maize streak virus" (SEQ ID NO.: 8) (kyivcareahk) and (SEQ ID NO.: 9) (kekkpskdeimrdiish); the "replication-associated protein of *Staphylococcus aureus* " (SEQ ID NO.: 10) (kkektthnk); the "DNA replication protein of bovine herpes virus 4" (SEQ ID NO.: 11) (hkinitngqk); and the "Mealigrid herpes virus 1 replication binding protein" (SEQ ID NO.: 12) (hkdlyrllmk). Previous studies of tomato leaf curl gemini virus show that the regulation of virus accumulation appears to involve binding of amino acids 1-160 of the "replicating protein" of that virus to leaf DNA and to other replication protein molecules during virus replication. Analysis of this sequence showed that amino acids 1-163 of this "replicating protein" contain five Replikins, namely: (SEQ ID NO.: 13) kfrinaknyfltyph, (SEQ ID NO.: 14) knletpvnklfiricrefh, (SEQ ID NO.: 15) hpniqaaksstdvk, (SEQ ID NO.: 16) ksstdvkaymdkdgdvldh, and (SEQ ID NO.: 17) kasalnilrekapkdfvlqfh.

Table 2 shows that Replikin-containing proteins also are associated frequently with redox functions, and protein synthesis or elongation, as well as with cell replication. The association with metal-based redox functions, the enrichment of the Replikin-containing glioma malignin concentration during anaerobic replication, and the cytotoxicity of antimalignin at low concentrations (picograms/cell) (FIGS. 4c-f), all suggest that the Replikins are related to central respiratory survival functions, have been found less often subjected to the mutations characteristic of non-Replikin amino acids.

Of particular interest, it was observed that at least one Replikin per 100 amino acids was found to be present in the hemagglutinin proteins of almost all of the individual strains of influenza viruses examined. The Replikin sequences that were observed to occur in the hemagglutinin proteins of isolates of each of the four prevalent strains of influenza virus, influenza B, H1N1, H2N2, and H3N2, for each year that amino acid sequence data are available (1902-2001), are shown in Tables 3, 4, 5 and 6, below.

TABLE 3

Replikin Sequences present in hemagglutinins of Influenza B
viruses in each year for which amino acid sequences were available (1902-2001).
Influenza B Replikins Year Detected in Influenza B strain

Figure 7:
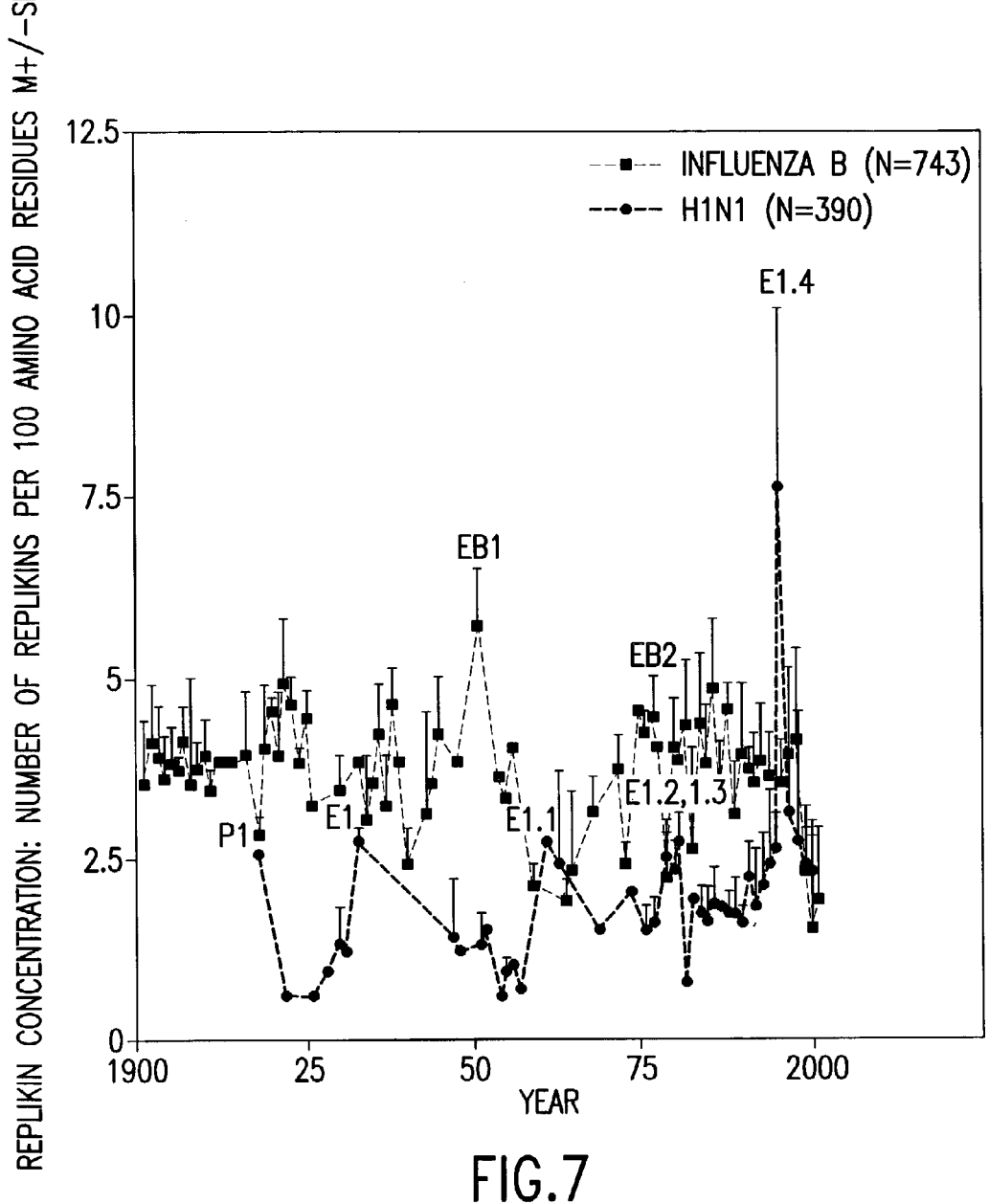
FIG. 7 is a graph showing the concentration of Replikins observed in hemagglutinin of influenza B and influenza A strain, H1N1, on a year by year basis from 1918 through 2001.

|  | (Peak in FIG. 7: EB1  EB2) |
|---|---|
| kshfanlk (SEQ ID NO. 91) | 1902, 19, 24, 38, 40, 43, <u>51</u>, 59, 75, 76, <u>77</u>, 89, 90, 93, 97, 98, 99, 00, 01 |
| kshfanlkgtk (SEQ ID NO. 92) | 1902, 19, 24, 38, 40, 43, <u>51</u>, 59, 75, 76, <u>77</u>, 89, 90, 93, 97, 98, 99, 00, 01 |
| kshfanlkgtktrgklcpk (SEQ ID NO. 93) | 1902, 19, 24, 38, 40, 43, <u>51</u>, 59, 75, 76, <u>77</u>, 89, 90, 93, 97, 98, 99, 00, 01 |
| hekygglnk (SEQ ID NO. 94) | 1902, 19, 24, 38, 40, 43, <u>51</u>, 59, 75, 76, <u>77</u>, 89, 90, 93, 97, 98, 99, 00, 01 |
| hekygglnksk (SEQ ID NO. 95) | 1902, 19, 24, 38, 40, 43, <u>51</u>, 59, 75, 76, <u>77</u>, 89, 90, 93, 97, 98, 99, 00, 01 |
| hekygglnkskpyytgehak (SEQ ID NO. 96) | 1902, 19, 24, 38, 40, 43, <u>51</u>, 59, 75, 76, <u>77</u>, 89, 90, 93, 97, 98, 99, 00, 01 |
| hakaigncpiwvk (SEQ ID NO. 97) | 1902, 19, 24, 38, 40, 43, <u>51</u>, 59, 75, 76, <u>77</u>, 89, 90, 93, 97, 98, 99, 00, 01 |
| hakaigncpiwvktplklangtk (SEQ ID NO. 98) | 1902, 19, 24, 38, 40, 43, <u>51</u>, 59, 75, 76, <u>77</u>, 89, 90, 93, 97, 98, 99, 00, 01 |
| hakaigncpiwvktplklangtkyrppak (SEQ ID NO. 99) | 1902, 19, 24, 38, 40, 43, <u>51</u>, 59, 75, 76, <u>77</u>, 89, 90, 93, 97, 98, 99, 00, 01 |
| hakaigncpiwvktplklangtkyrppakllk (SEQ ID NO. 100) | 1902, 19, 24, 38, 40, 43, <u>51</u>, 59, 75, 76, <u>77</u>, 89, 90, 93, 97, 98, 99, 00, 01 |
| hfanlkgtktrgk (SEQ ID NO. 101) | 1919, 76, 89, 90, 99, 00, 01 |
| hfanlkgtktrgklcpk (SEQ ID NO. 102) | 1919, 76, 90, 00, 01 |
| hsdneiqmvklygdsk (SEQ ID NO. 103) | 1919 |
| hsdneiqdkmvklygdskpqk (SEQ ID NO. 104) | 1919 |
| hsdneiqmvklygdskpqk (SEQ ID NO. 105) | 1919, 24, 97, 98, 00 |
| k(a/v)silhevk (SEQ ID NO. 106) | 1919, 40, 59, 90, 93 |
| kctgtipsakasilh (SEQ ID NO. 107) | 1919, 00 |
| kctgtipsakasilhevk (SEQ ID NO. 108) | 1919, 93, |
| kygglnkskpyytgeh (SEQ ID NO. 109) | 1919 |
| kvwcasgrskvikgslpligeadclh (SEQ ID NO. 110) | 1919, 38, 40, 43, 59, 75, 76, <u>77</u>, 89, 90, 98, 99, 00 |
| kpyytgehak (SEQ ID NO. 111) | 1919, 38, 40, 59, 89, 90, 93, 97, 98, 01 |
| kcmgtipsakasilhevk (SEQ ID NO. 112) | 1924, 43, 75, 76, <u>77</u>, 93 |
| hnvinaekapggpyk (SEQ ID NO. 113) | 1938, 93, 97, 00 |
| hsdnetqmaklygdsk (SEQ ID NO. 114) | 1938, 93, 97, 00 |
| hgvavaadlkstqeaink (SEQ ID NO. 115) | 1940, 59, 00 |
| hgvavaadlkstqeainkdtistqeaink (SEQ ID NO. 116) | 1940 |
| klygdskpqkftssangvtth (SEQ ID NO. 117) | 1943, 75, 76, <u>77</u>, 93, 97, 00 |
| hsdnetqmaklygdskpqk (SEQ ID NO. 118) | 1943, 75, 76, <u>77</u>, 93 |
| hfanlkgtqtrgk (SEQ ID NO. 119) | 1959 |
| kprsalkckgfh (SEQ ID NO. 120) | 1988 |
| kskpyytgehakai(g/a)ncpiwvk (SEQ ID NO. 121) | 2000 |

1. Influenza B has not been responsible for any human pandemic (global distribution).
2. Abbreviation for years: eg. "19" = 1919, "01" = 2001.
3. The first year that a given Replikin appears is indicated at the beginning of the series of years in which that Replikin has been found.
4. Overlapping Replikin sequences are listed separately.
5. Increase in number of new Replikin structures occurs in years of epidemics (underlined): eg. 1951 and 1977 and correlates with increased total Replikin concentration (number of Replikins per 100 amino acid residues). See FIG. 7.

TABLE 4

H1N1 Replikin Sequences present in H1N1 hemagglutinins of Influenza viruses
in each year for which amino acid sequences were available (1918-2000)
H1N1 Replikin Year Detected in Influenza
H1N1 Strain

|  | Peak in FIG. 7: P1    E1    E1.1, 1.2, 1.3    E1.4) |
|---|---|
| hp(v/i)tigecpkyv(r/k)(s/t)(t/a)k (SEQ ID NO. 122) | <u>1918</u>, 25, 28, 30, <u>31</u>, 35, 47, 48, 51, 52, 55, 56, 57, 59, <u>63</u>, <u>77</u>, <u>79</u>, 80, 81, 85, 87, 88, 89, 91, 92, 95, <u>96</u>, 97, 98, 99, 00 |
| hdsnvknly(e/g)kv(k/r)(n/s)ql(k/r)nnak (SEQ ID NO. 123) | <u>1918</u>, 28, 30, <u>31</u>, <u>77</u>, <u>79</u>, 80, 88, 91, 95, 98 |
| hdsnvknly(e/g)kv(k/r)(n/s)qlk (SEQ ID NO. 124) | <u>1918</u>, 28, 30, <u>31</u>, <u>77</u>, <u>79</u>, 80, 88, 91, 95, 98 |
| hkc(nn/dd)(a/t/e)cmesv(r/k)ngtydypkyseesklnre(e/k)idgvk (SEQ ID NO. 125) | <u>1918</u>, 30, 35, <u>77</u>, 80, 98 |
| hkc(nn/dd)(a/t/e)cmesv(r/k)ngtydypkyseesk (SEQ ID NO. 126) | <u>1918</u>, 30, 35, <u>77</u>, 80, 98 |
| hqn(e/g)qgsgyaadqkstqnai(d/n)gitnkvnsviekmntqftavgkefnklek (SEQ ID NO. 127) | <u>1918</u>, 28, 30, <u>31</u>, 35, 59, <u>79</u>, 95 |
| hqn(e/g)qgsgyaadqkstqnai(d/n)gitnkvnsviek (SEQ ID NO. 128) | <u>1918</u>, 28, 30, <u>31</u>, 35, 59, <u>79</u>, 95 |
| hqn(e/g)qgsgyaadqkstqnai(d/n)gitnk (SEQ ID NO. 129) | <u>1918</u>, 28, 30, <u>31</u>, 35, 59, <u>79</u>, 95 |
| kfeifpktsswpnh (SEQ ID NO. 130) | <u>1918</u>, <u>77</u> |
| kg(n/s/t)sypkl(n/s)ksy(v/t)nnkgkevlvlwgvh (SEQ ID NO. 131) | <u>1918</u>, 35, <u>77</u>, <u>96</u> |
| ksy(v/t)nnkgkevlvlwgvh (SEQ ID NO. 132) | <u>1918</u>, 35, <u>77</u>, <u>96</u> |
| hkcnnecmesvkngtydypkyseesklnrekidgvk (SEQ ID NO. 133) | 1928, <u>31</u>, 95 |
| hkcnnecmesvkngtydypkyseesk (SEQ ID NO. 134) | 1928, <u>31</u>, 95 |
| hkcnnecmesvkngtydypk (SEQ ID NO. 135) | 1928, <u>31</u>, 95 |
| hkcnnecmesvk (SEQ ID NO. 136) | 1928, <u>31</u>, 95 |
| hngkssfy(k/r)nllwlt(e/g)knglypnlsksyvnnkek (SEQ ID NO. 137) | 1928, 95, 00 |
| hngkssfy(k/r)nllwlt(e/g)knglypnlsksyvnnk (SEQ ID NO. 138) | 1928, <u>31</u>, 95, 00 |
| hngkssfy(k/r)nllwlt(e/g)knglypnlsk (SEQ ID NO. 139) | 1928, <u>31</u>, 95, 00 |
| hngkssfy(k/r)nllwlt(e/g)k (SEQ ID NO. 140) | 1928, <u>31</u>, 95, 00 |
| kssfyknllwlteknglypnlsksyvnnkekevlvlwgvh (SEQ ID NO. 141) | 1928, <u>31</u>, 95 |
| knllwlteknglypnlsksyvnnkekevlvlwgvh (SEQ ID NO. 142) | 1928, <u>31</u>, 95 |
| knglypnlsksyvnnkekevlvlwgvh (SEQ ID NO. 143) | 1928, <u>31</u>, 95, <u>96</u>, 00 |

TABLE 4-continued

H1N1 Replikin Sequences present in H1N1 hemagglutinins of Influenza viruses
in each year for which amino acid sequences were available (1918-2000)
H1N1 Replikin Year Detected in Influenza
H1N1 Strain

|  | Peak in FIG. 7: P1    E1    E1.1, 1.2, 1.3    E1.4) |
|---|---|
| ksy(v/a)nnkekev(l/-)(v/-)lwgvh (SEQ ID NO. 144) | 1928, <u>31</u>, 51, 95, <u>96</u>, 98, 00 |
| kesswpnhtvtk (SEQ ID NO. 145) | 1928, <u>31</u>, 95 |
| het(t/n)kgvtaacpyagassfyrnllwlvkkensypklsksyvnnk (SEQ ID NO. 146) | 1930, 35 |
| het(t/n)kgvtaacpyagassfyrnllwlvkkensypklsk (SEQ ID NO. 147) | 1930, 35 |
| kfeifpktsswpnevlvlwgvh (SEQ ID NO. 148) | 1930 |
| kerswpkh (SEQ ID NO. 149) | 1947, 51, 52, 55, 56, <u>79</u>, 82 |
| klsksyvnnkekevlvlwqvh (SEQ ID NO. 150) | 1947, 51 |
| knnkekevlvlwqvh (SEQ ID NO. 151) | 1947 |
| h(k/n)(g/q)kssfy(r/k)nllwltekng(l/s)yp(n/t)lsksyannkek (SEQ ID NO. 152) | 1948 <u>79</u>, 89, <u>96</u> |
| h(k/n)(g/q)kssfy(r/k)nllwltek (SEQ ID NO. 153) | 1948 <u>79</u>, 89, <u>96</u> |
| hakkssfyk (SEQ ID NO. 154) | <u>1951</u>, 57, 59 |
| hngklcrlkgk (SEQ ID NO. 155) | <u>1951</u>, 52, 55, 56, 57, 59, <u>79</u>, |
| hyklnn(q/g)kk (SEQ ID NO. 156) | 1956, 00 |
| hdiyrdeainnrfqiqgvkltqgyk (SEQ ID NO. 157) | 1956 |
| kgngcfeifhk (SEQ ID NO. 158) | 1956 |
| klnrliektndkyhqiek (SEQ ID NO. 159) | 1956 |
| klnrliektndkyh (SEQ ID NO. 160) | 1956 |
| kchtdkgslsttk (SEQ ID NO. 161) | 1956 |
| kinngdyaklyiwgvh (SEQ ID NO. 162) | 1956 |
| hngklcrkgiaplqlgk (SEQ ID NO. 163) | 1959, 82 |
| hetnrqvtaacpyagansffrnliwlvkkessypklsk (SEQ ID NO. 164) | <u>1963</u>, 81 |
| hetnrqvtaacpyagansffrnliwlvkkessypk (SEQ ID NO. 165) | <u>1963</u>, 81 |
| hpptstdqqslyqnadayifvgsskynrkfk (SEQ ID NO. 166) | <u>1963</u>, 81 |
| hpptstdqqslyqnadayifvgsskynrkfkpeia (SEQ ID NO. 167) | <u>1963</u>, 81 |
| hdiyrdeainnrfqiqgvkitqgyk (SEQ ID NO. 168) | <u>1977</u>, <u>79</u>, 91 |
| hqneqgsgyaadqkstqnaidgitnkvnsviekmntqftavgk (SEQ ID NO. 169) | <u>1977</u> |
| hqneqgsgyaadqkstqnaidgitnkvnsviek (SEQ ID NO. 170) | <u>1977</u> |
| hqneqgsgyaadqkstqnaingitnkvnsviekmntqftavgkefnklek (SEQ ID NO. 171) | <u>1979</u>, 91 |
| hngklcrlkgiaplqlgk (SEQ ID NO. 172) | <u>1979</u> |
| hkcnnecmesvk (SEQ ID NO. 173) | <u>1979</u> |
| kfeifpkasswpnh (SEQ ID NO. 174) | 1981 |
| hdsnvknlyekvrsqlmnak (SEQ ID NO. 175) | 1981 |
| kvnsvikkmntqfaavgkefnh (SEQ ID NO. 176) | 1981 |
| khngklck (SEQ ID NO. 177) | 1981 |
| kkgtsypklsksythnkgkevlvlwgvh (SEQ ID NO. 178) | 1981 |
| kgtsypklsksythnkgkevlvlwgvh (SEQ ID NO. 179) | 1981 |
| klsksythnkgkevlvlwgvh (SEQ ID NO. 180) | 1981 |
| ksythnkgkevlvlwgvh (SEQ ID NO. 181) | 1981 |
| kgvtascshk (SEQ ID NO. 182) | 1985, 87 |
| kgvtascshkgrssfyrnllwlteknglypnlsk (SEQ ID NO. 183) | 1985, 87 |
| kgnsypklsksyvnnkekevlvlwgih (SEQ ID NO. 184) | 1988 |
| kefnhlek (SEQ ID NO. 185) | 1988 |
| hpptstdqqslyqnadayvfvgsskynkkfkpeiatrpk (SEQ ID NO. 186) | 1988 |
| hpptstdqqslyqnadayvfvgsskynkkfk (SEQ ID NO. 187) | 1988 |
| hegkssfyrnllwltekegsypklknsyvnk (SEQ ID NO. 188) | 1991 |
| hegkssfyrnllwltekegsypk (SEQ ID NO. 189) | 1991 |
| hkcdnecmesvrngtydypkyseesk (SEQ ID NO. 190) | 1991 |
| kesswpnhtvtk (SEQ ID NO. 191) | 1991, 92 |
| knllwlteknglypnlsksyvnnkekeilvlwgvh (SEQ ID NO. 192) | 1991, 92, <u>96</u> |
| hngkssfy(k/m)(n/-)llwlt(e/g)(-/k)knglypnlsk (SEQ ID NO. 193) | 1991, 92, <u>96</u>, 00 |
| hngkssfyknllwltek (SEQ ID NO. 194) | 1991, 92, <u>96</u> |
| htvtkgvtascshngkssfyknllwlteknglypnlsksyvnnkekevlvlwgvh (SEQ ID NO. 195) | 1995 |
| htvt(k/g)gv(t/s)ascshngkssfy(k/m)(n/-)llwlt(e/g)k(-n/k)glypnlsk (SEQ ID NO. 196) | 1995, 00 |
| htvtkgvtascshngkssfyknllwltek (SEQ ID NO. 197) | 1995 |
| kyvrstklrmvtglrnipsiqsrglfgaiagfieggwtgmidgwygyh (SEQ ID NO. 198) | 1995 |
| hqneqgsgyaadqkstqnaingitnkvnsiiekmntqftavgk (SEQ ID NO. 199) | 1995 |
| hqneqgsgyaadqkstqnaingitnkvnsiiek (SEQ ID NO. 200) | 1995 |
| hqneqgsgyaadqkstqnaingitnk (SEQ ID NO. 201) | 1995 |
| hsgarsfyrnllwivkkgnsypk (SEQ ID NO. 202) | <u>1996</u> |
| hsgarsfyrnllwivkkgnsypklnk (SEQ ID NO. 203) | <u>1996</u> |
| hsgarsfyrnllwivkkgnsypklnksytndk (SEQ ID NO. 204) | <u>1996</u> |
| hsgarsfyrnllwivkkgnsypklnksytndkgk (SEQ ID NO. 205) | <u>1996</u> |
| htvskgvttscshngk (SEQ ID NO. 206) | <u>1996</u> |
| katswpnhettk (SEQ ID NO. 207) | <u>1996</u> |
| kqvttscshnqk (SEQ ID NO. 208) | <u>1996</u> |
| kgnsypklnksytndkgkevlviwgvh (SEQ ID NO. 209) | <u>1996</u> |
| klnksytndkgkevlviwgvh (SEQ ID NO. 210) | <u>1996</u> |
| ksytndkgkevlviwgvh (SEQ ID NO. 211) | <u>1996</u> |
| hnqkssfyrnllwlt(e/q)knglypnlsksy(v/a)annkek (SEQ ID NO. 212) | 1997, 98, 99 |
| hpitigecpkyvrsak (SEQ ID NO. 213) | 1997 |
| hqneqgsgyaadqkstqnaingitnkvnsviekmntqftavgk (SEQ ID NO. 214) | 1998 |

TABLE 4-continued

H1N1 Replikin Sequences present in H1N1 hemagglutinins of Influenza viruses
in each year for which amino acid sequences were available (1918-2000)
H1N1 Replikin Year Detected in Influenza H1N1 Strain

| | Peak in FIG. 7: P1 | E1 | E1.1, 1.2, 1.3 | E1.4) |
|---|---|---|---|---|
| hqneqgsgyaadqkstqnaingitnkvnsviek (SEQ ID NO. 215) | 1998 | | | |
| hngkssfyrnllwlteknglypnlsksyvnnkek (SEQ ID NO. 216) | 1998 | | | |

1. Influenza H1N1 was responsible for the human pandemic (global distribution) of 1918.
2. Abbreviation for years: eg. "96" = 1996.
3. The first year that a given Replikin appears is indicated at the beginning of the series of years in which that Replikin has been found in this work.
4. Overlapping Replikin sequences are listed separately.
5. Increase in number of new Replikin structures occurs in years of epidemics (underlined): eg. 1918 and 1977 and correlates with increased total Replikin concentration (number of Replikins per 100 amino acid residues). See FIG. 7.

TABLE 5

Replikin Sequences present in hemagglutinins of Influenza H2N2 viruses in years 1957-2000
Influenza H2N2 Replikins Year Detected in Influenza H2N2 strain

| | (Peak in FIG. 8: P2    E2) |
|---|---|
| khfekvkilpk (SEQ ID NO. 217) | <u>1957</u>, 58, 59, 60, 61, 64, <u>65</u>, 68, 78, 83, 84, 91 |
| khllssvkhfekvk (SEQ ID NO. 218) | <u>1957</u>, 58, 59, 60, 61, <u>65</u>, 68, 83, 84, 91 |
| ha(k/q/m)(d/n)ilekthngk (SEQ ID NO. 219) | <u>1957</u>, 58, 59, 60, 61, 64, <u>65</u>, 68, 78, 83, 84, 91, 95 |
| ha(k/q/m)(d/n)ilekthngklc(k/r) (SEQ ID NO. 220) | <u>1957</u>, 58, 59, 60, 61, 64, <u>65</u>, 68, 78, 83, 84, 91, 95 |
| hnvhpltigecpkyvksek (SEQ ID NO. 221) | <u>1957</u>, 58, 59, <u>65</u>, 68 |
| hpltigecpkyvksek (SEQ ID NO. 222) | <u>1957</u>, 58, 59, <u>65</u>, 68, 64, 65, 68, 78, 83, 84, 91 |
| khllssvkhfekvkilpk (SEQ ID NO. 223) | <u>1957</u>, 58, 59, 60, 61, 64, <u>65</u>, 68, 78 |
| krqssgimktegtlencetkcqtplgainttlpfhnvh (SEQ ID NO. 224) | <u>1957</u>, 59, 83 |
| kgsnyp(v/i)ak(g/r)synntsgeqmliiwq(v/i)h (SEQ ID NO. 225) | <u>1957</u>, 58, 59, 61, 83, 91, 95 |
| htttlgqsracavsgnpsffrnmvwltekgsnypvak (SEQ ID NO. 226) | <u>1957</u> |
| khfekvk (SEQ ID NO. 227) | <u>1957</u>, 59, <u>65</u> |
| kiskrgssgimktegtlencetkcqtplgainttlpfh (SEQ ID NO. 228) | <u>1957</u>, 59, <u>65</u>, 91 |
| krgssgimktegtlencetkcqtplgainttlpfh (SEQ ID NO. 229) | <u>1957</u>, 59, <u>65</u>, 91 |
| ktegtlencetkcqtplgainttlpfh (SEQ ID NO. 230) | <u>1957</u>, 59, <u>65</u>, 91 |
| kiskrgssgimktegtlencetkcqtplgainttlpfh (SEQ ID NO. 231) | <u>1957</u>, 59, <u>65</u>, 91 |
| ktegtlencetkcqtplgainttlpfhn(v/i)h (SEQ ID NO. 232) | <u>1957</u>, 59, <u>65</u>, 91 |
| kiskrgssgimktegtlencetkcqtplgainttlpfh (SEQ ID NO. 233) | <u>1957</u>, 59, <u>65</u>, 91 |
| k(e/g)snypvakgsynntsgeqmliiwgvh (SEQ ID NO. 234) | <u>1957</u>, 60, <u>65</u> |
| hpltigccpkyvksek (SEQ ID NO. 235) | <u>1957</u>, 60, <u>65</u> |
| kcqtplgaikttlpfh (SEQ ID NO. 236) | <u>1957</u>, <u>65</u> |
| hhsndqgsgyaadkestqka(f/i)dgitnkvnsviek-mntqfeavgklf(n/s)nleklenlnkk (SEQ ID NO. 237) | 1961, <u>65</u>, 68, 83, 84 |
| hsndqgsgyaadkestqka(f/i)dgitnkvnsviek-mntqfeavgklf(n/s)nleklenlnkk (SEQ ID NO. 238) | 1961 <u>65</u>, 68, 83, 84 |
| hsndqgsgyaadkestqka(f/i)dgitnk (SEQ ID NO. 239) | 1961, <u>65</u>, 68, 83, 84 |
| hdsnvrnlydkvrmqlrdnak (SEQ ID NO. 240) | 1964, 68, 76, 84, 91 |
| hkcddecmnsvkngtydypklnreikgvk (SEQ ID NO. 241) | 1964, <u>65</u>, 68, 76, 83, 84, 91 |
| hkcddecmnsvkngtydypklnrneik (SEQ ID NO. 242) | 1964, <u>65</u>, 68, 76, 83, 84, 91 |
| hkcddecmnsvkngtydypk (SEQ ID NO. 243) | 1964, <u>65</u>, 68, 76, 83, 84, 91 |
| hkcddecmnsvk (SEQ ID NO. 244) | 1964, <u>65</u>, 68, 76, 83, 84, 91 |
| kgsnypvakgsynntngeqiliiwgvh (SEQ ID NO. 245) | 1976, 78 |
| hsndqgsgyaadkestqkavdgitnkvnsviekmntqfeavgk (SEQ ID NO. 246) | 1976, 91 |
| krgssgimktegtlencetkcqtplgainttlpfh (SEQ ID NO. 247) | 1976, 78, 83, 84 |
| hpltigecpkyvksek (SEQ ID NO. 248) | 1976 |
| hakdilekthngklck (SEQ ID NO. 249) | 1976 |

1. Influenza H2N2 was responsible for the human pandemic (global distribution) of 1957.
2. Abbreviation for years: eg. "58" = 1958.
3. The first year that a given Replikin appears is indicated at the beginning of the series of years in which that Replikin has been found in this work.
4. Overlapping Replikin sequences are listed separately.
5. Increase in number of new Replikin structures occurs in years of epidemics (underlined): eg. 1957 and 1965 and correlates with increased total Replikin concentration (number of Replikins per 100 amino acid residues). See FIG. 8.

TABLE 6

H3N2 Replikin Sequences present in H3N2 hemagglutinins of Influenza viruses
in each year for which amino acid sequences were available (1968-2000)
Influenza H3N2 ReplikinsYear Detected in Influenza H3N2 strain Influenza Replikins

| | (Peak in Figure 8: P3　　E3　　E4) |
|---|---|
| hdvyrdealnnrfqikgvelksgyk (SEQ ID NO. 250) | 1968, 72, 75 96, 97, 98 |
| htidltdsemnklfertrk (SEQ ID NO. 251) | 1968 |
| kfhqiek (SEQ ID NO. 252) | 1968, 72, 75, 77 96, 97, 98 |
| ktnekfh(g/q)iek (SEQ ID NO. 253) | 1968 86 98 |
| klnr(v/l)iektnekfh (SEQ ID NO. 254) | 1968, 72, 75, 77 97, 98 |
| hqiekefsevegriqdlekyvedtk (SEQ ID NO. 255) | 1968, 72, 98 |
| kicnnphk (SEQ ID NO. 256) | 1975 |
| klnrvikktnekfh (SEQ ID NO. 257) | 1975 |
| hd(I,v)yrdealnnrfqik(g/q)ve(r/k)s(q/g)yk (SEQ ID NO. 258) | 1975, 76, 77, 86 |
| hqiekefsevegriqdlekyvedtk (SEQ ID NO. 259) | 1975 |
| kyvedtkidlwsynaellvalenqh (SEQ ID NO. 260) | 1975 |
| kyvkqnslklatgmrnvpekqtrglfgaiagfiengwegmidgwygfrh (SEQ ID NO. 261) | 1975 |
| kefsevegriqdlekyvedtkidlwsynaellvalenqh (SEQ ID NO. 262) | 1975 2000 |
| hqn(s/e)(e/q)g(t/s)g(q/y)aad(l/q)k--stq(a/n)a(i/l)d(q/g)I(n/t)(g/n)k(l/v)n(r/s)vi(e/c)k (SEQ ID NO. 263) | 1975 2000 |
| hcd(g/q)f(q,r)nekwdlf(v,/i)er(s/t)k (SEQ ID NO. 264) | 1975, 76, 77, 78, 80, 81, 82, 83, 84, 85, 86, 88, 89, 90, 91, 92, 93, 94, 95, 96, 97, 98 |
| htidltdsemnkklfertrk (SEQ ID NO. 265) | 1977, |
| ksgstypvlkvtmpnndnfdklyiwgvh (SEQ ID NO. 266) | 1977 |
| klnwltksgntypvlnvtmpnndnfdklviwgvh (SEQ ID NO. 267) | 1982 |
| htidltdsemnklfektrk (SEQ ID NO. 268) | 1986 |
| klnrliektnekfhqtek (SEQ ID NO. 269) | 1987 |
| htgkssvmrsdapidfcnsecitpnqsipndkpfqnvnkitygacpk (SEQ ID NO. 270) | 1994 |
| htgkssvmrsdapidfcnsecitpnqsipndkpfqnvnk (SEQ ID NO. 271) | 1994 |
| hpstdsdqtslyvrasgrvtvstkrsqqtvipk (SEQ ID NO. 272) | 1994 |
| kyvedtkidlwsynaellvalenqh (SEQ ID NO. 273) | 1997, 98 |
| klfertrkqlrenaedmgngcfkiyh (SEQ ID NO. 274) | 1998 |
| krrsiksffsrlnwlh (SEQ ID NO. 275) | 1998 |
| hpvtigecpky(v/r)kstk (SEQ ID NO. 276) | 2000 |
| kgnsypklsklsksyiinkkkevlviwgih (SEQ ID NO. 277) | 2000 |
| klsklsks(v/y)iinkkkevlviwgih (SEQ ID NO. 278) | 2000 |
| klsks(v/y)iinkkkevlviwgih (SEQ ID NO. 279) | 2000 |

1. Influenza H3N2 was responsible for the human pandemic (global distribution) of 1968.
2. Abbreviation for years: eg. "77" = 1977.
3. The first year that a given Replikin appears is indicated at the beginning of the series of years in which that Replikin has been found.
4. Overlapping Replikin sequences are listed separately.
5. Increase in number of new Replikin structures occurs in years of epidemics (underlined) : eg. 1975 and correlates with increased total Replikin concentration (number of Replikins per 100 amino acid residues). See FIG. 8.

Both the concentration and type, i.e., composition of Replikins observed, were found to relate to the occurrence of influenza pandemics and epidemics. The concentration of Replikins in influenza viruses was examined by visually scanning the hemagglutinin amino acid sequences published in the National Library of Medicine "PubMed" data base for influenza strains isolated world wide from human and animal reservoirs year by year over the past century, i.e., 1900 to 2001. These Replikin concentrations (number of Replikins per 100 amino acids, mean+/−SD) were then plotted for each strain.

The concentration of Replikins was found to directly relate to the occurrence of influenza pandemics and epidemics. The concentration of Replikins found in influenza B hemagglutinin and influenza A strain, H1N1, is shown in FIG. 7, and the concentration of Replikins found in the two other common influenza virus A strains, H2N2 and H3N2 is shown in FIG. 8 (H2N2, H3N2). The data in FIG. 8 also demonstrate an emerging new strain of influenza virus as defined by its constituent Replikins (H3N2(R)).

Each influenza A strain has been responsible for one pandemic: in 1918, 1957, and 1968, respectively. The data in FIGS. 7 and 8 show that at least one Replikin per 100 amino acids is present in each of the influenza hemagglutinin proteins of all isolates of the four common influenza viruses examined, suggesting a function for Replikins in the maintenance of survival levels of replication. In the 1990s, during the decline of the H3N2 strain, there were no Replikins in many isolates of H3N2, but a high concentration of new Replikins appeared in H3N2 isolates, which define the emergence of the H3N2(R) strain.

Several properties of Replikin concentration are seen in FIG. 7 and FIG. 8 to be common to all four influenza virus strains. First, the concentration is cyclic over the years, with a single cycle of rise and fall occurring over a period of two to thirty years. This rise and fall is consistent with the known waxing and waning of individual influenza virus strain predominance by hemagglutinin and neuramimidase classification. Second, peak Replikin concentrations of each influenza virus strain previously shown to be responsible for a pandemic were observed to relate specifically and individually to each of the three years of the pandemics. For example, for the pandemic of 1918, where the influenza virus strain, H1N1, was shown to be responsible, a peak concentration of the Replikins in H1N1 independently occurred (P1); for the pandemic of 1957, where H2N2 emerged and was shown to be responsible, a peak concentration of the Replikins in H2N2 occurred (P2); and for the pandemic of 1968, where H3N2 emerged and was shown to be the cause of the pandemic, a peak concentration of the Replikins in H3N2 occurred (P3). Third, in the years immediately following each of the above three pandemics, the specific Replikin concentration decreased markedly, perhaps reflecting the broadly distributed immunity generated in each case. Thus, this post-pandemic decline is specific for H1N1 immediately following the pandemic (P1) for which it was responsible, and is not a general property of all strains at the time. An increase of Replikin concentration in influenza B repeatedly occurred simultaneously with the decrease in Replikin concentration in H1N1, e.g., EB1 in 1951 and EB2 in 1976, both associated with influenza B epidemics having the highest mortality. (Stuart-Harris, et al., Edward Arnold Ltd. (1985). Fourth, a secondary peak concentration, which exceeded the primary peak increase in concentration, occurred 15 years after each of the three pandemics, and this secondary peak was accompanied by an epidemic: 15 years after the 1918 pandemic in an H1N1 'epidemic' year (E1); eight years after the 1957 pandemic in an H2N2 'epidemic' year (E2); and occurred seven years after the 1968 pandemic in an H3N2 'epidemic' year (E3). These secondary peak concentrations of specific Replikins may reflect recovery of the strain. Fifth, peaks of each strain's specific Replikin concentration frequently appear to be associated with declines in Replikin concentration of one or both other strains, suggesting competition between strains for host sites. Sixth, there is an apparent overall tendency for the Replikin concentration of each strain to decline over a period of 35 years (H2N2) to 60 years (influenza B). This decline cannot be ascribed to the influence of vaccines because it was evident in the case of influenza B from 1901 to 1964, prior to common use of influenza vaccines. In the case of influenza B, Replikin recovery from the decline is seen to occur after 1965, but Replikin concentration declined again between 1997 and 2000 (FIG. 7). This correlates with the low occurrence of influenza B in recent case isolates. H1N1 Replikin concentration peaked in 1978-1979 (FIG. 7) together with the reappearance and prevalence of the H1N1 strain, and then peaked in 1996 coincident with an H1N1 epidemic. (FIG. 7). H1N1 Replikin concentration also declined between 1997 and 2000, and the presence of H1N1 strains decreased in isolates obtained during these years. For H2N2 Replikins, recovery from a 35 year decline has not occurred (FIG. 8), and this correlates with the absence of H2N2 from recent isolates. For H3N2, the Replikin concentration of many isolates fell to zero during the period from 1996 to 2000, but other H3N2 isolates showed a significant, sharp increase in Replikin concentration. This indicates the emergence of a substrain of H3N2, which is designated herein as H3N2(R).

FIGS. 7 and 8 demonstrate that frequently, a one to three year stepwise increase is observed before Replikin concentration reaches a peak. This stepwise increase proceeds the occurrence of an epidemic, which occurs concurrently with the Replikin peak. Thus, the stepwise increase in concentration of a particular strain is a signal that particular strain is the most likely candidate to cause an epidemic or pandemic.

Currently, Replikin concentration in the H3N2(R) strain of influenza virus is increasing (FIG. 8, 1997 to 2000). Three similar previous peak increases in H3N2 Replikin concentration are seen to have occurred in the H3N2-based pandemic of 1968 (FIG. 8), when the strain first emerged, and in the H3N2-based epidemics of 1972 and 1975 (FIG. 8). Each of these pandemic and epidemics was associated with excess mortality. (Ailing, et al., Am J. Epidemiol., 113(1):30-43 (1981). The rapid ascent in concentration of the H3N2(R) subspecies of the H3N2 Replikins in 1997-2000, therefore, statistically represents an early warning of an approaching severe epidemic or pandemic. An H3N2 epidemic occurred in Russia in 2000 (FIG. 8, E4); and the CDC report of December 2001 states that currently, H3N2 is the most frequently isolated strain of influenza virus world wide. (Morbidity and Mortality Weekly Reports (MMWR), Center for Disease Control; 50(48):1084-68 (Dec. 7, 2001).

In each case of influenza virus pandemic or epidemic new Replikins emerge. There has been no observation of two of the same Replikins in a given hemagglutinin in a given isolate. To what degree the emergence of a new Replikin represents mutations versus transfer from another animal or avian pool is unknown. In some cases, each year one or more of the original Replikin structures is conserved, while at the same time, new Replikins emerge. For example, in influenza virus B hemagglutinin, five Replikins were constantly conserved between 1919 and 2001, whereas 26 Replikins came and went during the same period (some recurred after several years absence). The disappearance and re-emergence years later of a particular Replikin structure suggests that the Replikins return from another virus host pool rather than through de novo mutation.

In the case of H1N1 Replikins, the two Replikins present in the P1 peak associated with the 1918 pandemic were not present in the recovery E1 peak of 1933, which contains 12 new Replikins. Constantly conserved Replikins, therefore, are the best choice for vaccines, either alone or in combination. However, even recently appearing Replikins accompanying one year's increase in concentration frequently persist and increase further for an additional one or more years, culminating in a concentration peak and an epidemic, thus providing both an early warning and time to vaccinate with synthetic Replikins (see for example, H1N1 in the early 1990's, FIG. 7).

The data in FIGS. 7 and 8 demonstrate a direct relationship between the presence and concentration of a particular Replikin in influenza protein sequences and the occurrence of pandemics and epidemics of influenza. Thus, analysis of the influenza virus hemagglutinin protein sequence for the presence and concentration of Replikins provides a predictor of influenza pandemics and/or epidemics, as well as a target for influenza vaccine formulation.

Composition of Replikins in Strains of Influenza Virus B: Of a total of 26 Replikins identified in this strain (Table 3), the following ten Replikins are present in every influenza B isolate examined from 1902-2001. Overlapping Replikin sequences are listed separately. Lysines and histidines are in bold type to demonstrate homology consistent with the "3-point recognition."

kshfanlk (SEQ ID NO. 91)
kshfanlkgtk (SEQ ID NO. 92)
kshfanlkgtktrgklcpk (SEQ ID NO. 93)
hekygglnk (SEQ ID NO. 94)
hekygglnksk (SEQ ID NO. 95)
hekygglnkskpyytgehak (SEQ ID NO. 96)
hakaigncpiwvk (SEQ ID NO. 97)
hakaigncpiwvvkktplklangtk (SEQ ID NO. 98)
hakaigncpiwvktplklangtkyrppak (SEQ ID NO. 99)
hakaigncpiwvktplklangtkyrppakllk (SEQ ID NO. 100)

Tables 3 and 4 indicate that there appears to be much greater stability of the Replikin structures in influenza B hemagglutinins compared with H1N1 Replikins. Influenza B has not been responsible for any pandemic, and it appears not to have an animal or avian reservoirs. (Stuart-Harris et al., Edward Arnold Ltd., London (1985)).

Influenza H1N1 Replikins: Only one Replikin "hp(v/i)tigecpkyv(r/k)(s/t)(t/a)k" is present in every H1N1 isolate for which sequences are available from 1918, when the strain first appeared and caused the pandemic of that year, through 2000 (Table 4) ("(v/i)" indicates that the amino acid v or i is present in the same position in different years.) Although H1N1 contains only one persistent Replikin, H1N1 appears to be more prolific than influenza B. There are 95 different Replikin structures in 82 years on H1N1 versus only 31 different Replikins in 100 years of influenza B isolates (Table 4). An increase in the number of new Replikin structures occurs in years of epidemics (Tables 3, 4, 5 and 6) and correlates with increased total Replikin concentration (FIGS. 7 and 8).

Influenza H2N2 Replikins: Influenza H2N2 was responsible for the human pandemic of 1957. Three of the 20 Replikins identified in that strain for 1957 were conserved in each of the H2N2 isolates available for examination on PubMed until 1995 (Table 5).

ha(k/q/m)(d/n)ilekthngk (SEQ ID NO. 219)
ha(k/q/m)(d/n)ilekthngklc(k/r) (SEQ ID NO. 220)
kgsnyp(v/i)ak(g/r)synntsgeqmliiwq(v/i)h (SEQ ID No. 225)

However, in contrast to H1N1, only 13 additional Replikins have been found in H2N2 beginning in 1961. This paucity of appearance of new Replikins correlates with the decline in the concentration of the H2N2 Replikins and the appearance of H2N2 in isolates over the years (FIG. 8).

Influenza H3N2 Replikins: Influenza H3N2 was responsible for the human pandemic of 1968. Five Replikins which appeared in 1968 disappeared after 1977, but reappeared in the 1990s (Table 6). The only Replikin structure which persisted for 22 years was hcd(g/q)f(q/r)nekwdlf(v/i)er(s/t)$_k$, which appeared first in 1977 and persisted through 1998. The emergence of twelve new H3N2 Replikins in the mid 1990s (Table 6) correlates with the increase in Replikin concentration at the same time (FIG. 8), and with the prevalence of the H3N2 strain in recent isolates together with the concurrent disappearance of all Replikins from some of these isolates (FIG. 8), this suggests the emergence of the new substrain H3N2(R).

FIGS. 1 and 2 show that influenza epidemics and pandemics correlate with the increased concentration of Replikins in influenza virus, which is due to the reappearance of at least one Replikin from one to 59 years after its disappearance. Also, in the A strain only, there is an emergence of new strain-specific Replikin compositions (Tables 4-6). Increase in Replikin concentration by repetition of individual Replikins within a single protein appears not to occur in influenza virus, but is seen in other organisms.

It has been believed that changes in the activity of different influenza strains are related to sequence changes in influenza hemagglutinins, which in turn are the products of substitutions effected by one of two poorly understood processes: i) antigenic drift, thought to be due to the accumulation of a series of point mutations in the hemagglutinin molecule, or ii) antigenic shift, in which the changes are so great that genetic reassortment is postulated to occur between the viruses of human and non-human hosts. First, the present data suggests that the change in activity of different influenza strains, rather than being related to non-specific sequence changes, are based upon, or relate to the increased concentration of strain-specific Replikins and strain-specific increases in the replication associated with epidemics. In addition, the data were examined for a possible insight into which sequence changes are due to "drift" or "shift", and which are due to conservation, storage in reservoirs, and reappearance. The data show that the epidemic-related increase in Replikin concentration is not due to the duplication of existing Replikins per hemagglutinin, but is due to the reappearance of at least one Replikin composition from 1 to up to 59 years after its disappearance, plus in the A strains only, the emergence of new strain-specific Replikin compositions (Tables 3-6). Thus the increase in Replikin concentration in the influenza B epidemics of 1951 and 1977 are not associated with the emergence of new Replikin compositions in the year of the epidemic but only with the reappearance of Replikin compositions which had appeared in previous years then disappeared (Table 3). In contrast, for the A strains, in addition to the reappearance of previously disappeared virus Replikins, new compositions appear (e.g. in H1N1 in the year of the epidemic of 1996, in addition to the reappearance of 6 earlier Replikins, 10 new compositions emerged). Since the A strains only, not influenza B, have access to non-human animal and avian reservoirs, totally new compositions probably derive from non-human host reservoirs rather than from mutations of existing human Replikins which appear to bear no resemblance to the new compositions other than the basic requirements of "3-point recognition" (Tables 2-5). The more prolific nature of H1N1 compared with B, and the fact that pandemics have been produced by the three A strains only, but not by the B strain, both may also be a function of the ability of the human A strains to receive new Replikin compositions from non-human viral reservoirs.

Some Replikins have appeared in only one year, disappeared, and not reappeared to date (Tables 3-6). Other Replikins disappear from one to up to 81 years, when the identical Replikin sequence reappears. Key Replikin 'k' and 'h' amino acids, and the spaces between them, are conserved during the constant presence of particular Replikins over many years, as shown in Tables 23-6 for the following strain-specific Replikins: ten of influenza B, the single Replikin of H1N1, and the single Replikin of H2N3, as well as for the reappearance of identical Replikins after an absence. Despite the marked replacement or substitution activity of other amino acids both inside the Replikin structure and outside it in the rest of the hemagglutinin sequences, influenza Replikin histidine (h) appears never to be, and lysine (k) is rarely replaced. Examples of this conservation are seen in the H1N1 Replikin "hp(v/i)tigecpkyv(r/k)(s/t)(t/a)k," (SEQ ID NO. 122) constant between 1918 and 2000, in the H3N2 Replikin "hcd(g/q)f(q,r)nekwdlf(v/i)er(s/t)k" (SEQ ID NO. 264) constant between 1975 and 1998 and in the H3N2 Replikin "hqn(s/e)(e/q)g(t/s)g(q/y)aad(l/q)kstq(a/n)a(i/l)d(q/g)I(n/t)(g/n)k(l/v)n(r/s) vi(e/c)k" (SEQ ID NO. 263) which first appeared in 1975, disappeared for 25 years, and then reappeared in 2000. While many amino acids were substituted, the basic Replikin structure of 2 Lysines, 6 to 10 residues apart, one histidine, a minimum of 6% lysine in not more than approximately 50 amino acids, was conserved.

Totally random substitution would not permit the persistence of these H1N1 and H3N2 Replikins, nor from 1902 to 2001 in influenza B the persistence of 10 Replikin structures, nor the reappearance in 1993 of a 1919 18 mer Replikin after an absence of 74 years. Rather than a random type of substitution, the constancy suggests an orderly controlled process, or in the least, protection of the key Replikin residues so that they are fixed or bound in some way: lysines, perhaps bound to nucleic acids, and histidines, perhaps bound to respiratory redox enzymes. The mechanisms which control this conservation are at present unknown.

Conservation of Replikin Structures

Whether Replikin structures are conserved or are subject to extensive natural mutation was examined by scanning the protein sequences of various isolates of foot and mouth disease virus (FMDV), where mutations in proteins of these viruses have been well documented worldwide for decades. Protein sequences of FMDV isolates were visually examined for the presence of both the entire Replikin and each of the component Replikin amino acid residues observed in a particular Replikin.

Rather than being subject to extensive substitution over time as occurs in neighboring amino acids, the amino acids which comprise the Replikin structure are substituted little or not at all, that is the Replikin structure is conserved.

For example, in the protein VP1 of FMDV type O, the Replikin (SEQ ID NO.: 3) "hkqkivapvk" was found to be conserved in 78% of the 236 isolates reported in PubMed, and each amino acid was found to be conserved in individual isolates as follows: his, 95.6%; lys, 91.8%; gln 92.3%; lys, 84.1%; ile, 90.7%; val, 91.8%; ala, 97.3%; pro, 96.2%; ala, 75.4%; and lys, 88.4%. The high rate of conservation suggests structural and functional stability of the Replikin structure and provides constant targets for treatment.

Similarly, sequence conservation was found in different isolates of HIV for its Replikins, such as (SEQ ID NO.: 5) "kcfncgkegh" or (SEQ ID NO.: 6) "kvylawvpahk" in HIV Type 1 and (SEQ ID NO.: 7) "kcwncgkegh" in HIV Type 2 (Table 2). Further examples of sequence conservation were found in the HIV tat proteins, such as (SEQ ID NO.: 698) "hclvckqkkglgisygrkk," wherein the key lysine and histidine amino acids are conserved (See Table 7).

Similarly, sequence conservation was observed in plants, for example in wheat, such as in wheat ubiquitin activating enzyme E (SEQ ID NOs. 601-603). The Replikins in wheat even provided a reliable target for stimulation of plant growth as described within. Other examples of conservation are seen in the constant presence of malignin in successive generations, over ten years of tissue culture of glioma cells, and by the constancy of affinity of the glioma Replikin for antimalignin antibody isolated by immunoadsorption from 8,090 human sera from the U.S., U.K., Europe and Asia (e.g., FIG. 5 and U.S. Pat. No. 6,242,578 B1).

Similarly, conservation was observed in trans-activator (Tat) proteins in isolates of HIV. Tat (trans-activator) proteins are early RNA binding proteins regulating lentiviral transcription. These proteins are necessary components in the life cycle of all known lentiviruses, such as the human immunodeficiency viruses (HIV). Tat is a transcriptional regulator protein that acts by binding to the transactivating response sequence (TAR) RNA element and activates transcription Initiation and/or elongation from the LTR promoter. HIV cannot replicate without tat, but the chemical basis of this has been unknown. In the HIV tat protein sequence from 89 to 102 residues, we have found a Replikin that is associated with rapid replication in other organisms. The amino acid sequence of this Replikin is "hclvcfqkkglgisygrkk." In fact, we found that this Replikin is present in every HIV tat protein. Some tat amino acids are substituted frequently, as shown in Table 8, by alternate amino acids (in small size fonts lined up below the most frequent amino acid (Table 7), the percentage of conservation for the predominant Replikin "hclvcfqkkglgisygrkk"). These substitutions have appeared for most of the individual amino acids. However, the key lysine and histidine amino acids within the Replikin sequence, which define the Replikin structure, are conserved 100% in the sequence; while substitutions are common elsewhere in other amino acids, both within and outside the Replikin, none occurs on these key histidine amino acids.

As shown in Table 7, it is not the case that lysines are not substituted in the tat protein amino acid sequence. From the left side of the table, the very first lysine in the immediate neighboring sequence, but outside the Replikin sequence, and the second lysine (k) in the sequence inside the Replikin, but "extra" in that it is not essential for the Replikin formation, are both substituted frequently. However, the 3rd, 4th and 5th lysines, and the one histidine, in parentheses, which together set up the Replikin structure, are never substituted. Thus, these key amino acid sequences are 100% conserved. As observed in the case of the influenza virus Replikins, random substitution would not permit this selective substitution and selective non-substitution to occur due to chance.

TABLE 7

% Replikin CONSERVATION of each constituent amino acid in the first 117 different isolates of HIV tat protein as reported in PubMed:

| 38 | 100 | 57 | 86 | 100 | 100 | 66 | 76 | 100 | 99 | 57 | 49 | 100 | 94 | 100 | 97 | 98 | 85 | 97 | 99 | 100 | 100 | 100% |
|---|---|---|---|---|---|---|---|---|---|---|---|---|---|---|---|---|---|---|---|---|---|---|
| k | (c) | s | y | [(h) | (c) | l | v | (c) | f | q | k | (k) | g | (l) | g | i | s | y | g | (r) | (k) | (k)] |

Neighboring-Amino acids [tat Replikin]

below are the amino acid substitutions observed for each amino acid above:

| h |   | c | f |   |   | q | i |   | l | h | t |   | a |   | a | l | y | h | q |   |   |   |
| r |   | w | p |   |   | l | l |   | i | h |   |   | q |   | v |   |   |   |   |   |   |   |
| y |   |   | s |   |   |   | s |   | l | m |   |   | r |   | s |   |   |   |   |   |   |   |
| i |   |   |   |   |   |   | s |   | m | s |   |   |   |   |   |   |   |   |   |   |   |   |
| s |   |   |   |   |   |   | r |   | n |   |   |   |   |   |   |   |   |   |   |   |   |   |
| v |   |   |   |   |   |   |   |   |   |   |   |   |   |   |   |   |   |   |   |   |   |   |
| a |   |   |   |   |   |   |   |   |   |   |   |   |   |   |   |   |   |   |   |   |   |   |
| f |   |   |   |   |   |   |   |   |   |   |   |   |   |   |   |   |   |   |   |   |   |   |
| p |   |   |   |   |   |   |   |   |   |   |   |   |   |   |   |   |   |   |   |   |   |   |
| q |   |   |   |   |   |   |   |   |   |   |   |   |   |   |   |   |   |   |   |   |   |   |

The conservation of the Replikin structure suggests that the Replikin structure has a specific survival function for the HIV virus which must be preserved and conserved, and cannot be sacrificed to the virus 'defense' maneuver of amino acid substitution crested to avoid antibody and other 'attack.' These 'defense' functions, although also essential, cannot 'compete' with the virus survival function of HIV replication.

Further conservation was observed in different isolates of HIV for its Replikins such as "kcfncgkegh" (SEQ ID NO. 5) or "kvylawvpahk" (SEQ ID NO. 6) in HIV Type 1 and "kcwncgkegh" (SEQ ID NO. 7) in HIV Type 2.

The high rate of conservation observed in FMVD and HIV Replikins suggests that conservation also observed in the Replikins of influenza Replikins is a general property of viral Replikins. This conservation makes them a constant and reliable tarted for either destruction, for example by using specific Replikins such as for influenza, FMVD or HIV vaccines as illustrated for the glioma Replikin, or stimulation.

Similarly, as provided in examples found in viruses including influenza viruses, FMDV, and HIV, where high rates of conservation in Replikins suggest that conservation is a general property of viral Replikins and thus making Replikins a constant and reliable target for destruction or stimulation, conservation of Replikin structures occurs in plants. For example, in wheat plants, Replikins are conserved and provide a reliable target for stimulation. Examples of conserved Replikins in wheat plants ubiquitin activating enzyme E include:

E3 hkdrltkkvvdiarevakvdvpeyrrh (SEQ ID NO. 601)
E2 hkerldrkvvdvarevakvevpsyrrh (SEQ ID NO. 602)
E1 hkerldrkvvdvarevakmevpsyrrh (SEQ ID NO. 603)

Similarly to conservation found in the HIV tat protein, the Replikin in the wheat ubiquitin activating enzyme E is conserved. As with the HIV tat protein, substitutions of amino acids (designated with an '*') adjacent to the Replikin variant forms in wheat ubiquitin activating enzyme E are common. The key k and h amino acids that form the Replikin structure, however, do not vary whereas the 'unessential' k that is only 5 amino acids (from the first k on the left) is substituted.

Anti-Replikin Antibodies

Figure 3:
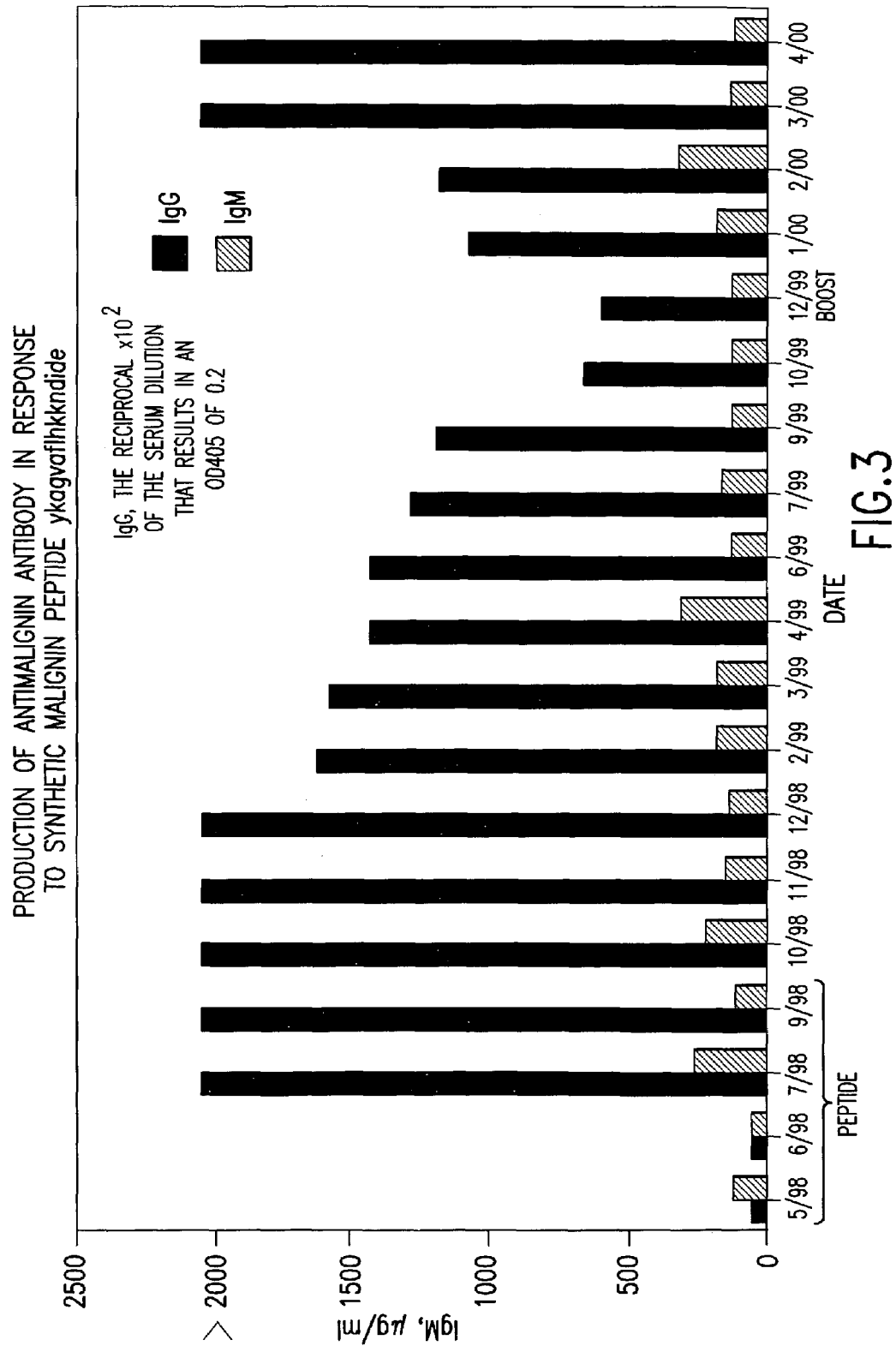
FIG. 3 is a bar graph showing amount of antimalignin antibody produced in response to exposure to the recognin 16-mer.

An anti-Replikin antibody is an antibody against a Replikin. Data on anti-Replikin antibodies also support Replikin class unity. An anti-Replikin antibody response has been quantified by immunoadsorption of serum antimalignin antibody to immobilized malignin (see Methods in U.S. Pat. No. 5,866,690). The abundant production of antimalignin antibody by administration to rabbits of the synthetic version of the 16-mer peptide whose sequence was derived from malignin, absent carbohydrate or other groups, has established rigorously that this peptide alone is an epitope, that is, provides a sufficient basis for this immune response (FIG. 3). The 16-mer peptide produced both IgM and IgG forms of the antibody. Antimalignin antibody was found to be increased in concentration in serum in 37% of 79 cases in the U.S. and Asia of hepatitis B and C, early, in the first five years of infection, long before the usual observance of liver cancer, which develops about fifteen to twenty-five years after infection. Relevant to both infectious hepatitis and HIV infections, transformed cells may be one form of safe haven for the virus: prolonging cell life and avoiding virus eviction, so that the virus remains inaccessible to anti-viral treatment.

Because administration of Replikins stimulates the immune system to produce antibodies having a cytotoxic effect, peptide vaccines based on the particular influenza virus Replikin or group of Replikins observed to be most concentrated over a given time period provide protection against the particular strain of influenza most likely to cause an outbreak in a given influenza season., e.g., an emerging strain or re-emerging strain For example, analysis of the influenza virus hemagglutinin amino acid sequence on a yearly or bi-yearly basis, provides data which are useful in formulating a specifically targeted influenza vaccine for that year. It is understood that such analysis may be conducted on a region-by-region basis or at any desired time period, so that strains emerging in different areas throughout the world can be detected and specifically targeted vaccines for each region can be formulated.

Influenza

Currently, vaccine formulations are changed twice yearly at international WHO and CDC meetings. Vaccine formulations are based on serological evidence of the most current preponderance of influenza virus strain in a given region of the world. However, prior to the present invention there has been no correlation of influenza virus strain specific amino acid sequence changes with occurrence of influenza epidemics or pandemics.

The observations of specific Replikins and their concentration in influenza virus proteins provides the first specific quantitative early chemical correlates of influenza pandemics and epidemics and provides for production and timely administration of influenza vaccines tailored specifically to treat the prevalent emerging or re-emerging strain of influenza virus in a particular region of the world. By analyzing the protein sequences of isolates of strains of influenza virus, such as the hemagglutinin protein sequence, for the presence, concentration and/or conservation of Replikins, influenza virus pandemics and epidemics can be predicted. Furthermore, the severity of such outbreaks of influenza can be significantly lessened by administering an influenza peptide vaccine based on the Replikin sequences found to be most abundant or shown to be on the rise in virus isolates over a given time period, such as about one to about three years.

An influenza peptide vaccine of the invention may include a single Replikinpeptide sequence or may include a plurality of Replikin sequences observed in influenza virus strains. Preferably, the peptide vaccine is based on Replikin sequence(s) shown to be increasing in concentration over a given time period and conserved for at least that period of time. However, a vaccine may include a conserved Replikin peptide(s) in combination with a new Replikin(s) peptide or may be based on new Replikin peptide sequences. The Replikin peptides can be synthesized by any method, including chemical synthesis or recombinant gene technology, and may include non-Replikin sequences, although vaccines based on peptides containing only Replikin sequences are preferred. Preferably, vaccine compositions of the invention also contain a pharmaceutically acceptable carrier and/or adjuvant.

The influenza vaccines of the present invention can be administered alone or in combination with antiviral drugs, such as gancyclovir; interferon; interleukin; M2 inhibitors, such as, amantadine, rimantadine; neuramimidase inhibitors, such as zanamivir and oseltamivir; and the like, as well as with combinations of antiviral drugs.

Replikin Decoys in Malaria

Analysis of the primary structure of a *Plasmodium falciparum* malaria antigen located at the merozoite surface and/or within the parasitophorous vacuole revealed that this organism, like influenza virus, also contains numerous Replikins (Table 8). However, there are several differences between the observation of Replikins in *Plasmodium falciparum* and influenza virus isolates. For example, *Plasmodium falciparum* contains several partial Replikins, referred to herein as "Replikin decoys." These decoy structures contain an abundance of lysine residues, but lack the histidine required of Replikin structures. Specifically, these decoys contain many lysines 6 to 10 residues apart in overlapping fashion, similar to the true malaria recognins but without histidine residues. It is believed that the decoy structure maximizes the chances that an anti-malarial antibody or other agent will bind to the relatively less important structure containing the lysines, i.e., the Replikin decoys, rather than binding to histidine, which is present in Replikin structure, such as Replikins in respiratory enzymes, which could result in destruction of the trypanosome. For example, an incoming antibody, with specificity for Replikin structures, might attach to the Replikin decoy structure, leaving the true Replikin structure remains untouched.

Therefore, anti-Replikin treatment of malaria requires two phases (dual treatment): i) preliminary treatment with proteolytic enzymes that cleave the Replikin decoys, permitting 'safe passage' of the specific anti-Replikin treatment; and ii) attacking malaria Replikins either with specific antibodies or by cellular immunity engendered by synthetic malaria Replikin vaccines or by organic means targeting the malaria Replikins.

Repetition and Overlapping of Replikin Structures

Another difference seen in *Plasmodium falciparum* is a frequent repetition of individual Replikin structures within a single protein, which was not observed with influenza virus. Repetition may occur by (a) sharing of lysine residues between Replikins, and (b) by repetition of a portion of a Replikin sequence within another Replikin sequence.

A third significant difference between Replikin structures observed in influenza virus isolates and *Plasmodium falciparum* is a marked overlapping of Replikin structures throughout malarial proteins, e.g., there are nine overlapping Replikins in the 39 amino acid sequence of SEQ ID NO. 380 (Replikin concentration=23.1/100 amino acids); and 15 overlapping Replikins in the 41 amino acids of SEQ ID NO. 454 (Replikin concentration=36.6/100 amino acids). Both of these overlapping Replikin structures occur in blood stage trophozoites and schizonts. In contrast, influenza virus Replikins are more scattered throughout the protein and the maximum Replikin concentration is about 7.5/100 amino acids (FIG. 7); and tomato leaf curl gemini virus, which was also observed to have overlapping Replikins has only about 3.1/100 amino acids.

This mechanism of lysine multiples is also seen in the Replikins of cancer proteins such as in gastric cancer transforming protein, ktkkgnrvsptmkvth (SEQ ID NO. 88), and in transforming protein P21B (K-RAS 2B) of lung, khkekmskdgkkkkkks (SEQ ID NO. 89).

The relationship of higher Replikin concentration to rapid replication is also confirmed by analysis of HIV isolates. It was found that the slow-growing low titer strain of HIV (NSI, "Bru," which is prevalent in early stage HIV infection) has a Replikin concentration of 1.1 (+/−1.6) Replikins per 100 amino acids, whereas the rapidly-growing high titer strain of HIV (SI, "Lai", which is prevalent in late stage HIV infection) has a Replikin concentration of 6.8 (+/−2.7) Replikins per 100 amino acid residues.

The high concentration of overlapping Replikins in malaria, influenza virus and cancer cells is consistent with the legendary high and rapid replicating ability of malaria organisms. The multitude of overlapping Replikins in malaria also provides an opportunity for the organism to flood and confuse the immune system of its host and thereby maximize the chance that the wrong antibody will be made and perpetuated, leaving key malaria antigens unharmed.

As in the case of influenza virus, for example, peptide vaccines based on the Replikin structure(s) found in the malaria organism can provide an effective means of preventing and/or treating malaria. Vaccination against malaria can be achieved by administering a composition containing one or a mixture of Replikin structures observed in *Plasmodium falciparum*. Furthermore, antibodies to malaria Replikins can be generated and administered for passive immunity or malaria detection Table 8 provides a list of several *Plasmodium falciparum* Replikin sequences. It should be noted that this list is not meant to be complete. Different isolates of the organism may contain other Replikin structures.

TABLE 8

Malaria Replikins
a) Primary structure of a Plasmodium falciparum malaria antigen located at the merozoite surface and within the parasitophorous vacuole a) i) DECOYS:

(C-Terminal)
keeeekekekekekeekekeekekekeekekekeekekekeekeeekk (SEQ ID NO. 280), or
keeeekekekekekeekekeekekeekekeekekekeekekeeekkek (SEQ ID NO. 281), or
keeeekekekekekeekekeekekekeekekeekekeekeekeeekk (SEQ ID NO. 282), or
keeeekekek (SEQ ID NO. 283)

ii) ReplikinS:

Hkklikalkkniesiqnkk (SEQ ID NO. 284)
hkklikalkkniesiqnkm (SEQ ID NO. 285)
hkklikalkk (SEQ ID NO. 286)
hkklikalk (SEQ ID NO. 287)
katysfvntkkkiislksqghkk (SEQ ID NO. 288)
katysfvntkkkiislksqghk (SEQ ID NO. 289)
katysfvntkkkiislksqgh (SEQ ID NO. 290)
htyvkgkkapsdpqca dikeeckellkek (SEQ ID NO. 291)
kiislksqghk (SEQ ID NO. 292)
kkkkfeplkngnvsetiklih (SEQ ID NO. 293)
kkkfeplkngnvsetiklih (SEQ ID NO. 294)
kkfeplkngnvsetiklih (SEQ ID NO. 295)
kngnvsetiklih (SEQ ID NO. 296)
klihlgnkdkk (SEQ ID NO. 297)
kvkkigvtlkkfeplkngnvsetiklihlgnkdkkh (SEQ ID NO. 298)
hliyknksynplllscvkkmnmlkenvdyiqnqnlfkelmnqkatysfvntkkkiislk (SEQ ID NO. 299)
hliyknksynplllscvkkmnmlkenvdyiqnqnlfkelmnqkatysfvntk (SEQ ID NO. 300)
hliyknksynplllscvkkmnmlkenvdyiqnqnlfkelmnqk (SEQ ID NO. 301)
hliyknksynplllscvkkmnmlkenvdyiqknqnlfk (SEQ ID NO. 302)
hliyknksynplllscvkkmnmlk (SEQ ID NO. 303)
ksannsanngkknnaeemknlvnflqshkklikalkkniesiqnkkh (SEQ ID NO. 304)
kknnaeemknlvnflqshkklikalkkniesiqnkkh (SEQ ID NO. 305)
knlvnflqshkklikalkkniesiqnkkh (SEQ ID NO. 306)

TABLE 8-continued

Malaria Replikins
a) Primary structure of a Plasmodium falciparum malaria antigen located at
the merozoite surface and within the parasitophorous vacuole kklikalkkniesiqnkkh (SEQ ID NO. 307)
klikalkkniesiqnkkh (SEQ ID NO. 308)
kkniesiqnkkh (SEQ ID NO. 309)
kniesiqnkkh (SEQ ID NO. 310)
knnaeemknlvnflqsh (SEQ ID NO. 311)
kklikalkkniesiqnkkqghkk (SEQ ID NO. 312)
kknnaeemknlvnflqshk (SEQ ID NO. 313)
knnaeemknlvnflqsh (SEQ ID NO. 314)
klikalkkniesiqnkkqghkk (SEQ ID NO. 315)
kvkkigvtlkkfeplkngnvsetiklih (SEQ ID NO. 316)
kngnvsetiklih (SEQ ID NO. 317)
klihlgnkdkk (SEQ ID NO. 318)
ksannsanngkknnaeemknlvnflqsh (SEQ ID NO. 319)
kknnaeemknlvnflqsh (SEQ ID NO. 320)
kklikalkkniesiqnkkh (SEQ ID NO. 321)
kalkkniesiqnkkh (SEQ ID NO. 322)
kkniesiqnkkh (SEQ ID NO. 323)
kelmnqkatysfvntkkkiislksqgh (SEQ ID NO. 324)
ksqghkk (SEQ ID NO. 325)
kkkiislksqgh (SEQ ID NO. 326)
kkiislksqgh (SEQ ID NO. 327)
kkniesiqnkkh (SEQ ID NO. 328)
kniesiqnkkh (SEQ ID NO. 329)
htyvkgkkapsdpqcadikeeckellkek (SEQ ID NO. 330)
htyvkgkkapsdpqcadikeeckellk (SEQ ID NO. 331)
b) "liver stage antigen-3" gene = "LSA-3" Replikins
henvlsaalentqseeekkevidvieevk (SEQ ID NO. 332)
kenvvttilekveettaesvttfsnileeiqentitndtieekleelh (SEQ ID NO. 333)
hylqqmkekfskek (SEQ ID NO. 334)
hylqqmkekfskeknnnvievtnkaekkgnvqvtnktekttk (SEQ ID NO. 335)
hylqqmkekfskeknnnvievtnkaekkgnvqvtnktekttkvdknnk (SEQ ID NO. 336)
hylqqmkekfskeknnnvievtnkaekkgnvqvtnktekttkvdknnkvpkkrrtqk (SEQ ID NO. 337)
hylqqmkekfskeknnnvievtnkaekkgnvqvtnktekttkvdknnkvpkkrrtqksk (SEQ ID NO. 338)
hvdevmkyvqkidkevdkevskaleskndvtnvlkqnqdffskvknfvkkyk (SEQ ID NO. 339)
hvdevmkyvqkidkevdkevskaleskndvtnvlkqnqdffskvknfvkk (SEQ ID NO. 340)
hvdevmkyvqkidkevdkevskaleskndvtnvlkqnqdffsk (SEQ ID NO. 341)
hvdevmkyvqkidkevdkevskaleskndvtnvlk (SEQ ID NO. 342)
hvdevmkyvqkidkevdkevskalesk (SEQ ID NO. 343)
hvdevmkyvqkidkevdkevsk (SEQ ID NO. 344)
hvdevmkyvqkidkevdk (SEQ ID NO. 345)
hvdevmkyvqkidk (SEQ ID NO. 346)
kdevidlivqkekriekvkakkkklekkveegvsglkkh (SEQ ID NO. 347)
kvkakkkklekkveegvsglkkh (SEQ ID NO. 348)
kakkkklekkveegvsglkkh (SEQ ID NO. 349)
kkkklekkveegvsglkkh (SEQ ID NO. 350)
kkklekkveegvsglkkh (SEQ ID NO. 351)
kklekkveegvsglkkh (SEQ ID NO. 352)
klekkveegvsglkkh (SEQ ID NO. 353)
kkveegvsglkkh (SEQ ID NO. 354)
kveegvsglkkh (SEQ ID NO.355)
hveqnvyvdvdvpamkdqflgilneagglkemffnledvfksesdvitveeikdepvqk (SEQ ID NO. 356)
hikgleeddleevddlkgsildmlkgdmelgdmdkesledvttklgerveslk (SEQ ID NO. 357)
hikgleeddleevddlkgsildmlkgdmelgdmdkesledvttk (SEQ ID NO. 358)
hikgleeddleevddlkgsildmlkgdmelgdmdk (SEQ ID NO. 359)
hikgleeddleevddlkgsildmlk (SEQ ID NO. 360)
hiisgdadvlssalgmdeeqmktrkkaqrpk (SEQ ID NO. 361)
hditttldevvelkdveedkiek (SEQ ID NO. 362)
kkleevhelk (SEQ ID NO. 363)
kleevhelk (SEQ ID NO. 364)
ktietdileekkkeiekdh (SEQ ID NO. 365)
kkeiekdhfek (SEQ ID NO. 366)
kdhfek (SEQ ID NO. 367)
kfeeeaeeikh (SEQ ID NO. 368)
c) 28 KDA ookinete surface antigen precursor Replikins:

kdgdtkctlecaqgkkcikhksdhnhksdhnhksdpnhkkknnnnnk (SEQ ID NO. 369)
kdgdtkctlecaqgkkcikhksdhnhksdhnhksdpnhkk (SEQ ID NO. 370)
kdgdtkctlecaqgkkcikhksdhnhksdhnhksdpnhk (SEQ ID NO. 371)
kdgdtkctlecaqgkkcikhksdhnhksdhnhk (SEQ ID NO. 372)
kdgdtkctlecaqgkkcikhksdhnhk (SEQ ID NO. 373)
kdgdtkctlecaqgkkcikhk (SEQ ID NO. 374)
kdgdtkctlecaqgkk (SEQ ID NO. 375)
kdgdtkctlecaqgk (SEQ ID NO. 376)

TABLE 8-continued

Malaria Replikins
a) Primary structure of a Plasmodium falciparum malaria antigen located at the merozoite surface and within the parasitophorous vacuole kciqaecnykecgeqkcvwdgih (SEQ ID NO. 377)
kecgeqkcvwdgih (SEQ ID NO. 378)
hieckcnndyvltnryecepknkctsledtnk (SEQ ID NO. 379)
d) Blood stage trophozoites and schizonts Replikins:

ksdhnhksdhnhksdhnhksdhnhksdpnhkkknnnnnk (SEQ ID NO. 380)
ksdhnhksdhnhksdhnhksdpnhkkknnnnnk (SEQ ID NO. 381)
ksdhnhksdhnhksdpnhkkknnnnnk (SEQ ID NO. 382)
ksdhnhksdpnhkkknnnnnk (SEQ ID NO. 383)
kkknnnnnkdnksdpnhk (SEQ ID NO. 384)
kknnnnnkdnksdpnhk (SEQ ID NO. 385)
knnnnnkdnksdpnhk (SEQ ID NO. 386)
kdnksdpnhk (SEQ ID NO. 387)
ksdpnhk (SEQ ID NO. 388)
hslyalqqneeyqkvknekdqneikkikqlieknk (SEQ ID NO. 389)
hslyalqqneeyqkvknekdqneikkik (SEQ ID NO. 390)
hslyalqqneeyqkvknekdqneikk (SEQ ID NO. 391)
hslyalqqneeyqkvknekdqneik (SEQ ID NO. 392)
hklenleemdk (SEQ ID NO. 393)
khfddntneqk (SEQ ID NO. 394)
kkeddekh (SEQ ID NO. 395)
keennkkeddekh (SEQ ID NO. 396)
ktssgilnkeennkkeddekh (SEQ ID NO. 397)
knihikk (SEQ ID NO. 398)
hikkkegidigyk (SEQ ID NO. 399)
kkmwtcklwdnkgneitknih (SEQ ID NO. 400)
kkgiqwnllkkmwtcklwdnkgneitknih (SEQ ID NO. 401)
kekkdsnenrkkkqkedkknpnklkkieytnkithffkaknnkqqnnvth (SEQ ID NO. 402)
kkdsnenrkkkqkedkknpnklkkieytnkithffkaknnkqqnnvth (SEQ ID NO. 403)
kdsnenrkkkqkedkknpnklkkieytnkithffkaknnkqqnnvth (SEQ ID NO. 404)
kkqkedkknpnklkkieytnkithffkaknnkqqnnvth (SEQ ID NO. 405)
kqkedkknpnklkkieytnkithffkaknnkqqnnvth (SEQ ID NO. 406)
kedkknpnklkkieytnkithffkaknnkqqnnvth (SEQ ID NO. 407)
knpnklkkieytnkithffkaknnkqqnnvth (SEQ ID NO. 408)
kkieytnkithffkaknnkqqnnvth (SEQ ID NO. 409)
kieytnkithffkaknnkqqnnvth (SEQ ID NO. 410)
kithffkaknnkqqnnvth (SEQ ID NO. 411)
hknnedikndnskdikndnskdikndnskdikndnnediknddnskdik (SEQ ID NO. 412)
hknnediknndnskdikndnskdikndnskdikndnnediknndnsk (SEQ ID NO. 413)
hknnediknndnskdikndnskdikndnskdikndnnedik (SEQ ID NO. 414)
hknnediknndnskdikndnskdikndnskdik (SEQ ID NO. 415)
hknnediknndnskdikndnskdikndnsk (SEQ ID NO. 416)
hknnediknndnskdikndnskdik (SEQ ID NO. 417)
hknnediknndnskdikndnsk (SEQ ID NO. 418)
hknnediknndnskdik (SEQ ID NO. 419)
hknnedik (SEQ ID NO. 420)
kkyddlqnkynilnklknsleekneelkkyh (SEQ ID NO. 421)
kyddlqnkynilnklknsleekneelkkyh (SEQ ID NO. 422)
kynilnklknsleekneelkkyh (SEQ ID NO. 423)
klknsleekneelkkyh (SEQ ID NO. 424)
knsleekneelkkyh (SEQ ID NO. 425)
kneelkkyh (SEQ ID NO. 426)
hmgnnqdinenvynikpqefkeeeeedismvntkk (SEQ ID NO. 427)
knsnelkrindnffklh (SEQ ID NO. 428)
kpclykkckisqclykkckisqvwwcmpvkdtfntyernnvlnskienniekiph (SEQ ID NO. 429)
hinneytnknpkncllykneernyndnnikdyinsmnfkk (SEQ ID NO. 430)
hinneytnknpkncllykneernyndnnikdyinsmnfk (SEQ ID NO. 431)
hinneytnknpkncllyk (SEQ ID NO. 432)
knktnqskgvkgeyekkketngh (SEQ ID NO. 433)
ktnqskgvkgeyekkketngh (SEQ ID NO. 434)
kgvkgeyekkketngh (SEQ ID NO. 435)
kgeyekkketngh (SEQ ID NO. 436)
ksgmytnegnkscecsykkkssssnkvh (SEQ ID NO. 437)
kscecsykkkssssnkvh (SEQ ID NO. 438)
kkkssssnkvh (SEQ ID NO. 439)
kkssssnkvh (SEQ ID NO. 440)
kssssnkvh (SEQ ID NO. 441)
himlksgmytnegnkscecsykkkssssnk (SEQ ID NO. 442)
himlksgmytnegnkscecsykkk (SEQ ID NO. 443)
himlksgmytnegnkscecsykk (SEQ ID NO. 444)
himlksgmytnegnkscecsyk (SEQ ID NO. 445)
kplaklrkrektqinktkyergdviidnteiqkiiirdyhetlnvhkldh (SEQ ID NO. 446)
krektqinktkyergdviidnteiqkiiirdyhetlnvhkldh (SEQ ID NO. 447)
ktqinktkyergdviidnteiqkiiirdyhetlnvhkldh (SEQ ID NO. 448)
kplaklrkrektqinktkyergdviidnteiqkiiirdyhetlnvh (SEQ ID NO. 449)

TABLE 8-continued

Malaria Replikins
a) Primary structure of a Plasmodium falciparum malaria antigen located at
the merozoite surface and within the parasitophorous vacuole kplaklrkrektqinktkyergdviidnteiqkiiirdyh (SEQ ID NO. 450)
klrkrektqinktkyergdviidnteiqkiiirdyh (SEQ ID NO. 451)
krektqinktkyergdviidnteiqkiiirdyh (SEQ ID NO. 452)
ktqinktkyergdviidnteiqkiiirdyh (SEQ ID NO. 453)
kkdkekkkdsnenrkkkqkedkknpndnklkkieytnkith (SEQ ID NO. 454)
kdkekkkdsnenrkkkqkedkknpndnklkkieytnkith (SEQ ID NO. 455)
kekkkdsnenrkkkqkedkknpndnklkkieytnkith (SEQ ID NO. 456)
kkkdsnenrkkkqkedkknpndnklkkieytnkith (SEQ ID NO. 457)
kkdsnenrkkkqkedkknpndnklkkieytnkith (SEQ ID NO. 458)
kdsnenrkkkqkedkknpndnklkkieytnkith (SEQ ID NO. 459)
kkkqkedkknpndnklkkieytnkith (SEQ ID NO. 460)
kkqkedkknpndnklkkieytnkith (SEQ ID NO. 461)
kqkedkknpndnklkkieytnkith (SEQ ID NO. 462)
kedkknpndnklkkieytnkith (SEQ ID NO. 463)
kknpndnklkkieytnkith (SEQ ID NO. 464)
knpndnklkkieytnkith (SEQ ID NO. 465)
klkkieytnkith (SEQ ID NO. 466)
kkieytnkith (SEQ ID NO. 467)
kieytnkith (SEQ ID NO. 468)
hgqikiedvnnenfnneqmknkyndeekmdiskskslksdflek (SEQ ID NO. 469)
hgqikiedvnnenfnneqmknkyndeekmdiskskslk (SEQ ID NO. 470)
hgqikiedvnnenfnneqmknkyndeekmdisksk (SEQ ID NO. 471)
hgqikiedvnnenfnneqmknkyndeekmdisk (SEQ ID NO. 472)
kkyddlqnkynilnklknsleekneelkkyh (SEQ ID NO. 473)
kyddlqnkynilnklknsleekneelkkyh (SEQ ID NO. 474)
kynilnklknsleekneelkkyh (SEQ ID NO. 475)
klknsleekneelkkyh (SEQ ID NO. 476)
knsleekneelkkyh (SEQ ID NO. 477)
kneelkkyh (SEQ ID NO. 478)
hmgnnqdinenvynikpqefkeeeeedismvntkkcddiqenik (SEQ ID NO. 479)
ktnlyniynnknddkdnildnenreglylcdvmknsnelkrindnffklh (SEQ ID NO. 480)
knsnelkrindnffklh (SEQ ID NO. 481)
krindnffklh (SEQ ID NO. 482)
hinneytnknpkncllykneernyndnnikdyinsmnfkk (SEQ ID NO. 483)
hinneytnknpkncllykneernyndnnikdyinsmnfk (SEQ ID NO. 484)
hinneytnknpkncllyk (SEQ ID NO. 485)
kpclykckisqvwwcmpvkdtfntyernnvlnskienniekiph (SEQ ID NO. 486)
kckisqvwwcmpvkdtfntyernnvlnskienniekiph (SEQ ID NO. 487)
kienniekiph (SEQ ID NO. 488)
knktngskgvkgeyekkketngh (SEQ ID NO. 489)
ktngskgvkgeyekkketngh (SEQ ID NO. 490)
kgvkgeyekkketngh (SEQ ID NO. 491)
kgeyekkketngh (SEQ ID NO. 492)
ktiekinkskswffeeldeidkplaklrkrektqinktkyergdviidnteiqkiirdyh (SEQ ID NO. 493)
kinkskswffeeldeidkplaklrkrektqinktkyergdviidnteiqkiirdyh (SEQ ID NO. 494)
kplaklrkrektqinktkyergdviidnteiqkiirdyh (SEQ ID NO. 495)
himlksqmytnegnkscecsykkksssnkvh (SEQ ID NO. 496)
klrkrektqinktkyergdviidnteiqkiirdyh (SEQ ID NO. 497)
krektqinktkyergdviidnteiqkiirdyh (SEQ ID NO. 498)
ktqinktkyergdviidnteiqkiirdyh (SEQ ID NO. 499)
kplaklrkrektqinktkyergdviidnteiqkiirdyhtlnvhkldh (SEQ ID NO. 500)
klrkrektqinktkyergdviidnteiqkiirdyhtlnvhkldh (SEQ ID NO. 501)
krektqinktkyergdviidnteiqkiirdyhtlnvhkldh(SEQ ID NO. 502)
ktqinktkyergdviidnteiqkiirdyhtlnvhkldh (SEQ ID NO. 503)
kplaklrkrektqinktkyergdviidnteiqkiirdyhtlnvh (SEQ ID NO. 504)
klrkrektqinktkyergdviidnteiqkiirdyhtlnvh (SEQ ID NO. 505)
krektqinktkyergdviidnteiqkiirdyhtlnvh (SEQ ID NO. 506)
ktqinktkyergdviidnteiqkiirdyhtlnvh (SEQ ID NO. 507)
himlksqmytnegnkscecsykkksssnkvh (SEQ ID NO. 508)
ksqmytnegnkscecsykkksssnkvh (SEQ ID NO. 509)
kscecsykkksssnkvh (SEQ ID NO. 510)
kkksssnkvh (SEQ ID NO. 511)
kksssnkvh (SEQ ID NO. 512)
ksssnkvh (SEQ ID NO. 513)
himlksqmytnegnkscecsykkksssnk (SEQ ID NO. 514)
himlksqmytnegnkscecsykkk (SEQ ID NO. 515)
himlksqmytnegnkscecsykk (SEQ ID NO. 516)
himlksqmytnegnkscecsyk (SEQ ID NO. 517)
hnnhniqiykdkrinfmnphkvmyhdnmsknertek (SEQ ID NO. 518)
hnnhniqiykdkrinfmnphkvmyhdnmsk (SEQ ID NO. 519)
hnnhniqiykdkrinfmnphk (SEQ ID NO. 520)
hkvmyhdnmsknertek (SEQ ID NO. 521)
hkvmyhdnmsk (SEQ ID NO. 522)

Replikins in Structural Proteins

It has also been determined that some structural proteins include Replikin structures. Structural proteins are molecules involved in tissue and organ support, such as collagen in skin and connective tissue and in membrane structures, for example amyloid A4 precursor protein (APP) in brain. Overproduction of these proteins is associated with disease; specifically, scleroderma in the case of overproduction of collagen in skin (Table 9) and Alzheimer's Disease in the case of overproduction of APP in the brain (Table 10).

The association of scleroderma and malignancy has been a source of controversy during recent years. Several mechanisms of interrelationship have been suggested in earlier reports. Recent long-term studies suggest an increased association-ratio of scleroderma and malignancy. However, the underlying mechanisms remain elusive. (Wenzel, J. Eur. J. Dermatol. 20002 May-June 12(3): 296-300).

Several proteins concerned with the excessive production of proteins in scleroderma have been found to contain Replikin structures. Thus, these provide further examples of unrecognized targets for inhibition or cessation of excessive collagen production. Table 9 provides a list of proteins in scleroderma and the associated Replikins.

The APP protein is the source of the amyloid beta A4 protein, which in excessive amounts forms placques in the extracellular spaces in the brain, producing toxic effects associated with nerve cell loss in Alzheimer's Disease. Most studies to date have focused on the inability to clear the excessive deposits of A4, but have not considered that, rather than a waste clearance problem, this may actually be a problem of overproduction of the precursor protein APP. The high concentration of the Replikins in APP (3.3 Replikins per 100 amino acids) strongly suggest that overproduction may well be the cause of Alzheimer's Disease (Table 10). Therefore, the Replikins contained in Table 10 can be blocked or inhibited by the same methods as illustrated in detail for the glioma Replikin.

TABLE 9

Proteins overproduced in scleroderma and associated Replikins:

PMC1 HUMAN:

hreictiqssggimllkdqvlrcskiagvkvaeitelilk (SEQ ID NO. 523)
hreictiqssggimllkdqvlresk (SEQ ID NO. 524)
34 KD nucleolar scleroderma antigen:

hreictiqssggimllkdqvlrcskiagvkvaeiteliklkalendqk (SEQ ID NO. 525)
hreictiqssggimllkdqvlrcskiagvkvaeitelilk (SEQ ID NO. 526)
Fibrillarin:

kkmqqenmkpqeqltlepyerdh (SEQ ID NO. 527)
kmqqenmkpqeqltlepyerdh (SEQ ID NO. 528)
SPOP HUMAN:

hemeeskknrveindvepevfkemmcfiytgkapnldk (SEQ ID NO. 529)
hemeeskknrveindvepevfkemmcfiytgk (SEQ ID NO. 530)
Centromere protein C:

khgelkvyk (SEQ ID NO. 531)
klilgpqeekgkqh (SEQ ID NO. 532)
hnrihhk (SEQ ID NO. 533)
hhnssrkstkktnqssk (SEQ ID NO. 534)
hnssrkstkktnqssk (SEQ ID NO. 535)
khhnilpktlandkhshkph (SEQ ID NO. 536)
hhnilpktlandkhshk (SEQ ID NO. 537)
hnilpktlandkhshk (SEQ ID NO. 538)
hnilpktlandk (SEQ ID NO. 539)
kntpdskkissrnindhh (SEQ ID NO. 540)
kntpdskkissrnindh (SEQ ID NO. 541)

TABLE 9-continued

Proteins overproduced in scleroderma and associated Replikins:

kdtciqspskecqkshpksvpvsskkk (SEQ ID NO. 542)
kdtciqspskecqkshpksvpvsskk (SEQ ID NO. 543)
hpksvpvsskkk (SEQ ID NO. 544)
hpksvpvsskk (SEQ ID NO. 545)
hpksvpvssk (SEQ ID NO. 546)
Factor CTCBF, KU antigen:

kalqekveikqlnh (SEQ ID NO. 547)
ktlfplieakkkdqvtageifgdnhedgptakklktegggah (SEQ ID NO. 548)
ktlfplieakkkdqvtageifqdnb (SEQ ID NO. 549)
klcvfkkierhsih (SEQ ID NO. 550)
klcvfkkierh (SEQ ID NO. 551)
kgpsfplkgiteqqkegleivk (SEQ ID NO. 552)
hgpsfplkgiteqqk (SEQ ID NO. 553)
ATP synthase subunit 6:

htllkilstflfk (SEQ ID NO. 554)
hllgnndknllpsk (SEQ ID NO. 555)
FBRL nuclear protein:

hrhegvficrgkedalvtk (SEQ ID NO. 556)
hegvficrgkedalvtk (SEQ ID NO. 557)
hsggnrgrgrggkrghqsgk (SEQ ID NO. 558)
krgnqsgknvmveph (SEQ ID NO. 559)
krgnqsgknvmvephrh (SEQ ID NO. 560)
kkmqqenmkpqeqltlepyerdh (SEQ ID NO. 561)
kmqqenmkpqeqltlepyerdh (SEQ ID NO. 562)
HP1Hs-alpha protein:

haypedaenkeketak (SEQ ID NO. 563)
keanvkcpqiviafyeerltwh (SEQ ID NO. 564)
kvldrrvvkgqveyllkwkgfseeh (SEQ ID NO. 565)
kgqveyllkwkgfseeh (SEQ ID NO. 566)
FM/Scl nucleolar protein:

ksevaagvkksgplpsaerlenvlfgphdcsh (SEQ ID NO. 567)
ksevaagvkksgplpsaerlenvlfgph (SEQ ID NO. 568)
kaaeygkkaksetfrllhakniirpqlk (SEQ ID NO. 569)
kaaeygkkaksetfrllhak (SEQ ID NO. 570)
ksetfrllhak (SEQ ID NO. 571)
hakniirpqlk (SEQ ID NO. 572)
hmnlkiaeelpk (SEQ ID NO. 573)
hsldhllklycnvdsnk (SEQ ID NO. 574)
hllklycnvdsnk (SEQ ID NO. 575)

TABLE 10

Amyloid beta A4 precursor protein (APP) Replikins:

kakerleakh (SEQ ID NO. 576)
kdrqhtlk (SEQ ID NO. 577)
kdrqhtlkh (SEQ ID NO. 578)
ketcsekstnlh (SEQ ID NO. 579)
kteeisevkmdaefgh (SEQ ID NO. 580)
kteeisevkmdaefghdsgfevrh (SEQ ID NO. 581)
kkyvraeqkdrqhtlkh (SEQ ID NO. 582)
kyvraeqkdrqhtlkh (SEQ ID NO. 583)
kkyvraeqkdrqh (SEQ ID NO. 584)
kyvraeqkdrqht (SEQ ID NO. 585)
hhvfnmlkkyvraeqk (SEQ ID NO. 586)
hvfnmlkkyvraeqk (SEQ ID NO. 587)
hhvfnmlkkyvraeqkdrqhtlkh (SEQ ID NO. 588)
hvfnmlkkyvraeqkdrqhtlkh (SEQ ID NO. 589)
hahfqkakerleakh (SEQ ID NO. 590)
hahfqkakerleak (SEQ ID NO. 591)
hfqkakerleak (SEQ ID NO. 592)
hqermdvcethlhwhtvaketcsekstnlh (SEQ ID NO. 593)
hqermdvcethlhwhtvaketcsek (SEQ ID NO. 594)
hwhtvaketcsek (SEQ ID NO. 595)
htvaketcsek (SEQ ID NO. 596)
hlhwhtvaketcsek (SEQ ID NO. 597)
hmnvqngkwesdpsgtktcigtk (SEQ ID NO. 598)
hmnvqngkwesdpsgtk (SEQ ID NO. 599)

Passive Immunity

In another embodiment of the invention, isolated Replikin peptides may be used to generate antibodies, which may be used, for example to provide passive immunity in an individual. Passive immunity to the strain of influenza identified by the method of the invention to be the most likely cause of future influenza infections may be obtained by administering antibodies to Replikin sequences of the identified strain of influenza virus to patients in need. Similarly, passive immunity to malaria may be obtained by administering antibodies to *Plasmodium falciparum* Replikin(s).

Various procedures known in the art may be used for the production of antibodies to Replikin sequences. Such antibodies include but are not limited to polyclonal, monoclonal, chimeric, humanized, single chain, Fab fragments and fragments produced by an Fab expression library. Antibodies that are linked to a cytotoxic agent may also be generated. Antibodies may also be administered in combination with an antiviral agent. Furthermore, combinations of antibodies to different Replikins may be administered as an antibody cocktail.

For the production of antibodies, various host animals or plants may be immunized by injection with a Replikin peptide or a combination of Replikin peptides, including but not limited to rabbits, mice, rats, and larger mammals.

Monoclonal antibodies to Replikins may be prepared by using any technique that provides for the production of antibody molecules. These include but are not limited to the hybridoma technique originally described by Kohler and Milstein, (Nature, 1975, 256:495-497), the human B-cell hybridoma technique (Kosbor et al., 1983, Immunology Today, 4:72), and the EBV hybridoma technique (Cole et al., Monoclonal Antibodies and Cancer Therapy, Alan R. Liss, Inc., pp. 77-96). In addition, techniques developed for the production of chimeric antibodies (Morrison et al., 1984, Proc. Nat. Acad. Sci USA, 81:6851-6855) or other techniques may be used. Alternatively, techniques described for the production of single chain antibodies (U.S. Pat. No. 4,946,778) can be adapted to produce Replikin-specific single chain antibodies.

Particularly useful antibodies of the invention are those that specifically bind to Replikin sequences contained in peptides and/or polypeptides of influenza virus. For example, antibodies to any of peptides observed to be present in an emerging or re-emerging strain of influenza virus and combinations of such antibodies are useful in the treatment and/or prevention of influenza. Similarly, antibodies to any Replikins present on malaria antigens and combinations of such antibodies are useful in the prevention and treatment of malaria.

Antibody fragments which contain binding sites for a Replikin may be generated by known techniques. For example, such fragments include but are not limited to F(ab')2 fragments which can be produced by pepsin digestion of the antibody molecules and the Fab fragments that can be generated by reducing the disulfide bridges of the F(ab')2 fragments. Alternatively, Fab expression libraries can be generated (Huse et al., 1989, Science, 246:1275-1281) to allow rapid and easy identification of monoclonal Fab fragments with the desired specificity.

Figure 4A:
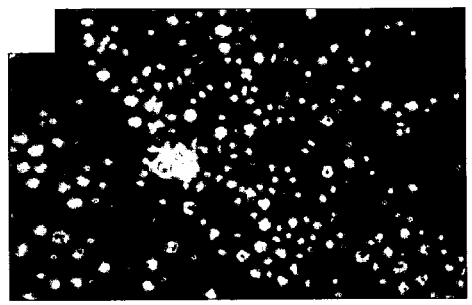
FIG. 4A is a photograph of a blood smear taken with ordinary and fluorescent light.
Figure 4B:
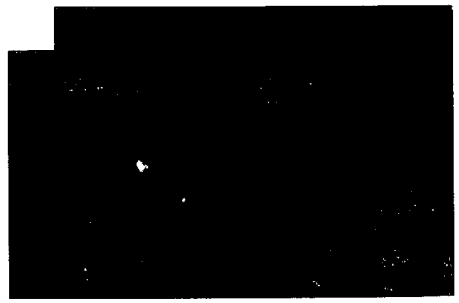
FIG. 4B is a photograph of a blood smear taken with ordinary and fluorescent light illustrating the presence of two leukemic cells.
Figure 4C:
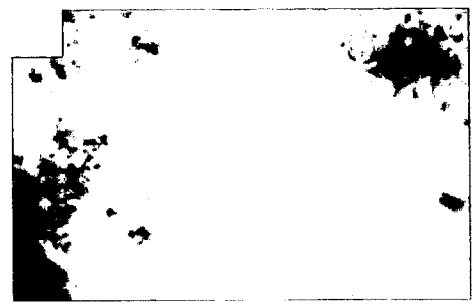
FIG. 4C is a photograph of a dense layer of glioma cells in the presence of antimalignin antibody.
Figure 4D:
FIG. 4D and FIG. 4E are photographs of the layer of cells in FIG. 4C taken at 30 and 45 minutes following addition of antimalignin antibody
Figure 4E:
Figure 4F:
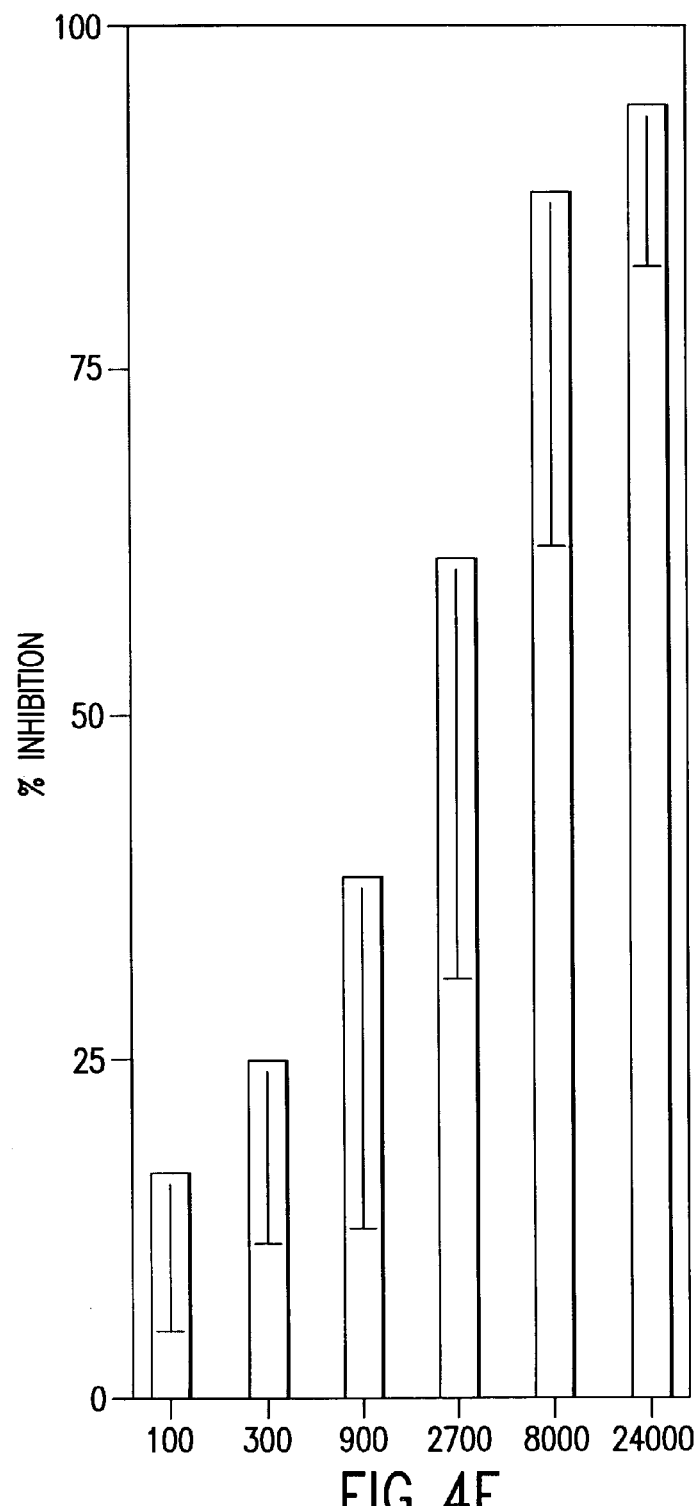
FIG. 4F is a bar graph showing the inhibition of growth of small cell lung carcinoma cells in vitro by antimalignin antibody.

The fact that antimalignin antibody is increased in concentration in human malignancy regardless of cancer cell type (FIG. 5), and that this antibody binds to malignant cells regardless of cell type now may be explained by the presence of the Replikin structures herein found to be present in most malignancies (FIG. 1 and Table 2). Population studies have shown that antimalignin antibody increases in concentration in healthy adults with age, and more so in high-risk families, as the frequency of cancer increases. An additional two-fold or greater antibody increase which occurs in early malignancy has been independently confirmed with a sensitivity of 97% in breast cancers 1-10 mm in size. Shown to localize preferentially in malignant cells in vivo, histochemically the antibody does not bind to normal cells but selectively binds to (FIG. 4a, b) and is highly cytotoxic to transformed cells in vitro (FIG. 4c-f). Since in these examples the same antibody is bound by several cell types, that is, brain glioma, hematopoietic cells (leukemia), and small cell carcinoma of lung, malignant Replikin class unity is again demonstrated.

Figure 5:
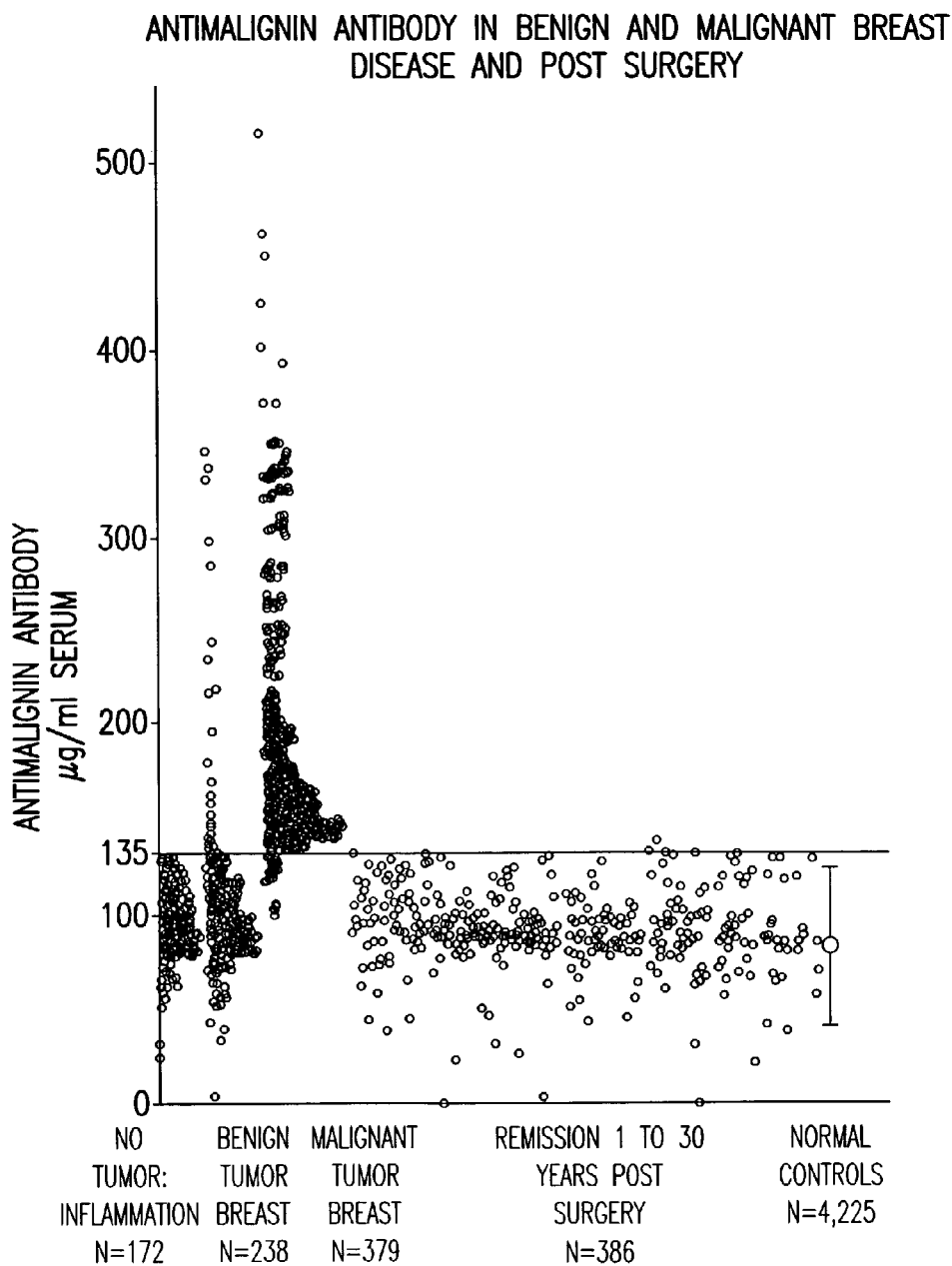
FIG. 5 is a plot of the amount of antimalignin antibody present in the serum of patients with benign or malignant breast disease pre-and post surgery.

Antimalignin does not increase with benign proliferation, but specifically increases only with malignant transformation and replication in breast in vivo and returns from elevated to normal values upon elimination of malignant cells (FIG. 5). Antimalignin antibody concentration has been shown to relate quantitatively to the survival of cancer patients, that is, the more antibody, the longer the survival. Taken together, these results suggest that anti-Replikin antibodies may be a part of a mechanism of control of cell transformation and replication. Augmentation of this immune response may be useful in the control of replication, either actively with synthetic Replikins as vaccines, or passively by the administration of anti-Replikin antibodies, or by the introduction of non-immune based organic agents, such as for example, carbohydrates, lipids and the like, which are similarly designed to target the Replikin specifically.

In another embodiment of the invention, immune serum containing antibodies to one or more Replikins obtained from an individual exposed to one or more Replikins may be used to induce passive immunity in another individual or animal. Immune serum may be administered via i.v. to a subject in need of treatment. Passive immunity also can be achieved by injecting a recipient with preformed antibodies to one or more Replikins. Passive immunization may be used to provide immediate protection to individuals who have been exposed to an infectious organism. Administration of immune serum or preformed antibodies is routine and the skilled practitioner can readily ascertain the amount of serum or antibodies needed to achieve the desired effect.

Synthetic Replikin Vaccine (Active Immunity)

Synthetic Replikin vaccines, based on Replikins such as the glioma Replikin (SEQ ID NO.: 1) "kagvaflhkk" or the hepatitis C Replikin (SEQ ID NO.: 18) "hyppkpgcivpak", or HIV Replikins such as (SEQ ID NO.: 5) "kcfncgkegh" or (SEQ ID NO.: 6) "kvylawvpahk" or preferably, an influenza vaccine based on conserved and/or emerging or re-emerging Replikin(s) over a given time period may be used to augment antibody concentration in order to lyse the respective virus infected cells and release virus extracellularly where chemical treatment can then be effective. Similarly, a malaria vaccine, based on Replikins observed in *Plasmodium falciparum* malaria antigens on the merozoite surface or within the parasitophorous vacuole, for example, can be used to generate cytotoxic antibodies to malaria.

Recognin and/or Replikin peptides may be administered to a subject to induce the immune system of the subject to produce anti-Replikin antibodies. Generally, a 0.5 to about 2 mg dosage, preferably a 1 mg dosage of each peptide is administered to the subject to induce an immune response. Subsequent dosages may be administered if desired.

The Replikin sequence structure is associated with the function of replication. Thus, whether the Replikins of this invention are used for targeting sequences that contain Replikins for the purpose of diagnostic identification, promoting replication, or inhibiting or attacking replication, for example, the structure-function relationship of the Replikin is fundamental.

It is preferable to utilize only the specific Replikin structure when seeking to induce antibodies that will recognize and attach to the Replikin fragment and thereby cause destruction of the cell. Even though the larger protein sequence may be known in the art as having a "replication associated function," vaccines using the larger protein often have failed or proven ineffective.

Although the present inventors do not wish to be held to a single theory, the studies herein suggest that the prior art vaccines are ineffective because they are based on the use of the larger protein sequence. The larger protein sequence invariably has one or more epitopes (independent antigenic sequences that can induce specific antibody formation); Replikin structures usually comprise one of these potential epitopes. The presence of other epitopes within the larger protein may interfere with adequate formation of antibodies to the Replikin, by "flooding" the immune system with irrelevant antigenic stimuli that may preempt the Replikin antigens, See, e.g., Webster, R. G., J. Immunol., 97(2):177-183 (1966); and Webster et al., J. Infect. Dis., 134:48-58, 1976; Klenerman et al, Nature 394:421-422 (1998) for a discussion of this well-known phenomenon of antigenic primacy whereby the first peptide epitope presented and recognized by the immune system subsequently prevails and antibodies are made to it even though other peptide epitopes are presented at the same time. This is another reason that, in a vaccine formulation, it is important to present the constant Replikin peptide to the immune system first, before presenting other epitopes from the organism so that the Replikin is not preempted but lodged in immunological memory.

The formation of an antibody to a non-Replikin epitope may allow binding to the cell, but not necessarily lead to cell destruction. The presence of structural "decoys" on the C-termini of malaria proteins is another aspect of this ability of other epitopes to interfere with binding of effective anti-Replikin antibodies, since the decoy epitopes have many lysine residues, but no histidine residues. Thus, decoy epitopes may bind anti-Replikin antibodies, but may keep the antibodies away from histidine-bound respiratory enzymes. Treatment may therefore be most efficacious in two stages: 1) proteases to hydrolize decoys, then; 2) anti-Replikin antibodies or other anti-Replikin agents.

It is well known in the art that in the course of antibody production against a "foreign" protein, the protein is first hydrolyzed into smaller fragments. Usually fragments containing from about six to ten amino acids are selected for antibody formation. Thus, if hydrolysis of a protein does not result in Replikin-containing fragments, anti-Replikin antibodies will not be produced. In this regard, it is interesting that Replikins contain lysine residues located six to ten amino acids apart, since lysine residues are known to bind to membranes.

Furthermore, Replikin sequences contain at least one histidine residue. Histidine is frequently involved in binding to redox centers. Thus, an antibody that specifically recognizes a Replikin sequence has a better chance of inactivating or destroying the cell in which the Replikin is located, as seen with anti-malignin antibody, which is perhaps the most cytotoxic anti-cancer antibody yet described, being active at picograms per cell.

One of the reasons that vaccines directed towards a particular protein antigen of a disease causing agent have not been fully effective in providing protection against the disease (such as foot and mouth vaccine which has been developed against the VP1 protein or large segments of the VP1 protein) is that the best antibodies have not been produced, that is—it is likey that the antibodies to the Replikins have not been produced. Replikins have not been produced. That is, either epitopes other than Replikins present in the larger protein fragments may interfere according to the phenomenon of antigenic primacy referred to above, and/or because the hydrolysis of larger protein sequences into smaller sequences for processing to produce antibodies results in loss of integrity of any Replikin structure that is present, e.g., the Replikin is cut in two and/or the histidine residue is lost in the hydrolytic processing. The present studies suggest that for an effective vaccine to be produced, the Replikin sequences, and no other epitope, should be used as the vaccine. For example, a vaccine of the invention can be generated using any one of the Replikin peptides identified by the three point recognition system.

Particularly preferred peptides—for example—an influenza vaccine include peptides that have been demonstrated to be conserved over a period of one or more years, preferably about three years or more, and/or which are present in a strain of influenza virus shown to have the highest increase in concentration of Replikins relative to Replikin concentration in other influenza virus strains, e.g., an emerging strain. The increase in Replikin concentration preferably occurs over a period of at least about six months to one year, preferably at least about two years or more, and most preferably about three years or more. Among the preferred Replikin peptides for use in an influenza virus vaccine are those Replikins observed to "re-emerge" after an absence from the hemagglutinin amino acid sequence for one or more years.

The Replikin peptides of the invention, alone or in various combinations are administered to a subject, preferably by i.v. or intramuscular injection, in order to stimulate the immune system of the subject to produce antibodies to the peptide. Generally the dosage of peptides is in the range of from about 0.1 μg to about 10 mg, preferably about 10 μg to about 1 mg, and most preferably about 50 μg to about 500 ug. The skilled practitioner can readily determine the dosage and number of dosages needed to produce an effective immune response.

Quantitative Measurement Early Response(S) to Replikin Vaccines

The ability to measure quantitatively the early specific antibody response in days or a few weeks to a Replikin vaccine is a major practical advantage over other vaccines for which only a clinical response months or years later can be measured.

Adjuvants

Various adjuvants may be used to enhance the immunological response, depending on the host species, including but not limited to Freund's (complete and incomplete), mineral gels, such as aluminum hydroxide, surface active substances such as lysolecithin, pluronic polyols, polyanions, peptides, oil emulsions, key limpet hemocyanin, dintrophenol, and potentially useful human adjuvants such as BCG and *Corynebacterium parvum*.

Replikin Nucleotide Sequences

Replikin DNA or RNA may have a number of uses for the diagnosis of diseases resulting from infection with a virus, bacterium or other Replikin encoding agent. For example, Replikin nucleotide sequences may be used in hybridization assays of biopsied tissue or blood, e.g., Southern or Northern analysis, including in situ hybridization assays, to diagnose the presence of a particular organism in a tissue sample or an environmental sample, for example. The present invention also contemplates kits containing antibodies specific for particular Replikins that are present in a particular pathogen of interest, or containing nucleic acid molecules (sense or antisense) that hybridize specifically to a particular Replikin, and optionally, various buffers and/or reagents needed for diagnosis.

Also within the scope of the invention are oligoribonucleotide sequences, that include antisense RNA and DNA molecules and ribozymes that function to inhibit the translation of Replikin- or recognin-containing mRNA. Both antisense RNA and DNA molecules and ribozymes may be prepared by any method known in the art. The antisense molecules can be incorporated into a wide variety of vectors for delivery to a subject. The skilled practitioner can readily determine the best route of delivery, although generally i.v. or i.m. delivery is routine. The dosage amount is also readily ascertainable.

Particularly preferred antisense nucleic acid molecules are those that are complementary to a Replikin sequence contained in a mRNA encoding, for example, an influenza virus polypeptide, wherein the Replikin sequence comprises from 7 to about 50 amino acids including:
  (1) at least one lysine residue located six to ten residues from a second lysine residue;
  (2) at least one histidine residue; and
  (3) at least 6% lysine residues.

More preferred are antisense nucleic acid molecules that are complementary to a Replikin present in the coding strand of the gene or to the mRNA encoding the influenza virus hemagglutinin protein, wherein the antisense nucleic acid molecule is complementary to a nucleotide sequence encoding a Replikin that has been demonstrated to be conserved over a period of six months to one or more years and/or which are present in a strain of influenza virus shown to have an increase in concentration of Replikins relative to Replikin concentration in other influenza virus strains. The increase in Replikin concentration preferably occurs over a period of at least six months, preferably about one year, most preferably about two or three years or more.

Similarly, antisense nucleic acid molecules that are complementary to mRNA those that are complementary to a mRNA encoding bacterial Replikins comprising a Replikin sequence of from 7 to about 50 amino acids including:
  (1) at least one lysine residue located six to ten residues from a second lysine residue;
  (2) at least one histidine residue; and
  (3) at least 6% lysine residues.

More preferred are antisense nucleic acid molecules that are complementary to the coding strand of the gene or to the mRNA encoding a protein of the bacteria.

Diagnostic Applications

For organisms such as diatom plankton, foot and mouth disease virus, tomato leaf curl gemini virus, hepatitis B and C, HIV, influenza virus and malignant cells, identified constituent Replikins are useful as vaccines, and also may be usefully targeted for diagnostic purposes. For example, blood collected for transfusions may be screened for contamination of organisms, such as HIV, by screening for the presence of Replikins shown to be specific for the contamination organism. Also, screening for Replikin structures specific for a particular pathological organism leads to diagnostic detection of the organism in body tissue or in the environment.

Replikin Stimulation of Growth

In another embodiment of the invention, Replikin structures are used to increase the replication rate of cells, tissues or organs. A method is available to increase replication rates by the addition of specific Replikin structures for other cells, tissues or organs that it is desired to replicate more rapidly, together with or without appropriate stimulae to cell division know in the art for said cells, tissues or organs to increase the rate of replication and yield. This may be accomplished, for example, by methods known in the art, by modifying or transforming a gene encoding for or associated with a protein or enzyme having a replication function in the organism with at least one Replikin structure.

In another aspect of the invention, Replikin structures are used to increase the replication of organisms. The present invention demonstrates that in influenza virus, for example, increased replication associated with epidemics is associated with increased concentration of Replikins. The increase is due to 1) the reappearance of particular Replikin structures, which were present in previous years, but which then disappeared for one or more years; and/or 2) by the appearance of new Replikin compositions. In addition, in malaria Replikins, repetition of the same Replikin in a single protein occurs.

Thus, the present invention provides methods and compositions for increasing the replication of organisms. Similarly, in the manner that Replikins of different organisms can be targeted to inhibit replication of any organism, Replikins can be used to increase the replication of any organism. For example, production of rice, maize, and wheat crops, which are critical to feeding large populations in the world, can be improved, for example, by increasing the concentration (number of Replikins/100 amino acid residues) of any particular strain of rice.

As an example, in the *Oryza sativa* strain of rice, catalase isolated from immature seeds was observed to contain the following different Replikins within the 491 amino acid sequence of the protein:
  kfpdvihafkpnprsh (SEQ ID NO. 625)
  kfpdvihafk (SEQ ID NO. 626)
  karyvkfhwk (SEQ ID NO.627)
  hpkvspelraiwvnylsqedeslgvkianlnvk (SEQ ID NO. 628)
  hrdeevdyypsrhaplrhapptpitprpvvgrrqkatihkqndfk (SEQ ID NO. 629)
  katihkqndfk (SEQ ID NO. 630)
  happtpitprpvvgrrqkatihkqndfk (SEQ ID NO.631)
  kfrpsssfdtkttttnagapvwndnealtvgprgpilledyhliekvah (SEQ ID NO. 632)
  kfrpsssfdtkttttnagapvwndnealtvgprgpilledyn (SEQ ID NO. 633)

Thus, by using recombinant gene cloning techniques well known in the art, the concentration of Replikin structures in an organism, such as a food crop plant, can be increased, which will promote increased replication of the organism. For example, inserting additional Replikin sequences like the Replikins identified above into the *Oryza sativa* catalase gene by methods well know in the art will promotethis organism's replication.

Similarly, in the NBS-LRR protein of *Oryza sativa* (japonica cultivar group), the following Replikins were found:
  kvkahfqkh (SEQ ID NO. 634)
  kvkahfqk (SEQ ID NO. 635)
  kdyeidkddlih (SEQ ID NO. 636)

hmkqcfafcavfpkdyeidk (SEQ ID NO. 637)
hmkqcfafcavfpk (SEQ ID NO. 638)
hvfwelvwrsffqnvkqigsifqrkvyrygqsdvttskihdlmhdlavh (SEQ ID NO. 639)
kqigsifqrkvrygpsdvttskihdlmhdlavh (SEQ ID NO. 640)
kqigsifqrkvyrygpsdvttskihdlmh (SEQ ID NO. 641)
kqigsifqrkvyrygqsdvttskih (SEQ ID NO. 642)

Further, for aspartic proteinase oryzasin 1 precursor protein, the following Replikins were found:
khgvsagik (SEQ ID NO. 643)
htvfdygkmrvgfak (SEQ ID NO. 644)
hsryksgqsstyqkngk (SEQ ID NO. 645)

Similarly, in the MADS-box protein FDRMADS3 transcription factor of *Oryza sativa* (indica cultivar-group), the following Replikins were found:
kqeamvlkqeinllqkglryiygnraneh (SEQ ID NO. 646)
kqeinllqkglryiygnraneh (SEQ ID NO. 647)
kskegmlkaaneilqekiveqnglidvgmmvadqqngh (SEQ ID NO. 648)
kaaneilqekiveqnglidvgmmvadqqngh (SEQ ID NO. 649)

Similarly, in LONI MAIZE (ATP-binding redox associated Hydrolase; Serine protease; Multigene family; Mitochondrion), the following Replikins were found:
kylaahrygik (SEQ ID NO. 650)
klkiamkhliprvleqh (SEQ ID NO. 651)
klkiamkh (SEQ ID NO. 652)
ktslassiakalnrkfirislggvkdeadirgh (SEQ ID NO. 653)
kalnrkfirislggvkdeadirgh (SEQ ID NO. 654)
kfirislggvkdeadirgh (SEQ ID NO. 655)
kvrlskatelvdrhlqsilvaekitqkvegqlsksqk (SEQ ID NO. 656)
hlqsilvaekitqkvegglsksqk (SEQ ID NO. 657)
kvrlskatelvdrh (SEQ ID NO. 658)
kvggsavesskqdtkngkepihwhskgvaaralh (SEQ ID NO. 659)
kvggsavesskqdtkngkepihwh (SEQ ID NO. 660)
kvggsavesskqdtkngkepih (SEQ ID NO. 661)
kqdtkngkepihwhskgvaaralh (SEQ ID NO. 662)
kqdtkngkepih (SEQ ID NO. 663)

Similarly, for Glyceraldehyde 3-phospate dehydrogenase A, a chloroplast precursor, the following Replikins are found:
hrdlrraraaalnivptstgaakavslylpnlk (SEQ ID NO. 664)
kvlddqkfgiikgtmtth (SEQ ID NO. 665)
hiqagakkvlitapgk (SEQ ID NO. 666)
hgrgdaspldviaindtggvkqashllk (SEQ ID NO. 667)
kqashllk (SEQ ID NO. 697)

Further, examples of rust resistance-like protein RP1-4 (*Zea mays*) found include the following Replikins:
kvrrylskdysslkqlmtlmmdddiskhlqiiesgleeredkvwmkeniik (SEQ ID NO. 668)
kvrrylskdysslkqlmtlmmdddiskh (SEQ ID NO. 669)
hlqiiesgleeredkvwmkeniik (SEQ ID NO. 670)
hdlreniimkaddlask (SEQ ID NO. 671)
hvqnlenvigkdealask (SEQ ID NO. 672)
kkqgyelrqlkdlnelggslh (SEQ ID NO. 673)
kqgyelrqlkdlnelggslh (SEQ ID NO. 674)
klylksrlkelilewssengmdamilh (SEQ ID NO. 675)
hlqllqlngmverlpnkvcnlsklrylrgykdqipnigk (SEQ ID NO. 676)
hlqllqlngmverlpnkvcnlskrylrgyk (SEQ ID NO. 677)
hlqllqlngmverlpnkvcnlsk (SEQ ID NO. 678)
hnsnklpksvgelk (SEQ ID NO. 679)
klpkvgelkh (SEQ ID NO. 680)
hlsvrvesmqkhkeiiyk (SEQ ID NO. 681)
khkeiiyk (SEQ ID NO. 682)
klrdilqesqfllvldlalfkh (SEQ ID NO. 683)
hafsgaeikdqllrmklqdtaeeiakrlgqcplaakvlgsrmcrrk (SEQ ID NO. 684)
hafsgaeikdqllrmk (SEQ ID NO. 685)
klqdtaeeiakrlgqclaakvlgsrmcrrkdiaewkaadvwfeksh (SEQ ID NO. 686)
kvlgsrmcrrkdiaewkaadvwfeksh (SEQ ID NO. 687)
kdiaewkaadvwfeksh (SEQ ID NO. 688)
kaadvwfeksh (SEQ ID NO. 689)
hvptttslptskvfgmsdrdrivkfllgktttaeasstk (SEQ ID NO. 690)
kailteakqlrdllglph (SEQ ID NO. 691)
kakaksgkgpllredessstattvmkpfh (SEQ ID NO. 692)
ksphrgklesw1rrlkeafydaedlldeh (SEQ ID NO. 693)
ksphrgkleswlrrlk (SEQ ID NO. 694)
hrgkleswlrrlk (SEQ ID NO. 695)
ksphrgk (SEQ ID NO. 696)

As discussed previously, the Replikin in wheat ubiquitin activating enzyme E (SEQ ID Nos. 601-603) is conserved. This conservation of Replikin structure provides reliable targets for stimulation of plant growth.

The close relationship of Replikins to redox enzymes is also clearly indicated in this structure in wheat. Thus, this wheat ubiquitin activating enzyme E activates ubiquitin by first adenylating with ATP its carboxy-terminal glycine residue and, thereafter, linking this residue to the side chain of a cysteine residue in E1 (SEQ ID NO. 603), yielding an ubiquitin-E1 thiolester and free AMP.

A further example of the relationship of wheat Replikins to redox enzymes was also found in the PSABWheat Protein, Photosystem I P700 chlorophyll A apoprotein A2 (PsaB) (PSI-B) isolated from bread Chinese spring wheat Chloroplast Triticum aestivum. This protein functions as follows: PsaA and PsaB bind 9700, the primary electron donor of photosystem I (PSI), as well as the electron acceptors A0, A1, and FX. PSI functions as a plastocyanin/cytochrome c6-ferredoxin oxidoreductase. Cofactor P700 is a chlorophyll A dimer, A0 is chlorophyll A, A1 is a phylloquinone and FX is a 4Fe-4S iron-sulfur center. The subunit A psaA/S heterodimer binds the P700 chlorophyll special pair and subsequent electron acceptors. The PSI reaction center of higher plants and algae is composed of one at least 11 subunits. This is an integral membrane protein of the Chloroplast thylakoid membrane. The 4Fe-4S iron-sulfur "center" to which 'h' bind is critical; hence the significance of 'h' in Replikin structure. Next to bacterial Replikins, these wheat Replikins and plant Replikins are the most primitive evolutionary illustrations of the importance of the Replikin structure to replication and the energy source needed for replication. This basic relationship carries through algae, virus Replikins, bacteria, cancer cells, and apparently all organisms with regard to replication.

Further examples of Replikins were found in the PSAB Wheat protein, which is critical fox wheat growth. These include:
hlqpkwkpslswfknaesrlnhh (SEQ ID NO. 604)
hlqpkwkpslswfk (SEQ ID NO. 605)
kwkpslswfknaesrlnhh (SEQ ID NO. 606)
kwkpslswfknaesrlnh (SEQ ID NO. 607)
kpslswfknaesrlnhh (SEQ ID NO. 608)
kpslswfknaesrlnh (SEQ ID NO. 609)
hhaialglhtttlilvkgaldargsklmpdkk (SEQ ID NO. 610)
haialglhtttlilvkgaldargsklmpdkk (SEQ ID NO. 611)
hhaialglhtttlilvkgaldargsk (SEQ ID NO. 612)
haialglhtttlilvkgaldargsk (SEQ ID NO. 613)
htttlilvkgaldargsklmpdkk (SEQ ID NO. 614)
htttlilvkgaldargsklmpdk (SEQ ID NO. 615)
htttlilvkgaldargsk (SEQ ID NO. 616)

A further example of the relationship of wheat Replikins to redox is provide in the PSAA_WHEAT Photosystem I 9700 chlorophyll A apoprotein A1, that include:

hhhlaiailfliaghmyrtnwgighglkdileahkgpftgqghk (SEQ ID NO. 617)

hhlaiailfliaghmyrtnwgighglkdileahkgpftgqghk (SEQ ID NO. 618)

hlaiailfliaghmyrtnwgighglkdileahkgpftgqghk (SEQ ID NO. 619)

hmyrtnwgighglkdileahkgpftgqghk (SEQ ID NO. 620)

hglkdileahkgpftgqghk (SEQ ID NO. 621)

hdileahkgpftgqghk (SEQ ID NO. 622)

hkgpftgqghk (SEQ ID NO. 623)

kgpftgqghk (SEQ ID NO. 624)

Computer Software for Identifying Replikins

The present invention also provides methods for identifying Replikin sequences in an amino acid or nucleic acid sequence. Visual scanning of over four thousand sequences was performed in developing the present 3-point-recognition methods. However, data banks comprising nucleotide and/or amino acid sequences can also be scanned by computer for the presence of sequences meeting the 3 point recognition requirements.

Figure 6:
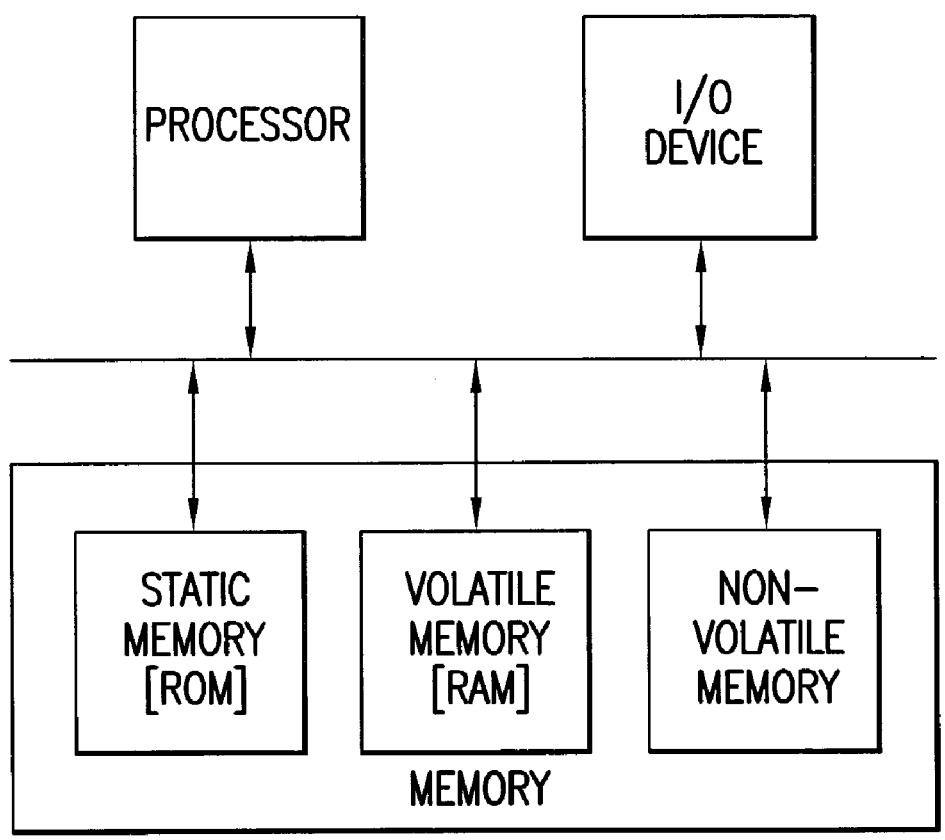
FIG. 6 is a box diagram depicting an embodiment of the invention wherein a computer is used to carry out the 3-point-recognition method of identifying Replikin sequences.

According to another embodiment of the invention, three-point recognition methods described herein may be performed by a computer. FIG. 6 is a block diagram of a computer available for use with the foregoing embodiments of the present invention. The computer may include a processor, an input/output device and a memory storing executable program instructions representing the 3-point-recognition methods of the foregoing embodiments. The memory may include a static memory, volatile memory and/or a nonvolatile memory. The static memory conventionally may be a read only memory ("ROM") provided on a magnetic, or an electrical or optical storage medium. The volatile memory conventionally may be a random accessmemory ("RAM") and may be integrated as a cache within the processor or provided externally from the processor as a separate integrated circuit. The non-volatile memory may be an electrical, magnetic or optical storage medium.

From a proteomic point of view the construction of a "3-point recognition" template based on the new glioma peptide sequence led directly to identification of a biology-wide class of proteins having related structures and functions. The operation of the 3-point-recognition method resembles identification by the use of a "keyword" search; but instead of using the exact spelling of the keyword "kagvaflhkk" (SEQ ID NO.: 1) as in a typical sequence homology search, or in the nucleotide specification of an amino acid, an abstraction of the keyword delimited by the "3-point-recognition" parameters is used. This delimited abstraction, although derived from a single relatively short amino acid sequence leads to identification of a class of proteins with structures that are defined by the same specifications. That particular functions, in this case transformation and replication, in addition to structures, turn out also to be shared by members of the exposed class suggests that these structures and functions are related. Thus, from this newly identified short peptide sequence, a molecular recognition 'language' has been formulated, which previously has not been described. Further, the sharing of immunological specificity by diverse members of the class, as here demonstrated for the cancer Replikins, suggests that B cells and their product antibodies recognize Replikins by means of a similar recognition language.

Other Uses of the Three Point Recognition Method

Since "3-point-recognition" is a proteomic method that specifies a particular class of proteins, using three or more different recognition points for other peptides similarly should provide useful information concerning other proteins classes. Further, the "3-point-recognition" method is applicable to other recognins, for example to the TOLL 'innate' recognition of lipopolyssacharides of organisms. The three point recognition method may also be modified to identify other useful compounds of covalently linked organic molecules, including other covalently linked amino acids, nucleotides, carbohydrates, lipids or combinations thereof. In this embodiment of the invention a sequence is screened for subsequences containing three or more desired structural characteristics. In the case of screening compounds composed of covalently linked amino acids, lipids or carbohydrates the subsequence of 7 to about 50 covalently linked units should contain (1) at least one first amino acid, carbohydrate or lipid residue located seven to ten residues from a second of the first amino acid, carbohydrate or lipid residue; (2) encoding at least one second amino acid, lipid or carbohydrate residue; and (3) at least 6% of the first amino acid, carbohydrate or lipid residue. In the case of screening nucleotide sequences, the subsequence of about 21 to about 150 nucleotides should contain (1) at least one codon encoding a first amino acid located within eighteen to thirty nucleotides from a second codon encoding the first amino acid residue; (2) at least one second amino acid residue; and (3) encodes at least 6% of said first amino acid residue.

Several embodiments of the present invention are specifically illustrated and described herein. However, it will be appreciated that modifications and variations of the present invention are encompassed by the above teachings and within the purview of the appended claims without departing from the spirit and intended scope of the invention.

EXAMPLE 1

Process for Extraction, Isolation and Identification of Replikins and the Use of Replikins to Target, Label or Destroy Replikin-Containing Organisms a) Algae The following algae were collected from Bermuda water sites and either extracted on the same day or frozen at −20 degrees C. and extracted the next day. The algae were homogenized in a cold room (at 0 to 5 degrees C.) in 1 gram aliquots in neutral buffer, for example 100 cc. of 0.005M phosphate buffer solution, pH 7 ("phosphate buffer") for 15 minutes in a Waring blender, centrifuged at 3000 rpm, and the supernatant concentrated by perevaporation and dialyzed against phosphate buffer in the cold to produce a volume of approximately 15 ml. The volume of this extract solution was noted and an aliquot taken for protein analysis, and the remainder was fractionated to obtain the protein fraction having a pK range between 1 and 4.

The preferred method of fractionation is chromatography as follows: The extract solution is fractionated in the cold room (4 degrees C.) on a DEAE cellulose (Cellex-D) column 2.5×11.0 cm, which has been equilibrated with 0.005M phosphate buffer. Stepwise eluting solvent changes are made with the following solutions:

Solution 1—4.04 g. NaH2P04 and 0.5 g NaH2P04 are dissolved in 15 liters of distilled water (0.005 molar, pH 7);

Solution 2—8.57 g. NaH2PO4 is dissolved in 2,480 ml. of distilled water;

Solution 3—17.1 g. of NaH2PO4 is dissolved in 2480 ml of distilled water (0.05 molar, pH 4.7);

Solution 4—59.65 g. of NaH2PO4 is dissolved in 2470 ml distilled water (0.175 molar);

Solution 5—101.6 g. of NaH2PO4 is dissolved in 2455 ml distilled water (pH 4.3);

Solution 6—340.2 g. of NaH2PO4 is dissolved in 2465 of distilled water (1.0 molar, pX-i 4.1);

Solution 7—283.63 g. of 80% phosphoric acid (H3PO4) is made up in 2460 ml of distilled water (1.0 molar, pH 1.0).

The extract solution, in 6 to 10 ml volume, is passed onto the column and overlayed with Solution 1, and a reservoir of 300 ml of Solution 1 is attached and allowed to drip by gravity onto the column. Three ml aliquots of eluant are collected and analyzed for protein content at OD 280 until all of the protein to be removed with Solution 1 has been removed from the column. Solution 2 is then applied to the column, followed in succession by Solutions 3, 4, 5, 6 and 7 until all of the protein which can, be removed with each Solution is removed from the column. The eluates from Solution 7 are combined, dialyzed against phosphate buffer, the protein content determined of both dialysands and dialyzate, and both analyzed by gel electrophoresis. One or two bands of peptide or protein of molecular weight between 3,000 and 25,000 Daltons are obtained in Solution 7. For example the algae *Caulerpa mexicana, Laurencia obtura, Cladophexa prolifera, Sargassum natans, Caulerpa verticillata, Halimeda tuna*, and *Penicillos capitatus*, after extraction and treatment as above, all demonstrated in Solution 7 eluates sharp peptide bands in this molecular weight region with no contaminants. These Solution 7 proteins or their eluted bands are hydrolyzed, and the amino acid composition determined. The peptides so obtained, which have a lysine composition of 6% or greater are Replikin precursors. These Replikin peptide precursors are then determined for amino acid sequence and the Replikins are determined by hydrolysis and mass spectrometry as detailed in U.S. Pat. No. 6,242,578 B1. Those which fulfill the criteria defined by the "3-point-recognition" method are identified as Replikins. This procedure can also be applied to obtain yeast, bacterial and any plant Replikins.

b) Virus

Using the same extraction and column chromatography separation methods as above in a) for algae, Replikens in virus-infected cells are isolated and identified.

c) Tumor Cells in vivo and in vitro Tissue Culture

Using the same extraction and column chromatography separation methods as above in a) for algae, Replikins in tumor cells are isolated and identified. For example, Replikin precursors of Astrocytin isolated from malignant brain tumors, Malignin (Aglyco lOB) isolated from glioblastoma tumor cells in tissue culture, MCF7 mammary carcinoma cells in tissue culture, and P3J Lymphoma cells in tissue culture each treated as above in a) yielded Replikin precursors with lysine content of 9.1%, 6.7%, 6.7%, and 6.5% respectively. Hydrolysis and mass spectrometry of Aglyco lOB as described in Example 10 U.S. Pat. No. 6,242,578 B1 produced the amino acid sequence, ykagvaflhkkndiide the 16-mer Replikin.

EXAMPLE 2

As an example of diagnostic use of Replikins: Aglyco lOB or the 16-mer Repliken may be used as antigen to capture and quantify the amount of its corresponding antibody present in serum for diagnostic purposes are as shown in FIGS. 2, 3, 4 and 7 of U.S. Pat. No. 6,242,578 B1.

As an example of the production of agents to attach to Replikins for labeling, nutritional or destructive purposes: Injection of the 16-mer Replikin into rabbits to produce the specific antibody to the 16-mer Replikin is shown in Example 6 and FIGS. 9A and 9B of U.S. Pat. No. 6,242,578 B1.

As an example of the use of agents to label Replikins: The use of antibodies to the 16-mer Replikin to label specific cells which contain this Replikin is shown in FIG. 5 and Example 6 of U.S. Pat. No. 6,242,578 B1.

As an example of the use of agents to destroy Replikins: The use of antibodies to the 16-mer Replikin to inhibit or destroy specific cells which contain this Replikin is shown in FIG. 6 of U.S. Pat. No. 6,242,578 B1.

EXAMPLE 3

Analysis of sequence data of isolates of influenza virus hemagglutinin protein or neuramimidase protein for the presence and concentration of Replikins is carried out by visual scanning of sequences or through use of a computer program based on the 3-point recognition system described herein. Isolates of influenza virus are obtained and the amino acid sequence of the influenza hemagglutinin and/or neuramimidase protein is obtained by any art known method, such as by sequencing the hemagglutinin or neuramimidase gene and deriving the protein sequence therefrom. Sequences are scanned for the presence of new Replikins, conservation of Replikins over time and concentration of Replikins in each isolate. Comparison of the Replikin sequences and concentrations to the amino acid sequences obtained from isolates at an earlier time, such as about six months to about three years earlier, provides data that are used to predict the emergence of strains that are most likely to be the cause of influenza in upcoming flu seasons, and that form the basis for seasonal influenza peptide vaccines or nucleic acid based vaccines. Observation of an increase in concentration, particularly a stepwise increase in concentration of Replikins in a given strain of influenza virus for a period of about six months to about three years or more is a predictor of emergence of the strain as a likely cause of influenza epidemic or pandemic in the future.

Peptide vaccines or nucleic acid-based vaccines based on the Replikins observed in the emerging strain are generated. An emerging strain is identified as the strain of influenza virus having the highest increase in concentration of Replikin sequences within the hemagglutinin and/or neuramimidase sequence during the time period. Preferably, the peptide or nucleic acid vaccine is based on or includes any Replikin sequences that are observed to be conserved in the emerging strain. Conserved Replikins are preferably those Replikin sequences which are present in the hemagglutinin or neuramimidase protein sequence for about two years and preferably longer. The vaccines may include any combination of Replikin sequences identified in the emerging strain.

For vaccine production, the Replikin peptide or peptides identified as useful for an effective vaccine are synthesized by any method, including chemical synthesis and molecular biology techniques, including cloning, expression in a host cell and purification therefrom. The peptides are preferably admixed with a pharmaceutically acceptable carrier in an amount determined to induce a therapeutic antibody reaction thereto. Generally, the dosage is about 0.1 µg to about 10 mg.

The influenza vaccine is preferably administered to a patient in need thereof prior to the onset of "flu season." Influenza flu season generally occurs in late October and lasts through late April. However, the vaccine may be administered at any time during the year. Preferably, the influenza vaccine is administered once yearly, and is based on Replikin sequences observed to be present, and preferably conserved in the emerging strain of influenza virus. Another preferred Replikin for inclusion in an influenza vaccine is a Replikin demonstrated to have re-emerged in a strain of influenza after an absence of one or more years.

EXAMPLE 4

Analysis of sequence data of isolates of *Plasmodium falciparum* antigens for the presence and concentration of Replikins is carried out by visual scanning of sequences or through use of a computer program based on the 3-point recognition method described herein. Isolates of *Plasmodium falciparum* are obtained and the amino acid sequence of the protein is obtained by any art known method, such as by sequencing the gene and deriving the protein sequence therefrom. Sequences are scanned for the presence of Replikins, conservation of Replikins over time and concentration of Replikins in each isolate. This information provides data that are used to form the basis for anti-malarial peptide vaccines or nucleic acid based vaccines.

Peptide vaccines or nucleic acid-based vaccines based on the Replikins observed in the malaria causing organism are generated. Preferably, the peptide or nucleic acid vaccine is based on or includes any Replikin sequences that are observed to be present on a surface antigen of the organism. The vaccines may include any combination of Replikin sequences identified in the malaria causing strain.

For vaccine production, the Replikin peptide or peptides identified as useful for an effective vaccine are synthesized by any method, including chemical synthesis and molecular biology techniques, including cloning, expression in a host cell and purification therefrom. The peptides are preferably admixed with a pharmaceutically acceptable carrier in an amount determined to induce a therapeutic antibody reaction thereto. Generally, the dosage is about 0.1 µg to about 10 mg.

Then malaria vaccine is preferably administered to a patient in need thereof at any time during the year, and particularly prior to travel to a tropical environment.

Another embodiment includes an antisense nucleic acid molecule complementary to the coding strand of the gene or the mRNA encoding organism for the replikins in organisms including, but not limited to, viruses, trypanosomes, bacteria, fungi, algae, amoeba, and plants, wherein said antisense nucleic acid molecules is complementary to a nucleotide sequence of a replikin containing organism.

What is claimed is:

1. An isolated or synthesized HIV trans-activator peptide consisting of 7 to 50 amino acids and consisting of a Replikin motif wherein said Replikin motif comprises:

(a) at least one lysine residue located at a first terminus of said motif and at least one lysine residue or at least one histidine residue located at a second terminus of said motif;

(b) a first lysine residue located 6 to 10 amino acid residues from a second lysine residue;

(c) at least one histidine residue; and (d) at least 6% lysine residues, and wherein said motif comprises the sequence set forth in SEQ ID NO: 600.

2. The peptide of claim 1, wherein said peptide consists of the sequence as set forth in SEQ ID NO: 600.

* * * * *